*(12)* United States Patent
Liu

(10) Patent No.: US 11,912,763 B2
(45) Date of Patent: Feb. 27, 2024

(54) ANTIBODY TARGETING CLDN18.2, BISPECIFIC ANTIBODY, ADC, AND CAR, AND APPLICATIONS THEREOF

(71) Applicant: L&L BIOPHARMA CO., LTD., Shanghai (CN)

(72) Inventor: Jiajian Liu, Shanghai (CN)

(73) Assignee: L & L BIOPHARMA CO., LTD., Shanghai (CN)

( * ) Notice: Subject to any disclaimer, the term of this patent is extended or adjusted under 35 U.S.C. 154(b) by 526 days.

(21) Appl. No.: 17/252,259

(22) PCT Filed: Jun. 6, 2019

(86) PCT No.: PCT/CN2019/090255
§ 371 (c)(1),
(2) Date: Dec. 14, 2020

(87) PCT Pub. No.: WO2019/242505
PCT Pub. Date: Dec. 26, 2019

(65) Prior Publication Data
US 2021/0230272 A1    Jul. 29, 2021

(30) Foreign Application Priority Data

Jun. 17, 2018 (CN) .......................... 201810610790.3
Nov. 1, 2018 (CN) .......................... 201811295845.2
Feb. 3, 2019 (CN) .......................... 201910108951.3
Apr. 8, 2019 (CN) .......................... 201910276473.7

(51) Int. Cl.
| | |
|---|---|
| *C07K 16/28* | (2006.01) |
| *A61K 47/68* | (2017.01) |
| *A61P 35/00* | (2006.01) |
| *A61K 31/537* | (2006.01) |
| *A61K 38/07* | (2006.01) |
| *C07K 14/725* | (2006.01) |
| *C07K 16/22* | (2006.01) |
| *C07K 16/24* | (2006.01) |
| *A61K 39/00* | (2006.01) |

(52) U.S. Cl.
CPC ............ *C07K 16/28* (2013.01); *A61K 31/537* (2013.01); *A61K 38/07* (2013.01); *A61K 47/6803* (2017.08); *A61K 47/6849* (2017.08); *A61P 35/00* (2018.01); *C07K 14/7051* (2013.01); *C07K 16/22* (2013.01); *C07K 16/244* (2013.01); *C07K 16/2803* (2013.01); *C07K 16/2809* (2013.01); *C07K 16/2818* (2013.01); *C07K 16/2827* (2013.01); *A61K 2039/505* (2013.01); *C07K 2317/21* (2013.01); *C07K 2317/24* (2013.01); *C07K 2317/31* (2013.01); *C07K 2317/622* (2013.01); *C07K 2317/732* (2013.01); *C07K 2317/734* (2013.01); *C07K 2317/76* (2013.01); *C07K 2317/92* (2013.01); *C07K 2319/02* (2013.01); *C07K 2319/03* (2013.01)

(58) Field of Classification Search
CPC ...................................................... C07K 16/28
See application file for complete search history.

(56) References Cited

U.S. PATENT DOCUMENTS

| | | | |
|---|---|---|---|
| 3,896,111 A | 7/1975 | Kupchan et al. | |
| 4,151,042 A | 4/1979 | Higashide et al. | |
| 7,750,116 B1 | 7/2010 | Doronina et al. | |
| 9,382,320 B2 | 7/2016 | Liu et al. | |
| 10,053,512 B2 | 8/2018 | Sahin et al. | |
| 2009/0202536 A1 | 8/2009 | Ebens, Jr. et al. | |
| 2014/0127211 A1 | 5/2014 | Geles et al. | |
| 2015/0147763 A1* | 5/2015 | Sahin ................. | C07K 16/3023 530/387.9 |
| 2017/0210806 A1 | 7/2017 | Liu | |
| 2018/0110875 A1 | 4/2018 | Liu et al. | |

FOREIGN PATENT DOCUMENTS

| | | |
|---|---|---|
| CN | 105315375 A | 2/2016 |
| CN | 105330740 A | 2/2016 |
| CN | 106188293 A | 12/2016 |
| CN | 106755107 A | 5/2017 |

(Continued)

OTHER PUBLICATIONS

Sep. 5, 2019 International Search Report issued in International Patent Application No. PCT/CN2019/090255.
Sep. 5, 2019 Written Opinion of the International Searching Authority issued in International Patent Application No. PCT/CN2019/090255.
Sahin U. et al., Claudin-18 splice variant 2 is a pan-cancer target suitable for therapeutic antibody delveopmen, Clin Cancer Res, vol. 14—No. 23, pp. 7642-7634,2008.
R Bird et al., Single-chain antigen-binding proteins, Science, vol. 242—No. 4877, pp. 423-426, Oct. 21, 1988.

(Continued)

*Primary Examiner* — Adam Weidner
*Assistant Examiner* — Ashley H. Gao
(74) *Attorney, Agent, or Firm* — Houston Beshining Law Office PLLC; Liangang Ye

(57) ABSTRACT

Provided is an antibody targeting CLDN18.2. The antibody targeting CLDN118.2 comprises VL and/or VH; the VL comprises the following CDR sequences: a VL CDR1 amino acid sequence as shown in SEQ ID NO: 11 or SEQ ID NO: 12; a VL CDR2 amino acid sequence as shown in SEQ ID NO: 13; and a VL CDR3 amino acid sequence as shown in SEQ ID NO: 14; and the VH comprises the following CDR sequences; a VH CDR1 amino acid sequence as shown in SEQ ID NO: 15; a VH CDR2 amino acid sequence as shown in SEQ ID NO: 16; and a VH CDR3 amino acid sequence as shown in SEQ ID NO: 17. Further disclosed are a bispecific antibody targeting CLDN18.2, a conjugates of the antibody, a CAR molecule targeting CLDN18.2 and a cell comprising same, and applications thereof.

20 Claims, 12 Drawing Sheets

Specification includes a Sequence Listing.

(56) References Cited

FOREIGN PATENT DOCUMENTS

| CN | 108047331 A | 5/2018 |
|---|---|---|
| CN | 108948193 A | 12/2018 |
| CN | 110172099 A | 8/2019 |
| EP | 3170842 A1 | 5/2017 |
| EP | 3176180 A1 | 6/2017 |
| JP | 2015517476 A | 6/2015 |
| WO | 2005081711 A2 | 9/2005 |
| WO | 2006034488 A2 | 3/2006 |
| WO | 2007046006 A2 | 4/2007 |
| WO | 2013019906 A1 | 2/2013 |
| WO | 2013167153 A1 | 11/2013 |
| WO | 2014140248 A1 | 9/2014 |
| WO | 2014146672 A1 | 9/2014 |
| WO | 2015118175 A2 | 8/2015 |
| WO | 2016015685 A1 | 2/2016 |
| WO | 2016165762 A1 | 10/2016 |
| WO | 2016166122 A1 | 10/2016 |
| WO | 2016180468 A1 | 11/2016 |
| WO | 2016180782 A1 | 11/2016 |
| WO | 2018054484 A1 | 3/2018 |
| WO | 2018075857 A1 | 4/2018 |

OTHER PUBLICATIONS

J S Huston et al., Protein engineering of antibody binding sites: recovery of specific activity in an anti-digoxin single-chain Fv analogue produced in *Escherichia coli*, Proc.Natl.Acad.Sci.USA, vol. 85, pp. 5879-5883, 1988.

Tin-Wein Yu et al., The biosynthetic gene cluster of the maytansinoid antitumor agent ansamitocin from Actinosynnema pretiosum, Proc Natl Acad Sci U S A, vol. 99—No. 12, pp. 7968-7973, Jun. 11, 2002.

Wayne C Widdison et al., Semisynthetic maytansine analogues for the targeted treatment of cancer, Journal of Medicinal Chemistry, vol. 49—No. 14, pp. 4392-4408, Jul. 13, 2006.

Aug. 2, 2021 Extended European Search Report issued in European Patent Application No. 19823355.3.

Aug. 19, 2021 the First Office Action issued in European Patent Application No. 19823355.3.

Apr. 4, 2023 Japanese Office Action issued in Japanese Patent Application No. 2020-571669.

Mar. 29, 2023 Chinese Office Action issued in Chinese Patent Application No. 201980019477.5.

* cited by examiner a b

SEQUENCE LISTING

<160> NUMBER OF SEQ ID NOS: 61

<210> SEQ ID NO 1
<211> LENGTH: 137
<212> TYPE: PRT
<213> ORGANISM: Artificial Sequence
<220> FEATURE:

<223> OTHER INFORMATION: TGFbeta RII

<400> SEQUENCE: 1

```
Gly Ile Pro Pro His Val Gln Lys Ser Val Asn Asn Asp Met Ile Val
1               5                   10                  15
Thr Asp Asn Asn Gly Ala Val Lys Phe Pro Gln Leu Cys Lys Phe Cys
            20                  25                  30
Asp Val Arg Phe Ser Thr Cys Asp Asn Gln Lys Ser Cys Met Ser Asn
        35                  40                  45
Cys Ser Ile Thr Ser Ile Cys Glu Lys Pro Gln Glu Val Cys Val Ala
    50                  55                  60
Val Trp Arg Lys Asn Asp Glu Asn Ile Thr Leu Glu Thr Val Cys His
65                  70                  75                  80
Asp Pro Lys Leu Pro Tyr His Asp Phe Ile Leu Glu Asp Ala Ala Ser
                85                  90                  95
Pro Lys Cys Ile Met Lys Glu Lys Lys Lys Pro Gly Glu Thr Phe Phe
            100                 105                 110
Met Cys Ser Cys Ser Ser Asp Glu Cys Asn Asp Asn Ile Ile Phe Ser
        115                 120                 125
Glu Glu Tyr Asn Thr Ser Asn Pro Asp
    130                 135
```

<210> SEQ ID NO 2
<211> LENGTH: 160
<212> TYPE: PRT
<213> ORGANISM: Artificial Sequence
<220> FEATURE:
<223> OTHER INFORMATION: IL10

<400> SEQUENCE: 2

```
Ser Pro Gly Gln Gly Thr Gln Ser Glu Asn Ser Cys Thr His Phe Pro
1               5                   10                  15
Gly Asn Leu Pro Asn Met Leu Arg Asp Leu Arg Asp Ala Phe Ser Arg
            20                  25                  30
Val Lys Thr Phe Phe Gln Met Lys Asp Gln Leu Asp Asn Leu Leu Leu
        35                  40                  45
Lys Glu Ser Leu Leu Glu Asp Phe Lys Gly Tyr Leu Gly Cys Gln Ala
    50                  55                  60
Leu Ser Glu Met Ile Gln Phe Tyr Leu Glu Glu Val Met Pro Gln Ala
65                  70                  75                  80
Glu Asn Gln Asp Pro Asp Ile Lys Ala His Val Asn Ser Leu Gly Glu
                85                  90                  95
Asn Leu Lys Thr Leu Arg Leu Arg Leu Arg Arg Cys His Arg Phe Leu
            100                 105                 110
Pro Cys Glu Asn Lys Ser Lys Ala Val Glu Gln Val Lys Asn Ala Phe
        115                 120                 125
Asn Lys Leu Gln Glu Lys Gly Ile Tyr Lys Ala Met Ser Glu Phe Asp
    130                 135                 140
Ile Phe Ile Asn Tyr Ile Glu Ala Tyr Met Thr Met Lys Ile Arg Asn
145                 150                 155                 160
```

<210> SEQ ID NO 3
<211> LENGTH: 469
<212> TYPE: PRT
<213> ORGANISM: Artificial Sequence
<220> FEATURE:
<223> OTHER INFORMATION: CAR1a protein

```
<400> SEQUENCE: 3

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro Phe Thr Phe Gly Gln Gly Thr Lys Leu Glu Ile
            100                 105                 110

Lys Gly Gly Gly Gly Ser Gly Gly Gly Gly Ser Gly Gly Gly Gly Ser
        115                 120                 125

Gln Val Gln Leu Val Gln Ser Gly Ala Glu Val Lys Lys Pro Gly Ser
    130                 135                 140

Ser Val Lys Val Ser Cys Lys Ala Ser Gly Tyr Ala Phe Ser Asn Tyr
145                 150                 155                 160

Leu Ile Glu Trp Val Lys Gln Ala Pro Gly Gln Gly Leu Glu Trp Ile
            165                 170                 175

Gly Leu Ile Asn Pro Gly Ser Gly Gly Thr Asn Tyr Asn Glu Lys Phe
        180                 185                 190

Lys Gly Lys Ala Thr Ile Thr Ala Asp Lys Ser Thr Ser Thr Ala Tyr
    195                 200                 205

Met Glu Leu Ser Ser Leu Arg Ser Glu Asp Thr Ala Val Tyr Tyr Cys
210                 215                 220

Ala Arg Val Tyr Tyr Gly Asn Ser Phe Ala Tyr Trp Gly Gln Gly Thr
225                 230                 235                 240

Leu Val Thr Val Ser Ser Thr Thr Thr Pro Ala Pro Arg Pro Pro Thr
            245                 250                 255

Pro Ala Pro Thr Ile Ala Ser Gln Pro Leu Ser Leu Arg Pro Glu Ala
        260                 265                 270

Cys Arg Pro Ala Ala Gly Gly Ala Val His Thr Arg Gly Leu Asp Phe
    275                 280                 285

Ala Cys Asp Ile Tyr Ile Trp Ala Pro Leu Ala Gly Thr Cys Gly Val
290                 295                 300

Leu Leu Leu Ser Leu Val Ile Thr Leu Tyr Cys Lys Arg Gly Arg Lys
305                 310                 315                 320

Lys Leu Leu Tyr Ile Phe Lys Gln Pro Phe Met Arg Pro Val Gln Thr
            325                 330                 335

Thr Gln Glu Glu Asp Gly Cys Ser Cys Arg Phe Pro Glu Glu Glu Glu
        340                 345                 350

Gly Gly Cys Glu Leu Arg Val Lys Phe Ser Arg Ser Ala Asp Ala Pro
    355                 360                 365

Ala Tyr Lys Gln Gly Gln Asn Gln Leu Tyr Asn Glu Leu Asn Leu Gly
370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
            405                 410                 415
```

-continued

```
Asn Glu Leu Gln Lys Asp Lys Met Ala Glu Ala Tyr Ser Glu Ile Gly
            420                 425                 430

Met Lys Gly Glu Arg Arg Gly Lys Gly His Asp Gly Leu Tyr Gln
        435                 440                 445

Gly Leu Ser Thr Ala Thr Lys Asp Thr Tyr Asp Ala Leu His Met Gln
450                 455                 460

Ala Leu Pro Pro Arg
465

<210> SEQ ID NO 4
<211> LENGTH: 712
<212> TYPE: PRT
<213> ORGANISM: Artificial Sequence
<220> FEATURE:
<223> OTHER INFORMATION: LB193 sequence comprising a heavy chain

<400> SEQUENCE: 4

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu Gly Gly Gly Ser Gly Gly
                245                 250                 255

Gly Gly Ser Gly Gly Gly Ser Gln Val Gln Leu Val Gln Ser Gly
            260                 265                 270

Ala Glu Val Lys Lys Pro Gly Ser Ser Val Lys Val Ser Cys Lys Ala
        275                 280                 285

Ser Gly Tyr Ala Phe Ser Asn Tyr Leu Ile Glu Trp Val Lys Gln Ala
    290                 295                 300
```

```
Pro Gly Gln Gly Leu Glu Trp Ile Gly Leu Ile Asn Pro Gly Ser Gly
305                 310                 315                 320
Gly Thr Asn Tyr Asn Glu Lys Phe Lys Gly Lys Ala Thr Ile Thr Ala
                325                 330                 335
Asp Lys Ser Thr Ser Thr Ala Tyr Met Glu Leu Ser Ser Leu Arg Ser
            340                 345                 350
Glu Asp Thr Ala Val Tyr Tyr Cys Ala Arg Val Tyr Tyr Gly Asn Ser
        355                 360                 365
Phe Ala Tyr Trp Gly Gln Gly Thr Leu Val Thr Val Ser Ser Ala Ser
370                 375                 380
Thr Lys Gly Pro Ser Val Phe Pro Leu Ala Pro Ser Ser Lys Ser Thr
385                 390                 395                 400
Ser Gly Gly Thr Ala Ala Leu Gly Cys Leu Val Lys Asp Tyr Phe Pro
                405                 410                 415
Glu Pro Val Thr Val Ser Trp Asn Ser Gly Ala Leu Thr Ser Gly Val
            420                 425                 430
His Thr Phe Pro Ala Val Leu Gln Ser Ser Gly Leu Tyr Ser Leu Ser
        435                 440                 445
Ser Val Val Thr Val Pro Ser Ser Ser Leu Gly Thr Gln Thr Tyr Ile
450                 455                 460
Cys Asn Val Asn His Lys Pro Ser Asn Thr Lys Val Asp Lys Lys Val
465                 470                 475                 480
Glu Pro Lys Ser Cys Asp Lys Thr His Thr Cys Pro Pro Cys Pro Ala
                485                 490                 495
Pro Glu Leu Leu Gly Gly Pro Ser Val Phe Leu Phe Pro Pro Lys Pro
            500                 505                 510
Lys Asp Thr Leu Met Ile Ser Arg Thr Pro Glu Val Thr Cys Val Val
        515                 520                 525
Val Asp Val Ser His Glu Asp Pro Glu Val Lys Phe Asn Trp Tyr Val
530                 535                 540
Asp Gly Val Glu Val His Asn Ala Lys Thr Lys Pro Arg Glu Glu Gln
545                 550                 555                 560
Tyr Asn Ser Thr Tyr Arg Val Val Ser Val Leu Thr Val Leu His Gln
                565                 570                 575
Asp Trp Leu Asn Gly Lys Glu Tyr Lys Cys Lys Val Ser Asn Lys Ala
            580                 585                 590
Leu Pro Ala Pro Ile Glu Lys Thr Ile Ser Lys Ala Lys Gly Gln Pro
        595                 600                 605
Arg Glu Pro Gln Val Tyr Thr Leu Pro Pro Ser Arg Asp Glu Leu Thr
610                 615                 620
Lys Asn Gln Val Ser Leu Thr Cys Leu Val Lys Gly Phe Tyr Pro Ser
625                 630                 635                 640
Asp Ile Ala Val Glu Trp Glu Ser Asn Gly Gln Pro Glu Asn Asn Tyr
                645                 650                 655
Lys Thr Thr Pro Pro Val Leu Asp Ser Asp Gly Ser Phe Phe Leu Tyr
            660                 665                 670
Ser Lys Leu Thr Val Asp Lys Ser Arg Trp Gln Gln Gly Asn Val Phe
        675                 680                 685
Ser Cys Ser Val Met His Glu Ala Leu His Asn His Tyr Thr Gln Lys
690                 695                 700
Ser Leu Ser Leu Ser Pro Gly Lys
705                 710
```

<210> SEQ ID NO 5
<211> LENGTH: 530
<212> TYPE: DNA
<213> ORGANISM: Artificial Sequence
<220> FEATURE:
<223> OTHER INFORMATION: anti-hCLDN18.2 monoclonal antibody light chain
      nucleotide sequence

<400> SEQUENCE: 5

```
taatgggctt caagatgaag tcacagtttc tggtcctcat gtccctgctg ttctgggtat    60
ctggtacctg tggggacatt gtgatgacac agtctccatc ctccctgact gtgacagcag   120
gagagaaggt cactatgagt tgcaagtcca gtcagagtct gttaaacagt ggaaatcaaa   180
agaactactt gacctggtac cagcagaaac agggcagcc tcctaaactg ttgatctact   240
gggcatccac tagggaatct ggggtccctg atcgcttcac aggcagtgga tctggaacac   300
atttcactct caccatcagc agtgtgcagg ctgaagacct ggcagtttat tactgtcaga   360
atgattattt ttatccattc acgttcggct cggggacaaa gttggaaaaa aaacgggctg   420
atgctgcacc aactgtatcc atcttcccac catccagtga gcagttaaca tctggaggtg   480
cctcagtcgt gtgcttctga acaactctac cccaaagacc atccatgccc              530
```

<210> SEQ ID NO 6
<211> LENGTH: 528
<212> TYPE: DNA
<213> ORGANISM: Artificial Sequence
<220> FEATURE:
<223> OTHER INFORMATION: anti-hCLDN18.2 monoclonal antibody heavy chain
      nucleotide sequence

<400> SEQUENCE: 6

```
taatgggatg gaccgggatc tttatctttc tcctgtcagt aactgcaggt gttcactccc    60
aggtccagct gcagcagtct ggagctgagc tgataggacc tgggacttca gtgaaggtgt   120
cctgcaaggc ctctggatac gccttcagta attacttgat agaatgggta aaacagaggc   180
ctgaacaggg ccttgagtgg attggtttga ttaatcctgg aagtggtggc actaactaca   240
atgagaagtt caagggcaag gcaacactga ctgcagacaa atcctccagc actgcctaca   300
tgcaactcag cagcctgaca tctgatgact ctgcggtcta cttctgtgca agggtctact   360
atggtaactc ctttgcttac tggggccaag ggactctggt cactgtctct gcagccaaaa   420
cgacaccccc atctgtctat ccactggccc ctggatctgc tgcccaaact aactccatgg   480
tgaccctggg atgcctggtc aagggctatt accgagcaag aaatgtcg                528
```

<210> SEQ ID NO 7
<211> LENGTH: 113
<212> TYPE: PRT
<213> ORGANISM: Artificial Sequence
<220> FEATURE:
<223> OTHER INFORMATION: mab5b light chain variable region

<400> SEQUENCE: 7

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60
```

```
Pro Asp Arg Phe Thr Gly Ser Gly Ser Gly Thr His Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Phe Tyr Pro Phe Thr Phe Gly Ser Gly Thr Lys Leu Glu Lys
            100                 105                 110

Lys
```

<210> SEQ ID NO 8
<211> LENGTH: 118
<212> TYPE: PRT
<213> ORGANISM: Artificial Sequence
<220> FEATURE:
<223> OTHER INFORMATION: mab5b heavy chain variable region

<400> SEQUENCE: 8

```
Gln Val Gln Leu Gln Gln Ser Gly Ala Glu Leu Ile Gly Pro Gly Thr
1               5                   10                  15

Ser Val Lys Val Ser Cys Lys Ala Ser Gly Tyr Ala Phe Ser Asn Tyr
                20                  25                  30

Leu Ile Glu Trp Val Lys Gln Arg Pro Glu Gln Gly Leu Glu Trp Ile
            35                  40                  45

Gly Leu Ile Asn Pro Gly Ser Gly Gly Thr Asn Tyr Asn Glu Lys Phe
50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Val Tyr Tyr Gly Asn Ser Phe Ala Tyr Trp Gly Gln Gly Thr
            100                 105                 110

Leu Val Thr Val Ser Ala
        115
```

<210> SEQ ID NO 9
<211> LENGTH: 220
<212> TYPE: PRT
<213> ORGANISM: Artificial Sequence
<220> FEATURE:
<223> OTHER INFORMATION: mab5b light chain

<400> SEQUENCE: 9

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr His Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Phe Tyr Pro Phe Thr Phe Gly Ser Gly Thr Lys Leu Glu Lys
            100                 105                 110

Lys Arg Thr Val Ala Ala Pro Ser Val Phe Ile Phe Pro Pro Ser Asp
        115                 120                 125
```

```
Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 10
<211> LENGTH: 448
<212> TYPE: PRT
<213> ORGANISM: Artificial Sequence
<220> FEATURE:
<223> OTHER INFORMATION: mab5b heavy chain

<400> SEQUENCE: 10

Gln Val Gln Leu Gln Gln Ser Gly Ala Glu Leu Ile Gly Pro Gly Thr
1               5                   10                  15

Ser Val Lys Val Ser Cys Lys Ala Ser Gly Tyr Ala Phe Ser Asn Tyr
            20                  25                  30

Leu Ile Glu Trp Val Lys Gln Arg Pro Glu Gln Gly Leu Glu Trp Ile
        35                  40                  45

Gly Leu Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Val Tyr Tyr Gly Asn Ser Phe Ala Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
        435                 440                 445

<210> SEQ ID NO 11
<211> LENGTH: 17
<212> TYPE: PRT
<213> ORGANISM: Artificial Sequence
<220> FEATURE:
<223> OTHER INFORMATION: Light chain CDR1

<400> SEQUENCE: 11

Lys Ser Ser Gln Ser Leu Leu Asn Ser Gly Asn Gln Lys Asn Tyr Leu
1               5                   10                  15

Thr

<210> SEQ ID NO 12
<211> LENGTH: 17
<212> TYPE: PRT
<213> ORGANISM: Artificial Sequence
<220> FEATURE:
<223> OTHER INFORMATION: Humanized light chain CDR1

<400> SEQUENCE: 12

Lys Ser Ser Gln Ser Leu Leu Asn Ser Gly Asn Asn Lys Asn Tyr Leu
1               5                   10                  15

Ala

<210> SEQ ID NO 13
<211> LENGTH: 7
<212> TYPE: PRT
<213> ORGANISM: Artificial Sequence
<220> FEATURE:
<223> OTHER INFORMATION: Light chain CDR2

<400> SEQUENCE: 13

Trp Ala Ser Thr Arg Glu Ser
1               5

<210> SEQ ID NO 14
```

```
<211> LENGTH: 9
<212> TYPE: PRT
<213> ORGANISM: Artificial Sequence
<220> FEATURE:
<223> OTHER INFORMATION: Light chain CDR3

<400> SEQUENCE: 14

Gln Asn Asp Tyr Phe Tyr Pro Phe Thr
1               5

<210> SEQ ID NO 15
<211> LENGTH: 10
<212> TYPE: PRT
<213> ORGANISM: Artificial Sequence
<220> FEATURE:
<223> OTHER INFORMATION: Heavy chain CDR1

<400> SEQUENCE: 15

Gly Tyr Ala Phe Ser Asn Tyr Leu Ile Glu
1               5                   10

<210> SEQ ID NO 16
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 16

Leu Ile Asn Pro Gly Ser Gly Gly Thr Asn Tyr Asn Glu Lys Phe Lys
1               5                   10                  15

Gly

<210> SEQ ID NO 17
<211> LENGTH: 9
<212> TYPE: PRT
<213> ORGANISM: Artificial Sequence
<220> FEATURE:
<223> OTHER INFORMATION: Heavy chain CDR3

<400> SEQUENCE: 17

Val Tyr Tyr Gly Asn Ser Phe Ala Tyr
1               5

<210> SEQ ID NO 18
<211> LENGTH: 5
<212> TYPE: PRT
<213> ORGANISM: Artificial Sequence
<220> FEATURE:
<223> OTHER INFORMATION: Heavy chain CDR1 (Kabat definition)

<400> SEQUENCE: 18

Asn Tyr Leu Ile Glu
1               5

<210> SEQ ID NO 19
<211> LENGTH: 10
<212> TYPE: PRT
<213> ORGANISM: Artificial Sequence
<220> FEATURE:
<223> OTHER INFORMATION: Heavy chain CDR1 (AbM definition)

<400> SEQUENCE: 19

Leu Ile Asn Pro Gly Ser Gly Gly Thr Asn
1               5                   10
```

```
<210> SEQ ID NO 20
<211> LENGTH: 7
<212> TYPE: PRT
<213> ORGANISM: Artificial Sequence
<220> FEATURE:
<223> OTHER INFORMATION: Heavy chain CDR1 (Chothia definition)

<400> SEQUENCE: 20

Gly Tyr Ala Phe Ser Asn Tyr
1               5

<210> SEQ ID NO 21
<211> LENGTH: 6
<212> TYPE: PRT
<213> ORGANISM: Artificial Sequence
<220> FEATURE:
<223> OTHER INFORMATION: Heavy chain  CDR2 (Chothia definition)

<400> SEQUENCE: 21

Asn Pro Gly Ser Gly Gly
1               5

<210> SEQ ID NO 22
<211> LENGTH: 13
<212> TYPE: PRT
<213> ORGANISM: Artificial Sequence
<220> FEATURE:
<223> OTHER INFORMATION: Light chain CDR1 (Contact definition)

<400> SEQUENCE: 22

Leu Asn Ser Gly Asn Gln Lys Asn Tyr Leu Thr Trp Tyr
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Humanized light chain CDR1 (Contact definition)

<400> SEQUENCE: 23

Leu Asn Ser Gly Asn Asn Lys Asn Tyr Leu Ala Trp Tyr
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Light chain CDR2 (Contact definition)

<400> SEQUENCE: 24

Lys Leu Leu Ile Tyr Trp Ala Ser Thr Arg Glu
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Light chain CDR3 (Contact definition)

<400> SEQUENCE: 25

Gln Asn Asp Tyr Phe Tyr Pro Phe
1               5

<210> SEQ ID NO 26
```

```
<211> LENGTH: 6
<212> TYPE: PRT
<213> ORGANISM: Artificial Sequence
<220> FEATURE:
<223> OTHER INFORMATION: Heavy chain CDR1 (Contact definition)

<400> SEQUENCE: 26

Ser Asn Tyr Leu Ile Glu
1               5

<210> SEQ ID NO 27
<211> LENGTH: 13
<212> TYPE: PRT
<213> ORGANISM: Artificial Sequence
<220> FEATURE:
<223> OTHER INFORMATION: Heavy chain CDR2 (Contact definition)

<400> SEQUENCE: 27

Trp Ile Gly Leu Ile Asn Pro Gly Ser Gly Gly Thr Asn
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Heavy chain CDR3 (Contact definition)

<400> SEQUENCE: 28

Ala Arg Val Tyr Tyr Gly Asn Ser Phe Ala
1               5                   10

<210> SEQ ID NO 29
<211> LENGTH: 113
<212> TYPE: PRT
<213> ORGANISM: Artificial Sequence
<220> FEATURE:
<223> OTHER INFORMATION: Light chain variable region sequence L14

<400> SEQUENCE: 29

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
                20                  25                  30

Gly Asn Gln Lys Asn Tyr Leu Thr Trp Tyr Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro Phe Thr Phe Gly Gln Gly Thr Lys Leu Glu Ile
            100                 105                 110

Lys

<210> SEQ ID NO 30
<211> LENGTH: 113
<212> TYPE: PRT
<213> ORGANISM: Artificial Sequence
<220> FEATURE:
<223> OTHER INFORMATION: Light chain variable region sequence L11

<400> SEQUENCE: 30
```

```
Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr His Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro Phe Thr Phe Gly Gln Gly Thr Lys Leu Glu Ile
                100                 105                 110

Lys

<210> SEQ ID NO 31
<211> LENGTH: 113
<212> TYPE: PRT
<213> ORGANISM: Artificial Sequence
<220> FEATURE:
<223> OTHER INFORMATION: Light chain variable region sequence L12

<400> SEQUENCE: 31

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
                20                  25                  30

Gly Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro Phe Thr Phe Gly Gln Gly Thr Lys Leu Glu Ile
                100                 105                 110

Lys

<210> SEQ ID NO 32
<211> LENGTH: 113
<212> TYPE: PRT
<213> ORGANISM: Artificial Sequence
<220> FEATURE:
<223> OTHER INFORMATION: Light chain variable region sequence L13

<400> SEQUENCE: 32

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Gly Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60
```

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Asp Tyr Phe Tyr Pro Phe Thr Phe Gly Gln Gly Thr Lys Leu Glu Ile
            100                 105                 110

Lys
```

<210> SEQ ID NO 33
<211> LENGTH: 113
<212> TYPE: PRT
<213> ORGANISM: Artificial Sequence
<220> FEATURE:
<223> OTHER INFORMATION: Light chain variable region sequence L15

<400> SEQUENCE: 33

```
Asp Ile Val Met Thr Gln Ser Pro Asp Ser Leu Ala Val Ser Leu Gly
 1               5                  10                  15

Glu Arg Ala Thr Ile Ser Cys Lys Ser Ser Gln Ser Leu Leu Asn Ser
                 20                  25                  30

Gly Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr His Phe Thr Leu Thr
 65                  70                  75                  80

Ile Ser Ser Leu Gln Ala Glu Asp Val Ala Val Tyr Tyr Cys Gln Asn
                 85                  90                  95

Asp Tyr Phe Tyr Pro Phe Thr Phe Gly Gln Gly Thr Lys Leu Glu Ile
            100                 105                 110

Lys
```

<210> SEQ ID NO 34
<211> LENGTH: 118
<212> TYPE: PRT
<213> ORGANISM: Artificial Sequence
<220> FEATURE:
<223> OTHER INFORMATION: Heavy chain variable region sequence H51

<400> SEQUENCE: 34

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Ser Asn Tyr
                 20                  25                  30

Leu Ile Glu Trp Val Lys Gln Ala Pro Gly Gln Gly Leu Glu Trp Ile
             35                  40                  45

Gly Leu Ile Asn Pro Gly Ser Gly Thr Asn Tyr Asn Glu Lys Phe
 50                  55                  60

Lys Gly Lys Ala Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Val Tyr Tyr Gly Asn Ser Phe Ala Tyr Trp Gly Gln Gly Thr
            100                 105                 110

Leu Val Thr Val Ser Ser
            115
```

<210> SEQ ID NO 35
<211> LENGTH: 118
<212> TYPE: PRT
<213> ORGANISM: Artificial Sequence
<220> FEATURE:
<223> OTHER INFORMATION: Heavy chain variable region sequence H52

<400> SEQUENCE: 35

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Tyr
            20                  25                  30

Leu Ile Glu Trp Val Lys Gln Ala Pro Gly Gln Gly Leu Glu Trp Ile
        35                  40                  45

Gly Leu Ile Asn Pro Gly Ser Gly Gly Thr Asn Tyr Asn Glu Lys Phe
    50                  55                  60

Lys Gly Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Val Tyr Tyr Gly Asn Ser Phe Ala Tyr Trp Gly Gln Gly Thr
            100                 105                 110

Leu Val Thr Val Ser Ser
        115
```

<210> SEQ ID NO 36
<211> LENGTH: 118
<212> TYPE: PRT
<213> ORGANISM: Artificial Sequence
<220> FEATURE:
<223> OTHER INFORMATION: Heavy chain variable region sequence H53

<400> SEQUENCE: 36

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Tyr
            20                  25                  30

Leu Ile Glu Trp Val Arg Gln Ala Pro Gly Gln Gly Leu Glu Trp Met
        35                  40                  45

Gly Leu Ile Asn Pro Gly Ser Gly Gly Thr Asn Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Tyr Tyr Gly Asn Ser Phe Ala Tyr Trp Gly Gln Gly Thr
            100                 105                 110

Leu Val Thr Val Ser Ser
        115
```

<210> SEQ ID NO 37
<211> LENGTH: 118
<212> TYPE: PRT
<213> ORGANISM: Artificial Sequence
<220> FEATURE:
<223> OTHER INFORMATION: Heavy chain variable region sequence H54

<400> SEQUENCE: 37

```
Gln Val Gln Leu Val Gln Ser Gly Ala Glu Val Lys Lys Pro Gly Ser
1               5                   10                  15
```

```
Ser Val Lys Val Ser Cys Lys Ala Ser Gly Tyr Ala Phe Ser Asn Tyr
            20                  25                  30

Leu Ile Glu Trp Val Arg Gln Ala Pro Gly Gln Gly Leu Glu Trp Met
        35                  40                  45

Gly Leu Ile Asn Pro Gly Ser Gly Gly Thr Asn Tyr Asn Glu Lys Phe
 50                  55                  60

Lys Gly Lys Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Val Tyr Tyr Gly Asn Ser Phe Ala Tyr Trp Gly Gln Gly Thr
            100                 105                 110

Leu Val Thr Val Ser Ser
        115

<210> SEQ ID NO 38
<211> LENGTH: 220
<212> TYPE: PRT
<213> ORGANISM: Artificial Sequence
<220> FEATURE:
<223> OTHER INFORMATION: Ab10/8/30/42 antibody light chain

<400> SEQUENCE: 38

Asp Ile Val Met Thr Gln Ser Pro Asp Ser Leu Ala Val Ser Leu Gly
 1               5                  10                  15

Glu Arg Ala Thr Ile Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                85                  90                  95

Asp Tyr Phe Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 39
<211> LENGTH: 448
<212> TYPE: PRT
<213> ORGANISM: Artificial Sequence
```

<220> FEATURE:
<223> OTHER INFORMATION: Ab10/7/6/15 antibody heavy chain

<400> SEQUENCE: 39

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Tyr
            20                  25                  30

Leu Ile Glu Trp Val Lys Gln Ala Pro Gly Gln Gly Leu Glu Trp Ile
        35                  40                  45

Gly Leu Ile Asn Pro Gly Ser Gly Gly Thr Asn Tyr Asn Glu Lys Phe
    50                  55                  60

Lys Gly Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Tyr Tyr Gly Asn Ser Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 40
<211> LENGTH: 220
<212> TYPE: PRT
<213> ORGANISM: Artificial Sequence
<220> FEATURE:
<223> OTHER INFORMATION: Ab7/9  antibody light chain

<400> SEQUENCE: 40

Asp Ile Val Met Thr Gln Ser Pro Asp Ser Leu Ala Val Ser Leu Gly
1               5                   10                  15

Glu Arg Ala Thr Ile Ser Cys Lys Ser Gln Ser Leu Leu Asn Ser
            20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr His Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 41
<211> LENGTH: 448
<212> TYPE: PRT
<213> ORGANISM: Artificial Sequence
<220> FEATURE:
<223> OTHER INFORMATION: Ab8/9 antibody heavy chain

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Tyr
            20                  25                  30

Leu Ile Glu Trp Val Lys Gln Ala Pro Gly Gln Gly Leu Glu Trp Ile
```

35                  40                  45
Gly Leu Ile Asn Pro Gly Ser Gly Thr Asn Tyr Asn Glu Lys Phe
 50                  55                  60

Lys Gly Lys Ala Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Val Tyr Tyr Gly Asn Ser Phe Ala Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 42

<211> LENGTH: 220
<212> TYPE: PRT
<213> ORGANISM: Artificial Sequence
<220> FEATURE:
<223> OTHER INFORMATION: Ab6/11/12/34/43 antibody light chain

<400> SEQUENCE: 42

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 43
<211> LENGTH: 448
<212> TYPE: PRT
<213> ORGANISM: Artificial Sequence
<220> FEATURE:
<223> OTHER INFORMATION: Ab11/13 antibody heavy chain

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Tyr
            20                  25                  30

Leu Ile Glu Trp Val Arg Gln Ala Pro Gly Gln Gly Leu Glu Trp Met
        35                  40                  45

Gly Leu Ile Asn Pro Gly Ser Gly Gly Thr Asn Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Tyr Tyr Gly Asn Ser Phe Ala Tyr Trp Gly Gln Gly Thr

```
            100                 105                 110
Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 44
<211> LENGTH: 448
<212> TYPE: PRT
<213> ORGANISM: Artificial Sequence
<220> FEATURE:
<223> OTHER INFORMATION: Ab12/14 antibody heavy chain

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Tyr
```

```
            20                  25                  30
Leu Ile Glu Trp Val Arg Gln Ala Pro Gly Gln Gly Leu Glu Trp Met
        35                  40                  45
Gly Leu Ile Asn Pro Gly Ser Gly Thr Asn Tyr Asn Glu Lys Phe
    50                  55                  60
Lys Gly Lys Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Val Tyr Tyr Gly Asn Ser Phe Ala Tyr Trp Gly Gln Gly Thr
            100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
            130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
            210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
            435                 440                 445
```

```
<210> SEQ ID NO 45
<211> LENGTH: 220
<212> TYPE: PRT
<213> ORGANISM: Artificial Sequence
<220> FEATURE:
<223> OTHER INFORMATION: Ab13/14/15 antibody light chain

<400> SEQUENCE: 45

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Asn Ser
            20                  25                  30

Gly Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 46
<211> LENGTH: 448
<212> TYPE: PRT
<213> ORGANISM: Artificial Sequence
<220> FEATURE:
<223> OTHER INFORMATION: Ab42/43 antibody heavy chain

<400> SEQUENCE: 46

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Ser Asn Tyr
            20                  25                  30

Leu Ile Glu Trp Val Lys Gln Ala Pro Gly Gln Gly Leu Glu Trp Ile
        35                  40                  45

Gly Leu Ile Asn Pro Gly Ser Gly Gly Thr Asn Tyr Asn Glu Lys Phe
    50                  55                  60

Lys Gly Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
```

```
                    85                  90                  95
Ala Arg Val Tyr Tyr Gly Asn Ser Phe Ala Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 47
<211> LENGTH: 17
<212> TYPE: PRT
<213> ORGANISM: Artificial Sequence
<220> FEATURE:
<223> OTHER INFORMATION: Light chain mutation design of deamidation
      sensitive site 1

<400> SEQUENCE: 47
```

Lys Ser Ser Gln Ser Leu Leu Thr Ser Gly Asn Asn Lys Asn Tyr Leu
1               5                   10                  15

Ala

<210> SEQ ID NO 48
<211> LENGTH: 17
<212> TYPE: PRT
<213> ORGANISM: Artificial Sequence
<220> FEATURE:
<223> OTHER INFORMATION: Light chain mutation design of deamidation
      sensitive site 2

<400> SEQUENCE: 48

Lys Ser Ser Gln Ser Leu Leu Asn Thr Gly Asn Asn Lys Asn Tyr Leu
1               5                   10                  15

Ala

<210> SEQ ID NO 49
<211> LENGTH: 9
<212> TYPE: PRT
<213> ORGANISM: Artificial Sequence
<220> FEATURE:
<223> OTHER INFORMATION: Heavy chain mutation design of deamidation
      sensitive site 1-1

<400> SEQUENCE: 49

Val Tyr Tyr Gly Thr Ser Phe Ala Tyr
1               5

<210> SEQ ID NO 50
<211> LENGTH: 10
<212> TYPE: PRT
<213> ORGANISM: Artificial Sequence
<220> FEATURE:
<223> OTHER INFORMATION: Heavy chain mutation design of deamidation
      sensitive site 1-2

<400> SEQUENCE: 50

Ala Arg Val Tyr Tyr Gly Thr Ser Phe Ala
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Heavy chain mutation design of deamidation
      sensitive site 2-1

<400> SEQUENCE: 51

Val Tyr Tyr Gly Asn Thr Phe Ala Tyr
1               5

<210> SEQ ID NO 52
<211> LENGTH: 10
<212> TYPE: PRT
<213> ORGANISM: Artificial Sequence
<220> FEATURE:
<223> OTHER INFORMATION: Heavy chain mutation design of deamidation
      sensitive site 2-2

<400> SEQUENCE: 52

Ala Arg Val Tyr Tyr Gly Asn Thr Phe Ala
1               5                   10

<210> SEQ ID NO 53

```
<211> LENGTH: 214
<212> TYPE: PRT
<213> ORGANISM: Artificial Sequence
<220> FEATURE:
<223> OTHER INFORMATION: LB302 light chain sequence

<400> SEQUENCE: 53
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 54
<211> LENGTH: 701
<212> TYPE: PRT
<213> ORGANISM: Artificial Sequence
<220> FEATURE:
<223> OTHER INFORMATION: LB302 sequence comprising a heavy chain

<400> SEQUENCE: 54
```

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Phe Tyr Pro Phe Thr Phe Gly Gln Gly Thr Lys Leu Glu Ile

```
                100                 105                 110
Lys Gly Gly Gly Ser Gly Gly Gly Ser Gly Gly Gly Ser
            115                 120                 125

Gln Val Gln Leu Val Gln Ser Gly Ala Glu Val Lys Lys Pro Gly Ser
        130                 135                 140

Ser Val Lys Val Ser Cys Lys Ala Ser Gly Tyr Ala Phe Ser Asn Tyr
145                 150                 155                 160

Leu Ile Glu Trp Val Lys Gln Ala Pro Gly Gln Gly Leu Glu Trp Ile
                165                 170                 175

Gly Leu Ile Asn Pro Gly Ser Gly Thr Asn Tyr Asn Glu Lys Phe
            180                 185                 190

Lys Gly Lys Ala Thr Ile Thr Ala Asp Lys Ser Thr Ser Thr Ala Tyr
            195                 200                 205

Met Glu Leu Ser Ser Leu Arg Ser Glu Asp Thr Ala Val Tyr Tyr Cys
    210                 215                 220

Ala Arg Val Tyr Tyr Gly Asn Ser Phe Ala Tyr Trp Gly Gln Gly Thr
225                 230                 235                 240

Leu Val Thr Val Ser Ser Gly Gly Gly Ser Gly Gly Gly Ser
                245                 250                 255

Gly Gly Gly Gly Ser Gln Val Gln Leu Val Glu Ser Gly Gly Gly Val
            260                 265                 270

Val Gln Pro Gly Arg Ser Leu Arg Leu Asp Cys Lys Ala Ser Gly Ile
        275                 280                 285

Thr Phe Ser Asn Ser Gly Met His Trp Val Arg Gln Ala Pro Gly Lys
        290                 295                 300

Gly Leu Glu Trp Val Ala Val Ile Trp Tyr Asp Gly Ser Lys Arg Tyr
305                 310                 315                 320

Tyr Ala Asp Ser Val Lys Gly Arg Phe Thr Ile Ser Arg Asp Asn Ser
                325                 330                 335

Lys Asn Thr Leu Phe Leu Gln Met Asn Ser Leu Arg Ala Glu Asp Thr
            340                 345                 350

Ala Val Tyr Tyr Cys Ala Thr Asn Asp Asp Tyr Trp Gly Gln Gly Thr
            355                 360                 365

Leu Val Thr Val Ser Ser Ala Ser Thr Lys Gly Pro Ser Val Phe Pro
    370                 375                 380

Leu Ala Pro Cys Ser Arg Ser Thr Ser Glu Ser Thr Ala Ala Leu Gly
385                 390                 395                 400

Cys Leu Val Lys Asp Tyr Phe Pro Glu Pro Val Thr Val Ser Trp Asn
                405                 410                 415

Ser Gly Ala Leu Thr Ser Gly Val His Thr Phe Pro Ala Val Leu Gln
            420                 425                 430

Ser Ser Gly Leu Tyr Ser Leu Ser Ser Val Val Thr Val Pro Ser Ser
            435                 440                 445

Ser Leu Gly Thr Lys Thr Tyr Thr Cys Asn Val Asp His Lys Pro Ser
        450                 455                 460

Asn Thr Lys Val Asp Lys Arg Val Glu Ser Lys Tyr Gly Pro Pro Cys
465                 470                 475                 480

Pro Pro Cys Pro Ala Pro Glu Phe Leu Gly Gly Pro Ser Val Phe Leu
                485                 490                 495

Phe Pro Pro Lys Pro Lys Asp Thr Leu Met Ile Ser Arg Thr Pro Glu
            500                 505                 510

Val Thr Cys Val Val Val Asp Val Ser Gln Glu Asp Pro Glu Val Gln
            515                 520                 525
```

```
Phe Asn Trp Tyr Val Asp Gly Val Glu Val His Asn Ala Lys Thr Lys
                525                 530                 535                 540

Pro Arg Glu Glu Gln Phe Asn Ser Thr Tyr Arg Val Val Ser Val Leu
545                 550                 555                 560

Thr Val Leu His Gln Asp Trp Leu Asn Gly Lys Glu Tyr Lys Cys Lys
                565                 570                 575

Val Ser Asn Lys Gly Leu Pro Ser Ser Ile Glu Lys Thr Ile Ser Lys
                580                 585                 590

Ala Lys Gly Gln Pro Arg Glu Pro Gln Val Tyr Thr Leu Pro Pro Ser
            595                 600                 605

Gln Glu Glu Met Thr Lys Asn Gln Val Ser Leu Thr Cys Leu Val Lys
            610                 615                 620

Gly Phe Tyr Pro Ser Asp Ile Ala Val Glu Trp Glu Ser Asn Gly Gln
625                 630                 635                 640

Pro Glu Asn Asn Tyr Lys Thr Thr Pro Pro Val Leu Asp Ser Asp Gly
                645                 650                 655

Ser Phe Phe Leu Tyr Ser Arg Leu Thr Val Asp Lys Ser Arg Trp Gln
                660                 665                 670

Glu Gly Asn Val Phe Ser Cys Ser Val Met His Glu Ala Leu His Asn
            675                 680                 685

His Tyr Thr Gln Lys Ser Leu Ser Leu Ser Leu Gly Lys
            690                 695                 700
```

<210> SEQ ID NO 55
<211> LENGTH: 214
<212> TYPE: PRT
<213> ORGANISM: Artificial Sequence
<220> FEATURE:
<223> OTHER INFORMATION: LB305 light chain sequence

<400> SEQUENCE: 55

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205
Phe Asn Arg Gly Glu Cys
    210
```

<210> SEQ ID NO 56
<211> LENGTH: 709
<212> TYPE: PRT
<213> ORGANISM: Artificial Sequence
<220> FEATURE:
<223> OTHER INFORMATION: LB305 sequence comprising a heavy chain

<400> SEQUENCE: 56

```
Asp Ile Val Met Thr Gln Ser Pro Asp Ser Leu Ala Val Ser Leu Gly
1               5                   10                  15
Glu Arg Ala Thr Ile Ser Cys Lys Ser Gln Ser Leu Leu Asn Ser
            20                  25                  30
Gly Asn Gln Lys Asn Tyr Leu Thr Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Asn
                85                  90                  95
Asp Tyr Phe Tyr Pro Phe Thr Phe Gly Gln Gly Thr Lys Leu Glu Ile
            100                 105                 110
Lys Gly Gly Gly Gly Ser Gly Gly Gly Gly Ser Gly Gly Gly Gly Ser
        115                 120                 125
Gln Val Gln Leu Val Gln Ser Gly Ala Glu Val Lys Lys Pro Gly Ser
    130                 135                 140
Ser Val Lys Val Ser Cys Lys Ala Ser Gly Tyr Ala Phe Ser Asn Tyr
145                 150                 155                 160
Leu Ile Glu Trp Val Lys Gln Ala Pro Gly Gln Gly Leu Glu Trp Ile
                165                 170                 175
Gly Leu Ile Asn Pro Gly Ser Gly Gly Thr Asn Tyr Asn Glu Lys Phe
            180                 185                 190
Lys Gly Lys Ala Thr Ile Thr Ala Asp Lys Ser Thr Ser Thr Ala Tyr
        195                 200                 205
Met Glu Leu Ser Ser Leu Arg Ser Glu Asp Thr Ala Val Tyr Tyr Cys
    210                 215                 220
Ala Arg Val Tyr Tyr Gly Asn Ser Phe Ala Tyr Trp Gly Gln Gly Thr
225                 230                 235                 240
Leu Val Thr Val Ser Gly Gly Gly Ser Gly Gly Gly Gly Ser
                245                 250                 255
Gly Gly Gly Gly Ser Glu Val Gln Leu Val Glu Ser Gly Gly Gly Leu
            260                 265                 270
Val Gln Pro Gly Gly Ser Leu Arg Leu Ser Cys Ala Ala Ser Gly Phe
        275                 280                 285
Thr Phe Ser Asp Ser Trp Ile His Trp Val Arg Gln Ala Pro Gly Lys
    290                 295                 300
Gly Leu Glu Trp Val Ala Trp Ile Ser Pro Tyr Gly Ser Thr Tyr
305                 310                 315                 320
Tyr Ala Asp Ser Val Lys Gly Arg Phe Thr Ile Ser Ala Asp Thr Ser
                325                 330                 335
```

```
Lys Asn Thr Ala Tyr Leu Gln Met Asn Ser Leu Arg Ala Glu Asp Thr
            340                 345                 350

Ala Val Tyr Tyr Cys Ala Arg Arg His Trp Pro Gly Gly Phe Asp Tyr
        355                 360                 365

Trp Gly Gln Gly Thr Leu Val Thr Val Ser Ser Ala Ser Thr Lys Gly
    370                 375                 380

Pro Ser Val Phe Pro Leu Ala Pro Ser Ser Lys Ser Thr Ser Gly Gly
385                 390                 395                 400

Thr Ala Ala Leu Gly Cys Leu Val Lys Asp Tyr Phe Pro Glu Pro Val
                405                 410                 415

Thr Val Ser Trp Asn Ser Gly Ala Leu Thr Ser Gly Val His Thr Phe
            420                 425                 430

Pro Ala Val Leu Gln Ser Ser Gly Leu Tyr Ser Leu Ser Ser Val Val
        435                 440                 445

Thr Val Pro Ser Ser Ser Leu Gly Thr Gln Thr Tyr Ile Cys Asn Val
    450                 455                 460

Asn His Lys Pro Ser Asn Thr Lys Val Asp Lys Lys Val Glu Pro Lys
465                 470                 475                 480

Ser Cys Asp Lys Thr His Thr Cys Pro Pro Cys Pro Ala Pro Glu Leu
                485                 490                 495

Leu Gly Gly Pro Ser Val Phe Leu Phe Pro Pro Lys Pro Lys Asp Thr
            500                 505                 510

Leu Met Ile Ser Arg Thr Pro Glu Val Thr Cys Val Val Val Asp Val
        515                 520                 525

Ser His Glu Asp Pro Glu Val Lys Phe Asn Trp Tyr Val Asp Gly Val
    530                 535                 540

Glu Val His Asn Ala Lys Thr Lys Pro Arg Glu Glu Gln Tyr Ala Ser
545                 550                 555                 560

Thr Tyr Arg Val Val Ser Val Leu Thr Val Leu His Gln Asp Trp Leu
                565                 570                 575

Asn Gly Lys Glu Tyr Lys Cys Lys Val Ser Asn Lys Ala Leu Pro Ala
            580                 585                 590

Pro Ile Glu Lys Thr Ile Ser Lys Ala Lys Gly Gln Pro Arg Glu Pro
        595                 600                 605

Gln Val Tyr Thr Leu Pro Pro Ser Arg Glu Glu Met Thr Lys Asn Gln
    610                 615                 620

Val Ser Leu Thr Cys Leu Val Lys Gly Phe Tyr Pro Ser Asp Ile Ala
625                 630                 635                 640

Val Glu Trp Glu Ser Asn Gly Gln Pro Glu Asn Asn Tyr Lys Thr Thr
                645                 650                 655

Pro Pro Val Leu Asp Ser Asp Gly Ser Phe Phe Leu Tyr Ser Lys Leu
            660                 665                 670

Thr Val Asp Lys Ser Arg Trp Gln Gln Gly Asn Val Phe Ser Cys Ser
        675                 680                 685

Val Met His Glu Ala Leu His Asn His Tyr Thr Gln Lys Ser Leu Ser
    690                 695                 700

Leu Ser Pro Gly Lys
705

<210> SEQ ID NO 57
<211> LENGTH: 600
<212> TYPE: PRT
<213> ORGANISM: Artificial Sequence
<220> FEATURE:
```

<223> OTHER INFORMATION: LB401 sequence comprising a heavy chain

<400> SEQUENCE: 57

```
Gln Val Gln Leu Val Gln Ser Gly Ala Glu Val Lys Lys Pro Gly Ser
  1               5                  10                  15

Ser Val Lys Val Ser Cys Lys Ala Ser Gly Tyr Ala Phe Ser Asn Tyr
             20                  25                  30

Leu Ile Glu Trp Val Lys Gln Ala Pro Gly Gln Gly Leu Glu Trp Ile
         35                  40                  45

Gly Leu Ile Asn Pro Gly Ser Gly Gly Thr Asn Tyr Asn Glu Lys Phe
 50                  55                  60

Lys Gly Lys Ala Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Val Tyr Tyr Gly Asn Ser Phe Ala Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Ala
        435                 440                 445

Gly Gly Gly Gly Ser Gly Gly Gly Gly Ser Gly Gly Gly Gly Ser Gly
        450                 455                 460

Ile Pro Pro His Val Gln Lys Ser Val Asn Asn Asp Met Ile Val Thr
465                 470                 475                 480

Asp Asn Asn Gly Ala Val Lys Phe Pro Gln Leu Cys Lys Phe Cys Asp
                485                 490                 495

Val Arg Phe Ser Thr Cys Asp Asn Gln Lys Ser Cys Met Ser Asn Cys
        500                 505                 510

Ser Ile Thr Ser Ile Cys Glu Lys Pro Gln Glu Val Cys Val Ala Val
        515                 520                 525

Trp Arg Lys Asn Asp Glu Asn Ile Thr Leu Glu Thr Val Cys His Asp
        530                 535                 540

Pro Lys Leu Pro Tyr His Asp Phe Ile Leu Glu Asp Ala Ala Ser Pro
545                 550                 555                 560

Lys Cys Ile Met Lys Glu Lys Lys Pro Gly Glu Thr Phe Phe Met
                565                 570                 575

Cys Ser Cys Ser Ser Asp Glu Cys Asn Asp Asn Ile Ile Phe Ser Glu
                580                 585                 590

Glu Tyr Asn Thr Ser Asn Pro Asp
            595                 600

<210> SEQ ID NO 58
<211> LENGTH: 623
<212> TYPE: PRT
<213> ORGANISM: Artificial Sequence
<220> FEATURE:
<223> OTHER INFORMATION: LB433 sequence comprising a heavy chain

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Tyr
            20                  25                  30

Leu Ile Glu Trp Val Lys Gln Ala Pro Gly Gln Gly Leu Glu Trp Ile
        35                  40                  45

Gly Leu Ile Asn Pro Gly Ser Gly Gly Thr Asn Tyr Asn Glu Lys Phe
    50                  55                  60

Lys Gly Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Tyr Tyr Gly Asn Ser Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160
```

-continued

```
Ser Gly Ala Leu Thr Ser Gly Val His Thr Phe Pro Ala Val Leu Gln
            165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
            195                 200                 205
Asn Thr Lys Val Asp Lys Lys Val Glu Pro Lys Ser Cys Asp Lys Thr
            210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
            245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
            325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
            405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Ala
            435                 440                 445
Gly Gly Gly Gly Ser Gly Gly Gly Gly Ser Gly Gly Gly Gly Ser Ser
            450                 455                 460
Pro Gly Gln Gly Thr Gln Ser Glu Asn Ser Cys Thr His Phe Pro Gly
465                 470                 475                 480
Asn Leu Pro Asn Met Leu Arg Asp Leu Arg Asp Ala Phe Ser Arg Val
            485                 490                 495
Lys Thr Phe Phe Gln Met Lys Asp Gln Leu Asp Asn Leu Leu Leu Lys
            500                 505                 510
Glu Ser Leu Leu Glu Asp Phe Lys Gly Tyr Leu Gly Cys Gln Ala Leu
            515                 520                 525
Ser Glu Met Ile Gln Phe Tyr Leu Glu Glu Val Met Pro Gln Ala Glu
            530                 535                 540
Asn Gln Asp Pro Asp Ile Lys Ala His Val Asn Ser Leu Gly Glu Asn
545                 550                 555                 560
Leu Lys Thr Leu Arg Leu Arg Leu Arg Arg Cys His Arg Phe Leu Pro
            565                 570                 575
Cys Glu Asn Lys Ser Lys Ala Val Glu Gln Val Lys Asn Ala Phe Asn
```

```
              580                 585                 590
Lys Leu Gln Glu Lys Gly Ile Tyr Lys Ala Met Ser Glu Phe Asp Ile
            595                 600                 605

Phe Ile Asn Tyr Ile Glu Ala Tyr Met Thr Met Lys Ile Arg Asn
        610                 615                 620

<210> SEQ ID NO 59
<211> LENGTH: 623
<212> TYPE: PRT
<213> ORGANISM: Artificial Sequence
<220> FEATURE:
<223> OTHER INFORMATION: LB4333 sequence comprising a heavy chain

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Tyr
            20                  25                  30

Leu Ile Glu Trp Val Lys Gln Ala Pro Gly Gln Gly Leu Glu Trp Ile
        35                  40                  45

Gly Leu Ile Asn Pro Gly Ser Gly Gly Thr Asn Tyr Asn Glu Lys Phe
    50                  55                  60

Lys Gly Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Tyr Tyr Gly Asn Ser Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
```

```
                    325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
            405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Ala
            435                 440                 445
Gly Gly Gly Gly Ser Gly Gly Gly Ser Gly Gly Gly Gly Ser Ser
            450                 455                 460
Pro Gly Gln Gly Thr Gln Ser Glu Asn Ser Cys Thr His Phe Pro Gly
465                 470                 475                 480
Asn Leu Pro Asn Met Leu Arg Asp Leu Arg Asp Ala Phe Ser Arg Val
            485                 490                 495
Lys Thr Phe Phe Gln Met Lys Asp Gln Leu Asp Asn Leu Leu Leu Lys
            500                 505                 510
Glu Ser Leu Leu Glu Asp Phe Lys Gly Tyr Leu Gly Cys Gln Ala Leu
            515                 520                 525
Ser Glu Met Ile Gln Phe Tyr Leu Glu Glu Val Met Pro Gln Ala Glu
            530                 535                 540
Asn Gln Asp Pro Asp Ile Lys Ala His Val Asn Ser Leu Gly Glu Asn
545                 550                 555                 560
Leu Lys Thr Leu Arg Leu Arg Leu Arg Arg Cys His Arg Phe Leu Pro
            565                 570                 575
Cys Glu Asn Lys Ser Lys Ala Val Glu Gln Val Lys Asn Ala Phe Asn
            580                 585                 590
Lys Leu Gln Glu Lys Gly Ile Tyr Lys Ala Met Ser Glu Phe Asp Ile
            595                 600                 605
Phe Ile Asn Tyr Ile Glu Ala Tyr Met Thr Met Lys Ile Arg Asn
            610                 615                 620

<210> SEQ ID NO 60
<211> LENGTH: 620
<212> TYPE: PRT
<213> ORGANISM: Artificial Sequence
<220> FEATURE:
<223> OTHER INFORMATION: LB4331 sequence comprising a heavy chain

<400> SEQUENCE: 60

Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ala Phe Ser Asn Tyr
            20                  25                  30
Leu Ile Glu Trp Val Lys Gln Ala Pro Gly Gln Gly Leu Glu Trp Ile
            35                  40                  45
Gly Leu Ile Asn Pro Gly Ser Gly Gly Thr Asn Tyr Asn Glu Lys Phe
        50                  55                  60
Lys Gly Lys Ala Thr Ile Thr Ala Asp Lys Ser Thr Ser Thr Ala Tyr
```

```
            65                  70                  75                  80
Met Glu Leu Ser Ser Leu Arg Ser Glu Asp Thr Ala Val Tyr Tyr Cys
                    85                  90                  95

Ala Arg Val Tyr Tyr Gly Asn Ser Phe Ala Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
                180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Ala Gly Gly Gly
            435                 440                 445

Gly Ser Gly Gly Gly Gly Ser Gly Gly Gly Ser Ser Pro Gly Gln
            450                 455                 460

Gly Thr Gln Ser Glu Asn Ser Cys Thr His Phe Pro Gly Asn Leu Pro
465                 470                 475                 480

Asn Met Leu Arg Asp Leu Arg Asp Ala Phe Ser Arg Val Lys Thr Phe
                485                 490                 495
```

```
Phe Gln Met Lys Asp Gln Leu Asp Asn Leu Leu Lys Glu Ser Leu
                500                 505                 510

Leu Glu Asp Phe Lys Gly Tyr Leu Gly Cys Gln Ala Leu Ser Glu Met
            515                 520                 525

Ile Gln Phe Tyr Leu Glu Glu Val Met Pro Gln Ala Glu Asn Gln Asp
530                 535                 540

Pro Asp Ile Lys Ala His Val Asn Ser Leu Gly Glu Asn Leu Lys Thr
545                 550                 555                 560

Leu Arg Leu Arg Leu Arg Arg Cys His Arg Phe Leu Pro Cys Glu Asn
                565                 570                 575

Lys Ser Lys Ala Val Glu Gln Val Lys Asn Ala Phe Asn Lys Leu Gln
            580                 585                 590

Glu Lys Gly Ile Tyr Lys Ala Met Ser Glu Phe Asp Ile Phe Ile Asn
            595                 600                 605

Tyr Ile Glu Ala Tyr Met Thr Met Lys Ile Arg Asn
610                 615                 620

<210> SEQ ID NO 61
<211> LENGTH: 623
<212> TYPE: PRT
<213> ORGANISM: Artificial Sequence
<220> FEATURE:
<223> OTHER INFORMATION: LB4335 sequence comprising a heavy chain

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Asn Tyr
            20                  25                  30

Leu Ile Glu Trp Val Lys Gln Ala Pro Gly Gln Gly Leu Glu Trp Ile
        35                  40                  45

Gly Leu Ile Asn Pro Gly Ser Gly Gly Thr Asn Tyr Asn Glu Lys Phe
    50                  55                  60

Lys Gly Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Tyr Tyr Gly Asn Ser Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Ala
        435                 440                 445

Gly Gly Gly Gly Ser Gly Gly Gly Ser Gly Gly Gly Gly Ser Ser
    450                 455                 460

Pro Gly Gln Gly Thr Gln Ser Glu Asn Ser Cys Thr His Phe Pro Gly
465                 470                 475                 480

Asn Leu Pro Asn Met Leu Arg Asp Leu Arg Asp Ala Phe Ser Arg Val
                485                 490                 495

Lys Thr Phe Phe Gln Met Lys Asp Gln Leu Asp Asn Leu Leu Leu Lys
            500                 505                 510

Glu Ser Leu Leu Glu Asp Phe Lys Gly Tyr Leu Gly Cys Gln Ala Leu
        515                 520                 525

Ser Glu Met Ile Gln Phe Tyr Leu Glu Glu Val Met Pro Gln Ala Glu
    530                 535                 540

Asn Gln Asp Pro Asp Ile Lys Ala His Val Asn Ser Leu Gly Glu Asn
545                 550                 555                 560

Leu Lys Thr Leu Arg Leu Arg Leu Arg Arg Cys His Arg Phe Leu Pro
                565                 570                 575

Cys Glu Asn Lys Ser Lys Ala Val Glu Gln Val Lys Asn Ala Phe Asn
            580                 585                 590

Lys Leu Gln Glu Lys Gly Ile Tyr Lys Ala Met Ser Glu Phe Asp Ile
        595                 600                 605

Phe Ile Asn Tyr Ile Glu Ala Tyr Met Thr Met Lys Ile Arg Asn
    610                 615                 620
```

ANTIBODY TARGETING CLDN18.2, BISPECIFIC ANTIBODY, ADC, AND CAR, AND APPLICATIONS THEREOF

REFERENCE TO SEQUENCE LISTING

The Sequence Listing is submitted concurrently with the specification as an ASCII formatted text file via EFS-Web, with a file name of "P20414659US-2-seq", a creation date of Dec. 14, 2020, and a size of 109,668 bytes. The Sequence Listing filed via EFS-Web is part of the specification and is incorporated in its entirety by reference herein.

The present application is a National Stage of International Application No. PCT/CN2019/090255, filed on Jun. 6, 2019, which claims priority of the Chinese Patent Application No. CN 201810610790.3 filed on Jun. 17, 2018, Chinese Patent application CN 201811295845.2 filed on Nov. 1, 2018, Chinese Patent application CN 201910108951.3 filed on Feb. 3, 2019, and Chinese Patent application CN 201910276473.7 filed on Apr. 8, 2019, the contents of which are incorporated herein by reference in their entireties.

TECHNICAL FIELD

The present disclosure relates to the field of biological medicine, and in particular to an antibody targeting CLDN18.2, a bispecific antibody, ADC, and CAR, and applications thereof.

BACKGROUND

Cancer is a great threat to human health and is one of the important reasons for death in the field of diseases. Since the development of various treatments including surgery, chemotherapy, targeting drugs, tumor immunotherapy and combination therapy, etc., cancer treatment has made significant achievements in recent years. In numerous cancer patients, the treatment approach for patients with cancers such as lung cancer, gastric cancer, pancreatic cancer, esophageal cancer and ovarian cancer, has a lot of room for improvement. The treatment approaches for these types of tumors, comprising macromolecular targeting drugs such as new monoclonal antibodies, as well as the combination of these monoclonal antibodies and existing tumor immunotherapy approaches, such as antibodies against immune checkpoint inhibitor PD-1 and PD-L1, provide new possibilities and options for the huge unmet clinical treatment needs.

The tight junction proteins Claudins (CLDNs), which are expressed in human and species belonging to murine, etc., are a type of intercellular sheet seal-associated protein, and plays an important role in the control of intercellular sheet ion flow, maintenance of cell polarity and intercellular signal transduction. As many as 29 proteins of the CLDN family have been identified, and CLDN18 is one of them. CLDN18 has two homologous molecules, which are respectively referred to as claudin18.1 (CLDN18.1) and claudin18.2 (CLDN18.2). Human claudin18.1 (hCLDN18.1) and human claudin18.2 (hCLDNi18.2) are highly homologous, with up to 92% amino acid homology. The expression of hCLDN18.2 in normal tissues is very limited, and is only found in differentiated epithelial cells of the gastric mucosa, but has a very high expression in gastric cancer tissues including metastatic gastric cancer tissues (Sahin U. et al. Claudin-18 splice variant 2 is a pan-cancer target suitable for therapeutic antibody development. Clin Cancer Res. 2008; 14 (23): 7642-34). It is further found that CLDN18.2 is expressed in the tumor tissues of different cancer patients, in about 70% of gastric cancer, 50% of pancreatic cancer, 30% of esophageal cancer, 25% of lung cancer and ovarian cancer, et cetera. Therefore, CLDN18.2 has become an ideal tumor biochemical marker and a target for anti-tumor drug development, in particular the development of antibody targeting CLDN18.2 for tumor treatment. However, due to the specificity of the target, the development of therapeutic antibodies against CLDN18.2 is very difficult. Human CLDN18.2 protein has 261 amino acids in full length, which can be viewed in NCBI public sequence NP 001002026.1 claudin-18 isoform 2, in which amino acid 1-23 form a signal peptide. CLDN18.2 protein is a transmembrane protein with two extracellular domains after the signal peptide. The two extracellular domains are respectively Extracellular loop 1 (ECL1) of about 55 amino acids and ECL2 of 23 amino acids. This structure is very similar to that of human CLDN18.1, and the ECL2 regions of human CLDN18.2 and human CLDN18.1 are identical. Therefore, for the development of antibodies targeting human CLDN18.2 protein, there is a need to find the antibodies against the ECL1 domain or spatial structure of human CLDN18.2 protein. This makes this work more difficult.

In addition, the antibodies against human CLDN18.2 membrane protein exerts effects thereof comprising at least inducing tumor cell apoptosis, inhibiting tumor cell growth and exerting tumor cell killing effects mediated by effector cells of patient immune cells, including antibody-dependent cell-mediated cytotoxicity (ADCC) and complement dependent cytotoxicity (CDC). It will be more difficult to find antibodies with such functions. At present, for the research of antibodies against human CLDN18.2, only antibody IMAB362 (see WO 2014/146672) is in the clinical trial phase. IMAB362 is a human-murine chimeric antibody against human CLDN18.2, which has an immunogenicity risk and a low affinity. Cytological experiments have proven that IMAB362 has no endocytic activity, is not suitable for ADC development, and has a very limited therapeutic effect, which has also been verified in the tumor model efficacy evaluation of the present disclosure. In addition, there is no bispecific antibodies against CLDN18.2 target in the clinical stage or early stage of research and development. At present, there are no antibody-drug conjugate (ADC) drugs against CLDN 18.2 target in clinical development. Chimeric antigen receptor (CAR) T cells (abbreviated as CART or CAR-T) are T cells isolated from patients modified by CAR in vitro and enabled to specifically recognize cancer cells. The modified CART cells are amplified and transfused back into patients to achieve a tumor-treating effect. CN201410341504.X discloses a T lymphocyte targeting CLD18A2 (i.e. Claudin18.2), and a preparation method therefor and applications thereof and reports clinical data, but there is still a very large space for improving the efficacy and safety of CART.

Therefore, there is a lack of effective antibodies, in particular humanized antibodies, targeting human CLDN18.2 protein, bispecific antibodies, antibody-drug conjugate (ADC) drugs with better cell activity, PK activity and animal efficacy, as well as more effective chimeric antigen receptors (CARs) and cells containing same in the field.

Content of the Present Disclosure

In order to overcome the technical problem of the lack of antibodies targeting CLDN18.2, bispecific antibodies, antibody-drug conjugates and CAR molecules in the art, an antibody targeting CLDN18.2, a humanized antibody, a bispecific antibody and an antibody drug conjugate thereof and a CAR molecule, a preparation method and applications therefor are provided.

In order to solve the above-mentioned technical problem, the technical solution of the first aspect of the present disclosure is: an antibody targeting CLDN18.2, which comprises a light chain variable region (VL) and/or a heavy chain variable region (VI), wherein the VL comprises the following complementary determining region (CDR) sequences:

a VL CDR1 amino acid sequence as shown in SEQ ID NO: II or SEQ ID NO: 12; a VL CDR2 amino acid sequence as shown in SEQ ID NO: 13; a VL CDR3 amino acid sequence as shown in SEQ ID NO: 14;

and the VH comprises the following CDR sequences:

a VH CDR1 amino acid sequence as shown in SEQ ID NO: 15; a VH CDR2 amino acid sequence as shown in SEQ ID NO: 16; and a VH CDR3 amino acid sequence as shown in SEQ ID NO: 17.

The antibody targeting CLDN18.2 has a better specific binding activity to human and murine CLDN18.2, a higher Emax; a high affinity (KinExA) (preferably up to 10 pM); a better CDC activity in human blood cell; a better activity for inducing apoptosis of CLDN18.2+ cells, a better activity for inhibiting tumor cell growth, a better animal efficacy, and a good pharmacokinetics (PK) in vivo, in particular a longer T1/2. The antibody targeting CLDN18.2 has a better binding activity to murine CLDN18.2.

In a preferred embodiment, in the antibody targeting CLDN18.2 as mentioned above, the VL comprises amino acid sequences of VL CDR1 as shown in SEQ ID NO: 11, VL CDR2 as shown in SEQ ID NO: 13 and VL CDR3 as shown in SEQ ID NO: 14; the VH comprises amino acid sequences of VH CDR1 as shown in SEQ ID NO: 15, VH CDR2 as shown in SEQ ID NO: 16 and VH1 CDR3 as shown in SEQ ID NO: 17; or, the VL comprises amino acid sequences of VL CDR1 as shown in SEQ ID NO: 12, VL CDR2 as shown in SEQ ID NO: 13 and VL CDR3 as shown in SEQ ID NO: 14; and the VH comprises amino acid sequences of VH CDR1 as shown in SEQ ID NO: 15, VH CDR2 as shown in SEQ ID NO: 16 and VH CDR3 as shown in SEQ ID NO: 17.

In a preferred embodiment of the present disclosure, the anti body targeting CLDN18.2 as described above is provided, wherein the CDR region of the antibody is a CDR sequence optimized for deamination sensitive site; preferably, the CDR sequence optimized for deamination sensitive site in the CDR region is a light chain CDR sequence; preferably, the CDR sequence optimized for deamination sensitive site in the CDR region is a CDR1 sequence optimized at position L30A and/or L30B of light chain CDR1.

In a preferred embodiment of the present disclosure, the antibody targeting CLDN18.2 as described above is provided, wherein the NS at position L30A and/or L30B of the light chain CDR1 of the antibody is mutated to NT, provided that position L30E is not Q and position L34 is not T.

In a preferred embodiment of the present disclosure, the antibody targeting CLDN18.2 as described above is provided, wherein the NS at position L30A and/or L30B of the light chain CDR1 of the antibody is mutated to NT, provided that the light chain CDR1 is the sequence as shown in SEQ ID NO: 12 before mutation.

In a preferred embodiment of the present disclosure, the antibody targeting CLDN18.2 as described above is provided, wherein the CDR region of the antibody is a CDR sequence optimized for deamination sensitive site; preferably, the CDR sequence optimized for deamination sensitive site in the CDR region is a heavy chain CDR sequence; preferably, the CDR sequence optimized for deamination sensitive site in the CDR region is a CDR sequence optimized at position H99 and/or H100 of heavy chain CDR3.

In a preferred embodiment of the present disclosure, the antibody targeting CLDN18.2 as described above is provided, wherein the NS at position H99 and/or H100 of the heavy chain CDR3 of the antibody is mutated to NT, provided that in the light chain CDR1, position L30E is not Q and position L34 is not T.

In a preferred embodiment of the present disclosure, the antibody targeting CLDN18.2 as described above is provided, wherein the NS at position 1-199 and/or H1100 of the heavy chain CDR3 of the antibody is mutated to NT, provided that the light chain CDR1 is the sequence as shown in SEQ ID NO: 12 before mutation.

The position L30A, L30B, L30E and L34 of the light chain CDR1 as described above and the position H99 and H100 of the heavy chain CDR3 are defined by the Kabat numbering rule.

In a preferred embodiment, the antibody targeting CLDN18.2 as described above is provided, wherein the antibody targeting CLDN18.2 is a murine-derived antibody; The murine-derived CLDN18.2 antibody is an affinity mature antibody, and the affinity thereof is increased by 3-10 times or more, preferably 10 times or more.

Preferably, the VL of the murine-derived antibody is the amino acid sequence as shown in SEQ ID NO: 7 or a variant thereof; and/or, the VH of the murine-derived antibody is the amino acid sequence as shown in SEQ ID NO: 8 or a variant thereof;

the variant has the deletion, substitution or insertion of one or more amino acid residues on the amino acid sequence of the VL and/or VH, and the amino acid sequence of the variant has at least 85% sequence identity to the amino acid sequence of the VL and/or VH, and the variant retains or improves the binding of the antibody to CLDN18.2; the at least 85% sequence identity is preferably at least 90% sequence identity; more preferably, at least 95% sequence identity; most preferably, at least 99% sequence identity.

In a preferred embodiment, the antibody targeting CLDN18.2 as described above is provided, wherein the antibody targeting CLDN18.2 comprises a variable region from a murine-derived antibody and a constant region from a murine or human antibody; the constant region from a murine antibody includes the heavy chain constant region of murine IgG1, IgG2a, IgG2b or IgG3 and κ or λ type light chain constant region, and the constant region from a human antibody includes the heavy chain constant region of human IgG1, IgG2, IgG3 or IgG4 and κ or λ type light chain constant region.

Preferably, the antibody targeting CLDN18.2 is a chimeric antibody composed of a variable region from a murine-derived antibody and a constant region from a human antibody. The chimeric antibody is an affinity mature antibody, and the affinity thereof is increased by 3-10 times or more, preferably 10 times or more.

More preferably, the light chain amino acid sequence of the chimeric antibody is the amino acid sequence as shown in SEQ ID NO: 9 or a variant thereof; and/or, the heavy chain amino acid sequence of the chimeric antibody is the amino acid sequence as shown in SEQ ID NO: 10 or a variant thereof.

In a preferred embodiment, the antibody targeting CLDN18.2 as described above is provided, wherein the antibody targeting CLDN18.2 is a humanized antibody.

In a preferred embodiment of the present disclosure, the antibody targeting CLDN18.2 as described above is provided, wherein the light chain variable region framework (FR) sequence of the humanized antibody is selected from human germline light chain sequence, and FR sequence preferably comprises 1-10 amino acid reverse mutations.

In a preferred embodiment of the present disclosure, the antibody targeting CLDN18.2 as described above is provided, wherein the light chain variable region CDR sequence of the humanized antibody can be defined according to numbering rules, such as CCG, Kabat, Chothia, AbM or Contact respectively, and the CDR sequence comprises light chain CDR sequences listed in table 4—table 8 or a variant thereof.

preferably, the VL of the humanized antibody comprises the amino acid sequence as shown in any one of SEQ ID NO: 29-33 or a variant thereof; the variant has the deletion, substitution or insertion of one or more amino acid residues on the amino acid sequence of the VL and/or VH1, and the amino acid sequence of the variant has at least 85% sequence identity to the amino acid sequence of the V-L and/or VH, and the variant retains or improves the binding of the antibody to CLDN18.2; the at least 85% sequence identity is preferably at least 90% sequence identity; more preferably, at least 95% sequence identity; most preferably, at least 99% sequence identity.

more preferably, position L30E and L34 of light chain CDR1 are optimized (mutated) to the amino acid at the corresponding site of human germline CDR1.

In a preferred embodiment of the present disclosure, the antibody targeting CLDN18.2 as described above is provided, wherein the heavy chain variable region framework (FR) sequence of the humanized antibody is selected from human germline heavy chain sequence, and FR sequence preferably comprises 0-10 amino acid reverse mutations.

In a preferred embodiment of the present disclosure, the antibody targeting CLDN18.2 as described above is provided, wherein the heavy chain variable region CDR sequence of the humanized antibody can be defined according to numbering rules, such as CCG, Kabat, Chothia, AbM or Contact respectively, and the CDR sequence comprises heavy chain CDR sequences listed in table 4—table 8 or a variant sequence thereof.

In a preferred embodiment of the present disclosure, the antibody targeting CLDN18.2 as described above is provided, wherein the heavy chain variable region sequence of the humanized antibody comprises the amino acid sequence as shown in any one of SEQ ID NO: 34-37 or a variant thereof.

In a preferred embodiment of the present disclosure, the anti body targeting CLDN18.2 as described above is provided, wherein the humanized antibody comprises a combination of the sequence of the light chain variable region of the amino acid sequence as shown in any one of SEQ ID NO: 29-33 or a variant thereof and the sequence of the heavy chain variable region of the amino acid sequence as shown in any one of SEQ ID NO: 34-37 or a variant thereof.

In a preferred embodiment, the antibody targeting CLDN18.2 as described above is provided, and the light chain of the antibody comprises the light chain constant region selected from human antibody K or X type or a variant thereof; and/or, the heavy chain of the antibody comprises the heavy chain constant region selected from human IgG1, IgG2, IgG3 and IgG4 or a variant thereof;

preferably, the heavy chain constant region or a variant thereof comprises positions 234, 235 and 243 of human IgG1 Fc region, or mutations at position 239, 330 and 332;

more preferably, the heavy chain constant region or the variant thereof comprises a variant having EEM or DEL at positions 356-358 of human IgG1 Fc region.

In a preferred embodiment, the antibody targeting CLDN18.2 as described above is provided, and the light chain comprises the amino acid sequence as shown in SEQ ID NO: 38, SEQ ID NO: 40, SEQ ID NO: 42 or SEQ ID NO: 45 or a variant thereof; and/or, the heavy chain comprises the amino acid sequence as shown in SEQ ID NO: 39, SEQ ID NO: 41, SEQ ID NO: 43, SEQ ID NO: 44 or SEQ ID NO: 46 or a variant thereof.

In a preferred embodiment, the antibody targeting CLDN18.2 as described above is provided, which comprises the following light chains and heavy chains:

the heavy chain is as shown in the amino acid sequence of SEQ ID NO: 39, and the light chain is as shown in the amino acid sequence of SEQ ID NO: 38; or, the heavy chain is as shown in the amino acid sequence of SEQ ID NO: 39, and the light chain is as shown in the amino acid sequence of SEQ ID NO: 40; or, the heavy chain is as shown in the amino acid sequence of SEQ ID NO: 41, and the light chain is as shown in the amino acid sequence of SEQ ID NO: 38; or, the heavy chain is as shown in the amino acid sequence of SEQ ID NO: 41, and the light chain is as shown in the amino acid sequence of SEQ ID NO: 40; or, the heavy chain is as shown in the amino acid sequence of SEQ ID NO: 39, and the light chain is as shown in the amino acid sequence of SEQ ID NO: 42; or, the heavy chain is as shown in the amino acid sequence of SEQ ID NO: 43, and the light chain is as shown in the amino acid sequence of SEQ ID NO: 42; or, the heavy chain is as shown in the amino acid sequence of SEQ ID NO: 44, and the light chain is as shown in the amino acid sequence of SEQ ID NO: 42; or, the heavy chain is as shown in the amino acid sequence of SEQ ID NO: 43, and the light chain is as shown in the amino acid sequence of SEQ ID NO: 45; or, the heavy chain is as shown in the amino acid sequence of SEQ ID NO: 44, and the light chain is as shown in the amino acid sequence of SEQ ID NO: 45; or, the heavy chain is as shown in the amino acid sequence of SEQ ID NO: 39, and the light chain is as shown in the amino acid sequence of SEQ ID NO: 45; or, the heavy chain is as shown in the amino acid sequence of SEQ ID NO: 46, and the light chain is as shown in the amino acid sequence of SEQ ID NO: 38.

In a preferred embodiment, the antibody targeting CLDN18.2 as described above is provided, wherein the antibody targeting CLDN18.2 comprises an immunoglobulin, Fab, Fab', F(ab')$_2$, Fv or a single-chain Fv fragment (scFv).

In order to solve the above-mentioned technical problem, the technical solution of the second aspect of the present disclosure is that: a bispecific antibody is provided, which comprises a first protein functional region and a second protein functional region, and the first protein functional region is an antibody targeting CLDN18.2 as described in the technical solution of the first aspect; the second protein functional region is an antibody targeting a non-CLDN1T8.2 antigen. The bispecific antibody can not only retain the binding activity and functional activity of a single CLDN18.2 antibody, but also retain the binding and functional activity of the other protein functional region. Moreover, the bispecific antibody has a structure similar to that of a normal IgG antibody, can be expressed and purified according to the conventional antibody expression and purification method, and is stable.

The bispecific antibody of the present disclosure is a Sequence-based IgG like bispecific antibody (SBody).

In a particular embodiment, the bispecific antibody as described above is provided, the non-CLDN18.2 antigen is an immune checkpoint antigen or a therapeutic target of tumor, wherein the immune checkpoint antigen includes PD-1, PD-L1, Tim3, LAG3 and CD47; the therapeutic target of tumor includes SIRPα, (signal regulatory protein α), etc., and SIRPα is a membrane protein, and is mainly expressed in myeloid cells, including macrophages, dendritic cells, et cetera. More preferably, the second protein functional region comprises an anti-PD-1 antibody, an anti-PD-L1 antibody, an anti-Tim3 antibody, an anti-LAG3 antibody, an anti-CD47 antibody, an anti-CD3 antibody and an anti-CSF-1R antibody. Most preferably, the anti-PD-1 antibody is Nivolumab (abbreviated as Nivo), Pembrolizumab (abbreviated as Pem) or Ba08 (i.e., the Ba08-1 described in patent application CN201410369300). The anti-PD-L1 antibody is Atezolumab (abbreviated as Atezo), Avelumab (abbreviated as Avel) or Durvalumab (abbreviated as Durv), and the anti-CD3 antibody is an antibody constructed using the sequences of light and heavy chain variable regions that bind to CD3 in Blincyto or AMG420.

or, the second protein functional region is a cytokine and a cytokine receptor or a fragment thereof; preferably, the cytokine or the fragment thereof comprises TGFβ, IL10 and CSF-1, and the cytokine receptor or the fragment thereof comprises TGFβRII, an IL10 receptor and a macrophage colony stimulating factor 1 receptor (CSF-1R).

In some specific embodiments, the bispecific antibody as described above is provided, and the antibody is an immunoglobulin, scFv (single chain Fv, also called single-chain variable fragment), Fab, Fab' or F(ab')$_2$. More preferably, the constant region of the immunoglobulin is a human antibody constant region, the human antibody constant region comprises a human antibody light chain constant region and a human antibody heavy chain constant region, the human antibody light chain constant region is preferably κ chain or λ chain, and the human antibody heavy chain constant region is preferably the heavy chain constant region of hIgG1, higG2 or hIgG4.

In order to design a bispecific antibody with a simple production process and the retention of an effective activity, the form of the bispecific antibody of the present disclosure is a structure similar to normal IgG, specifically, the protein functional regions capable of targeting the light chain and/or heavy chain variable regions of two targets are designed on the structure of the bispecific antibody, and the two protein functional regions share the same heavy chain Fc region. Preferably, the antibody molecule against one target is linked to one end of the light chain or heavy chain of a complete antibody against the other target in the form of one or more scFvs, or a complete cytokine or a fragment thereof, or a complete cytokine receptor or a fragment thereof. In this way, the heterogeneous expression products caused by the expression of different heavy chain Fc and/or different light chain can be avoided, such as the co-expression of Fc in Knob form and Fc in Hole form, and there will be heterogeneous Fc-Fc pairing form in the expression process, which will result in a lot of inconvenience during the purification process; The influence of cross design of a partial region of light and heavy chain on the structure activity, and the Fe mismatch during the process can also be avoided. The activity against a specific target can also be adjusted by one or more scFv designs.

In some specific embodiments, the bispecific antibody as described above is provided. The first protein functional region is an immunoglobulin, and the second protein functional region is one or more scFvs, cytokines or fragments thereof, or cytokine receptors or fragments thereof; or, the second protein functional region is an immunoglobulin, and the first protein functional region is one or more scFvs; wherein, the scFv comprises a heavy chain variable region and a light chain variable region, the heavy chain variable region is linked to the light chain variable region via a linker, and the linker is preferably (Gly-Gly-Gly-Gly-Ser)$_w$ [hereinafter referred to as (G4S)$_w$]; the scFv, the cytokine or the fragment thereof, or the cytokine receptor or the fragment thereof is linked to the immunoglobulin via a linker, and the linker may be selected from common peptide segments or (G4S)$_w$ in the art; and the w is preferably an integer number between 0 to 10, more preferably 1, 2, 3 or 4.

The bispecific design is summarized in the following table (general formula 1).

TABLE 01

| Schemes | A sequence comprising a light chain | A sequence comprising a heavy chain |
|---|---|---|
| 1 | T2 (scFv)$_{n1}$-T1VL-Lc-T2 (scFv)$_{n2}$ | T2 (scFv)$_{n3}$-T1VH-Hc-T2 (scFv)$_{n4}$ |
| 2 | T1 (scFv)$_{n1}$-T2VL-Lc-T1 (scFv)$_{n2}$ | T1 (scFv)$_{n3}$-T2VH-Hc-T1 (scFv)$_{n4}$ |
| 3 | T2 (scFv)$_{n1}$-T1VL-Lc-T1 (scFv)$_{n2}$ | T2 (scFv)$_{n3}$-T1VH-Hc-T1 (scFv)$_{n4}$ |
| 4 | T1 (scFv)$_{n1}$-T2VL-Lc-T2 (scFv)$_{n2}$ | T1 (scFv)$_{n3}$-T2VH-Hc-T2 (scFv)$_{n4}$ |

In table 01, "A sequence comprising a light chain" means that the sequence, in addition to a light chain sequence, can also comprises a scFv linked to the light chain sequence; "A sequence comprising a heavy chain" means that the sequence, in addition to a heavy chain sequence, can also comprises a scFv linked to the heavy chain sequence. For the convenience of presentation, the scFv in the table, unless specified otherwise herein, can also be the sequence of a cytokine and a cytokine receptor or a fragment thereof in addition to the meaning understood by those skilled in the art. Wherein, T1 represents the first protein functional region against target 1, and T2 represents the second protein functional region against target 2. T1 (scFv) represents the scFv sequence of the antibody against target 1; and T2 (scFv) represents the scFv sequence of the antibody against target 2.

n1, n2, n3 and n4 in (scFv)$_{n1}$, (scFv)$_{n2}$, (scFv)$_{n3}$ and (scFv)$_{n4}$ are respectively natural numbers, which can be 0, 1, 2, 3, etc. In the specific embodiment of the present disclosure, at least 1 value of n1, n2, n3 and n4 is 1, and the rest of which are 0. VL represents an antibody light chain variable region sequence against target 1 or 2; VH represents an antibody heavy chain variable region sequence against target 1 or 2. Lc represents a constant region sequence of a light chain (κ or λ), preferably a human light chain constant region sequence; He represents a heavy chain, which comprises a constant region sequence of IgG1, IgG2, IgG3 and IgG4 etc., preferably a human heavy chain constant region sequence. When the C-terminal of a heavy chain constant region is linked to a scFv or other protein sequences, the C-terminal amino acid K or the heavy chain constant region can be mutated, preferably mutated to A. Thus, in scheme 1, T1 is an immunoglobulin, and T2 is a scFv; in scheme 2, T2 is an immunoglobulin, and T1 is a scFv; the scFvs are against the is the same target; and in schemes 3 and 4, the scFvs at two ends are against two different targets.

When the scFv in table 01 is a conventional scFv, which is namely not a sequence of a cytokine and a cytokine receptor or a fragment thereof, the scFv is light chain variable region-linker-heavy chain variable region, and the N-terminal of the light chain variable region of the scFv or the C-terminal of the heavy chain variable region of the scFv is correspondingly linked to the C-terminal or N-terminal of the light chain and/or heavy chain of an immunoglobulin via a linker; or the scFv is heavy chain variable region-linker-light chain variable region, and the N-terminal of the heavy chain variable region of the scFv or the C-terminal of the light chain variable region of the scFv is correspondingly linked to the C-terminal or N-terminal of the light chain and/or heavy chain of an immunoglobulin via a linker.

It should be noted that when the above-mentioned scFv is light chain variable region-linker-heavy chain variable region, the linking manner thereof is that the C-terminal of the light chain variable region is linked to a linker, and then the linker is linked to the N-terminal of the heavy chain variable region, thus exposing the N-terminal of the light chain variable region and the C-terminal of the heavy chain variable region of the scFv, so that the scFv can be linked to the light chain and or heavy chain of an immunoglobulin via the linker. In the present disclosure, when the scFv is linked to the light chain of an immunoglobulin, in some specific embodiments, the C-terminal of the heavy chain variable region of the scFv is preferably used for linking to the N-terminal of the light chain of the immunoglobulin via a linker; when the scFv is linked to the heavy chain of an immunoglobulin, in some specific embodiments, the N-terminal of the light chain variable region of the scFv is preferably used for linking to the C-terminal of the heavy chain of the immunoglobulin.

when the scFv is heavy chain variable region-linker-light chain variable region, the linking manner thereof is that the N-terminal of the light chain variable region is linked to a linker, and then the linker is linked to the C-terminal of the heavy chain variable region, thus exposing the C-terminal of the light chain variable region and the N-terminal of the heavy chain variable region of the scFv, so that the scFv can be linked to the light chain and or heavy chain of an immunoglobulin via the linker. In this case, when the scFv is linked to the light chain of an immunoglobulin, in some specific embodiments, the C-terminal of the light chain variable region of the scFv is preferably used for linking to the N-terminal of the light chain of the immunoglobulin; when the scFv is linked to the heavy chain of an immunoglobulin, in some specific embodiments, the N-terminal of the heavy chain variable region of the scFv is preferably used for linking to the C-terminal of the heavy chain of the immunoglobulin. Preferably, the linker is $(G_4S)_3$, and/or, the number of the scFv is two and the scFvs are symmetrically linked to the light chain and/or heavy chain of an immunoglobulin.

More preferably, the bispecific antibody is selected from any one of the following:

(1) the first protein functional region is an immunoglobulin, and the immunoglobulin comprises a light chain amino acid sequence as shown in SEQ ID NO: 38 and a heavy chain amino acid sequence as shown in SEQ ID NO: 39; the second protein functional region is scFv; wherein the C-terminals of the heavy chain variable regions of the two scFvs are symmetrically linked to the N-terminals of the two heavy chains of the immunoglobulin via a linker; and, the light chain variable region of the scFv is the light chain variable region of, Atezo, and the heavy chain variable region of the scFv is the heavy chain variable region of Atezo; or, the C-terminals of the heavy chain variable regions of the two scFvs are symmetrically linked to the N-terminals of the two heavy chain variable regions of the immunoglobulin via a linker; and, the light chain variable region of the scFv is the light chain variable region of Hu5F9, and the heavy chain variable region of the scFv is the light chain variable region of Hu5F9; or, The N-terminals of the heavy chain variable regions of the two scFvs are symmetrically linked to the C-terminals of the two heavy chains of the immunoglobulin via a linker; and, the light chain variable region of the scFv is the light chain variable region of AMG420, and the heavy chain variable region of the scFv is the heavy chain variable region of AMG420.

In addition, the bispecific antibody may also comprise the following structure, the first protein functional region is an immunoglobulin, and the immunoglobulin comprises a light chain amino acid sequence as shown in SEQ ID NO: 38 or SEQ ID NO: 42 and a heavy chain amino acid sequence as shown in SEQ ID NO: 39; the second protein functional region is a scFv:

the light chain variable region of the scFv is the light chain variable region of iMab (i.e. WO 2018075857_4 sequence), and the heavy chain variable region is the heavy chain variable region of iMab (i.e. WO 2018075857_3 sequence); or, the sequence of the light chain variable region of the scFv is the light chain variable region of Tim3 (as shown in SEQ ID NO: 27 in patent application CN201710348699.4), and the heavy chain variable region of the scFv is the heavy chain variable region of Tim3 (as shown in SEQ ID NO: 36 in patent application CN201710348699.4); or, the sequence of the light chain variable region of the scFv is the light chain variable region of BlincytoCD3, and the heavy chain variable region of the scFv is the heavy chain variable region of BlincytoCD3; or, the sequence of the light chain variable region of the scFv is the light chain variable region of Pem, and the heavy chain variable region of the scFv is the heavy chain variable region of Pem; or, (2) the first protein functional region is scFv, and the second protein functional region is an immunoglobulin; the C-terminals of the heavy chain variable regions of the two scFvs are symmetrically linked to the N-terminals of the two heavy chains of the immunoglobulin via a linker; the sequence of the light chain variable region of scFv is as shown in SEQ ID NO: 29, and the sequence of the heavy chain variable region of scFv is as shown in SEQ ID NO: 34; wherein the immunoglobulin comprises the amino acid sequences of the light chain variable region of Nivo, the light chain constant region K chain, the heavy chain variable region of Nivo and the heavy chain constant region of hIgG4; or, the immunoglobulin comprises the amino acid sequences of the light chain variable region of Pem, the light chain constant region K chain, the heavy chain variable region of Pem and the heavy chain constant region of hIgG4; or, the immunoglobulin comprises the amino acid sequences of the light chain variable region of Atezo, the light chain constant region K chain, the heavy chain variable region of Atezo and the heavy chain constant region of hIgG1.

Similarly, the bispecific antibody may also comprise the following immunoglobulin: the first protein functional region is a scFv, and the second protein functional region is an immunoglobulin which has the amino acid sequence of the light chain constant region K chain and the heavy chain constant region of hIgG1; wherein, the light chain variable region of the immunoglobulin is the light chain variable region of iMab (i.e. WO 2018075857_4 sequence), and the heavy chain variable region is the heavy chain variable region of iMab (i.e. WO 2018075857_3 sequence); or, the light chain variable region of the immunoglobulin is the light chain variable region of Tim3 (as shown in SEQ ID NO: 27 in patent application CN201710348699.4), and the heavy chain variable region of the immunoglobulin is the heavy chain variable region of Tim3 (as shown in SEQ ID NO: 36 in patent application CN201710348699.4); or, the light chain variable region of the immunoglobulin is the light chain variable region of Hu5F9, and the heavy chain variable region is the light chain variable region of Hu5F9; the sequence of the light chain variable region of the immunoglobulin is the light chain variable region of Avel, and the heavy chain variable region of the immunoglobulin is the heavy chain variable region of Avel; or, the sequence of the light chain variable region of the immunoglobulin is the light chain variable region of Blincy to CD3, and the heavy chain variable region of the immunoglobulin is the heavy chain variable region of Blincy to CD3.

when the scFv in T1 (scFv) and T2 (scFv) in table 01 is a cytokine or a fragment thereof, or a cytokine receptor or a fragment thereof, the structure of the scFv is linker-cytokine receptor and variant sequence thereof, or cytokine and variant sequence thereof-linker. the other end of the linker is linked to the N-terminal and/or C-terminal of the light chain and/or heavy chain of the immunoglobulin, preferably the linker is $(G_4S)_w$, and w is 0, 1, 2, 3 and 4; preferably w=3 or w=4.

In a specific embodiment, the bispecific antibody as described above is provided. The first protein functional region is an immunoglobulin, and the second protein functional region is a cytokine or a fragment thereof, or a cytokine receptor or a fragment thereof, the number of the cytokine or the fragment thereof, or the number of the cytokine receptor or the fragment thereof is preferably two or four; the cytokine or the fragment thereof, or the cytokine receptor or the fragment thereof is symmetrically linked to the C-terminals and/or N-terminals of the two light chains and/or two heavy chains of the immunoglobulin via a linker, and the linker is preferably $(G_4S)_3$;

preferably, the immunoglobulin comprises the light chain amino acid sequence as shown in SEQ ID NO: 38; and the heavy chain amino acid sequence as shown in SEQ ID NO: 39; wherein the cytokine or the fragment thereof, or the cytokine receptor or the fragment thereof is TGFβRII, and the sequence of TGFβRII is as shown in SEQ ID NO: 1, and the number of TGFβRII is two; the TGFβRIIs are symmetrically linked to the C-terminals of the two heavy chains of the immunoglobulin, and the C-terminal amino acid is mutated from K to A; or, the cytokine or the fragment thereof, or the cytokine receptor or the fragment thereof is IL10, and the sequence of IL10 is as shown in SEQ ID NO: 2, and the number of IL10 is two; the IL10s are symmetrically linked to the C-terminals of the two heavy chains of the immunoglobulin, and the C-terminal amino acid is mutated from K to A.

In some preferred specific embodiments, the bispecific antibody as mentioned above is provided, and the bispecific antibody comprises the following light chain amino acid sequences and the amino acid sequences containing heavy chains:

the light chain amino acid sequence as shown in SEQ ID NO: 53, and the amino acid sequence comprising a heavy chain as shown in SEQ ID NO: 54; or, the light chain amino acid sequence as shown in SEQ ID NO: 55, and the amino acid sequence comprising a heavy chain as shown in SEQ ID NO: 56; or, the light chain amino acid sequence as shown in SEQ ID NO: 38, and the amino acid sequence comprising a heavy chain as shown in SEQ ID NO: 57; or, the light chain amino acid sequence as shown in SEQ ID NO: 38, and the amino acid sequence comprising a heavy chain as shown in SEQ ID NO: 58; or, the light chain amino acid sequence as shown in SEQ ID NO: 38, and the amino acid sequence comprising a heavy chain as shown in SEQ ID NO: 59; or, the light chain amino acid sequence as shown in SEQ ID NO: 38, and the amino acid sequence comprising a heavy chain as shown in SEQ ID NO: 60; or, the light chain amino acid sequence as shown in SEQ ID NO: 38, and the amino acid sequence comprising a heavy chain as shown in SEQ ID NO: 61; or, the light chain amino acid sequence as shown in SEQ ID NO: 38, and the amino acid sequence comprising heavy chain as shown in SEQ ID NO: 4.

Or, the bispecific antibody of the present disclosure is DVD-Ig (Dual-variable domain Ig) bispecific antibody, and the structure thereof is that the VL and Vl of another antibody are respectively linked to the N-terminals of the light and heavy chains of a normal antibody, and the dual function is realized by binding of two antibody variable regions to two targets.

The design of the bispecific antibody is summarized in the following table (general formula 2)

TABLE 02

| DVD structure design of bispecific antibodies | |
|---|---|
| A sequence comprising a light chain | A sequence comprising a heavy chain |
| T2 VL-Linker-T1VL-Lc | T2 VH-Linker-T1VH-Hc |
| TI VL-Linker-T2VL-Lc | T1 VH-Linker-T2VH-Hc |

T1 and T2 represent directing against target 1 and target 2 respectively. In table 02 "a sequence comprising a light chain" means that the sequence, in addition to the normal and complete light chain sequence, also comprises another light chain variable region sequence. "A sequence comprising a heavy chain" means that the sequence, in addition to the normal and complete heavy chain sequence, also comprises another heavy chain variable region sequence. The light chain variable region and the complete light chain, and the heavy chain variable region and the complete heavy chain are linked via a linker.

In a specific embodiment, the bispecific antibody is a DVD-Ig bispecific antibody. More preferably, the second protein functional region comprises a complete light chain and heavy chain of a normal antibody, and the first protein functional region comprises a light chain variable region and a heavy chain variable region; or, the first protein functional region comprises a complete light chain and heavy chain of a normal antibody, and the second protein functional region comprises a light chain variable region and a heavy chain variable region. More preferably, the light chain and the light chain variable region, and the heavy chain and the heavy chain variable region are linked via a linker; and the linker is preferably $(G_4S)_w$ and the w is preferably an integer number between 0 to 10, more preferably 1, 2, 3 or 4.

In a preferred specific embodiment, the bispecific antibody consists of a sequence comprising a light chain and a sequence comprising a heavy chain. the bispecific antibody is selected from following combination: the sequence comprising a light chain is Ab10 VL-$(G_4S)_3$-NivoVL-Lc (κ chain), and the sequence comprising a heavy chain is Ab10ViH-$(G_4S)_3$-NivoViH-Hc (hIgG4); or, the sequence comprising a light chain is AtezoVL-$(G_4S)_3$-Ab10VL-Le (κ chain), and the sequence comprising a heavy chain is AtezoVH-$(G_4S)_3$-Ab10VH-Hc (hIgG1); or, the sequence comprising a light chain is Hu5F9VL-$(G_4S)_3$-Ab10VL-Lc (κ chain), and the sequence comprising a heavy chain is Hu5F9VH-$(G_4S)_3$-Ab10VH-Hc (hIgG1).

or, the bispecific antibody of the present disclosure comprises a first protein functional region and a second protein functional region, one of the protein functional regions is an immunoglobulin and the other protein functional region is Fab' or F(ab')$_2$.

In order to solve the above-mentioned technical problem, the technical solution of the third aspect of the present disclosure is that: an antibody drug conjugate (ADC) is provided, which has a structure as shown in formula I:

$$Ab\text{-}[(L_2)_n\text{-}L_1\text{-}D]_y \qquad \text{formula I}$$

wherein, D is a small molecule drug having cytotoxicity, and $L_1$ and $L_2$ are linkers respectively linking the drug and the antibody; n is 0 or 1; y represents an average number of D conjugated to Ab, and $0<y\leq10$, preferably $2\leq y\leq7$; more preferably $3\leq y\leq6$; most preferably 4.4 or 4.8;

and the Ab is the antibody targeting CLDN18.2 as described in the first aspect of the present disclosure, or the bispecific antibody as described in the second aspect of the present disclosure.

In the preparation process of the antibody drug conjugate, according to the conjugating method, if a site-directed conjugating method is employed, the number of drugs carried by the antibody is an exact number, and the antibody drug conjugate can be a single product (not a mixture). If a site-random conjugating is employed, the number of drug conjugate molecules carried on different antibodies is actually different. Therefore, the antibody drug conjugate of the present disclosure is actually a mixture, and γ in the general formula reflects the average value of the drug conjugates carried by the antibodies in the mixture. After numerical calculation, y usually is a non-integer positive number, such as 4.4 or 4.8. The average number of drug moieties of each antibody in the ADC preparation from the conjugating reaction can be characterized by conventional methods such as mass spectrometry, ELISA assay and HPLC. The quantitative distribution of ADC can also be determined. In some cases, the separation, purification and characterization of uniform ADC with a certain value of y from ADC with other drug loading amounts can be achieved by methods such as reverse phase HPLC or electrophoresis.

In the general formula of the present disclosure, if the linker $L_2$ exists (i.e., n is 1), the number of $L_2$, $L_1$ and D is the same, in this case, the antibody drug conjugate is Ab-[$L_2$-$L_1$-D]y; If $L_2$ does not exist (i.e., n is 0), i.e., only one linker is included, the number of $L_1$ and D is the same, in this case, the antibody drug conjugate should be Ab-[$L_1$-D]$_y$ actually. In addition, the antibody drug conjugate shown in the general formula of the present disclosure is actually an antibody drug conjugate in an ideal state, i.e., only the number of $L_2$ (if present) linked to linker $L_1$ and the number of $L_1$ linked to D are taken into account in the general formula. It is well known to those skilled in the art that there should be a linker not linked to D in an antibody drug conjugate actually synthesized, therefore, the average number of drug molecules actually conjugated with the antibody should be $\leq y$, i.e., y is a theoretical maximum value of the drug conjugated to the antibody.

In a preferred embodiment of the present disclosure, an antibody drug conjugate is provided, and the small molecule drug is a cytotoxic agent selected from toxins, chemotherapeutic agents, antibiotics, radioisotopes and nucleolytic enzymes.

Preferably, the small molecule drug is selected from the following group: monomethyl auristatin, maytansine alkaloids, camptothecin alkaloids, calicheamicin, doxorubicin (adriamvcin), duocarmycin, or a combination thereof. More preferably, the monomethyl auristatin is monomethyl auristatin E (NLAE) or monomethyl auristatin F (MMAF), the maytansines is $N_2$'-deacetylation-$N_2$'-(3-mercapto-1-oxopropyl)-maytansine (DMl), $N_2$'-deacetylation-$N_2$'-(4-mercapto-1-oxopentyl)-maytansine (DM3) and $N_2$'-deacetylation-$N_2$'-(4-mercapto-4-methyl-1-oxopentyl)-maytansine (DM4).

In a preferred embodiment of the present disclosure, an antibody drug conjugate is provided, and the $L_1$ is selected from a cleavable linker, a uncleavable linker, a hydrophilic linker, a precharged linker and a dicarboxylic acid-based linker. Preferably, the linker is selected from N-succinimidyl 4-(2-pyridyldithio) valerate (SPP), N-succinimidyl (4-iodacetyl) aminobenzoate ester (SLAB), N-succinimidyl 4-(maleimidomethyl) cyclohexanecarboxylate ester (SMCC), 6-maleiminocaproyl (MC), maleiminopropionyl (MP), valine-citrulline (VC), alanine-phenylalanine (ala-phe), p-aminobenzyloxycarbonyl (PAB) and MC-VC-PAB.

In a preferred embodiment of the present disclosure, an antibody drug conjugate is provided, the $L_2$ is a compound as shown in the following formula II:

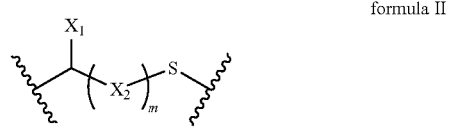

formula II wherein, $X_1$ is selected from a hydrogen atom, a halogen, hydroxyl, cyano, alkyl, alkoxy and cycloalkyl;

$X_2$ is selected from alkyl, cycloalkyl and heterocyclyl; m is 0-5; S is a sulfur atom;

preferably, when $X_1$ is a hydrogen atom, $X_2$ is alkyl and n is 1, the compound as shown in formula II is S-(3-carbonylpropyl) thioacetate ester.

In a preferred embodiment of the present disclosure, an antibody drug conjugate is provided, the small molecule drug is DM1, the linker $L_1$ is SMCC, and n is 0, thereby forming an antibody drug conjugate as shown in the following formula III:

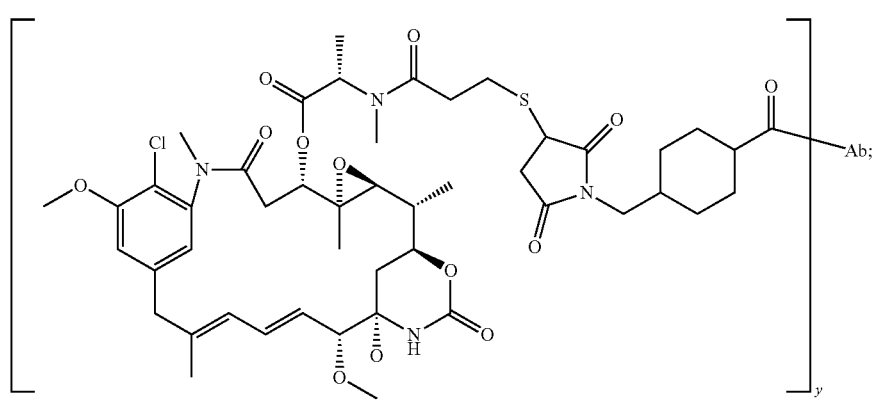

formula III or, the small molecule drug is MMAF, the linker $L_1$ is MC-VC-PAB, $L_2$ is S-(3-carbonylpropyl) thioacetate ester, and n is 1, thereby forming an antibody drug conjugate as shown in the following formula IV:

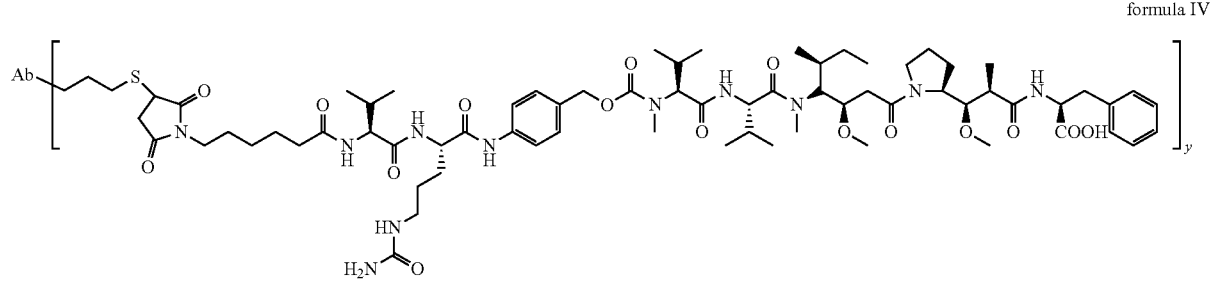

formula IV

In a preferred embodiment of the present disclosure, an antibody drug conjugate as described above is provided. In some embodiments, the number y (or load, or DAR) of the cytotoxic agent or small molecule drug conjugated to a single antibody molecule which is linked to the linker is 1, 2, 3, 4, 5, 6, 7, 8, 9 or 10, but due to the particularity of the linking reaction, the DAR of the small molecule drug conjugated on the antibody which is linked to the linker is actually an average value between 0 to 10, 1 to 8, 2 to 7, 3 to 6 or 4 to 5. That is to say, the antibody conjugate of the present disclosure is actually a mixture of antibodies linked to different numbers of linkers-drugs or only linkers, therefore y value is an average value of the number of conjugated drugs and the value is an integer or a non-integer. In certain embodiments, the scope of drug load of ADC of the present disclosure ranges from 1 to about 8; about 2 to about 7; about 3 to about 6; about 4 to about 5; about 4.1 to about 4.9; about 4.2 to about 4.8; about 4.3 to about 4.7; about 4.4 to about 4.6; about 4.4, 4.6 to about 4.8.

In a preferred embodiment of the present disclosure, an antibody drug conjugate is provided, and the antibody drug conjugate is an antibody drug conjugate as shown in the following formula V:

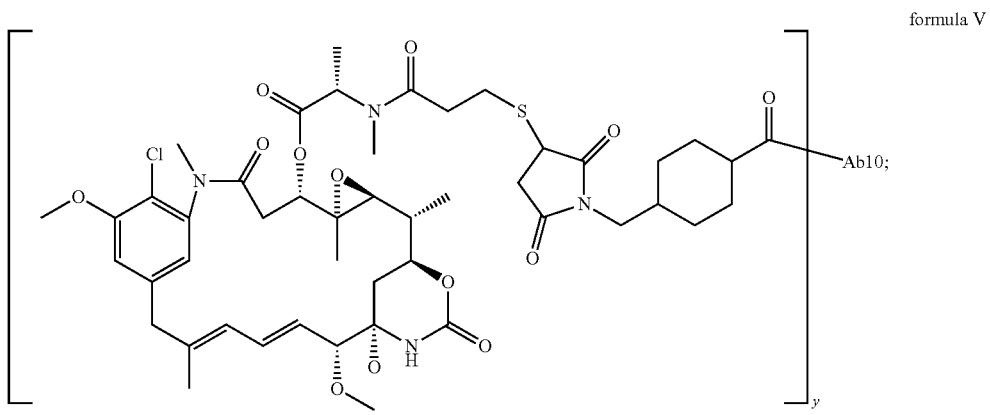

formula V or, an antibody drug conjugate as shown in the following formula VI:

formula VI

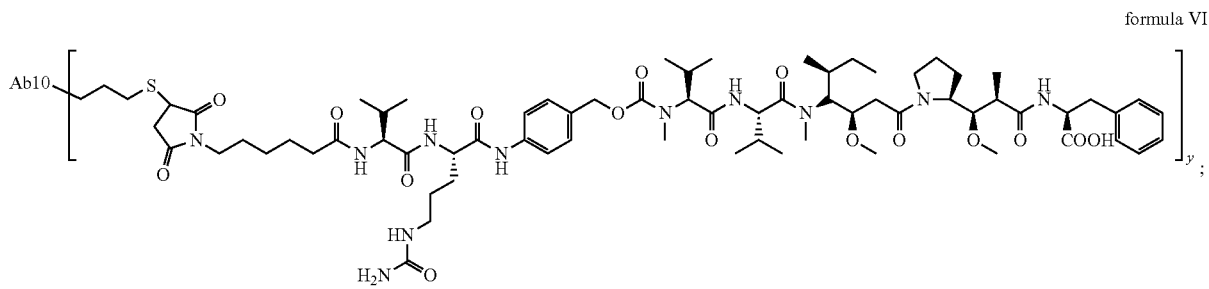

or, an antibody drug conjugate as shown in the following formula VII:

formula VII

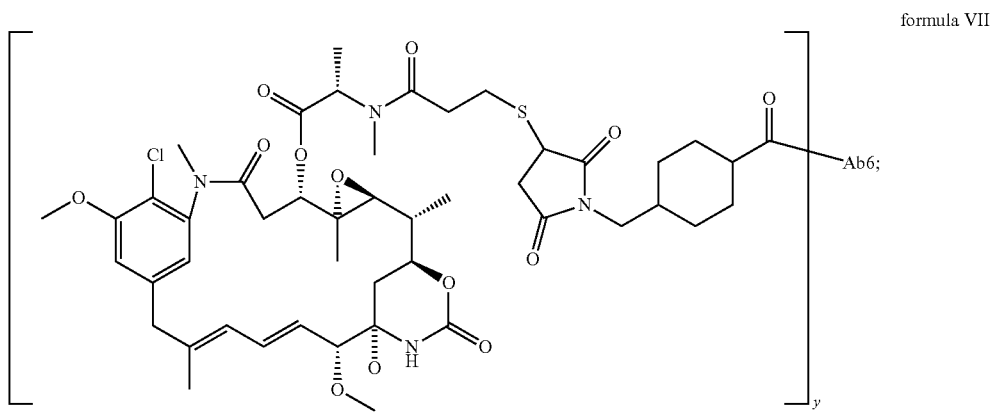

or, an antibody drug conjugate as shown in the following formula VIII:

formula VIII

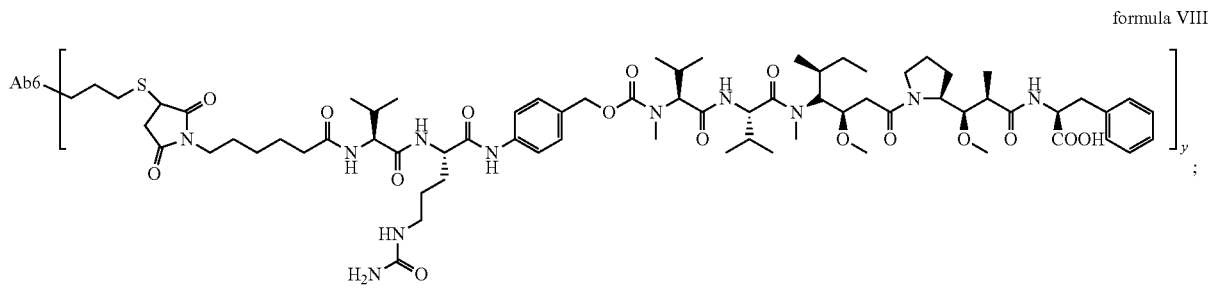

wherein, the Ab10 comprises a light chain as shown in SEQ ID NO: 38 and a heavy chain as shown in SEQ ID NO: 39; the Ab6 comprises a light chain as shown in SEQ ID NO: 42 and a heavy chain as shown in SEQ ID NO: 39.

In order to solve the above-mentioned technical problem, the technical solution of the fourth aspect of the present disclosure is that: a method for preparing the antibody drug conjugate is provided, when n is 1, the preparation method includes the following steps:

(1) preparation of intermediate 1: the antibody is mixed with the linker $L_2$ in a solution, after reaction and purification, a solution containing intermediate 1 is obtained, and the intermediate 1 is shown in the following formula IX:

formula IX

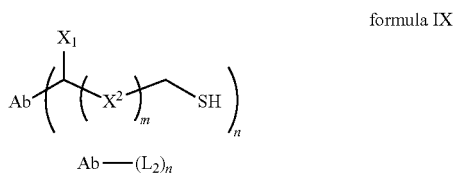

wherein, $X_1$ is selected from a hydrogen atom, a halogen, hydroxyl, cyano, alkyl, alkoxy and cycloalkyl;

$X_2$ is selected from alkyl, cycloalkyl and heterocyclyl; m is 0-5; S is a sulfur atom;

preferably, $X_1$ is hydrogen atom, $X_2$ is alkyl, and m is 1, i.e., $L_2$ is S-(3-carbonylpropyl) thioacetate ester;

(2) preparation of intermediate 2: the linker $L_1$ and the drug are prepared into an intermediate 2: $L_1$-D;

(3) the solution containing intermediate 1 obtained in step (1) is mixed with the solution containing intermediate 2 obtained in step (2), after reaction and purification, a solution containing the antibody drug conjugate is obtained;

when n is 0, the preparation method includes the following steps:

(1) preparation of intermediate 3: the antibody is mixed with the linker $L_1$ in a solution, after reaction and purification, a solution containing intermediate 3 is obtained;

(2) the solution containing intermediate 3 obtained in step (1) is mixed with a solution containing the drug, after reaction and purification, a solution containing the antibody drug conjugate is obtained;

preferably, the reaction temperature is 25° C. in the step (1) and/or (2); the reaction time is 2 to 4 hours; and/or, the purification is gel filtration purification, and more preferably Sephadex G25 gel column desalination purification.

In order to solve the above-mentioned technical problem, the technical solution of the fifth aspect of the present disclosure is that: a chimeric antigen receptor (CAR) targeting Claudin18.2 is provided.

When designing CAR, the selection of an antibody gene against a specific antigen is a key. In view of the complexity of gene expression in vivo and various uncontrollable factors, it is very difficult to select a suitable gene for CAR. Moreover, for many tumor specific antigens, it is difficult to find specific molecules against same and suitable for the construction of CAR cells. After the construction of CAR, it is usually impossible to obtain an active extracellular binding region, which is also the difficulty in developing CAR technology. In addition, although CAR cells have attractive prospects in tumor immunotherapy, the higher risk thereof should also be considered. For example, since low expression of specific antigens recognized by CAR in some normal tissues, CAR cells may damage normal tissue expressing the corresponding antigens. In the prior art, the effect of specific binding of the antibody targeting Claudin18.2 to Claudin18.2 is not good, and the effect of CAR cells targeting Claudin18.2 is also not promising. However, it is well-known that it is very difficult to develop CAR cells targeting Claudin18.2 with both effectiveness and safety. Through experiments, the inventor has unexpectedly found that the antibody binding activity/affinity of the CAR of the present disclosure is high, which means that the CAR of the present disclosure can better bind to target cells with better specificity and reduce the side effects caused by the binding of non-target cells under the same process (the same virus titer and transfection efficiency). The CAR of the present disclosure can work even at a very small dose and has an extremely high application value. The antigen binding part (antibody) of the CAR cell against CLDN18.2 in the present disclosure is a humanized sequence, which can reduce the immunogenic risk caused by CAR treatment. Through a new generation of CAR design, specifically, cytokines, cytokines and receptor binding complexes thereof, etc., which can effectively kill tumors are introduced into the C-terminal of the CAR, and these factors and/or complexes can be secreted into extracellular and tumor cell regions, a better tumor inhibition effect is achieved.

The CAR comprises: (a) an extracellular binding domain scFv specifically recognizing CLDN18.2; (b) a hinge domain; (c) a transmembrane domain; (d) a co-stimulatory intracellular domain; and (e) a signaling domain;

wherein, the extracellular binding domain comprises the light chain variable region and a heavy chain variable region of the antibody targeting CLDN18.2 as described in the first aspect of the present disclosure.

In a preferred specific embodiment, in the CAR as described above, (1) the hinge domain is selected from hinge regions of one or more of the following molecules: CD8α, CD28, CD152, PD1 and IgG1 heavy chain;

(2) the transmembrane domain is selected from transmembrane regions of one or more of the following molecules: α, β and ζ chain of TCR, $CD3_\varepsilon$, $CD3_\zeta$, CD4, CD5, CD8α, CD9, CD16, CD22, CD27, CD28, CD33, CD37, CD45, CD64, CD80, CD86, CD134, 4-1BB, CD152, CD154 and PD1;

(3) the co-stimulatory intracellular domain is selected from intracellular regions of one or more of the following molecules: CARD11, CD2, CD7, CD27, CD28, CD30, CD40, CD54, CD83, OX40, CD134, 4-1BB, CD150, CD152, CD223, CD270, PD-$L_2$, PD-L1, CD278, DAP10, NKD2C SLP76, TRIM, FcεFRIγ and MyD88, preferably CD28 intracellular region and/or 4-1BB intracellular region; and/or, (4) the signaling domain is selected from intracellular regions of one or more of the following molecules: Igα, Igβ, TCRξ, FcR1γ, FcR1β, CD3γ, CD3δ, $CD3_\varepsilon$, CD2, CD5, CD22, CD28, CD79a, CD79b, CD278, CD66d and CD3ζ; preferably CD3ζ intracellular region.

In a preferred embodiment, in the CAR, the hinge domain is CD8α hinge region, the transmembrane domain is CD8α transmembrane domain, the co-stimulatory intracellular domain is CD28 intracellular region and/or 4-1BB intracellular region, and the signaling domain is CD3ζ intracellular region (abbreviated as CD3ζ in the CAR general formula of embodiments);

preferably, the CD8α hinge region is human CD8α hinge region; the CD8α transmembrane region is human CD8α transmembrane region; the CD28 intracellular region is human CD28 intracellular region; the 4-1B13 intracellular region is human 4-1BB intracellular region; and/or, the CD3ζ intracellular region is human CD3ζ intracellular region.

In order to solve the above-mentioned technical problem, the technical solution of the sixth aspect of the present disclosure is that: a nucleic acid construct containing CAR targeting Claudin18.2 is provided, and the nucleic acid construct has a structure as shown in formula car-[(IRES)—f]$_q$, wherein, IRES is an internal ribosome entry site sequence as shown in the nucleic sequence of SEQ ID NO: 55; f encodes a functional protein F, q is 0 or a non-zero natural number; Car encodes CAR including the CAR of the fifth aspect mentioned above.

In a preferred embodiment, in the nucleic acid construct as described above, when q is a non-zero natural number, preferably 1, the functional protein F comprises:

(1) a cytokine or a fragment thereof, preferably IL10 or IL15 or an active fragment thereof; more preferably, the amino acid sequence of IL10 is as shown in SEQ ID NO: 54;

(2) a cytokine receptor or an active fragment thereof, preferably IL15 Rα or a fragment thereof or IL15 Rα fragment (sushi) or IL 15 Rα fragment (sushi+); or, (3) a fusion protein of a cytokine receptor or an active fragment thereof and a cytokine, preferably a fusion fragment of IL15Rα or a fragment thereof or IL15Rα (sushi) or IIL15Rα (sushi+) and IL15.

In a preferred embodiment, the structure of the nucleic acid construct is:

(1) scFv-human CD8α hinge region-human CD8α transmembrane region-human 4-1BB intracellular region-human CD3ζ intracellular region; preferably, the amino acid sequence encoded thereby is as shown in SEQ ID NO: 3; a preferred nucleotide construct herein is named CAR1a below; or, (2) scFv-human CD8α hinge region-human CD8α transmembrane region-human 4-1BB intracellular region-human CD3ζ intracellular region-(IRES)-IL 15; a preferred nucleotide construct herein is named CAR3ab below; or, (3) scFv-human CD8α hinge region-human CD8α transmembrane region-human 4-1BB intracellular region-human CD3ζ intracellular region-(IRES)-IL 10; a preferred nucleotide construct herein is named CAR3ab below; or, (4) scFv-human CD8α hinge region-human CD8α transmembrane region-human 4-1BB intracellular region-human CD3ζ intracellular region-(IRES)-IL15Rα (sushi+)-IL15; a preferred nucleotide construct herein is named CAR4a below.

Those skilled in the art need to know that the above-mentioned constructs are nucleic acids. For the sake of simplicity, the four structures of the constructs omit the expression "the nucleotide sequence encoding". For example, the scFv in the above-mentioned construct structure is actually "the nucleotide sequence encoding scFv", the human CD8α hinge region is actually "the nucleotide sequence encoding the human CD8α hinge region", and so on. Furthermore, the IL10 and IL15 in the above-mentioned structure can be wild-type IL10 and IL15 and can also be mutants of IL10 and IL 15 or an active fragment thereof.

In the above-mentioned nucleic acid constructs, CD27 T cell memory and survival signaling domain, and/or self-destructible domains, such as the nucleotide sequence encoding inducible caspase (iCasp) or the nucleotide sequence encoding herpes simplex virus-thymidine kinase (HSV-TK) may be further comprised. The self-destructible domain can regulate the antigen recognition signaling pathway, minimize the damage of CAR cells to normal tissues and reduce off-target effects. When adverse reactions occur, under the stimulation of non-toxic precursor drugs, a suicide gene is activated, CAR cell apoptosis is induced, and the treatment is terminated.

In order to solve the above-mentioned technical problem, the technical solution of the seventh aspect of the present disclosure is that: an isolated nucleic acid is provided, and the isolated nucleic acid encodes the antibody targeting CLDN18.2 as described above, or the bispecific antibody as described above.

In order to solve the above-mentioned technical problem, the technical solution of the eighth aspect of the present disclosure is that: an expression vector is provided, and the expression vector comprises the isolated nucleic acid as described above, or the nucleic acid construct as described above.

Preferably, the expression vector is selected from a retrovirus vector, a lentiviral vector, an adenovirus vector and an adeno-associated virus vector, more preferably a lentiviral vector, and the backbone of the plasmid for the expression vector can be pBABEpuro.

In order to solve the above-mentioned technical problem, the technical solution of the ninth aspect of the present disclosure is that: a genetically modified cell is provided, and the genetically modified cell is transfected with the nucleic acid construct or the expression vector as described above; preferably, the genetically modified cell is an eukaryotic cell, more preferably an isolated human cell; furthermore preferably an immune cell such as a T cell, or a NK cell such as a NK92 cell line.

In order to solve the above-mentioned technical problem, the technical solution of the tenth aspect of the present disclosure is that: a method for preparing the genetically modified cell is provided, and the method includes the following steps: transferring the nucleic acid construct, the expression vector, or the virus into cells to be modified to obtain the genetically modified cell;

more preferably, the genetically modified cell is a eukaryotic cell, preferably an isolated human cell; more preferably an immune cell such as a T cell or a NK cell; furthermore preferably a NK92 cell line.

In order to solve the above-mentioned technical problem, the technical solution of the eleventh aspect of the present disclosure is that: a pharmaceutical composition is provided, and the pharmaceutical composition comprises the antibody targeting CLDN18.2, the bispecific antibody, the genetically modified cell or the antibody drug conjugate, and a pharmaceutically acceptable carrier; preferably, the pharmaceutical composition further comprises an immune checkpoint antibody.

In order to solve the above-mentioned technical problem, the technical solution of the twelfth aspect of the present disclosure is that: the use of the antibody targeting CLDN18.2, the bispecific antibody, the antibody drug conjugate, the nucleic acid construct, the expression vector, the virus, the genetically modified cell or the pharmaceutical composition in the preparation of drugs for treating tumors is provided; more preferably, the tumors are CLDN18.2 positive tumors, preferably gastric cancer, esophageal cancer, lung cancer, melanoma, kidney cancer, breast cancer, colorectal cancer, liver cancer, pancreatic cancer, bladder cancer, glioma or leukemia.

On the basis of meeting common knowledge in the art, the above-mentioned various preferred conditions can be combined in any form, such that various preferred examples of the present disclosure are obtained. The reagents and raw materials used in the present disclosure are commercially available.

The present disclosure has the following positive improvement effects:

through innovative immune and screening methods and a variety of innovative designs, provided is a brand new antibody targeting CLDN18.2, preferably a humanized antibody, which has a better specific binding activity to human and murine CLDN18.2, a higher Emax; a high affinity (KinExA) (preferably up to 10 pM); a better CDC activity in human blood cell; a better activity for inducing apoptosis of CLDN18.2+ cells, a better activity for inhibiting tumor cell growth, a better animal efficacy, and a good pharmacokinetics (PK) in vivo, in particular a longer T1/2. The antibody also has a better binding activity to murine CLDN18.2.

The present disclosure provides a bispecific antibody, one target of the antibody is CLDN18.2, and the other is a target other than CLDN18.2. Innovative design unexpectedly discovered that the obtained preferred molecule of double specific antibody (SBody) retained the binding activity and functional activity for double targets; moreover, the double specific design is similar to IgG structure, and the purification process is simple and the product (bispecific antibody) is stable. This will bring convenience to the preparation of antibody by a process in the later development. Meanwhile, when the designed targets include immune checkpoint antigens such as PD-1/PD-L1, the bispecific antibody binds to CLDN18.2, which can achieve the combined effect of tumor immunity and targeted antibody in one molecule, resulting in an effect equal to combined 2 molecules or better synergistic effect and bringing more convenient options for drug development for the combination of tumor immunotherapy and targeted therapy.

The present disclosure first creates an antibody drug conjugate (ADC) against CLDN18.2. The effects of the antibody molecule are as described above. The ADC molecule obtained by conjugation of the antibody with cytotoxin retains the characteristics of the excellent specific binding activity against human and murine CLDN18.2, endocytosis and highly effective killing tumor cells, meanwhile, the ADC molecule carries cytotoxic toxin and can target and kill tumor cells more specifically, target and specifically inhibit tumor cell proliferation, and produce an unexpected and excellent efficacy in the treatment of tumors. These characteristics make the ADC drug of the present disclosure, the pharmaceutical salt thereof, the solvent compound thereof or the combination thereof with other drugs provide more specific, effective and better treatment options, means and methods for tumor patients, especially for CLDN18.2 positive cancer patients. In addition, the antibody drug conjugate/antibody provided by the present disclosure has a better pharmacokinetic performance, a large safety window and lower toxic and side effects.

The present disclosure provides a novel CAR molecule targeting Claudin18.2, which has a higher activity and affinity and can better target tumor cells; the CAR molecule does not bind to Claudin18.1, has an excellent specificity and reduces the side effects of non-target cell binding; the antigen binding sequence of the CAR molecule is preferably humanized so as to reduce the immunogenic risk and achieve a better safety; The combined use of the CAR molecule with a cytokine or a cytokine receptor has a better therapeutic effect; The immune cell containing the CAR molecule of the present disclosure has a better therapeutic effect, in particular, in a preferred embodiment, the CAR molecule of the present disclosure has a nearly 100% cancer-inhibitive effect.

DETAILED DESCRIPTION OF THE PREFERRED EMBODIMENT

Figure 1:
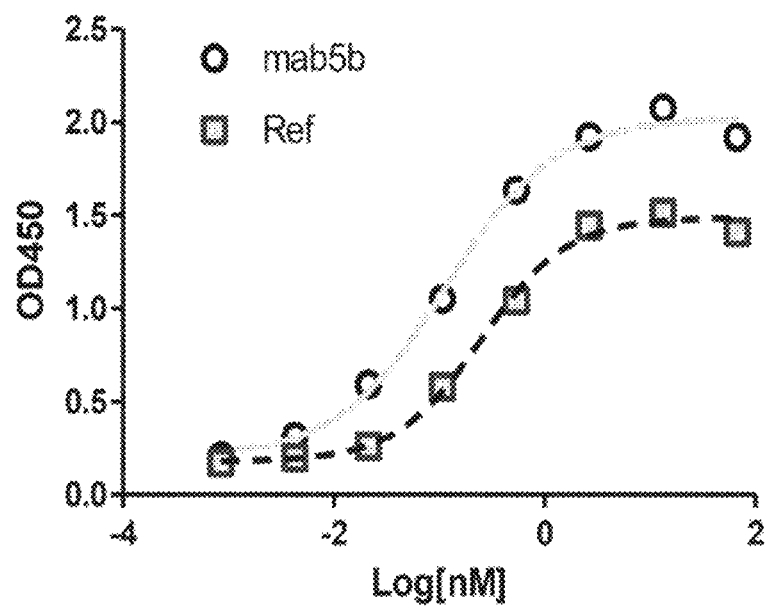
FIG. 1 is the binding activity of murine-derived anti-human CLDN18.2 antibody mab5b of the present disclosure to human CLDN18.2 (FIG. 1a) and murine CLDN18.2 (FIG. 1b) (ELISA)
Figure 1:
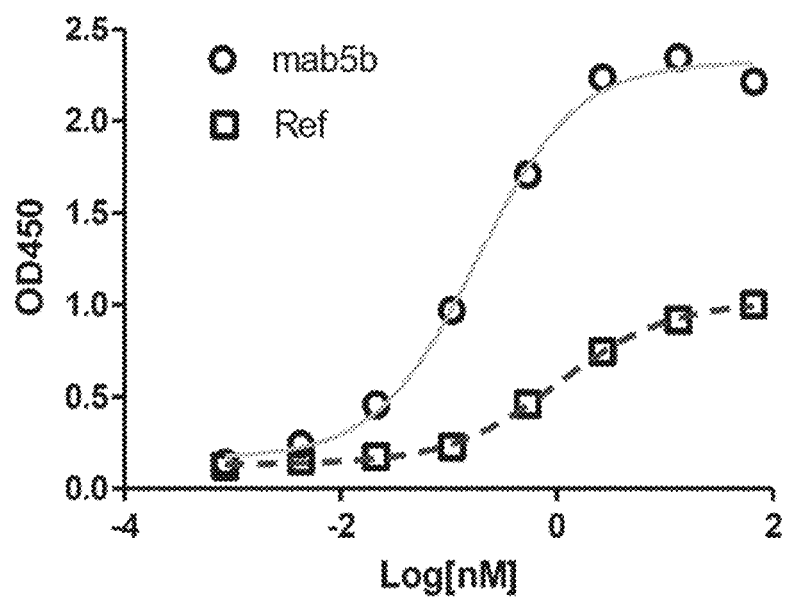

Explanation of terms:

In the present disclosure, all scientific and technical terms used herein have the meanings commonly understood by a person skilled in the art unless specified otherwise. In addition, the laboratory operation steps related to the cell culture, molecular genetics, nucleic acid chemistry and immunology as used herein are conventional steps that are widely used in the corresponding art. To better understand the present disclosure, definitions and explanations of related terms are provided below.

The three-letter code and one-letter code of amino acids as used in the present disclosure are known to those skilled in the art or described in J. Biol. Chem, 243, p3558 (1968).

As used herein, the term "include" or "comprise" is intended to indicate that the composition and method include elements, but do not exclude other elements. "Consisting essentially of" when used to define compositions and methods shall mean the exclusion of other elements having any substantial effect for the combination for intended use. For example, the composition consisting essentially of the element as defined herein will not exclude trace pollutants (for example, phosphate-buffered saline, preservatives, etc.) from separation and purification methods and pharmaceutically acceptable carriers. "Consisting of" should indicate excluding other ingredients that are more than trace elements and substantial method steps for applying the compositions disclosed herein. Aspects defined through each of these transitional terms is within the scope of the present disclosure.

The term "CLDN18.2" includes isoforms, CLDN18.2 of mammalian (for example, human), species homologs of human CLDN18.2, and analogs comprising at least one common epitope with CLDN18.2. The amino acid sequence of CLDN18.2 (for example human CLDN18.2) is known in the art, as shown in NCBI database.

The term "CLDN18.1" includes isoforms, CLDN18.1 of mammalian (for example, human), species homologs of human CLDN18.1, and analogs comprising at least one common epitope with CLDN18.1. The amino acid sequence of CLDN18.1 (for example human CLDN18.1) is known in the art, as shown in NCBI database.

The "CLDN18.2 antibody", "anti-CLDN18.2 antibody", "CLDN18.2 antibody molecule" and "anti-CLDN18.2 antibody molecule" of the present disclosure can be used interchangeably. The term "epitope" refers to the part of an antigen (for example, human CLDN18.2) that specifically interacts with an antibody molecule. The term "competition" in the present disclosure refers to the ability of an antibody molecule to interfere with the binding of an anti-CLDN18.2 antibody molecule to a target (for example, human CLDN18.2). Interference with binding action may be direct or indirect (for example, through allosteric regulation effect of antibody molecules or targets). Competitive binding assay (e.g., FACS, ELISA, or BIACORE) can be used to determine whether an antibody molecule can interfere with the degree of binding of another antibody molecule to the target thereof.

The term "antibody" of the present disclosure includes an immunoglobulin, which is a tetrapeptide chain structure of two identical heavy chains and two identical light chains linked by an interchain disulfide bond. The amino acid composition and arrangement of immunoglobulin heavy chain constant region is different; therefore, the antigenicity thereof is also different. According to this, immunoglobulins can be divided into five classes, or referred to as the isoforms of immunoglobulins, namely IgM, IgD, IgG, IgA and IgE, and the corresponding heavy chains thereof are respectively µ chain, δ chain, γ chain, α chain and ε chain. According to the difference in terms of the amino acid composition of the hinge region and the number and position of heavy chain disulfide bonds, the same class of Ig can also be divided into different subclasses, for example, IgG can be divided into IgG1, IgG2, IgG3 and IgG4. A light chain can be divided into κ chain or λ chain according to different constant regions. Each class of Ig of the five classes of Igs may have a κ chain or a λ chain.

In the present disclosure, the antibody light chain variable region of the present disclosure may further comprise a light chain constant region, and the light chain constant region comprises human or murine-derived κ, λ chain or a variant thereof. In the present disclosure, the antibody heavy chain variable region of the present disclosure may further comprise a heavy chain constant region, and the heavy chain constant region comprises human or murine-derived IgG1, IgG2, IgG3, IgG4 or a variant thereof.

The sequence of about 110 amino acids near the N-terminal of heavy chain and light chain of an antibody varies greatly and is a variable region (V region); the rest amino acid sequence near the C-terminal are relatively stable and is constant region (C region). The variable region comprises 3 hypervariable regions (HVR) and 4 skeleton regions (FR) with relatively conserved sequences. The 3 hypervariable regions determine the specificity of the antibody, and also are referred to as complementary determinant region (CDR). Each of the light chain variable region (VL) and the heavy chain variable region (VH) consist of 3 CDR regions and 4 FR regions and is arranged from the amino end to the carboxyl end in the order of: FRI, CDR1, FR2, CDR2, FR3, CDR3 and FR4. The 3 CDR regions of the light chain refer to LCDR1, LCDR2 and LCDR3; and the 3 CDR regions of the heavy chain refer to HCDR1, ICDR2 and HCDR3.

In the light chain and heavy chain, the variable region and constant region are linked by the "J" region of about 12 or more amino acids, and the heavy chain also comprises the "D" region of about 3 or more amino acids. Each heavy chain consists of a heavy chain variable region (VH) and a heavy chain constant region (CH). The heavy chain constant region consists of 3 domains (CHI, CH2 and CH3). Each light chain consists of a light chain variable region (VL) and a light chain constant region (CL). The light chain constant region consists of one domain CL. The constant region of the antibody can mediate the binding of immunoglobulins to host tissues or factors (including various cells (for example, effector cells) of the immune system) and the first component of the classical complement system (C1q). The VH region and VL region can also be subdivided into regions with high variability called complementary determining region (CDR), among which more conservative regions called framework regions (FRs) are interspersed. Each VH and VL consists of 3 CDRs and 4 FRs arranged from amino end to carboxyl end in the order of: FRI, CDR1, FR2, CDR2, FR3, CDR3 and FR4. The variable regions corresponding to each heavy chain/light chain (V H and VL) form an antibody binding site respectively. In particular, the heavy chain can also comprise more than 3 CDRs, such as 6, 9 or 12. For example, in the bispecific antibody of the present disclosure, for the heavy chain, the N-terminal of the heavy chain of the IgG antibody is linked to the ScFv of another antibody, in this case, the heavy chain contains 9 CDRs.

The number and position of CDR amino acid residues in the VL region and V-J region of the antibody or antigen binding fragment of the present disclosure conform to known Kabat, Contact, CCG, AbM and Chothia numbering rules. For example, Kabat numbering rule follows the definition of Kabat E A. Et al., Sequences of Proteins of Immunological Interest [National Institutes of Health, Bethesda, Md. (1987 and 1991)], and Chothia numbering rule follows the definition of Chothia & Lesk 1987) Mol. Biol. 196: 901-917; Chothia et al. (1989) Nature 342: 877-883. The boundary of a given CDR may vary depending on the scheme used for identification. The definition rules of the present disclosure and the CDR sequence defined by the antibody are shown in Tables 3-8. For example, Kabat scheme is based on structural alignment, while Chothia scheme is based on structural information. The numbers used for Kabat and Chothia schemes are based on the most commonly used antibody region sequence length, inserting letters to adjust inserts (e.g., "30a") and the presence of deletions in some antibodies. In the two schemes, some inserts and deletions ("indel") are placed in different positions, resulting in a different numbering. The Contact scheme is based on the analysis of the crystal structure of the complex and is similar to the Chothia numbering scheme in many respects. Therefore, unless otherwise specified, the terms "CDR" and "complementary determining region" of a given antibody or a region thereof (for example, a variable region) and the individual CDR of the antibody or the region thereof (for example, "CDR-H1, CDR-H2) should be understood to cover a complementary determining region defined by any of the above-mentioned known schemes described herein. In some cases, a scheme for identifying one or more specific CDRs is specified, for example, CDRs are defined by Kabat, Chothia or Contact method. In other cases, the specific amino acid sequence of CDR is given.

The term "murine-derived antibody" in the present disclosure is a monoclonal antibody against human CLDN18.2 prepared according to the knowledge and skills in the art. When preparation, CLDN18.2 antigen is injected into an experimental subject, and then hybridomas expressing the antibody with desired sequence or functional properties are isolated. In a preferred embodiment of the present disclosure, the murine-derived CLDN18.2 antibody or the antigen binding fragment thereof can further comprise a light chain constant region of murine-derived κ and λ chains or the variants thereof, or further comprises a heavy chain constant region of murine-derived IgG1, IgG2, IgG3 or IgG4 or the variants thereof.

The term "human antibody" includes the antibody with the variable region and constant region of the human germline immunoglobulin sequence. The human antibody of the present disclosure can include the amino acid residues not encoded by the human germline immunoglobulin sequence (for example, mutations introduced by random or site-specific mutagenesis in vitro or by somatic mutation in vivo). However, the term "human antibody" does not include an antibody in which a CDR sequence derived from another mammalian species, such as a mouse, has been transplanted into a human backbone sequence (i.e., a "humanized antibody").

The term "chimeric antibody" refers to an antibody generated by fusing the variable region of a murine-derived antibody with the constant region of a human antibody, which can reduce the immune response induced by the murine-derived antibody. To construct a chimeric antibody, the hybridoma secreting murine-derived monoclonal antibody should be selected and established, and then the variable region gene is cloned from mouse hybridoma cells, and then the constant region gene of human antibody is cloned according to the need. The mouse variable region gene and the human constant region gene are liked to form a chimeric gene which is then inserted into a vector. Finally, the chimeric antibody molecule is expressed in eukaryotic cells, an industrial system or a prokaryotic industrial system. In a preferred embodiment of the present disclosure, the antibody light chain variable region of the CLDN18.2 chimeric antibody further comprises the light chain FR region of murine-derived x or r types or a variant thereof. The antibody heavy chain variable region of the CLDN18.2 chimeric antibody further comprises the heavy chain RF region of murine-derived IgG1, IgG2, IgG3 and IgG4 or a variant thereof. The human antibody constant region can be selected from the heavy chain constant region of human IgG1, IgG2, IgG3 or IgG4 or a variant thereof, preferably comprises the heavy chain constant region of human IgG1 or IgG4, or IgG1 with altered ADCC (antibody-dependent cell-mediated cytotoxicity) and CDC (complement dependent cytotoxicity) activity after amino acid mutation. The effector function of ADCC and CDC of the antibody can be reduced or eliminated, or enhanced by modifying the Fc segment of IgG. The modification refers to mutations in the heavy chain constant region of the antibody, and the mutations are for example selected from N297A, L234A and L235A in IgG1; IgG2/4 chimera, F235E in IgG4, or L234A1E235A, F243L, or S239D/A330L/11332E mutation.

The term "humanized antibody", also known as CDR-grafted antibody, refers to the antibody produced by transplanting a mouse CDR sequence into a human antibody variable region framework. In particular, the CDR of the CLDN18.2 antibody of the present disclosure is the antibody produced by transplanting each CDR sequence defined according to numbering rules such as CCG, Kabat, AbM, Chothia or Contact into the human antibody variable region framework. Preferably, for the CDR of the CLDN18.2 antibody of the present disclosure, preferably the 0-5 sites in the light chain CDR1 are mutated into the amino acids at corresponding sites in the human antibody CDR. These can overcome the strong antibody variable antibody reaction induced by chimeric antibodies which carry a large amount of mouse protein ingredients. The human FR germline sequence can be obtained from the websites www.imgt.org and www.vbase2.org of ImMunoGeneTics (IMGT).

As used herein, the term "specific binding" with respect to an antibody refers to the antibody that recognizes a specific antigen but does not substantially recognize or bind to other molecules in the sample. For example, an antibody that specifically bind to an antigen from one species can also bind to the antigen from one or more species. However, such interspecific cross-reactivity itself does not change the classification of antibodies according to specificity. In another example, the antibody that specifically bind to an antigen can also bind to different allelic forms of the antigen. However, such cross-reactivity itself does not change the classification of antibodies according to specificity. In some cases, the term "specific binding" or "specifically binding" can be used to refer to the interaction of an antibody, a protein, or a peptide with a second chemical substance, meaning that the interaction depends on the presence of a specific structure (for example, an antigenic determinant or epitope) on the chemical substance; for example, an antibody generally recognize and bind to a specific protein structure rather than a protein. If an antibody is specific to epitope "A", the presence of a molecule containing epitope A (or free, unlabeled A) in a reaction containing the labeled "A" and the antibody will reduce the amount of the labeled A bound to the antibody.

In a preferred embodiment of the present disclosure, the mouse CDR sequence of CLDN18.2 humanized antibody is selected from SEQ ID NO: 11-28. The framework of human antibody variable region is designed and selected, in which the sequence of the light chain FR region on the antibody light chain variable region is derived from the combined sequence SEQ ID NO: 29-33 of human germline light chain IGKV4-1*01(F) and hJK2.1, comprising FRI, FR2, FR3 regions of human germline light chain IGKV4-1*01(F) and FR4 region of hJK2.1; wherein the heavy chain FR region sequence on the antibody heavy chain variable region is derived from the combined sequence SEQ ID NO: 34-37 of human germline heavy chain IGHV1-69*01(F) and hJH4.1, comprising FRI, FR2 and FR3 region of human germline heavy chain IGHV1-69*01(F) and FR4 region of hJ-14.i. In order to avoid a decrease in activity caused by a decrease in immunogenicity at the same time, the variable region of the human antibody can be subject to minimal reverse mutation to retain the activity. In a preferred embodiment of the present disclosure, the reverse mutation of a humanized antibody variable region is 0, i.e., a full humanized antibody.

The term "deamidation" refers to the removal of an amino group from a site or a certain site in a molecule. A "deamination sensitive site" refers to the molecule and the certain site of a molecule that are easier and more prone to deamination.

The term "antigen binding fragment" refers to the antigen binding fragment and antibody analogue of an antibody, which generally includes an antigen binding region or a variable region (for example, one or more CDRs) of at least part of the parental antibody. The antibody fragment retains at least some binding specificities of the parental antibody.

Generally, when the activity is expressed on a molar basis, the antibody fragment retains at least 10% of the parental binding activity. Preferably, the antibody fragment retains at least 50%, 60%, 70%, 80%, 90%, 95%, 99% or 100% or more of the binding affinity of the parental antibody to a target. Examples of antigen binding fragments include, but are not limited to: Fab, Fab', F(ab'), a Fv fragment, a linear antibody, a single chain antibody, a nanobody, a domain antibody and a multispecific antibody. The engineered antibody variants are reviewed in Holliger and Hudson (2005) Nat. Biotechnol. 23: 1126-1136.

"Fab fragment" consists of one light chain and CH1 and a variable region of one heavy chain. The heavy chain of a Fab molecule cannot form a disulfide bond with another heavy chain molecule. The "Fc" region contains two heavy chain fragments comprising the CH1 and C1H2 domains of an antibody. The two heavy chain fragments are held together by two or more disulfide bonds and the hydrophobic interaction of the CH3 domain. The "Fab' fragment" contains one light chain and a part of one heavy chain comprising the VH domain and CH1 domain and the region between the CH1 and CH2 domains, thereby, an interchain disulfide bond can be formed between the two heavy chains of two Fab' fragments to form a F(ab')2 molecule. The "F(ab')2 fragment" contains two light chains and two heavy chains comprising a part of the constant region between the CH1 and CH2 domains, thereby forming an interchain disulfide bond between the two heavy chains. Therefore, the F(ab')2 fragment consists of two Fab' fragments held together by disulfide bonds between two heavy chains. The term "Fv" refers to an antibody fragment composed of the VL and VH domains of the single arm of an antibody, but lacking a constant region.

In some cases, the antigen binding fragment of an antibody is a single chain binding fragment (for example, scFv), wherein the VL and VH domains are paired to form a univalent molecule via a linker that links the VL and VH domains to form a single polypeptide chain [see, for example, Bird et al., Science 242:423-426 (1988) and Huston et al., Proc. Natl. Acad. Sci. USA 85:5879-5883 (1988)]. Such scFv molecules can have a general structure: N112-VL-linker-VH-COOH or N112-VH1-linker-VL-COOH. A suitable prior art linker consists of repeated $G_4S$ amino acid sequence or a variant thereof. For example, a linker with the amino acid sequence $(G_4S)_4$ or $(G_4S)_3$ can be used, but the variant thereof can also be used.

The term "multispecific antibody" is used in the broadest sense thereof to cover antibodies with multiple epitope specificity. These multispecific antibody includes but are not limited to: an antibody comprising a heavy chain variable region (VH) and a light chain variable region (VL), wherein the VH-VL unit is multiepitope specific; an antibody having two or more VL and VH regions, each VH-VL unit binds to different targets or different epitopes of the same target; an antibody having two or more single variable regions, each single variable region binds to different targets or different epitopes of the same target; a full-length antibody, an antibody fragment, a diabody, a triabody, an antibody fragment that is covalently or non-covalently linked together, etc.

An antibody molecule comprises a diabody and a single chain molecule, and an antigen binding fragment of an antibody (for example, Fab, F(ab')$_2$, scFv and Fv). An antibody molecule comprises or consists of one heavy chain and one light chain (referred to in the present disclosure as a hapten). Fab', F(ab')$_2$, Fc, Fd, Fv, a single chain antibody (for example, scFv), a single variable domain antibody, a diabody (Dab) (bivalent and bispecific), and a chimeric (for example, humanized) antibody can be produced by modifying a complete antibody or synthesized de novo using a recombinant DNA technology. These functional antibody fragments retain the ability to selectively bind to the corresponding antigens or receptors thereof. Antibodies and antibody fragments may be from any class of antibody, including but not limited to IgG, IgA, IgM, IgD, and IgE, and from any antibody subclass (for example, IgG1, IgG2, IgG3, and IgG4). The antibody molecule can be monoclonal or polyclonal. The antibody can also be a human antibody, a humanized antibody, a CDR transplantation antibody or an antibody produced in vitro. The antibody may have a heavy chain constant region selected from, for example, IgG1, IgG2, IgG3 or IgG4. The antibody may also have a light chain selected from, for example, a κ or λ type.

The antibody disclosed in the present disclosure can also be a single domain antibody. The single domain antibody can include an antibody whose complementary determining region is a component of a single domain polypeptide. Examples include, but are not limited to, heavy chain antibodies, antibodies that naturally lack light chains, single domain antibodies derived from conventional 4-chain antibodies, engineered antibodies, and single domain scaffolds other than those scaffolds derived from antibodies. The single domain antibody can be any antibody in the prior art or any single domain antibody in the future. The single domain antibody can be derived from any species, including but not limited to mice, humans, camels, alpacas, goats, rabbits and cattle. According to some aspects, the single domain antibody is a naturally occurring single domain antibody called a heavy chain antibody that lacks light chains. For clarity, such variable domain derived from the heavy chain antibody that naturally lacks light chains is referred to in the present disclosure as VHH or a nanobody to distinguish same from the conventional VI of a four-chain immunoglobulin. Such VHH molecule can be derived from the antibody produced in camelidae species, such as camels, alpacas, dromedaries, alpacas and guanacos. Other species other than camels can produce the heavy chain antibody that naturally lacks light chains, and such VHH is also considered. VH region and VL region can be further divided into a hypervariable region called a "complementary determinant region" (CDR), among which a more conservative region called the "framework region" (FR) is interspersed. The scope of the framework region and CDR has been defined in many ways.

The antibody of the present disclosure includes a monoclonal antibody. The monoclonal antibody or mAb or Ab of the present disclosure refers to the antibody obtained from a single clonal cell strain, and the cell strain is not limited to an eukaryotic, prokaryotic or phage clonal cell strain. The host cell of the vector of the present disclosure can be, but is not limited to, eukaryotic cells, bacterial cells, insect cells or human cells. Suitable eukaryotic cells include but are not limited to Vero cells, Hela cells, COS cells, CHO cells, HEK293 cells, 293T, 293E, BHK cells, and suitable insect cells, including but not limited to Sf9 cells.

Monoclonal antibodies or antigen binding fragments can be obtained by recombination using hybridoma technology, recombinant technology, phage display technology, synthesis technology (such as CDR-grafting), or other prior art. Methods for producing and purifying antibodies and antigen binding fragments are well known and can be found in the prior art, such as the technical guide for antibody experiment of Cold Spring Harbor. Antigen binding fragments can also be prepared by conventional methods.

As used herein, the term "chimeric antigen receptor" or "CAR" refers to: an extracellular domain (extracellular binding domain) that can bind to an antigen, a hinge domain, a transmembrane domain (transmembrane region) and a polypeptide that transmits the cytoplasmic signal to the domain (i.e., intracellular signal domain). The hinge domain can be considered as a part which is used to provide flexibility to the extracellular antigen binding region. The intracellular signal domain refers to the protein that transmits information into cells to regulate cell activity by the production of a second messenger via a certain signaling pathway, or the protein that acts as an effector by corresponding to such messengers, thereby producing signals that can promote the immune effector function of CAR cells (such as CART cells). The intracellular signal domain includes a signaling domain and may also include a costimulatory intracellular domain derived from a costimulatory molecule.

The term "signaling domain" refers to the part of CAR that transduces effector functional signals and directs cells to perform the specific functions thereof. Examples of signaling domains include, but are not limited to, the L chain of a T-cell receptor complex or any homolog thereof.

As used herein, the term "CD3ζ" is defined as the protein provided by GenBank accession number BAG36664.1, or equivalent residues from non-human species such as mice, rodents, monkeys, apes, etc. The "CD3ζ intracellular region" is defined as amino acid residues from the cytoplasmic domain of the (chain, and is sufficient to functionally transmit the initial signal required for T cell activation. In one aspect, CD3ζ intracellular region includes residues 52 to 164 of GenBank accession number BAG36664.1, and the functional homologs thereof which are from the equivalent residues of non-human species such as mice, rodents, monkeys, apes, etc. As used herein, the term "CD3ζ signaling domain" or "CD3ζ intracellular region" refers to a specific protein fragment associated with the name, and any other molecules of the similar biological functions having at least 80%, or alternatively at least 90% identity, preferably at least about 95%, more preferably at least about 97%, more preferably at least about 98%, and most preferably at least about 99% identity with the amino acid sequence of the CD3ζ intracellular region shown herein.

The term "costimulatory intracellular domain" refers to the intracellular region of a costimulatory molecule, is an associated binding partner on T cells, and specifically binds to costimulatory ligands, thereby mediating costimulatory responses of immune cells, such as but not limited to proliferation. Costimulatory molecules are cell surface molecules or ligands thereof of non-antigen receptors required for effective immune response. Costimulatory molecules include, but are not limited to, the intracellular regions of the following molecules: such as MHC class I molecules, BTLA and Toll ligand receptors, and OX40, CD2, CD27, CD28, CDS, ICAM-1, LFA-1 (CD11a/CD18) and 4-1B13 (CD137).

As used herein, the term "4-1BB" refers to a member of the TNFR superfamily, which has the amino acid sequence of GenBank accession number AAA62478.2, or equivalent residues from non-human species such as mice, rodents, monkeys, apes, etc.; The "4-1BB" costimulatory intracellular domain is defined as the amino acid sequence 214-255 of GenBank accession number AAA62478.2, or the equivalent residues from the unclassified species such as mice, rodents, monkeys, apes, etc., or any other molecules with similar biological functions having at least 80%, or alternatively at least 90% amino acid sequence identity, preferably at least 95% sequence identity, more preferably at least 97%, 98% or 99% sequence identity with the sequence of the 4-1BB costimulatory domain of the present application.

As used herein, the term "CD28 costimulatory domain" is a human CD28 costimulatory domain or a specific protein fragment associated with the name, and any other molecules with similar biological functions having at least 80%, or alternatively at least 90% amino acid sequence identity, preferably at least 95% sequence identity, more preferably at least 97%, 98% or 99% sequence identity with the sequence of the human CD28 costimulatory domain.

In one aspect of the present disclosure, the CAR comprises a chimeric fusion protein, which comprises an extracellular antigen recognition domain, a transmembrane domain, a costimulatory domain and a signaling domain. In one aspect, the CAR comprises a chimeric fusion protein, which comprises an extracellular binding domain that recognizes an extracellular antigen, a transmembrane domain, a costimulatory domain and a signaling domain. In one aspect, the CAR comprises a chimeric fusion protein, which comprises an extracellular binding domain, a costimulatory domain and a signaling domain, and the costimulatory domain comprises at least two functional signaling domains derived from one or more costimulatory molecules. In one aspect, the CAR comprises an optional leader sequence (or signal peptide) at the N-terminal of the CAR fusion protein. In one aspect, the CAR also comprises a leader sequence at the N-terminal of the extracellular antigen recognition domain, wherein the leader sequence is optionally cut off from the N-terminal of the antigen recognition domain (such as scFv) during the cell processing of CAR and the localization of CAR to the cell membrane.

"Homology", "variation sequence" and "mutation" refer to the sequence similarity between two polynucleotide sequences or between two polypeptides. When positions in the two compared sequences are occupied by the same base or amino acid monomer subunit, e.g., if each position in two DNA molecules is occupied by adenine, then the molecules are homologous at that position. The percent of homology between two sequences is a function of the number of matching or homologous positions shared by the two sequences divided by the number of positions compared× 100. For example, when the sequences are optimally aligned, if 6 of 10 positions in two sequences match or are homologous, then two sequences are 60% homologous. In general, comparisons are made when the maximum percentage of homology is obtained by aligning two sequences. "Optimization" refers to a mutation that retains or improves the binding of an antibody to an antigen, and in the present disclosure, a mutation that retains, keeps or improves the binding to CLDN18.2.

The terms "polypeptide", "peptide" and "protein" (if a single chain) are used interchangeably in the present disclosure. The terms "nucleic acid", "nucleic acid sequence", "nucleotide sequence" or "polynucleotide sequence" and "polynucleotide" are used interchangeably.

The term "amino acid modification" includes amino acid substitution, insertion and/or deletion, and "amino acid substitution" and "conservative amino acid substitution" means that an amino acid residue is replaced by another amino acid residue and by an amino acid residue with a similar side chain, respectively.

The terms "IL10", "interleukin 10" and "interleukin-10" can be used interchangeably and have the same meaning. Similarly, the terms "IL15", "interleukin 15" and "interleukin-15" can be used interchangeably and have the same meaning. Appropriate amino acid modifications can be easily implemented, and can ensure that the biological activity of the resulting molecules is not changed. These techniques enlighten those in the art to recognize that, in general, changing a single amino acid in a non-essential region of a polypeptide does not substantially alter the biological activity. The active fragments of IL10 or IL15 can be applied in the present disclosure. Herein, the meaning of the biological active fragment refers to that the polypeptide, which is used as a part of a full-length polypeptide, can still retain all or part of the function of the full-length polypeptide. Generally, the bioactive fragment retains at least 50% of the activity of the full-length polypeptide. Under a more preferred condition, the active fragment can retain 80%, 90%, 95%, 97%, 98%, 99%, or 100% activity of the full-length polypeptide. Based on the IL10 or IL10 polypeptide sequence, the modified or improved polypeptide can also be applied in the present disclosure, for example, a polypeptide modified or improved to promote the half-life, effectiveness, metabolism, and/or the efficacy of the polypeptide may be used. That is to say, any variation form that does not affect the biological activity of the polypeptide can be used in the present disclosure.

It is well known to those skilled in the art that IL15 binds to IL15 receptor to exert the biological function thereof. IL15 receptor has three subunits, which are respectively IL15 receptor α, ILI15Rβ (CD122) and γ (also referred to CD132). The extracellular region of IL15Rα is the part that binds to IL15, and the sushi domain of the extracellular region of IL15Rα binds to IL15 to exert the biological function of IL15. In the present disclosure, "sushi+" means that in addition to the sushi fragment, other polypeptide fragments are included. The amino acid sequences of the above-mentioned IL15Rα, IL15Rα (sushi) and ILI1Rα (sushi+) can be seen in CN106755107A. The binding of IL15 to IL15Rα of a cell not only activates the cell, but also transmit signals to another cell to activate cell activity due to the mediation of IL15Rα. These activities include the selective expansion of CD8+ T cells, NK cells, etc., and do not activate regulatory T cells like IL2, thereby playing different roles in anti-tumor immune response.

As used herein, the term "lentivirus" refers to the genus of retroviridae family. Lentivirus is unique in retroviruses, which can infect nondividing cells; They can deliver a significant amount of genetic information to the DNA of host cells, so they are one of the most effective methods for gene delivery. HIV, SIV and FIV are all examples of lentivirus. Vectors from lentivirus provide a means to achieve a significant level of gene transfer in vivo.

The term "vector" or a grammatical variant thereof as used herein is a composition that comprises an isolated nucleic acid and can be used to deliver the isolated nucleic acid to the interior of the cell. Many vectors are known in the art, including but not limited to linear polynucleotides, polynucleotides associated with ions or amphipathic compounds, plasmids, and viruses. Thus, the term "vector" or a grammatical variant thereof includes autonomously replicating plasmids or viruses. The term should also be interpreted as including non-plasmid and non-viral compounds that promote the transfer of nucleic acids into cells, such as polylysine compounds, liposomes, etc. Examples of viral vectors include but are not limited to adenovirus vectors, adeno-associated virus vectors, retroviral vectors, etc.

The expressions "cell", "cell line" and "cell culture" or grammatical variants thereof used in the present disclosure can be used interchangeably, and all such names include descendants. The term "host cell" or a grammatical variant thereof refers to the cells into which vectors can be introduced, including, but not limited to, prokaryotic cells such as *Escherichia coli*, fungal cells such as yeast cells, or animal cells such as fibroblasts, CHO cells, COS cells, NSO cells, HeLa cells, BHK cells, HEK 293 cells or human cells.

The term "transfection" or a grammatical variant thereof refers to the introduction of an exogenous nucleic acid into a eukaryotic cell. Transfection can be achieved by various means known in the art, including calcium phosphate-DNA coprecipitation, DEAE-dextran mediated transfection, polybrene mediated transfection, electroporation, microinjection, liposome fusion, lipid transfection, protoplast fusion, retroviral infection and biolistics.

The term "immune cell" or a grammatical variant thereof refers to a cell that triggers an immune response, and "immune cell" and other grammatical forms can refer to immune cells of any origin. "Immune cell" or a grammatical variant thereof includes, for example, white blood cells (leukocyte), lymphocytes (T cells, B cells, natural killer (INK) cells) derived from hematopoietic stem cells (HSC) produced in bone marrow, and bone marrow-derived cells (neutrophils, eosinophils, basophils, monocytes, macrophages and dendritic cells). The term "immune cell" can also be human or nonhuman immune cell.

As used herein, the term "T cell" or a grammatical variant thereof refers to a class of lymphocytes that mature in the thymus. T cells play an important role in cell-mediated immunity, and T cells differ from other lymphocytes (such as B cells) in that there are T cell receptors on the cell surface. "T cell" includes all types of immune cells that express CD3, including T helper cells (CD4+ cells), cytotoxic T cells (CD8+ cells), natural killer T cells, T regulatory cells (Treg) and γ-δT cells. "Cytotoxic cell" or a grammatical variant thereof includes CD8+ T cells, natural killer (NK) cells and neutrophils, these cells can mediate cytotoxic reactions. As used herein, the term "NK cell" or a grammatical variant thereof refers to a class of lymphocytes that originate from bone marrow and play an important role in the innate immune system. NK cells provide a rapid immune response to virus infected cells, tumor cells or other stress cells, even if there are no antibodies and major histocompatibility complexes on the cell surface.

For example, immune cells can be derived from blood, such as autologous T cells, allogeneic T cells, autologous NK cells and allogeneic NK cells, or can be derived from cell lines, such as INK cell lines prepared by EBV virus infection, NK cells induced and differentiated from embryonic stem cells and iPSC, and NK92 cell lines.

"Optional," "any one," "any" or "any one of" means that the event or circumstance subsequently described may but need not to occur, and the description includes the occasions where the events or circumstances occur or do not occur. For example, "optionally comprising 1 antibody heavy chain variable region" means that the antibody heavy chain variable region of a specific sequence may but need not be present. As used in the present disclosure, "a" or "an" refers to one or more than one grammatical object in the present disclosure. Unless indicated in the context clearly, the term "or" used in the present disclosure means the term "and/or" and is used interchangeably with "and/or". "About" and "approximately" should generally mean the acceptable degree of error of the quantity measured, in view of the nature or accuracy of the measurement. The degree of exemplary error is generally within the range of 10% of the degree of exemplary error and more generally within the range of 5% of the degree of exemplary error. The methods and compositions of the present disclosure cover peptides and nucleic acids, which have a designated sequence, a mutated sequence, or a sequence substantially identical or similar thereto, e.g., the sequence having at least 85%, 90%, 95%, 99% or more identity to the sequence designation. In the case of the amino acid sequence, the term "substantially identical" refers to the first amino acid sequence in the present disclosure.

As used herein, the term "KD" refers to the dissociation equilibrium constant (KD) of a specific antibody-antigen interaction, which is used to describe the binding affinity between the antibody and the antigen. The smaller the equilibrium dissociation constant, the closer the antibody-antigen binding, and the higher the affinity between the antibody and the antigen. In general, an antibody binds to an antigen at a dissociation equilibrium constant less than about $10^{-5}$M, for example, less than about $10^{-6}$M, $10^{-7}$M, $10^{-8}$M, $10^{-9}$M, M or $10^{-10}$M or less, for example, as determined by surface plasmon resonance (SPR) in a BIACORE instrument. For example, the affinity of an antibody with a cell is detected on the KINEXA 400 instrument by means of KINEXA method. As used herein, the term $EC_{50}$ refers to concentration for 50% of maximal effect, that is, the concentration that can cause 50% maximum effect.

The pharmaceutical composition of the present disclosure can be prepared into various dosage forms as required, and the dosage beneficial to patients can be determined by the physician according to factors, such as the patient types, age, weight, general conditions and mode of administration. For example, the mode of administration may be injection or other treatment methods.

As used herein, the terms "antibody drug conjugate," "coupling compound," "conjugate," or "ADC" can be used interchangeably, referring to the drug conjugate of an antibody with structures shown in formulas I, III, IV, V, VI, or VII, etc.

Orestatin is a totally synthetic drug, and the chemical structure thereof is relatively easy to modify in order to optimize the physical properties and medicine properties of orestatin. The derivatives of orestatin used for conjugating to an antibody mainly include monomethyl auristatin E (MMAE) and monomethyl auristatin F (MMAF). The former is a synthetic pentapeptide derived from natural tubulin polymerase inhibitor dolastatin-10 by adding a 2-amino-1-phenylpropyl-1-ol at the C-terminal. The inhibitory activity of MMAE on a variety of human tumor cell strains was less than one nanomole. In order to reduce the cytotoxic activity of MMAE itself, a phenylalanine is added to the C-terminal of dolastatin-10. Because of the introduction of a carboxyl group on the structure, the cell membrane permeability of MMAF is poor, therefore the biological activity effect on the cells is significantly reduced, but the inhibitory activity effect on the cells is greatly increased after conjugating with an antibody (US7750116).

In some embodiments, the antibody cytotoxic drug conjugate or a pharmaceutically acceptable salt or a solvate thereof comprises an antibody of the present disclosure conjugated with one or more maytansinoid molecules. Maytansinoids are mitotic inhibitors which inhibit tubulin polymerization so that tubulin polymerization does not work. Maytansine was originally isolated and obtained from the Maytenusserrata (U.S. Pat. No. 3,896,111). Subsequently, it was found that some microorganisms also produced maytansinoids, such as maytansinol and C-3 maytansinol vinegar (U.S. Pat. No. 4,151,042). Maytansinoid drug modules are attractive drug modules in antibody-drug conjugate, because they: (i) are relatively easy to be prepared by fermentation or chemical modification or derivatization of fermentation products; (ii) are easy to be derivatized with functional groups suitable for conjugating with antibodies by non-disulphide linker; (iii) are stable in plasma; and (iv) are effective against a variety of tumor cell lines. Maytansine compounds suitable for use as maytansinoid drug modules are well known in the art and can be isolated from natural sources according to known methods or produced by genetic engineering techniques (see Yu et al. (2002) PNAS99: 7968-7973). Maytansinol and maytansinol analogues can also be prepared according to known synthetic methods. An exemplary embodiment of the maytansinoid drug modules includes: DM1, DM3 and DM4, as disclosed herein.

The terms "linking unit" and "linker" as used in the present disclosure refer to groups applicable in the present disclosure for linking the antibody of the present disclosure to a small molecule drug. Exemplary linkers include MC, MP, val-cit, ala-phe, PAB, SPP, SMCC and SIAB. In an embodiment, the linker is MC-vc-PAB.

Drug loading is represented by y, which is the average number of drug modules per antibody in the general formula I, III, IV, V and VI, and is also known as drug antibody ratio (DAR). The average number of drug modules per antibody in the ADC preparation from the conjugating reaction can be characterized by conventional means such as mass spectrometry, ELISA, and HPLC. The quantitative distribution of ADC in terms of y can also be determined. In some cases, the separation, purification and characterization of homogeneous ADC with a certain value of y from ADC with other drug loading can be achieved by means such as reverse phase HPLC or electrophoresis. The scope of drug loading can be 0.8-10 drug modules (D) per antibody.

The loading (drug/antibody ratio DAR) of ADC can be controlled in different ways, for example by: (i) limiting the excess mole amount of the drug-linker intermediate or a linker reagent relative to the antibody, (ii) limiting the time or temperature of the conjugating reaction, (iii) the part with cysteine mercaptan modification or limiting reductive conditions, and (iv) engineering the amino acid sequence of the antibody by recombinant techniques, so that the number and position of cysteine residues are changed in order to control the number and/or position of the linker-drug attachment (such as thioMab or thioFab prepared as described herein and in WO2006/034488 (incorporated by reference herein in its entirety)).

The method, composition and combination therapy of the present disclosure can be combined with other active agents or therapeutic methods. The method of the present disclosure includes the administration of the anti-CLDN18.2 antibody molecule of the present disclosure to a subject in the amount effective for treatment or prevention of diseases (e.g., cancers), optionally, in combination with one or more inhibitors of PD-1, PD-L1, PD-L2, LAG-3, CTLA-4, Tim-3 antibody (immunotherapy) or other tumor therapeutic antibodies, Her-2, EGFR, VEGF, VEGFR antibody, etc., as well as ADC (antibody drug conjugate, such as T-DM1), bispecific antibody, chemotherapy drug, etc. The method also includes the administration of anti-CLDN18.2 antibody molecule, additional active agents or all can be administered in such amount or dose that is higher, lower, or equal to the amount or dose of each active agent used alone (e.g., as a monotherapy). The administered amount or dose of anti-CLDN18.2 antibody, additional active agents or both of them is lower (e.g., at least 20%, at least 30%. at least 40% or at least 50%) than the amount or dose of each active agent used alone (e.g., as a monotherapy).

In addition, as described in the embodiment of the present disclosure, the anti-CLDN18.2 antibody and the drug conjugate of CLDN18.2 antibody can bind to CLDN18.2 to induce the apoptosis of target cells (tumor cells), inhibit the growth of tumor cells, increase the ADCC and CDC killing effect of effector cells in vivo on tumor cells, so as to achieve the purpose of treating cancer patients. Therefore, in some embodiments, the anti-CLDN18.2 antibody and the drug conjugate of CLDN18.2 antibody described in the present disclosure show the anti-tumor effect of the antibody of the present disclosure by these mechanisms, and the method of inhibiting the growth of tumor cells, includes the administration of a therapeutically effective amount of the anti-CLDN18.2 antibody and the drug conjugate of the CLDN18.2 antibody of the present disclosure to a subject. This method is suitable for cancer treatment in vivo. In order to obtain target-specific therapeutic effects, anti-CLDN18.2 antibody molecule can be administrated together with other antibodies. When the CLDN18.2 antibody and the drug conjugate of the CLDN18.2 antibody are administrated in combination with one or more active agents, each in the combination may be administered in any order or at the same time in patients having cancers, especially in patients having tumors with high CLDN18.2 expression. In some aspects, the treatment (e.g., reduction or alleviation) of hyperplastic conditions or diseases (e.g., cancers) is provided in the subject. The method includes the administration of one or more anti-CLDN18.2 antibodies or drug conjugates of CLDN18.2 antibody to a subject alone or in combination with other active agents or therapeutic methods.

The combination further includes inhibitors or activators of immune checkpoint regulators, such as anti-PD-L1 antibody molecules, anti-PD-1 antibody molecules, or CTLA-4 inhibitors (e.g., anti-CTLA-4 antibodies), or inhibitors or activators of non-immune checkpoint regulators (e.g., chemical drugs, small molecule targeting drugs, and macromolecules including antibody targeting drugs, such as antibodies of anti-Her2, anti-VEG, anti-VEGFR, anti-EGFR, antibody-drug conjugates, bispecific antibodies, CAR-T cell combination, etc.) or any combination thereof. CLDN18.2 antibody therapy can also be combined with standard cancer therapy.

The term "immune checkpoint" and a grammatical variant thereof refers to a group of molecules on the cell surface of immune cells, which can act as a "gate" to reduce or inhibit immune responses, such as anti-tumor immune response, and thus can be combined with the antibodies of the present disclosure to treat tumors. Immune checkpoint molecules include but are not limited to PD-1, PD-L1, cytotoxic T-lymphocyte antigen 4 (CTLA-4), B7-H1, B7-H3, OX-40, 4-1BB (CD137), CD40, and lymphocyte activating gene 3 (LAG-3), etc.

Anti-CLDN18.2 antibody molecules alone or in combination with another immunomodulator (such as anti-LAG-3, anti-Tim-3, anti-PD-1 or anti-PD-L1 and anti-CTLA-4 antibody molecule) are used to treat gastric cancer, pancreatic cancer, lung cancer, esophageal cancer, ovarian cancer, etc. Anti-CLDN18.2 antibody molecule can be administered in combination with one or more of the following: immune based strategies, targeting drugs (e.g., VEGF inhibitors such as monoclonal antibodies against VEGF); VEGF tyrosine kinase inhibitors such as sunitinib, sorafenib, and apatinib; RNAi inhibitors or inhibitors of downstream mediators of VEGF signaling, such as inhibitors of rapamycin mammalian target (mTOR).

As used herein, the terms "carcinoma", "cancer", "cancer patient" are intended to include all types of cancerous growth or tumorigenic process, metastatic tissue or malignant transformed cells, tissues or organs, regardless of the histopathological type or aggressive stage. Examples include, but are not limited to, solid tumors, hematological cancers, soft tissue tumors, and metastatic lesions.

The non-limited examples of cancers suitable for treatment by using the antibody targeting CLDN18.2, bispecific antibody, ADC and CAR cell or a combination thereof disclosed in the present disclosure include lung cancer, gastric cancer, esophageal cancer, ovarian cancer, head and neck cancer, melanoma, kidney cancer, breast cancer, colorectal cancer, liver cancer, pancreatic cancer, bladder cancer and leukemia, etc., or metastatic lesions thereof.

Example 1: Construction of Cell Lines which Highly Express Claudin 18.1 and Claudin 18.2 (CLDN18.1, CLDN18.2)

The cell lines which highly express human CLDN18.1, human CLDN18.2, mice CLDN18.1, and mice CLDN18.2 used in the present disclosure are completed through the stable cell line construction platform of the present company. The steps were specifically as follows:

On the first day of the experiment, 293T cells (Cell Bank of the Type Culture Collection Committee of the Chinese Academy of Sciences Cat #GNHu17) were inoculated into two 6 cm culture dishes, and the number of cells in each culture dish reached $7.5 \times 10^5$. Day 2, 4 µg of each of the packaging plasmid (including pGag-pol, pVSV-G, BioVector Science Lab, Inc) and the plasmid pBabe-CLDN18.2 or pBabe-CLDN18.1 cloned with human or mice CLDN18.2 or CLDN18.1 gene are added into OPTI-MEM (Thermofisher Scientific Cat #31985070), so the final volume reached 200 µl. In addition, 200 µl of OPTI-IEM is prepared and added with 36 al of transfection reagent fectin (Shanghai BasalMedia Technologies Co., Ltd, Cat #F210), the two are mixed and placed at room temperature for 5 min, and then the mixture (200 µl per dish) are added dropwise into the cultured 293T cells. Day 3, the 293T cell culture medium was replaced with 4 ml of DMEM (high glucose) medium (Shanghai BasalMedia Technologies Co., Ltd/BasalMedia: Cat #310KJ). Day 4, CHO-KI cells (Cell Bank of the Type Culture Collection Committee of the Chinese Academy of Sciences Cat #SCSP-507) were inoculated into a 10 cm culture dish, and the number of cells reached $5 \times 10^5$. Day 5, the 293T cell supernatant (virus) was collected, filtered with a 0.45 jam filter membrane into the cultured CHO-K1 cells, while 10 µg/ml polybrene (Shanghai Yeasen Biotech Co., Ltd, Cat #40804ES76) was added, mixed well and then placed in an incubator, which was replaced with DMFEM/F12 medium with 10% FBS (BasalMedia, Cat #L3I10KJ) after 3 to 4 h. Day 7, CHO-K1 cells were passaged, and day 8, 10 µg/ml puromycin were added to the passaged cells for screening (BasalMedia, Cat #S250J0). After 2-3 days, the cells died in large numbers. The medium was replaced for further culture until the cells did not die any more. The cells were amplified in large numbers, and monoclonal cell lines were screened, amplified and cultured, and cryopreserved for species preservation.

The cell lines stably expressing CLDN18 which are constructed by the present disclosure were respectively marked as: human CLDN18.1+ cell (hCLDN18.1+ cell), human CLDN18.2+ cell (hCLDN18.2+ cell), mice CLDN18.1+ cell (mCLDN18.1+ cell) and mice CLDN18.2+ cell (mCLDN18.2+ cell). The protein sequences used are derived from published databases, and the amino acid sequences of the proteins are as follows.

Human CLDN18.1 (hCLDN18.1):>NP_057453.1, claudin-18 isoform 1 precursor [Homo sapiens], derived from NCBI database. Human CLDN18.2 (hCLDN18.2): >NP 001002026.1 claudin-18 isoform 2 [Homo sapiens], derived from NCBI database. Mice CLDN18.1 (mCLDN18.1): >NP_062789.1 claudin-18 isoform A1.1 precursor, derived from NCBI database. Mice CLDN18.2 (mCLDN18.2): NP_001181850.1 claudin-18 isoform A2.1 [Mus musculus], derived from NCBI database.

Example 2: Binding Experiment of Anti-CLDN18.2 Antibodies to CLDN18.2+ and CLDN18.1+ Cell Lines (ELISA)

The monoclonal cell lines which highly express human CLDN18.1, human CLDN18.2, mice CLDN18.1 or mice CLDN18.2 in cells obtained in Example 1 were amplified and cultured, and then plated on a 96-well plate at $5\times10^4$/well, and after overnight incubation in a 37° C. incubator, the supernatant was removed, and fixed with 100 μl/well of immunostaining fixative solution (Shanghai Beyotime Biotechnology Co., Ltd, Cat #P0098) for half an hour at room temperature. After washing once with PBS (BasalMedia, Cat #B320), plates were blocked with 5% milk at 37° C. for 2 hours and then washed with PBST 3 times. A sample to be tested (human- or murine-derived antibody, Jackson Immuno Research) was added. Same was incubated at 37° C. for 1 hour, then washed with PBST 3 times. Anti-human or mouse HRP (1:2500) was added at 50 μl/well and incubated at 37° C. for 1 hour, then washed with PBST 3 times, and developed with TMB (Surmodic Cat #TTMB-1000-01), and 1M $H_2SO_4$ was added at 50 μl/well to stop the reaction. Reading was performed on Microplate reader (MultiskanGO Thermo model 51119200), and data analysis was carried out using Graphpad Prism 5.

Example 3: Cloning, Expression and Purification of Recombinant Proteins and Antibodies, and Activity Detection (ELISA, Blocking Assay)

The cloning, expression and purification of the recombinant proteins/antibodies used in the present disclosure were all performed according to molecular cloning methods well known to a person skilled in the art.

Specifically, the expression vector used in the present disclosure was purchased from Changsha Ubao Biotechnology Co., Ltd, and EcoRI restriction enzyme site (GAATTC) was then introduced by L&L Biopharma Co., Ltd., Shanghai, China, which makes it easy to clone foreign genes with double enzyme digestion or by homologous recombination methods. Gene synthesis was completed by companies such as Sangon Biotech (Shanghai) Co., Ltd (Sangon Biotech). 293 cells and CHO-K were purchased from Cell Bank of the Type Culture Collection Committee of the Chinese Academy of Sciences.

The recombinant protein and antibody in the present disclosure were obtained by transiently transfecting, expressing and purifying in the 293-cell system. The specific steps involve amplification and culture of the 293 cells in Gibco FreeStyle 293 Expression Medium (Gibco, Cat #12338018). The day before transient transfection, the cell concentration was adjusted to 6 to $8\times10^5$ cell/ml, and cultured with 1% FBS (Aus Gene X FBS Excellent, supplier: AusGeneX, China, Cat #FBSSA500-S) in a shaker at 37° C. under 8% $CO_2$ for 24 h. The survival rate of additional microscopic examination was >95%, and the cell concentration was $1.2\times10^6$ cell/ml.

300 ml cells were prepared, 150 kg of each of heavy chain and light chain plasmids were dissolved in 15 ml of Opti-MEM (Gibco, Cat #31985070) and sterilized by filtration with a 0.22 μm filter. Additional 15 ml of Opti-MEM was taken and in which 600 μl of 1 μg/ml PEI (Polysciences, Inc, Cat #23966-2) was dissolved and then left to stand for 5 min. In 500 ml of culture system, 250 kg of each of heavy chain and light chain plasmids was dissolved in 25 ml of Opti-MEM (Gibco, Cat #31985070), and sterilized by filtration with a 0.22 μm filter. Additional 25 ml of Opti-MEM was taken and in which 1000 μl of 1 μg/ml PEI was dissolved and then left to stand for 5 min. PEI was slowly added to the plasmids, incubated at room temperature for 10 min, and the plasmid-PEI mixed solution was slowly dropped into a culture flask while shaking, and incubated in a shaker at 37° C. under 8% $CO_2$ for 5 days to collect samples, and the supernatant was obtained and purified (3300G for 10 min).

Purification: The samples were centrifuged at a high speed to remove impurities, and the gravity column (Shanghai Sangon Biotech, Cat #F506606-0001) containing Protein A (Mabselect, GE Healthcare Life Science, Cat #71-5020-91 AE) was equilibrated with PBS with pH 7.4, and flushed with 2-5 times the column volume. The samples were passed through the column. The column was flushed with PBS with 5-10 times the column volume (Shanghai Sangon Biotech, Cat ##B548117-0500). Then the target protein was eluted with 0.1M acetic acid with pH 3.5, and then adjusted to neutral with Tris-HCl at pH 8.0, and the concentration was measured by a microplate reader, then split packed and stored for later use.

The recombinant human CLDN18.2 (claudin18.2) extracellular region (the fragment of position 20 being D—position 70 is fragment A) and the Fc fusion protein in the present disclosure are purified after transient transfection by the 293 system. The protein can be used to detect serum titer of immunized mice.

In some experiments of the present disclosure, an anti-human CLDN18.2 (anti-hCLDN18.2) antibody (referred to as control molecule or positive molecule) was used for comparison. The antibody is abbreviated as Ref (Reference) in the present disclosure, and the sequence is derived from WO 2014146672.

Antigen-Coated-Plate ELISA: The antigens expressed in the present disclosure such as the human PD-1, PD-L1, CD47, LAG3 and Tim3; or TGFβ1 (Cat #100-21-10), TGFβ2 (Cat #t 100-35B), TGFβ3 (Cat #100-36E) purchased from Peprotech; IL10 (Cat. No. SEKA10947) and FcγR I/CD64 (Cat. No. 1257-FC-050, R&D Systems) purchased from Sino biological, were diluted to a concentration of 1-2 μg/ml with PBS buffer with pH 7.4 according to different assays and added into 96-well ELISA plate (Corning, CLS3590-100EA) at a volume of 50 μl/well, and placed in a 37° C. incubator for 2 hours. After the liquid was discarded, a blocking solution of 5% skimmed milk (Shanghai Sangon Biotech Co., Ltd, A600669-0250) diluted with PBS at 200 μl/well was added and incubated in a 37° C. incubator for 3 hours or placed at 4° C. overnight (16-18 hours) for blocking. After the blocking solution was discarded and the plate was washed 5 times with PBST buffer (PBS with pH 7.4 containing 0.05% tweeen-20), the antibody to be tested on which a 5 fold serial dilution with 1% BSA was performed was added at 50 μl/well, and incubated at 37° C. for 1 hour, and the plate was washed 5 times with PBST, and same was added at 50 μl/well with a 1:2500 diluted HRP labeled secondary antibody (Jackson Immuno Research, 115-035-003), and incubated at 37° C. for 1 hour. After the plate was washed 5 times with PBST, TMB chromogenic substrate (KPL, 52-00-03) was added at 50 μl/well, incubated at room temperature for 5-10 min, added at 50 μl/well with 1M $H_2SO_4$ to stop the reaction, and the absorption value at 450 nm was read using MULTISKAN Go microplate reader (ThermoFisher, 51119200) and the EC50 was calculated based on the OD value.

Experiment of Antibodies Preventing the Binding of Antigens to Ligands Thereof (Blocking assay)

The antigens PD-1, PD-L1, and CD47 expressed in the present disclosure were diluted to a concentration of 2 μg/ml with PBS buffer with pH 7.4, and added into a 96-well ELISA plate (Corning, CLS3590-100EA) at a volume of 50 μl/well, and incubated at 37° C. for 2 hours. After the liquid was discarded, a blocking solution of 5% skimmed milk (Shanghai Sangon Biotech Co., Ltd, A600669-0250) diluted with PBS at 200 μl/well was added and incubated at 37° C. for 3 hours for blocking. After the blocking solution was discarded and the plate was washed 5 times with PBST (PBS with pH 7.4 containing 0.05% tweeen-20), 25 μl of the sample to be tested on which a 5 fold serial dilution with 1% BSA was performed and 25 μl of biotin labeled ligand (PD-1, PD-L1, SIRPα, etc., expressed and purified in the present disclosure) with a final concentration of 10 μg/ml were added to each well, and incubated at 37° C. for 1 hour, the plate was washed 5 times with PBST, and same was added at 50 μl/well with a 1: 1000 diluted RP labeled secondary antibody (GenScript, M00091), and incubated at 37° C. for 1 hour. After the plate was washed 5 times with PBST, TMB chromogenic substrate (KPL, 52-00-03) was added at 50 μl/well, incubated at room temperature for 5-10 min, added at 50 μl/well with 1M $H_2SO_4$ to stop the reaction, and the absorption value at 450 nm was read using a MULTISKAN Go microplate reader (ThermoFisher, 51119200) and the IC50 was calculated based on the OD value.

The Biotin labeling kit is Biotin Labeling Kit-NH2, purchased from Dojindo Laboratories (Shanghai) Co., Ltd, Cat. No. LK03. The operation was carried out according to the instructions, and the labeled antibody was used after the concentration being detected with a Multiskan GO (ThermoFisher) microplate reader.

Example 4: Discovery of Anti-Human CLDN18.2 Antibody

The anti-human CLDN18.2 monoclonal antibody of the present disclosure was obtained by following steps: a mouse was immunized with the cell lines (hCLDN18.2+ cells) which highly express human CLDN18.2 obtained in Example 1, the spleen of the immunized mouse was taken for hybridoma fusion, and screening and optimization were performed on millions of hybridoma clones.

Experimental mice are female, 4 weeks old (SJL, purchased from Beijing Vital River Laboratory Animal Technology Co., Ltd, animal production license number: SCXK (Beijing) 2016-0011; Balb/c, purchased from Shanghai Sippr-BK Laboratory Animal Co., Ltd). After the mice were purchased, they were fed under a laboratory environment for 1 week, with an adjusted cycle of light at day/darkness at night, and the temperature was 20-25° C.; humidity is 40%-60%. Mice were divided into 3/group/cage.

The cell lines which highly express human CLDN18.2 (hCLDN18.2+ cells, human CLDN18.2+ cells) constructed in Example 1 were cultured, digested with trypsin and then washed with DMEM medium (BasalMedia, Cat #L310KJ), and resuspended in DMEM medium. Mice were immunized by intraperitoneal injection at 100 μl/1×$10^7$ cells/mouse. For the first immunization, Titermax (Sigma-Aldrich, T2684) was mixed with the cells at a ratio of 1:1 for immunization. Then immunization was performed once a week, and after immunization 10 times, the human CLDN18.1+ cells and human CLDN]8.2+ cells were planked onto plates at the same time, or the recombinantly expressed human CLDN18.2 extracellular (ECL1) protein in the above-mentioned Example 3 was coated onto plates, to detect the serum titer of immunized mice, and the ELISA value obtained when plated with human CLDN18.1—cells was used as a background to calculate the mice serum immune titer (titer). After 12-15 immunizations, the mice with high serum titers and titers reaching a plateau were selected for spleen cell fusion. The mice were boosted immunized with 200 μl/2×$10^7$ cells/mouse before fusion, and after 3 days, the mouse spleen lymphocytes and the myeloma cells Sp2/0 cells (ATCC® CRL-8287™) were taken for fusion to obtain the hybridoma cells to planked into 96-well plates.

The hybridoma cell supernatant from the 96-well plate was taken and human CLDN18.1+ cells and human CLDN18.2+ cells were plated at the same time to detect the antibody binding in hybridoma cells. Table 1a shows the detection results of supernatants of part of the hybridomas.

TABLE 1a

Detection of binding activity of hybridoma fusion clone to human CLDN18.2+ cells and human CLDN18.1+ cells

| No. | Initial hybridoma clone number | Human CLDN18.2+ cell binding activity (ELISA) | Human CLDN18.1+ cell binding activity (ELISA) |
|---|---|---|---|
| mab1 | F2A4 | 1.617 | 1.192 |
| mab2 | F6B1 | 0.176 | 0.123 |
| mab3 | C6F9 | 0.671 | 0.448 |
| mab4 | C11A11 | 0.436 | 0.524 |
| mab5 | C13C1 | 1.41 | 0.09 |

Because human CLDN18.2 and CLDN18.1 have up to 92% of homology (240/261), and the proteins are transmembrane proteins, only a small part of the peptide fragment of which are extracellular (such as ECL1 of 51 amino acids), and the immunogenicity of which is extremely low, leading to the possibility of producing specific antibodies being very small. Therefore, in the above screening, there are only a few hybridomas that can secrete antibodies that recognize CLDN18, but also in a few hybridomas, most of the antibodies in the supernatant of hybridomas are antibodies that can simultaneously bind to human CLDN18.2 and CLDN18.1

Very unexpectedly, a hybridoma clone is discovered in the present disclosure, and the supernatant secreted thereby only binds to human CLDN18.2+ cells and does not bind to human CLDN18.1+ cells, see mab5 in Table 1a, clone number C13C1. The data in Table 1a shows that under the same screening conditions, the clone supernatant only binds to human CLDN18.2+ cells with a detection value of 1.41, while hardly binds to the human CLDN18.1+ cells with the reading value of binding activity being only 0.09.

It was further confirmed that the hybridoma cell line C13CI unexpectedly discovered in the present disclosure can secrete unique anti-human CLDN18.2 antibody. The C13C1 hybridoma cells were subjected to multiple limited dilutions, and the monoclonal cells after each dilution were carefully and finely optimized and screened. Finally, a monoclonal cell line capable of secreting unique anti-human CLDN18.2 antibodies was discovered, and the results are shown in Table 1b.

TABLE 1b

Hybridoma monoclonal cell lines discovered at optimization and screening of hybridoma C13C1

| No. | Initial hybridoma clone number | Number of monoclonal cell lines discovered at optimization and screening | Binding activity to hCLDN18.2+ cells (ELISA) | Binding activity to hCLDN18.1+ cells (ELISA) |
|---|---|---|---|---|
| mab1b | F2A4 | F2A4F6F3E4 | 0.543 | 0.702 |
|  | F2A4 | F2A4F6F3H7 | 0.618 | 0.651 |
| mab5b | C13C1 | C13C1F1D3G6 | 0.8895 | 0.0859 |
| mab5b2 | C13C1 | C13C1F1D3H5 | 0.8778 | 0.0756 |

It can be seen from the results in Table 1b that the antibodies secreted by the monoclonal cell lines C13C1F1D3G6 and C13C1F1D3H5 obtained by fine optimization and screening of the initial hybridoma clone C13C1 obtained by the present disclosure retain the binding activity to human CLDN18.2 cells, and the reading values are 0.8895 and 0.8778, respectively; however, they do not bind to human CLDN18.1 cells, and the reading values are 0.0859 and 0.0756, respectively. The reading values are close to the background of this ELISA, 0.081. Likewise, the initial hybridoma clone F2A4 is screened simultaneously to obtain monoclonal cell lines F2A4F6F3E4 and F2A4F6F3H17. As expected, these monoclonal cell lines have the same binding activities as human CLDN18.2 cells and human CLDN18.1 cells, and the data is shown in Table 1b. These results indicate that the monoclonal cell lines discovered in the present disclosure, such as C13C1F1D3G6, can secrete unique antibodies, and unexpectedly, the secreted antibodies can only bind to human CLDN 18.2, but not to human CLDN 18.]L This means that the antibodies unexpectedly discovered in the present disclosure can effectively recognize human CLDN18.2 protein only and has the potential as a monoclonal antibody to treat tumors, especially for the treatment of cancers in patients with human CLDN18.2 protein overexpression, including but not limited to pancreatic cancer, stomach cancer, esophageal cancer, lung cancer, etc. Since not binding to human CLDN18.1 protein at all, it is expected that toxic and side effects caused by non-specific binding of therapeutic antibodies to human CLDN18.1 protein can be avoided.

Example 5: Screening and Identification of Murine-Derived Anti-Human CLDN18.2 Antibodies of the Present Disclosure The sequence of the antibody secreted by the hybridoma monoclonal cell line C13C1F1D3G6 (Table 1b) obtained in the above examples was extracted from the cell line to obtain the murine-derived antibody mab5b sequence of the present disclosure. The process of extracting antibody sequences from the preferred monoclonal cell lines from hybridomas is a well-known and commonly used method by a person skilled in the art.

Specifically, in the present disclosure, the hybridoma monoclonal cells C13C1F1D3G6 discovered in the above example were amplified and cultured, $1\times10^6$ cells were collected, and RNAs were extracted with Trizol (Invitrogen, 15596-018) (according to the steps in the kit instructions), and the extracted RNAs were reversely transcribed into cDNAs, wherein the reverse transcription kit was purchased from Sangon Biotech (Shanghai) Co., Ltd, Cat #B532435. The cDNA obtained by reverse transcription was used as a template for PCR amplification, and then the amplified product is sequenced to obtain the antibody light and heavy chain variable region sequences of mab5b. The primers used refer to the manual published by Novagen (TB326 Rev. C0308).

The light chain nucleotide sequence (SEQ ID NO: 5) and heavy chain nucleotide sequence (SEQ ID NO: 6) of the anti-human CLDN18.2 (anti-hCLDN18.2) monoclonal antibodies were obtained from the preferred hybridoma monoclonal cell line C13C1F1D3G6 of the present disclosure.

The amino acid sequence of the light chain variable region of the murine-derived anti-human CLDN18.2 (anti-hCLDN18.2) monoclonal antibody mab5b extracted from the hybridoma monoclonal cell line discovered in the present disclosure can be obtained by translating the above-mentioned light chain base sequence, and is:

(SEQ ID NO: 7)
DIVMTQSPSSLTVTAGEKVTMSCKSSQSLLNSGNQKNYLTWYQQKPGQPP

KLLIYWASTRESGVPDRFTGSGSGTHFTLTISSVQAEDLAVYYCQNDYFY

PFTFGSGTKLEKK

The amino acid sequence of the heavy chain variable region of the murine-derived anti-human CLDN18.2 (anti-hCLDN18.2) monoclonal antibody mab5b extracted from the hybridoma monoclonal cell line discovered in the present disclosure can be obtained from the above-mentioned heavy chain base sequence, and is:

(SEQ ID NO: 8)
QVQLQQSGAELIGPGTSVKVSCKASGYAFSNYLIEWVKQRPEQGLEWIGL

INPGSGGTNYNEKFKGKATLTADKSSSTAYMQLSSLTSDDSAVYFCARVY

YGNSFAYWGQGTLVTVSA

For the above-mentioned antibody mab5b extracted from the hybridoma monoclonal cell line discovered in the present disclosure, using the method described in Example 3, the light and heavy chain variable regions and constant regions of the antibodies are cloned (sequences are as follows) for recombinant expression, respectively. After purification, the antibodies, along with the control antibody Ref, were detected for binding activities to human hCLDN18.1, hCLDN18.2, and mice mCLDN18.1 and mCLDN18.2, and the results are shown in Table 2a and Table 2b below, and FIG. 1.

The light chain (L Chain) of anti-hCLDN18.2 antibody mab5b of the present disclosure is as shown in SEQ ID NO: 9; and the heavy chain (H Chain) is as shown in SEQ ID NO: 10.

TABLE 2a

Binding activity of anti-hCLDN18.2 murine-derived antibody mab5b of the present disclosure to human CLDN18 + cells

| Sample | Binding activity to hCLDN18.2 + cells | | Binding activity to hCLDN18.1 + cells | |
|---|---|---|---|---|
| | EC50 (nM) | Emax | EC50 (nM) | Emax |
| mab5b | 0.115 | 1.92 | ND | Close to background |
| Ref | 0.249 | 1.41 | ND | Close to background |

TABLE 2b

Binding activity of anti-hCLDN18.2 murine-derived antibody mab5b of the present disclosure to mice CLDN18 + cells

| Sample | Binding activity to mCLDN18.2 + cells | | Binding activity to mCLDN18.1 + cells | |
|---|---|---|---|---|
| | EC50 (nM) | Emax | EC50 (nM) | Emax |
| mab5b | 0.182 | 2.21 | ND | Background |
| Ref | 1.04 | 1.0 | ND | Background |

The results in Table 2a and FIG. 1a indicate that both the anti-hCLDN18.2 murine-derived antibody mab5b discovered in the present disclosure and the control antibody (Ref) do not bind to hCLDN18.1+ cells, with undetectable (ND) EC50, and the binding activity is still undetectable even at a high concentration of 200 nM, and the binding value Emax (refers to the binding value when the sample concentration increases and the binding reaches a plateau, namely, the maximum specific binding value) is still the background, namely, the background value. However, both antibodies have good binding activities to hCLDN18.2+ cells. Surprisingly, the binding activity of the antibody mab5b of the present disclosure is more than 1 time better than that of Ref (EC50 being 0.115 nM vs 0.249 nM). More surprisingly, the maximum binding value Emax that mab5b can achieve is 36% higher than that of Ref [(1.92-1.41)/1.41].

The results in Table 2b and FIG. 1b indicate that both the anti-hCLDN18.2 murine-derived antibody mab5b discovered in the present disclosure and the control antibody (Ref) do not bind to CLDN18.1+ cells, with undetectable (ND) EC50, and the binding activity is still undetectable even at a high concentration of 200 nM, and the binding value Emax is still the background, namely, the background value. However, both antibodies have good binding activity to CLDN18.2+ cells. Surprisingly, the binding activity of the antibody mab5b of the present disclosure is more than 4 times better than that of Ref (EC50 being 0.182 nM vs 1.04 nM). More surprisingly, the maximum binding value Emax that mab5b can achieve is more than 1 time higher than that of Ref [2.21 vs 1.0].

The above-mentioned results indicate that the binding activity (EC50 and Emax) of the new molecule mab5b discovered in the present disclosure is better than that of the control molecule. Moreover, having no binding activity to hCLDN18.1 and mCLDN18.1, indicates that mab5b not only has better binding activity, but also has excellent specificity. This indicates that mab5b can provide advantages of better efficacy and safety for tumor treating product development. The antibody also has a better binding to mice CLDN18.2, which provides a more convenient non-primate choice for preclinical research on mice.

Example 6: Humanization of Antibody mab5b of the Present Disclosure

The activity of the antibody mab5b discovered in the present disclosure is better than that of Ref, showing that the antibody can be used for the development of tumor treating drugs. In order to reduce the risk of immunogenicity and other aspects during the drug development, for example, humanization of murine-derived antibodies, and optimization of the molecular characteristics after humanization were performed to facilitate drug development, and humanized screening and sequence optimization of mab5b were performed in the present disclosure. The specific process is described as follows.

There are many other different methods for defining an antibody CDR in the art, and these methods for labeling CDRs can be summarized in Table 3 below.

TABLE 3

Summary of different methods for defining antibody CDR in the art*

| Regions | CCG definition | Kabat definition | AbM definition | Chothia definition | Contact definition |
|---|---|---|---|---|---|
| Light chain CDR1 | L24-L34 | L24-L34 | L24-L34 | L24-L34 | L30-L36 |
| Light chain CDR2 | L50-L56 | L50-L56 | L50-L56 | L50-L56 | L45-L55 |
| Light chain CDR3 | L89-L97 | L89-L97 | L89-L97 | L89-L97 | L89-L96 |
| Heavy chain CDR1 | H26-H35 | H31-H35 | H26-H35 | H26-H32 | H30-H35 |
| Heavy chain CDR2 | H50-H65 | H50-H65 | H50-H58 | H52-H56 | H47-H58 |
| Heavy chain CDR3 | H95-H102 | H95-H102 | H95-H102 | H95-H102 | H93-H101 |

*For more information, please refer to the website: http://www.bioinf.org.uk/abs/#cdrdef According to various definition methods in Table 3, the CDR sequences of the murine-derived anti-human CLDN18.2 antibody mab5b obtained in the above-mentioned Example 5 are marked/annotated as follows.

TABLE 4

CDR sequences of the anti-human CLDN18.2 (anti-hCLDN18.2) antibody mab5b of the present disclosure defined according to CCG

| Antibody | mab5b CDRs |
|---|---|
| Light chain CDR1 | KSSQSLLNSGNQKNYLT (SEQ ID NO: 11) or humanized optimized sequence KSSQSLLNSGNNKNYLA (SEQ ID NO: 12, wherein these underlined are amino acids different from SEQ ID NO: 11) |
| Light chain CDR2 | WASTRES (SEQ ID NO: 13, CDR2 sequence of the selected fully humanized human germline antibody) |
| Light chain CDR3 | QNDYFYPFT (SEQ ID NO: 14) |
| Heavy chain CDR1 | GYAFSNYLIE (SEQ ID NO: 15) |
| Heavy chain CDR2 | LINPGSGGTNYNEKFKG (SEQ ID NO: 16) |
| Heavy chain CDR3 | VYYGNSFAY (SEQ ID NO: 17) |

TABLE 5

CDR sequences of the anti-human antibody of the present disclosure defined according to Kabat

| Antibody | mab5b CDRs |
|---|---|
| Light chain CDR1 | KSSQSLLNSGNQKNYLT (SEQ ID NO: 11) or humanized optimized sequence KSSQSLLNSGNNKNYLA (SEQ ID NO: 12) |
| Light chain CDR2 | WASTRES (SEQ ID NO: 13) |
| Light chain CDR3 | QNDYFYPFT (SEQ ID NO: 14) |
| Heavy chain CDR1 | NYLIE (SEQ ID NO: 18) |
| Heavy chain CDR2 | LINPGSGGTNYNEKFKG (SEQ ID NO: 16) |
| Heavy chain CDR3 | VYYGNSFAY (SEQ ID NO: 17) |

TABLE 6

CDR sequences of the antibody of the present disclosure defined according to AbM

| Antibody | mab5b CDRs |
|---|---|
| Light chain CDR1 | KSSQSLLNSGNQKNYLT (SEQ ID NO: 11) or humanized optimized sequence KSSQSLLNSGNNKNYLA (SEQ ID NO: 12) |
| Light chain CDR2 | WASTRES (SEQ ID NO: 13) |
| Light chain CDR3 | QNDYFYPFT (SEQ ID NO: 14) |
| Heavy chain CDR1 | GYAFSNYLIE (SEQ ID NO: 15) |
| Heavy chain CDR2 | LINPGSGGTN (SEQ ID NO: 19) |
| Heavy chain CDR3 | VYYGNSFAY (SEQ ID NO: 17) |

TABLE 7

CDR sequences of the antibody of the present disclosure defined according to Chothia

| Antibody | mab5b CDRs |
|---|---|
| Light chain CDR1 | KSSQSLLNSGNQKNYLT (SEQ ID NO: 11) or humanized optimized sequence KSSQSLLNSGNNKNYLA (SEQ ID NO: 12) |
| Light chain CDR2 | WASTRES (SEQ ID NO: 13) |
| Light chain CDR3 | QNDYFYPFT (SEQ ID NO: 14) |
| Heavy chain CDR1 | GYAFSNY (SEQ ID NO: 20) |
| Heavy chain CDR2 | NPGSGG (SEQ ID NO: 21) |
| Heavy chain CDR3 | VYYGNSFAY (SEQ ID NO: 17) |

TABLE 8

CDR sequences of the antibody of the present disclosure defined according to Contact

| Antibody | mab5b CDRs |
|---|---|
| Light chain CDR1 | LNSGNQKNYLTWY (SEQ ID NO: 22) or humanized optimized sequence LNSGNNKNYLAWY (SEQ ID NO: 23) |
| Light chain CDR2 | KLLIYWASTRE (SEQ ID NO: 24) |
| Light chain CDR3 | QNDYFYPF (SEQ ID NO: 25) |
| Heavy chain CDR1 | SNYLIE (SEQ ID NO: 26) |
| Heavy chain CDR2 | WIGLINPGSGGTN (SEQ ID NO: 27) |
| Heavy chain CDR3 | ARVYYGNSFA (SEQ ID NO: 28) |

On the basis that the CDR regions (as above) of the light and heavy chains of the antibody are labeled and identified for the above-mentioned CDR analysis of the anti-hCLDN18.2 antibody (mab5b) of the present disclosure according to the antibody labeling system, the light and heavy variable region sequences of the murine-derived antibody mab5b are respectively compared with the human antibody germline database (v-base) to find out the human antibody light and heavy chain germlines with high homology. On this basis, a model is established by the computer to simulate the sites, reversion mutation key sites and combinations in the antibody structure that may affect binding to the antigen, and to screen out humanized antibody molecules with preferred activities.

Specifically, through the comparison and analysis of sequence homology, it was found that the human antibody germlines with better homology to the mab5b light chain comprise IGKV4-1*01 (F), IGKV2-28*01 (F), IGKV2D-28*01 (F), IGKV1-27*01 (F), IGKV1-39*01 (F), IGKV1D-39*01 (F), IGKV2-40*01(F), IGKV2D-29*01 (F), IGKV2D-40*01 (F) and IGKV3-15*01 (F). Through further comparison and analysis, the human antibody germline light chain IGKV4-1*01 (F) is preferred. In particular, the CDR2 sequence of the selected human germline light chain IGKV4-1*01 (F) is WASTRES, which is exactly the same as the CDR2 sequence of the murine-derived antibody mab5b light chain discovered in the present disclosure. Through sequence comparison, it is found that the J gene region of the mab5b light chain has high homology to the human antibody germlines hJK1, hJK2.1, hJK2.2, hJK2.3 and hJK2.4, and through further comparison and analysis, hJK2.1 is preferably used for mab5b light chain humanized human antibody germline J region for humanized design, screening and sequence optimization.

Through comparison and analysis of sequence homology, it is found that human antibody germlines with better homology to mab5b heavy chain include IGHV1-69*02 (F), IGHV1-69*06 (F), IGHIV1-69*08 (F), IGHV1-69*09 (F), IGH1-V-69*10 (F), IGHV1-69*04 (F), IGHV1-69*14 (F), IGHV1 μl/OR15-2*02 (P), IGHV1-69*01 (F) and IGHV1-69*11 (F), and through further comparison and analysis, the human germline heavy chain IGHV1-69*01 (F) sequence is preferably used for the humanization of the antibody of the present disclosure. Through sequence comparison, it is found that the J gene region of the mab5b light chain has high homology to the human antibody germline heavy chain J genes hJh4.1, hJh4.2, hJh4.3, hJh1, hJh2, hJh3.1 and hJh3.2, and through further comparison and analysis, hJh4.1 is preferably used for mab5b heavy chain humanized human antibody germline J region of the present disclosure for humanized design, screening and sequence optimization.

The CDR region of the antibody mab5b of the present disclosure (see the definition of CDR above) was transplanted onto the selected humanized light and heavy chain human antibody germline template, and then recombined with the IgG light and heavy chain constant regions. Then, based on the three-dimensional structure of the murine-derived antibody, reversion mutations were performed on the embedded residues, residues that directly interact with the CDR region, and residues that have an important effect on the conformation of VL and VI, and these mutations and the combination of mutations were screened for checking the effect on antibody activities, and the chemically unstable amino acid residues in the CDR region were optimized, to obtain an antibody molecule sequence with an optimized structure and activity, etc., which is the optimized antibody molecule of humanized series of the anti-human CLDN18.2 murine-derived antibody mab5b of the present disclosure.

Specifically, through the analysis of the antibody mab5b light chain of the present disclosure, it was found that the sequence comprising CDR1 (positions L24-L34) and CDR2 (positions L50-L56) has a very high homology to the sequence of the preferred humanized human germline light chain IGKV4-1*01 (F) of the present disclosure. L24-L34 CDR1 has only 5 different amino acids, which are at positions L29, L30A, L30C, L30E and L34 respectively, see Table 9a below. However, 150-L56 CDR2 is exactly the same (see Table 9b below). In the present disclosure, reversion mutations were performed on the five sites (L29, L30A, L30C, L30E and L34) of mab5b CDR1 to the amino acids corresponding to the human germline IGKV4-1*01 (F) sites, and the combination design is as shown in Table 9a below.

TABLE 9a

Amino acids at positions L24-L34 (CDR1, SEQ ID NO: 11) of the sequence of the murine-derived anti-hCLDN18.2 antibody mab5b of the present disclosure defined according to Kabat, and humanization

| | Amino acid position number | | | | | | | | | | | | | | | |
|---|---|---|---|---|---|---|---|---|---|---|---|---|---|---|---|---|
| | L24 | L25 | L26 | L27 | L28 | L29 | L30 | L30A | L30B | L30C | L30D | L30E | L30F | L31 | L32 | L33 | L34 |
| mab5b | K | S | S | Q | S | L | L | N | S | G | N | Q | K | N | Y | L | T |
| IGKV4-1*01 (F) | | | | | | V | | Y | | S | | N | | | | | A |
| Var1 | | | | | | V | | | | | | | | | | | |
| Var2 | | | | | | V | | | | | | | | | | | A |
| Var3 | | | | | | | | | | | | N | | | | | A |
| Var4 | | | | | | | | Y | | S | | | | | | | |
| Var5 | | | | | | | | Y | | S | | | | | | | A |
| Var6 | | | | | | V | | Y | | S | | | | | | | A |
| Var7 | | | | | | V | | Y | | S | | N | | | | | A |
| Var8 | | | | | | | | | | | | | | | | | A |

TABLE 9b

Amino acids at positions L50-L56 (CDR2) of the sequence of the murine-derived anti-hCLDN18.2 antibody mab5b of the present disclosure

| | Amino acid position number | | | | | | |
|---|---|---|---|---|---|---|---|
| | L50 | L51 | L52 | L53 | L54 | L55 | L56 |
| mab5b CDR2 | W | A | S | T | R | E | S |
| IGKV4-1 *01 (F) CDR2 | W | A | S | T | R | E | S |

The above-mentioned humanized molecules Var1, Var2, Var3, Var4, Var5, Var6, Var7, Var8 and mab5b were cloned, expressed and purified according to the preceding Example 3, and tested for the binding activity to human CLDN18.2+ cells according to Example 2, and the results are as shown in Table 10 below.

TABLE 10

Humanized optimization of CDR1 sequence of the antibody light chain of the present disclosure

| Antibody | $EC_{50}$ (nM) | $E_{max}$ |
|---|---|---|
| mab5b | 0.215 | 1.93 |
| Var1 | 0.461 | 1.83 |
| Var2 | 0.221 | 1.7 |
| Var3 | 0.143 | 1.46 |
| Var4 | 0.434 | 1.7 |
| Var5 | 0.656 | 1.37 |
| Var6 | 7.67 | 1.14 |
| Var7 | 9.51 | 1.02 |
| Var8 | 0.20 | 1.79 |

The above-mentioned results indicate that the humanized optimized light chain CDR1 sequence of the antibody mab5b of the present disclosure retains the same (close) binding activity as that of mab5b.

Furthermore, mab5b was humanized using the above-mentioned humanization method, the preferred sequences of the humanized light chain variable region of the mab5b antibody of the present disclosure were preferably obtained, which are as follows:

L14:
(SEQ ID NO: 29)
DIVMTQSPDSLAVSLGERATISCKSSQSLLNSGNQKNYLTWYQQKPGQPP

KLLIYWASTRESGVPDRFSGSGSGTDFTLTISSLQAEDVAVYYCONDYFY

PFTFGQGTKLEIK

L11: SEQ ID NO: 30;

L12:
(SEQ ID NO: 31)
DIVMTQSPDSLAVSLGERATISCKSSQSLLNSGNNKNYLAWYQQKPGQPP

KLLIYWASTRESGVPDRFSGSGSGTDFTLTISSLQAEDVAVYYCONDYFY

PFTFGQGTKLEIK

L13: SEQ ID NO: 32;

L15:
(SEQ ID NO: 33)
DIVMTQSPDSLAVSLGERATISCKSSQSLLNSGNNKNYLAWYQQKPGQPP

KLLIYWASTRESGVPDRFSGSGSGTHFTLTISSLQAEDVAVYYCONDYFY

PFTFGQGTKLEIK

The preferred sequences of the humanized heavy chain variable region of the present disclosure obtained by the above-mentioned method are as follows:

H51:
(SEQ ID NO: 34)
QVQLVQSGAEVKKPGSSVKVSCKASGYAFSNYLIEWVKQAPGQGLEWIG

LINPGSGGTNYNEKFKGKATITADKSTSTAYMELSSLRSEDTAVYYCAR

VYYGNSFAYWGQGTLVTVSS

H52: SEQ ID NO: 35; H53: SEQ ID NO: 36,

H54:
(SEQ ID NO: 37)
QVQLVQSGAEVKKPGSSVKVSCKASGYAFSNYLIEWVRQAPGQGLEWMGL

INPGSGGTNYNEKFKGKVTITADKSTSTAYMELSSLRSEDTAVYYCARVY

YGNSFAYWGQGTLVTVSS

The above-mentioned light chain variable region sequences, comprising the listed L14, L11, L12, L13, and L15, and any of the sequences not listed, were combined with K or; light chain constant regions of the human antibody light chain to obtain the light chain sequence of the humanized antibody of the present disclosure. The above-mentioned heavy chain variable region sequences, comprising the listed H51, 1152, 1153, L54, etc., and the unlisted heavy chain variable region sequences, were combined with the constant region sequences of different subtypes such as hIgG1, 2, 3 and 4 to obtain heavy chain sequences of the antibody of the present disclosure. The humanized antibody of the present disclosure can be obtained from any combination of the light chains and heavy chains, and the sequences of part of the humanized antibodies are as shown in Table 11 bel ow.

TABLE 11

Part of preferred sequences of the humanized antibody of the present disclosure

| | Light chain | | Heavy chain | |
|---|---|---|---|---|
| Humanized antibody | Variable region | Constant region | Variable region | Constant region |
| Ab10 | L14 | κ or λ light chain | H51 | hIgG4 or |
| Ab7 | L11 | | H51 | hIgG1 or |
| Ab8 | L14 | | H52 | hIgG2 or |
| Ab9 | L11 | | H52 | hIgG3 |
| Ab6 | L12 | | H51 | |
| Ab11 | L12 | | H53 | |
| Ab12 | L12 | | H54 | |
| Ab13 | L13 | | H53 | |
| Ab14 | L13 | | H54 | |
| Ab15 | L13 | | H51 | |
| Ab16 | L12 | | H52 | |
| Ab17 | L13 | | H52 | |
| Ab18 | L14 | | H53 | |
| Ab19 | L14 | | H54 | |

TABLE 11-continued

Part of preferred sequences of the humanized antibody of the present disclosure

| Humanized antibody | Light chain | | Heavy chain | |
|---|---|---|---|---|
| | Variable region | Constant region | Variable region | Constant region |
| Ab20 | L11 | | H53 | |
| Ab5 | L11 | | H54 | |
| Ab1 | L15 | | H51 | |
| Ab2 | L15 | | H52 | |
| Ab3 | L15 | | H53 | |
| Ab4 | L15 | | H54 | |

Amino acid sequences of the humanized Ab110 antibody:
Light chain:

(SEQ ID NO: 38)
DIVMTQSPDSLAVSLGERATISCKSSQSLLNSGNQKNYLTWYQQKPGQPP

KLLIYWASTRESGVPDRFSGSGSGTDFTLTISSLQAEDVAVYYCQNDYFY

PFTFGQGTKLEIKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC

Heavy chain:

(SEQ ID NO: 39)
QVQLVQSGAEVKKPGSSVKVSCKASGYAFSNYLIEWVKQAPGQGLEWIGL

INPGSGGTNYNEKFKGKATITADKSTSTAYMELSSLRSEDTAVYYCARVY

YGNSFAYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK

Figure 2:
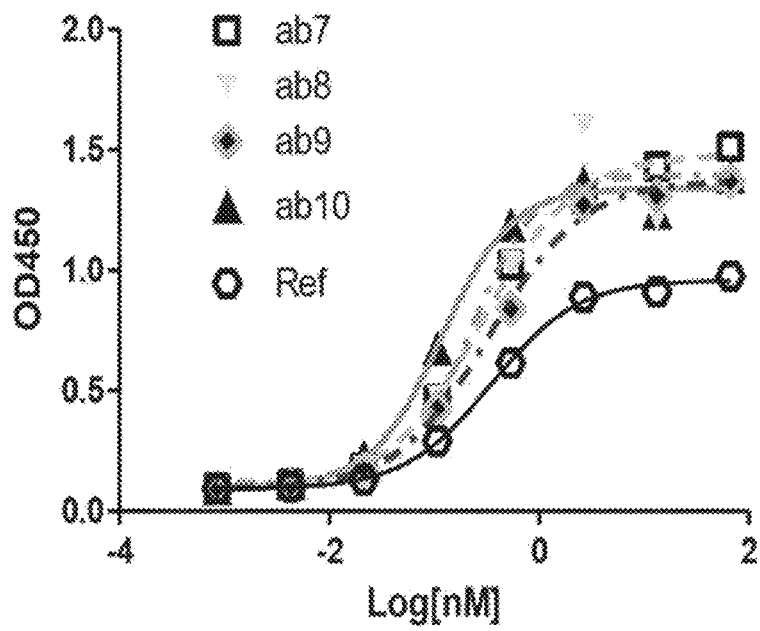
FIG. 2 is the binding activity of the humanized antibody (FIG. 2a) and the humanized optimized antibody (FIG. 2b) of the anti-human CLDN18.2 antibody mab5b of the present disclosure to human CLDN18.2 (ELISA)
Figure 2:
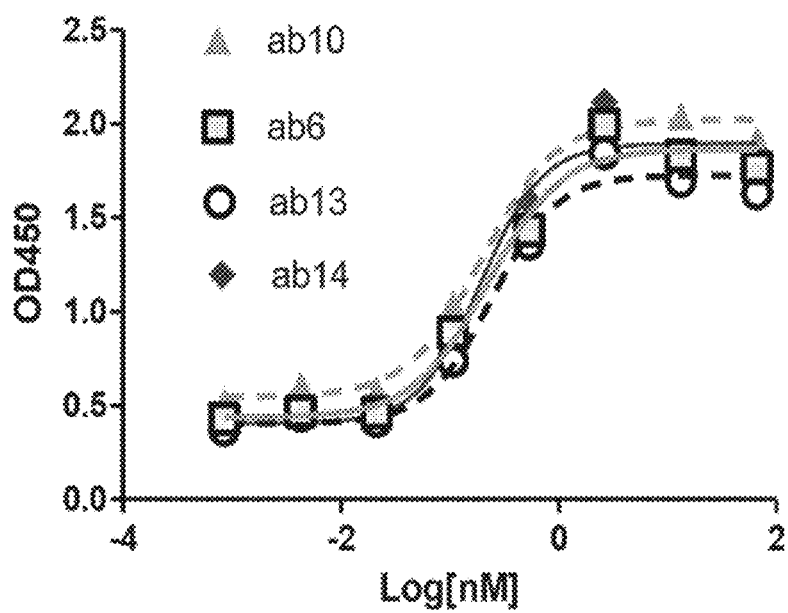

Light chain of humanized Ab7 antibody amino acid sequence: SEQ ID NO: 40; Heavy chain: SEQ ID NO: 39;
Light chain of humanized Ab8 antibody amino acid sequence: SEQ ID NO: 38; Heavy chain: SEQ ID NO: 41;
Light chain of humanized Ab9 antibody amino acid sequence: SEQ ID NO: 40; Heavy chain: SEQ ID NO: 41;
Light chain of humanized Ab6 antibody amino acid sequence:
DIVMTQSPDSLAVSLGERATISCK-SSQSLLNSGNNKNYLAWYQQKPGQPPKL LIYWAST-RESGVPDRFSGSGSGTDFTLTISSLQAEDVAVYYCQN-DYFYPFTFGQGTKL EIKRFVAAPSVFIFPPSDEQLKSGTASVVCLLNNFY-PREAKVQWKVDNALQSGNSQES VTEQDSKDSTYS-LSSTLTLSKADYEKHKVYACE-VTHQGLSSPVTKSFNRGEC (SEQ ID NO: 42)
Heavy chain: SEQ ID NO: 39;
Light chain of humanized Ab11 antibody amino acid sequence: SEQ ID NO: 42; Heavy chain: SEQ ID NO: 43;
Light chain of humanized Ab12 antibody amino acid sequence: SEQ ID NO: 42; Heavy chain: SEQ ID NO: 44;
Light chain of humanized Ab13 antibody amino acid sequence: SEQ ID NO: 45; Heavy chain: SEQ ID NO: 43;
Light chain of humanized Ab14 antibody amino acid sequence: SEQ ID NO: 45; Heavy chain: SEQ ID NO: 44;
Light chain of humanized Ab15 antibody amino acid sequence: SEQ ID NO: 45; Heavy chain: SEQ ID NO: 39;

The recombinant antibody was cloned, expressed and purified by the method described in Example 3 of the present disclosure, and the ELISA method described in Example 2 was used to detect and screen the binding activities of the above-mentioned humanized antibodies to hCLDN18.2+ cells and hCLDN18.1+ cells, and the results are shown in the Table 12 below and FIG. 2a.

TABLE 12

Binding activities of the humanized anti-hCLDN18.2 antibodies of the present disclosure to hCLDN18.2 + cells and hCLDN18.1 + cells

| | Binding activity to hCLDN18.2 + cells | | | Binding activity to hCLDN18.1 + cells | |
|---|---|---|---|---|---|
| Sample | $EC_{50}$ (nM) | $E_{max}$ | $E_{max}$ higher than that of Ref (%) | $EC_{50}$ (nM) | $E_{max}$ |
| Ab10 | 0.117 | 1.39 | 41.8 | ND* | Close to background |
| Ab7 | 0.282 | 1.51 | 54.1 | ND | Close to background |
| Ab8 | 0.227 | 1.38 | 40.8 | ND | Close to background |
| Ab9 | 0.339 | 1.37 | 39.8 | ND | Close to background |
| Ref | 0.345 | 0.98 | NA | ND | Close to background |

NA—Not applicable; ND—Not detected

The results in Table 12 indicate that the antibody mab5b discovered in the present disclosure retains the advantage of higher binding activity of a murine-derived antibody than the that of control antibody Ref after humanization, and the EC 50 of the humanized antibody Ab10 is 2 times better than that of Ref (0.117 vs 0.345). Not only that, the highest binding value Emax of these humanized optimized molecules is 39.8%-54.1% higher than that of the control antibody Ref. Compared with the murine-derived antibody mab5b, the molecules are much better than the control antibody.

In order to further optimize the humanized molecule of the present disclosure, it is preferred that the final sequence is as consistent as possible with the human antibody germline light and heavy chains to reduce possible immunogenicity caused by a small number of sequences in the murine-derived antibody. The humanized optimized light chain CDR1 sequence Var3 (see Table 9) was preferred for designing a series of humanized antibodies, which are screened for specific binding activity. The results are as shown in Table 13 below and FIG. 2b.

TABLE 13

Binding activity of the optimized antibodies of the humanized anti-hCLDN18.2 antibodies of the present disclosure to hCLDN18.2 + cells and hCLDN18.1 + cells

| | Binding activity to hCLDN18.2 + cells | | Binding activity to hCLDN18.1 + cells | |
|---|---|---|---|---|
| Sample | EC50 (nM) | Emax | EC50 (nM) | Emax |
| Ab6 | 0.222 | 1.77 | ND* | Close to background |
| Ab10 | 0.200 | 1.91 | ND | Close to background |
| Ab11 | 0.229 | 1.70 | ND | Close to background |

TABLE 13-continued

Binding activity of the optimized antibodies of the humanized anti-hCLDN18.2 antibodies of the present disclosure to hCLDN18.2 + cells and hCLDN18.1 + cells

| Sample | Binding activity to hCLDN18.2 + cells | | Binding activity to hCLDN18.1 + cells | |
|---|---|---|---|---|
|  | EC50 (nM) | Emax | EC50 (nM) | Emax |
| Ab12 | 0.190 | 1.77 | ND | Close to background |
| Ab13 | 0.240 | 1.63 | ND | Close to background |
| Ab14 | 0.191 | 1.78 | ND | Close to background |
| Ab15 | 0.219 | 1.77 | ND | Close to background |

ND—Not detected

The above-mentioned results indicate that in the humanized antibodies obtained by further optimization of the present disclosure (Table 13 and FIG. 2b), the number of back mutations of these humanized antibodies are different, including Ab1-Ab20 (see Table 11). Specifically, 6 back mutations occurred, such as in Ab10 (in the light chain, and 5 in the heavy chain); 6 back mutations occur and the light chain CDR1 is subjected to humanized optimization, such as in Ab6 (1 in the light chain, and 5 in the heavy chain); 2 back mutations occur, such as in Ab14 (0 in light chain, and 2 in heavy chain); only 1 back mutation occurs, such as in Ab 1 (1 in light chain, and 0 in heavy chain); and no back mutation occurs at all, such as in Ab]3. The activities including EC50 and Emax of these optimized humanized molecules, retain the same level as Ab10 (the optimized mab5b humanized molecules in Table 12) and do not bind to hCLDN18.1+ cells.

The Ab13 antibody molecules that are unexpectedly discovered do not have any back mutations, namely, the antibody molecules are fully humanized antibody molecules, and the CDR1 sequence after humanized optimization has the same binding activity (EC50 and Emax) as Ab6 and Ab10.

The above-mentioned results indicate that the antibody molecules obtained by humanizing, optimizing and screening the murine-derived antibody mab5b sequence of the present disclosure comprises sequence Var3 in which only the FR region is humanized, while the light chain CDR1 remains wild type (without mutation), such as Ab10; or in which not only the FR region, but also the light chain CDR1 is subjected to humanized optimization, and the obtained Ab6, Ab11-15, etc., all retain the binding activity thereof and are better than that of the control molecules, wherein the EC50 is 1 time better than that of the control molecules, and Emax is 30%-50% higher than that of the control molecules; and do not bind to hCLDN18.1+ cells.

Example 7: Optimization of Deamidation Sensitive Site Sequences of the Antibody Sequence of the Present Disclosure Through the computer structure simulation analysis of the mab5b sequence of the present disclosure and the humanized and optimized sequence (Tables 9a, 9b, 11 above), especially through the analysis of the potential post-translational modification (PTM) sites of the CDR regions, including the analysis of antibody aggregation, deamidation sensitive (asparagine deamidation) sites (NG, NS, NH, etc.), aspartic acid isomerization (DG, DP) sensitive sites, N-glycosylation (N-{P}SIT) sensitive sites, oxidation sensitive sites, etc., it is found that NS is at positions L30A and L30B of the light chain CDR1 (CDR1, L Chain) of the antibody of the present disclosure, and NS is at positions H99 and H100 of the heavy chain CDR3 (CDR3, H Chain), wherein, asparagine (N) at positions L30A and H99 may be sensitive to deamidation. In order to reduce the druggability-related risks of antibody molecules when the antibodies of the present disclosure are used for pharmaceutical formulations, we have performed sequence optimization on these two possible sensitive sites. Specifically, the positions L30A and L30B (NS) of the light chain CDR1; and the positions H99 and H100 (NS) of the heavy chain CDR3 of the antibody of the present disclosure are mutated, and the referred scheme is as follows:

TABLE 14

Optimized design of deamidation sensitive site sequences of the antibody sequence of the present disclosure

| Mutation design | CDR sequence | Light chain CDR1 | Heavy chain CDR3 |
|---|---|---|---|
| Wild type (namely, no mutation) | KSSQSLLNSGNNKNYLA (SEQ ID NO: 12) | NA* | NA |
| Mutation design 1 | KSSQSLLTSGNNKNYLA (SEQ ID NO: 47) | NS→TS | NA |
| Mutation design 2 | KSSQSLLNTGNNKNYLA (SEQ ID NO: 48) | NS→NT | NA |
| Wild type (no mutation introduced) | VYYGNSFAY (SEQ ID NO: 17) or ARVYYGNSFA (SEQ ID NO: 28) | NA | NA |
| Mutation design 1-1, 1-2 | 1-1: VYYGTSFAY (SEQ ID NO: 49) or 1-2: ARVYYGTSFA (SEQ ID NO: 50) | NA | NS→TS |
| Mutation design 2-1, 2-2 | 2-1: VYYGNTFAY (SEQ ID NO: 51) or 2-2: ARVYYGNTFA (SEQ ID NO: 52) | NA | NS→NT |

*NA, not applicable (no changes made)

The above-mentioned optimized sequences of the deamidation sensitive sites after the optimized design are used in a way in which different light and heavy chains are combined for body expression, and then further screened for binding activity. The part of the antibody combinations is shown in the table below.

TABLE 15

Antibody with optimized deamidation sensitive sites of the antibody of the present disclosure

| Antibody number | Variable region sequence number | | Deamidation optimization design | |
|---|---|---|---|---|
| | L Chain | H Chain | Light chain CDR1 | Heavy chain CDR3 |
| Ab21 | L20 | H60 | NS->TS in L13 | NS->TS in H54 |
| Ab22 | L20 | H61 | NS->TS in L13 | NS->NT in H54 |
| Ab23 | L21 | H60 | NS->NT in L13 | NS->TS in H54 |
| Ab56 | L21 | H61 | NS->NT in L13 | NS->NT in H54 |
| Ab25 | L21 | HS1 | NS->NT in L13 | —* |
| Ab26 | L21 | H53 | NS->NT in L13 | — |
| Ab27 | L20 | H54 | NS->TS in L13 | — |
| Ab28 | L21 | H54 | NS->NT in L13 | — |
| Ab29 | L14 | H60 | — | NS->TS in H54 |
| Ab30 | L14 | H61 | — | NS->NT in H54 |
| Ab31 | L13 | H60 | — | NS->TS in H54 |
| Ab32 | L13 | H61 | — | NS->NT in H54 |
| Ab33 | L12 | H60 | — | NS->TS in H54 |
| Ab34 | L12 | H61 | | NS->NT in H54 |
| Ab35 | L22 | H62 | NS->NT in L14 | NS->NT in H51 |
| Ab36 | L23 | H62 | NS->NT in L12 | NS->NT in H51 |

*— represents no mutation

The above-mentioned preferred antibodies were expressed and purified according to the method of Example 3 and then the binding activity thereof to human CLDN118.24 cells was detected using the method of Example 2, and the results are shown in Tables 16a, 16b and Table 16c.

TABLE 16a

Activities of antibodies with optimized deamidation sensitive sites of humanized anti-hCLDN18.2 antibody of the present disclosure

| | Binding activity to hCLDN18.2 + cells | |
|---|---|---|
| Sample | EC50 (nM) | Emax |
| Ab21 | >16 | 0.145 |
| Ab22 | 1.37 | 0.827 |
| Ab23 | >40 | 0.147 |
| Ab56 | 0.295 | 1.27 |
| Ab14* | 0.35 | 1.54 |

*Ab14 was used as the control sample for this assay (no NT mutation)

TABLE 16b

Activities of antibodies with optimized deamidation sensitive sites of humanized anti-hCLDN18.2 antibody of the present disclosure

| | Binding activity to hCLDN18.2 + cells | |
|---|---|---|
| Sample | EC50 (nM) | Emax |
| Ab24 | 0.143 | 1.60 |
| Ab25 | 0.127 | 1.51 |
| Ab28 | 0.154 | 1.56 |
| Ab30 | 11.4 | 0.67 |
| Ab32 | 0.197 | 1.41 |
| Ab34 | 0.151 | 1.42 |
| Ab14* | 0.145 | 1.64 |

*Ab14 was used as the control sample for this assay (no NT mutation)

TABLE 16c

Activities of antibodies with optimized deamidation
sensitive sites of humanized anti-hCLDN18.2
antibody of the present disclosure

| Sample | Binding activity to hCLDN18.2 + cells | |
|---|---|---|
|  | EC50 (nM) | Emax |
| Ab10 | 0.208 | 1.71 |
| Ab35 | 62.11 | 1.18 |
| Ab6 | 0.220 | 1.87 |
| Ab36 | 0.211 | 1.37 |

The results in Table 16a indicate that Ab21 (NS->TS in light chain CDR1 and NS->TS in heavy chain CDR3) has "almost no" binding activity (>16 nM). Ab23 (NS->NT in light chain CDR1 and NS->TS in heavy chain CDR3) also has "almost no" binding activity (>40 nM). The binding activity of Ab22 (NS->TS in light chain CDR1, NS->NT in heavy chain CDR3) is decreased, but not completely disappeared (EC50=1.37 nM vs Ab14 EC50=0.35). That is to say, in the case of N->T at position L3OA of the light chain CDR1, as N at position 1-199 of the heavy chain CDR3 is not mutated, the binding activity of the antibody is restored from "almost no" to 1.37 nM, which is nearly 3 times less than that of the normal Ab14. The binding activity of Ab56 (NS->NT in light chain CDR1, NS->NT in heavy chain CDR3) is the same as that of the normal molecule Ab14, with EC50 thereof=0.295 nM.

According to the results in Table 16a, it shows that the N at position L30A of the light chain CDR1 and the N at position H99 of the heavy chain CDR3 of the antibody of the present disclosure are very important for the binding of the antibody of the present disclosure. Mutations at these sites (such as mutated to T) directly result in loss of activity or no activity at all. However, the mutations of both S at position L30B of the light chain and S at position H100 of the heavy chain CDR3 to T have no effect on the binding activity.

The data in Table 16b further prove that the mutation of S at position L30B of the light chain to T alone, or the mutation of S at position 11100 of the heavy chain CDR3 to T alone, has no effect on the binding activity.

Very surprisingly, the data in Table 16b indicates that Ab3O (heavy chain CDR3, NS->NT) completely loses the binding activity (EC50>11 nM, namely, the binding curve is actually same as the negative control, and has no specific binding effect to the antigen), but Ab34 comprising the same heavy chain (CDR3, NS->NT) does not lose the activity. This illustrates that the activity loss of Ab30 is not caused by the changes in CDR3, NS->NT. In view of the only difference between the two molecules lies in the light chain CDR1, namely, Ab30 light chain is L14, and CDR1 thereof is KSSQSLLNSGNQKNYL1 (SEQ ID NO: 11); Ab34 light chain is L12, and the CDR1 thereof is KSSQSLLNSGNNK-NYL_A (SEQ ID NO: 12), and the underlined parts are the differences between the two CDR1 sequences. This unexpected finding indicates that when the S at position 11100 of the heavy chain CDR3 is mutated to T (to avoid potential deamidation), the CDR1 sequence of the light chain must be KSSQSLLNSGNNKNYLA (SEQ ID NO: 12, namely, Var3 with optimized CDR1 sequence, see Table 9a). If the light chain CDR1 is KSSQSLLNSGNQKNYLT (SEQ ID NO: 11, the underlined parts are the differences between the two CDR1 sequences), the entire antibody molecule completely loses the binding activity (Ab30). This finding indicates that, in the CDR1 of the antibody of the present disclosure, if Q is at position L30E and T is at position L34 (underlined), the S at position 11100 of the heavy chain cannot be mutated, for example, to avoid the mutation of S at position H100 of potential deamidation to T; otherwise the entire antibody will lose the binding activity.

In order to further confirm the effect of the difference between light chain CDR1 sequence KSSQSLLNSGNQK-NYLT (SEQ ID NO: 11, Q at position L30E and T at position L34) and humanized optimized CDR1 sequence KSSQSLLNSGNNKNYLA (SEQ ID NO: 12, N at position L30E and A at position L34) of the antibody of the present disclosure on the NS mutation in the light chain CDR1 and heavy chain CDR3 of the antibody of the present disclosure (to avoid potential deamidation), we compared Ab10 (CDR1: KSSQSLLNSGNQKNYLT, SEQ ID NO: 11) with Ab6 (CDR1: KSSQSLLNSGNNKNYLA, SEQ ID NO: 12), and the only difference between these two molecules lies in the light chain CDR1 thereof (the underlined amino acids are the differences between the two). Moreover, NT->NS mutation was simultaneously performed on the light chain CDR1 and heavy chain CDR3 of these two molecules to obtain two antibodies, Ab35 and Ab36. The results in Table 16c indicate that Ab35 completely loses the binding activity (EC50>62 nM).

This data confirms that N is at position L30E and A is at position L34 (underlined) in the light chain CDR1 sequence KSSQSLLNSGNNKNYLA (SEQ ID NO: 12) discovered in the present disclosure, namely, the humanized optimized sequence of CDR1 does not affectthe S at position L30B of the light chain CDR1 (italicized), and/or the S at position 11100 of the heavy chain is mutated to avoid potential deamidation (such as mutation of S at position L30B to T or/and mutation of S at position H100 to T).

If Q is at position L30E and T is at position L34 (underlined) in the CDR1 sequence KSSQSLLNSGN_QK-NYLT (SEQ ID NO: 11), S at position L30B of CDR1 (italicized) or S at position 1-100 of heavy chain cannot be mutated (such as mutation of S at position L3013 to T or mutation of S at position H100 to T), and any such mutation will make the binding activity of the antibody disappear.

The above-mentioned results indicate that NS at positions L30A and L30B of the light chain CDR1; NS at positions H99 and H100 of heavy chain CDR3 of the antibody of the present disclosure can reduce the risk of potential deamidation via an optimized mutation of NS->NT, which, however, can only be achieved when N is at position L30E and Ais at position L34 in CDR1 (namely, the sequence is humanized optimized sequence KSSQSLLNSGNNKNYLA, SEQ ID NO: 12). If the sequence of this region is KSSQSLLNSGN_QKNYLT (SEQ ID NO: 11), the antibody will completely lose the activity (the underlined parts are the differences between the sequences of two).

Example 8: Activity Analysis of Fc Sequence (Variant) of the Antibody of the Present Disclosure Different antibody variant forms can be obtained from the combinations of the variable regions of the antibody of the present disclosure with the different light and heavy chain constant regions of human antibodies, including but not limited to the combinations of different light chains (x, X light chains, etc.) and heavy chain constant regions (hIgG2, hIgG4, hIgG1) of the human antibodies listed in Example 3, especially human IgG1Fc sequence variants, such as in different forms having DEL or EEM at positions 356-358. Table 17 lists a part of variant forms of the antibody of the present disclosure and Fc sequences, including one in which DEL or EEM are at positions 356-358 of the Fc region sequence.

TABLE 17

Antibodies with different light and heavy chains and heavy chain constant regions of the antibody of the present disclosure

| No. | Light chain | Heavy chain | hIgG1, positions 356-358 |
|---|---|---|---|
| Ab10 | L14 | H51 | DEL |
| Ab42 | L14 | H51 | EEM |
| Ab6 | L12 | H51 | DEL |
| Ab43 | L12 | H51 | EEM |
| Ab13 | L13 | H53 | DEL |
| Ab48 | L13 | H53 | EEM |
| Ab51 | L21 | H64 | DEL |
| Ab52 | L21 | H64 | EEM |
| Ab14 | L13 | H54 | DEL |
| Ab53 | L13 | H54 | EEM |
| Ab24 | L21 | H61 | DEL |
| Ab56 | L21 | H61 | EEM |

The amino acid sequences of the Ab42 antibody are as follows:

Light chain: SEQ ID NO: 38; Heavy chain: SEQ ID NO: 46;

The above-mentioned preferred antibodies were expressed and purified according to the method of Example 3 and then the binding activity thereof to human CLDN18.2+ cells was detected using the method of Example 2, and the results are shown in Table 18. The results indicate that the above-mentioned changes in the constant regions of the light and heavy chains, including DEL or EEM respectively being at positions 356-358 of higG1, do not affect the activity of the antibody of the present disclosure.

TABLE 18

Binding activity of the humanized anti-hCLDN18.2 antibody of the present disclosure with DEL or EEM being at positions 356-358 of IgG1 Fc

| Sample | Binding activity to hCLDN18.2 + cells | |
|---|---|---|
| | EC50 (nM) | Emax |
| Ab24 | 0.373 | 1.67 |
| Ab56 | 0.428 | 1.44 |

Example 9: Sequence Optimization of Fc Region (Human IgGI) of the Antibody of the Present Disclosure for ADCC and CDC Activity One of the mechanisms of tumor treatment via specific binding of the antibody of the present disclosure to human CLDN18.2 is that the antibody Fc can mediate the killing of tumor cells by effector cells to achieve the purpose of treating tumor. The human Fc region (hIgG1 Fc) of the antibody of the present disclosure mediating the effects of effector cells on ADCC and CDC, can specifically enhance the effect of targeting tumor cells, and causes target-off side effects for non-specific targets. There have been many studies on the effects of ADCC and CDC mediated by the human antibody Fc region (hIgG1 Fc). The present disclosure confirms the effect of the Fe region of the discovered antibody molecules on human blood cells (ADCC and CDC). Specifically, different mutations were performed in the human antibody Fe region (hIgG1 Fc) of the antibody of the present disclosure to evaluate the ADCC and CDC activities of these mutants. The mutation design is shown in Table 19, and the activity data is shown in Tables 20a and 20b.

TABLE 19

Design of active sites of Fc (IgG1) of the antibody of the present disclosure for ADCC and CDC

| No. | Light chain | Heavy chain | hIgG1, Fc region |
|---|---|---|---|
| Ab10 | L14 | H51 | WT |
| Ab57 | L14 | H51 | F243L |
| Ab572 | L14 | H51 | L234A |
| Ab573 | L14 | H51 | L235A |
| Ab573 | L14 | H51 | L234A/L235A |
| Ab58 | L14 | H51 | S239D/A330L/I332E |
| Ab6 | L12 | H51 | WT |
| Ab59 | L12 | H51 | F243L |
| Ab60 | L12 | H51 | S239D/A330L/I332E |
| Ab24 | L21 | H61 | WT |
| Ab65 | L21 | H61 | F243L |
| Ab66 | L21 | H61 | S239D/A330L/I332E |

The above-mentioned preferred antibodies were expressed and purified according to the method of Example 3 to obtain antibodies, ADCC (antibody-dependent cytotoxicity test) and CDC (complement-dependent cytotoxicity test) were performed to detect the activities of the antibodies with optimized Fc sequences. Specifically, ADCC involves the following steps.

The hCLDN18.2+ cells constructed in Example 1 were cultured according to standard conditions as the target cells for ADCC in this experiment. The medium was DMEM/F12 plus 10% FBS (Shanghai BasalMedia Technologies Co., LTD, Cat #L310KJ).

The day before the experiment, the cultured hCLDN18.2±cells were taken, and counted 5000 cells/well to plate a 96-well plate. On the day of the experiment, PBMC cells (which in the present disclosure were isolated from human peripheral blood donated by volunteers from the present company) were prepared, and suspended in a serum-free RPM11640 medium (BasalMedia, Cat #L210KJ) at a concentration of 150000 cells/50 μl. The drug to be tested was prepared with the serum-free RPMI1640, and the initial concentration of 40 μg/ml was diluted by 3-fold.

The cultured target cells (hCLDN18.2+ cells) were taken out, the supernatant was carefully aspirated and removed, and added with the prepared PBMC at 50 μl/well; At the same time, prepared samples to be tested of different concentrations were added at 50 µl/well, and then the target cells were incubated in a 37° C. and 5% $CO_2$ incubator for 4 hours to detect LDH.

The LDH kit is Cytotoxicity LDH Assay Kit-WST, purchased from Dojindo Laboratories (Shanghai) Co., Ltd, Cat. No. CK12. The operation was carried out according to the instructions. The well plate was taken out, 100 µl of WorkingSolution was added into each well, wrapped with aluminum foil to avoid light, reaction was carried out at room temperature for 10-40 min, reading was performed on a MultiskanGO (ThermoFisher) microplate reader at 490 nM, and the detection was performed every 10 min. The Data at a suitable reaction time was analyzed and processed with Graphpad Prism 5.

CDC involves the following steps.

The hCLDN18.2+ cells constructed in Example 1 were used as target cells for this CDC experiment. hCLDN18.2+ cells were cultured in standard conditions, the medium was DMEM/F12 plus 10% FBS (same as ADCC). The day before the experiment, the target cells were collected, counted, cells prepared at $1\times10^5$ ml, and added at 100 µl/well to a 96-well cell culture plate. The cells were incubated overnight at 37° C. under 5% $CO_2$ for later use.

On the day of the experiment, the medium was removed from the cells in the 96-well plate and washed 2 times with PBS for later use. The antibody to be tested was diluted with a serum-free medium (RPMI1640), and the initial antibody concentration is 20 µg/ml, which was diluted by 5-fold. The diluted antibody was added at 50 µl/well to the PBS-washed target cell culture plate (0 µg/ml antibody-containing wells, added with a fresh medium at 100 µl/well as a control well), and 6 replicate wells were set for each concentration point. The plates were incubated at 37° C. under 5% $CO_2$ for 15 min.

Preparation of complements: Fresh serum was taken in a sterile centrifuge tube. Half of the serum was taken and incubated in a 56° C. water bath kettle for 30 minutes to inactivate the complement, as a negative control. The inactivated and non-inactivated serums were respectively prepared with the RPMI1640 medium with serum: RPMI1640 medium=40% 60%, namely, 40% is serum, and 60% is RPMI1640.

Diluted serum at 50 µl/well was added to target cell culture plates containing different concentrations of antibodies to be tested, namely, the final concentration of serum was 20%; and the initial concentration of the sample (antibody) was 10 µg/ml. The serum with complements was added to the first 3 replicate wells, and the serum with inactivated complements was added to the last 3 replicate wells. The plates were incubated in a 37° C. and 5% $CO_2$ incubator for 2 hours, and then taken out for testing using LDH kit.

The LDH kit is Cytotoxicity LDH Assay Kit-WST, purchased from Dojindo Laboratories (Shanghai) Co., Ltd, Cat. No. CK12. The operation was carried out according to the instructions. The well plate was taken out, 100 µl of Working Solution was added into each well, wrapped with aluminum foil to avoid light, reaction was carried out at room temperature and the detection was performed every 10 min. The Data at a suitable reaction time and reading on a MultiskanGO (ThermoFisher) microplate reader at 490 nM were analyzed and processed with Graphpadprism5.

TABLE 20a

Detection of ADCC activity of Fc (IgG1) mutants of the antibody of the present disclosure

| Sample | $EC_{50}$ (µg/ml) |
| --- | --- |
| Ab6 | 1.40 |
| Ab59 | Not detectable (no binding) |
| Ab60 | 0.431 |
| Neg IgG* | Not detectable (no binding) |

*Neg IgG: is a non-specific antibody that does not bind to the target

TABLE 20b

Detection of CDC activity of Fc (IgG1) mutants of the antibody of the present disclosure

| Sample | $EC_{50}$ (µg/ml) |
| --- | --- |
| Ab6 | 0.290 |
| Ab59 | Not detectable (no binding) |
| Ab60 | 0.973 |
| Ab24 | 0.255 |
| Ab65 | Not detectable (no binding) |
| Ab66 | 0.927 |
| Neg IgG* | Not detectable (no binding) |

*Neg IgG: is a non-specific antibody that does not bind to the target

The results indicate that if the antibody of the present disclosure is the hIgG1 subtype, wherein single site F at position 243 in the Fc region is mutated, such as F243L, L234A, L235A and L234A/L235A, the ADCC and/or CDC activity of the antibody of the present disclosure will completely lose; if the combined three sites at positions 239, 330, and 332 in the Fc region are mutated, such as S239D/A330L/I332E, the CDC activity of the antibody of the present disclosure will be weakened.

Figure 3:
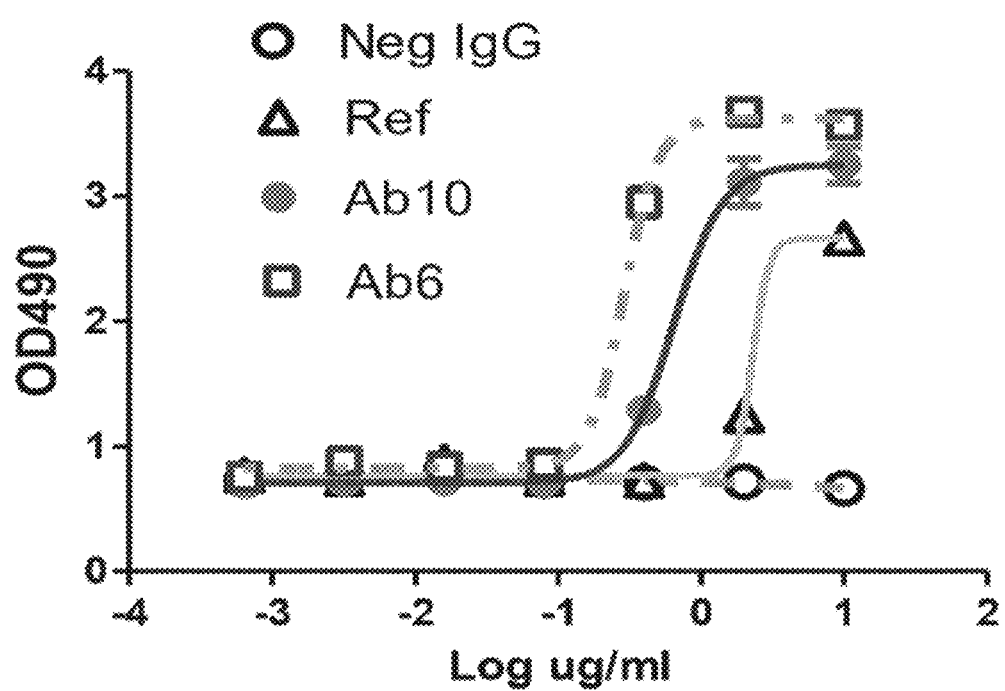
FIG. 3 is the CDC activity evaluation of the humanized anti-human CLDN18.2 antibody and the humanized optimized antibody of the present disclosure.

Example 10: Evaluation of ADCC and CDC Activities of Different Humanized Molecules of the Antibody of the Present Disclosure In order to evaluate the ADCC and CDC activities of the humanized antibody molecule of the present disclosure, the ADCC and CDC activities of the humanized molecule of the present disclosure, along with the control molecule (Ref), were detected using the same method as the above-mentioned examples. The results are shown in Tables 21a and 21b below, and FIG. 3.

TABLE 21a

Evaluation of ADCC activities of different humanized molecules of the antibody of the present disclosure

| Sample | $EC_{50}$ (µg/ml) |
| --- | --- |
| Ab10 | 1.55 |
| Ab6 | 1.40 |
| Ref | 1.39 |
| Neg IgG* | Not detectable (no binding) |

*Neg IgG: is a non-specific antibody that does not bind to the target, the same below TABLE 21b Evaluation of CDC activities of different humanized molecules of the antibody of the present disclosure

| Sample | EC$_{50}$ (μg/ml) |
| --- | --- |
| Ab10 | 0.648 |
| Ab35 | Not detectable (no binding) |
| Ab6 | 0.293 |
| Ab36 | 1.75 |
| Ab14 | 0.265 |
| Ab24 | 1.30 |
| Ab13 | 0.374 |
| Ab51 | 2.12 |
| Ref | 2.31 |
| Neg IgG* | Not detectable (no binding) |

The above-mentioned results indicate that the ADCC activity of the humanized antibody of the present disclosure is comparable to that of the control antibody (Ref) (Table 21a). Unexpectedly, the CDC activities of the humanized molecules of the present disclosure, including those comprising different back mutations, Ab6, Ab13, Ab14, etc. are similar (EC50 are 0.293 μg/ml, 0.374 μg/ml, and 0.265 μg/ml, respectively) and more than 1 time better than that of Ab10 (0.648 μg/ml). Especially unexpected is that the CDC activities of Ab6, Ab13, Ab14, etc. are nearly 10 times better than that of the control antibody (EC50=2.31 μg/ml) (see Table 21b and FIG. 3). The CDC activities of Ab36 and Ab24 are also better than that of the control antibody Ref.

Because of the loss of binding activity, the CDC activity of Ab35 (CDR1, CDR3 NS mutant, see Example 7, Table 16c) is not detected.

Example 11: Evaluation of the Activity of the Antibody of the Present Disclosure in Inducing Apoptosis of Tumor Cells (hCLDN18.2+ Cells)

In order to detect the effect of the antibody of the present disclosure, especially the preferred humanized antibody in inducing the apoptosis of hCLDN18.2+ cells (tumor cells), we used the hCLDN18.2+ cells constructed in Example 1 of the present disclosure to detect the activity of the antibody of the present disclosure in inducing the apoptosis of tumor cells. hCLDN18.2+ cells were cultured normally (the medium was DMEM/F12 containing 10% FBS, supplier: Shanghai BasalMedia Technologies Co., LTD, Cat. No.: L310), and used as the cells for this experiment. At the beginning of the experiment, hCLDN18.2+ cells were plated on a 96-well plate with a plated density of 2×10$^4$/well. The cells were subjected to overnight adherent culture at 37° C. under 5% CO$_2$. Preparation of antibody samples: The serum-free DMEM/F12 medium was used to prepare 0 μg/ml, 1 μg/ml, 3 μg/ml, and 10 μg/ml of antibody samples. The hCLDN18.2+ cells that were subjected to overnight adherent culture were taken out, the medium was discarded, and the cells were washed twice with PBS. The prepared antibody samples at different concentrations were added, at 100 μl/well. After for another 24 hours, LDH was detected.

The LDH kit is Cytotoxicity LDH Assay Kit-WST, purchased from Dojindo Laboratories (Shanghai) Co., Ltd, Cat. No. CK12. The operation was carried out according to the instructions. The well plate was taken out, 100 μl of Working Solution was added into each well, a method such as wrapping with aluminum foil was used to avoid light, and reaction was carried out at room temperature. Reading was performed on a Multiskan GO (ThermoFisher) microplate reader at 490 nM at different time points (10 min, 20 min, 30 min, 40 min, 50 min) to find out the best reaction time, and the data of the reading values was analyzed and processed with Graphpad Prism 5.

Figure 4:
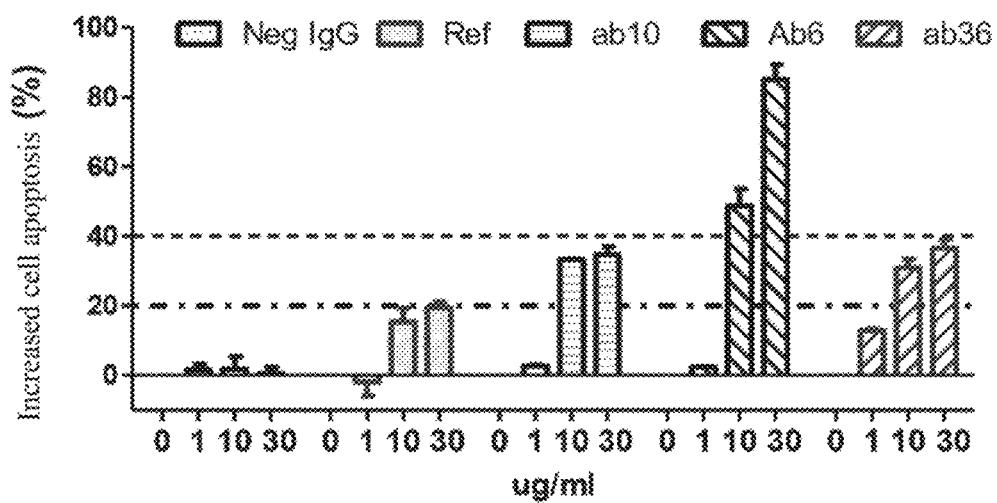
FIG. 4 is the activity of the humanized anti-human CLDN18.2 antibody and the humanized optimized antibody of the present disclosure in inducing tumor cell apoptosis (FIG. 4a, FIG. 4b)
Figure 4:
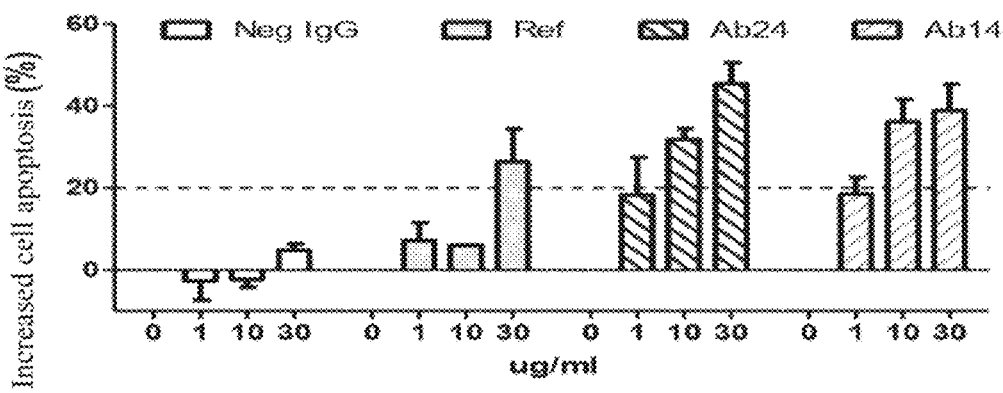

The results are shown in FIG. 4a and FIG. 4b. The results of FIGS. 4a and 4b indicate that the activity of the humanized antibodies such as Ab10, Ab6, Ab14, Ab24 and Ab36 of the present disclosure in inducing the apoptosis of tumor cells is better than that of the control molecule (Ref), and the activity is 3-10 times better/stronger. The activities of these molecules at a concentration of 10 μg/ml is already comparable to that of the control molecules at 30 μg/ml or even stronger than that of the positive molecules at 30 μg/ml.

Specifically, the activity of Ab6 at 10 μg/ml in inducing the apoptosis of tumor cells (46.7%) is more than 2 times better than that of the positive control at the same concentration (15.3%), which is even more than 1 time better than that of the positive control at 30 μg/ml (19.6%); and at a concentration of 30 μg/ml, the activity in inducing the apoptosis of tumor cells (85.1%) was more than 3 times better than that of the control antibody at the same concentration (19.6%).

More surprisingly, the activity of Ab6 at 10 μg/ml in inducing the apoptosis of tumor cells (46.7%) is 41% better than that of Ab10 at the same concentration (33.2%); at 30 gg/ml concentration, the activity in inducing the apoptosis of tumor cells (85.1%) was more than 1 time stronger than that of Ab10 at the same concentration (34.7%).

Example 12: Inhibitory Effect of the Antibody of the Present Disclosure on the Proliferation of Tumor Cells (hCLDN18.2+ Cells)

In order to detect the inhibitory effect of the antibody of the present disclosure on the proliferation of tumor cells, an activity detection was performed on the hCLDN18.2+ cells constructed in Example 1. Specifically, hCLDN8.2+ cells were cultured normally (the medium was DMEM/F12 containing 10% FBS, supplier: Shanghai BasalMedia Technologies Co., LTD, Cat. No.: L310). At the beginning of the experiment, the hCLDN18.2+ cells at the logarithmic phase were taken and spread onto a 96-well plate with a plating density of 3×10$^3$/well. The cells were subjected to overnight adherent culture at 37° C. under 5% CO2. Preparation of antibody samples: DMEM/F12 (BasalMedia) containing 10% FBS was used to prepare 1 μg/ml, 10 μg/ml, and 30 μg/ml of antibody samples. The hCLDN18.2+ cells that were subjected to overnight adherent culture were taken out, the medium was discarded, and the cells were washed once with PBS, and then the prepared antibody samples at different concentrations were added, at 100 μl/well. After culture for another 72 h, CCK-8 kit was used for detection.

The CCK-8 kit is Cell Counting Kit-8, purchased from Dojindo Laboratories (Shanghai) Co., Ltd, Cat. No. CK04. The operation was carried out according to the instructions. The 96-well plate was taken out and added with 10 μl CCK-8 solution to each well (be careful not to allow the formation of air bubbles in the wells, otherwise the reading will be affected), and the culture plate was incubated in an incubator for 1-4 h, the optimal detection time points were found out for performing reading on the Multiskan GO (ThermoFisher) microplate reader at 450 nM, and the data of the reading values was analyzed and processed with Graphpad prism 5. The results are shown in table 22 below:

TABLE 22

Activity of preferred humanized antibody of the present disclosure for inhibiting the proliferation of tumor cells (hCLDN18.2 + cells) (inhibition rate %)

| Sample/concentration | 1 µg/ml | 10 µg/ml | 30 µg/ml |
|---|---|---|---|
| Neg IgG | 0 | 0.34 | 0.1 |
| Ab10 | 2.17 | 2.93 | 3.16 |
| Ab6 | 3.29 | 6.12 | 6.2 |
| Ref | 2.34 | 2.94 | 3.9 |

The results in Table 22 indicate that the activity for inhibiting tumor cells (inhibition rate) by negative antibodies at concentrations of 1 µg/ml, 10 µg/ml, and 30 µg/ml is below 1%, which is the background level. The activity for inhibiting tumor cells (inhibition rate) by 1 g/mil, 10 µg/ml, 30 µg/mli of Ab10 is between 2.17%-3.16%, which is close to 2.34%-3.9% of the inhibition rate of Ref. The activity for inhibiting tumor cells by Ab6 is much stronger than that of Ref. For example, the inhibition rate at 10 µg/ml is 6.12% which is more than 2 times than that of Ref (2.94%).

Example 13: Detection of Binding Activities of Humanized Antibodies of the Present Disclosure to Mice CLDN18

According to the method of the preceding Example 2, the binding activities of the preferred humanized antibodies of the present disclosure to mice CLDN18.1+ cells and mice CLDN18.2+ cells were detected. During the screening, we screened and obtained a clone (antibody L180), which binds to both human CLDN18.1 and mice CLDN18.1. As a control of this assay, the EC50 for the binding activity of L180 to mCLDN18.1+ cells is 0.48 nM, indicating that the mice CLDN18.1+ cells constructed in the present disclosure specifically bind to the anti-CLDN18.1 antibody. However, the preferred humanized antibodies of the present disclosure do not bind to the mCLDN18.1+ cells, and all retain the same binding activity to the mCLDN18.2+ cells as the murine-derived antibody mab5b, as shown in Table 23 below.

TABLE 23

Binding activities of preferred humanized antibodies of the present disclosure to mCLDN18.2 + cells

| Sample | $EC_{50}$ (nM) | $E_{max}$ |
|---|---|---|
| mab5b | 0.375 | 2.17 |
| Ab10 | 0.371 | 2.27 |
| Ab35 | ND# | ND |
| Ab6 | 0.594 | 2.47 |
| Ab36 | 0.518 | 2.18 |
| Ab14 | 0.399 | 2.39 |
| Ab24 | 0.574 | 2.22 |
| Ab13 | 0.422 | 2.37 |
| Ab51 | 0.474 | 1.91 |
| Neg IgG* | No binding | 0.19 (background) |

Not detected.

The above-mentioned results indicate that the preferred humanized antibodies of the present disclosure all retain the binding activity to mCLDN18.2+ cells. EC50 of the preferred humanized antibodies of the present disclosure and mab5b before humanization (EC50=0.375 nM in the same assay) shows the same binding activity. Emax is between 1.91 (Ab51) to 2.47 (Ab6), which is close to that of mab5b (2.17).

Example 14: Evaluation of the In Vivo Pharmacological Activity of the Antibody of the Present Disclosure In order to evaluate the anti-tumor activity of the antibody of the present disclosure, an animal efficacy model established with BALB/c nude mice subcutaneously transplanted with hCLND18.2+ cells (as constructed in Example 1) or gastric cancer cell line NUGC4 (Shanghai Suer Biotechnology Co., Ltd) was used to evaluate the in vivo efficacy of the antibody of the present disclosure.

Specifically, the medium was DMEM/F12 (BasalMedia) plus 10% of fetal bovine serum (Shanghai BioSun Sic & Tech Co., Ltd, Cat. No. BS-0002-500) for hCLDN18.2+ cells. The medium is RPMI1640 (BasalMedia) plus 10% of fetal bovine serum for NUGC4 cells. The culture conditions are 37° C., 5% $CO_2$. BALB/c nude mice, female, 4 weeks old, weight 18-20 g, were purchased from Shanghai Sippr-BK Laboratory Animal Co., Ltd (production license number: SCXK (Beijing) 2012-0001), adaptively fed at room temperature of 20-25° C. and at 40%-60% humidity for 3-4 days, free to eat and drink water. The beddings were changed, and cages were cleaned in due course. The cells at logarithmic growth phase were taken, collected and counted.

For the hCLDN18.2+ cell allograft model, the hCLDN18.2+ cells were taken and washed 2 times with PBS, and then resuspended to formulate cells at $1\times10^8$/ml. The mice were inoculated subcutaneously in the left flank at $1\times10^7$ cells/mouse with a total of 0.1 ml. The mice with a tumor size of approximately 120-180 mm$^3$ were selected, and grouped randomly, with 5-6 mice in each group.

For the gastric cancer NUGC4 cell allograft model, NUGC4 cells were taken and washed 2 times with RPMI1640, and Matrigel was added so that the ratio of Matrigel to RPMI640 was 1:1, and the mixture was resuspended to formulate cells at $1\times10^8$/ml. The mice were inoculated subcutaneously in the left flank at $1\times10^7$ cells/mouse with a total of 0.1 ml. The mice with a tumor size of approximately 150-200 mm$^3$ were selected, and grouped randomly, with 5-6 mice in each group.

The sample to be tested was prepared with PBS and sterilized. Blank is PBS control with no sample, an antibody that has nothing to do with the target, namely, a negative antibody (Neg IgG) control. Intraperitoneal injection was performed at 200 µg/100 µl/mouse, BIW for several weeks. The day of sample injection is day 0. Body weight and tumor volume were measured before each administration and recorded.

Calculation formula for tumor sizes: Tumor volume TV (mm$^3$)=0.5×(tumor long diameter tumor short diameter$^2$). Relative tumor growth rate (T/C %)=100%*(T-T0)/(C-C0). Tumor inhibition rate (TGI)=(1−T/C)*100%. TO and T are the tumor volumes at the beginning and end of the experiment in the sample group, respectively; C0 and C are the tumor volumes at the beginning and end of the experiment in the control group, respectively.

Figure 5:
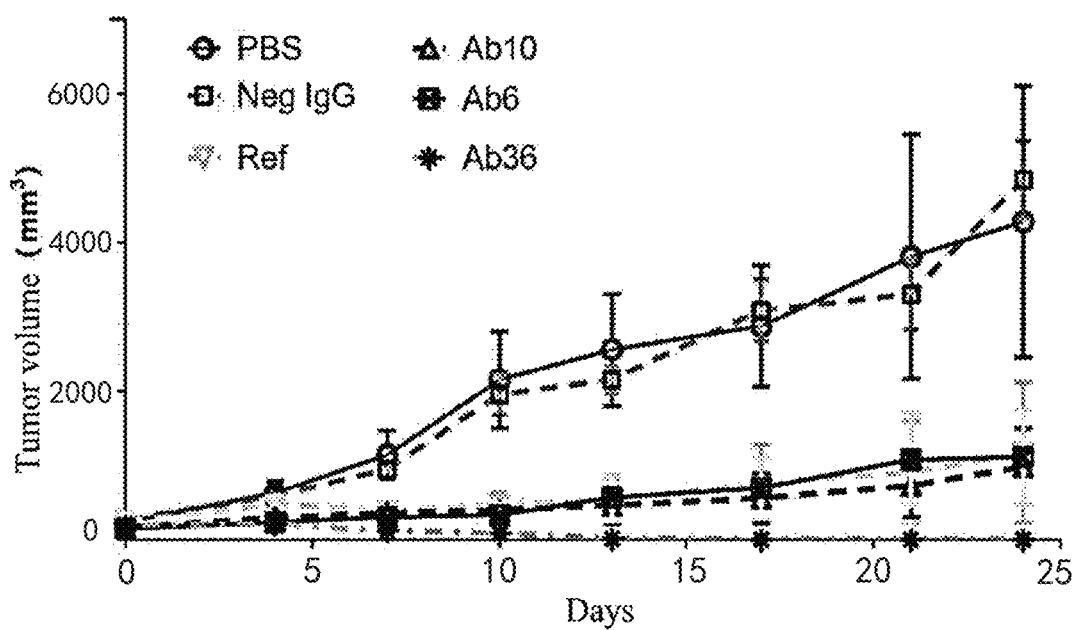
FIG. 5 is the pharmacodynamic evaluation in vivo of the animal model of the humanized anti-human CLDN18.2 antibody and the humanized optimized antibody of the present disclosure (FIG. 5a, FIG. 5b)
Figure 5:
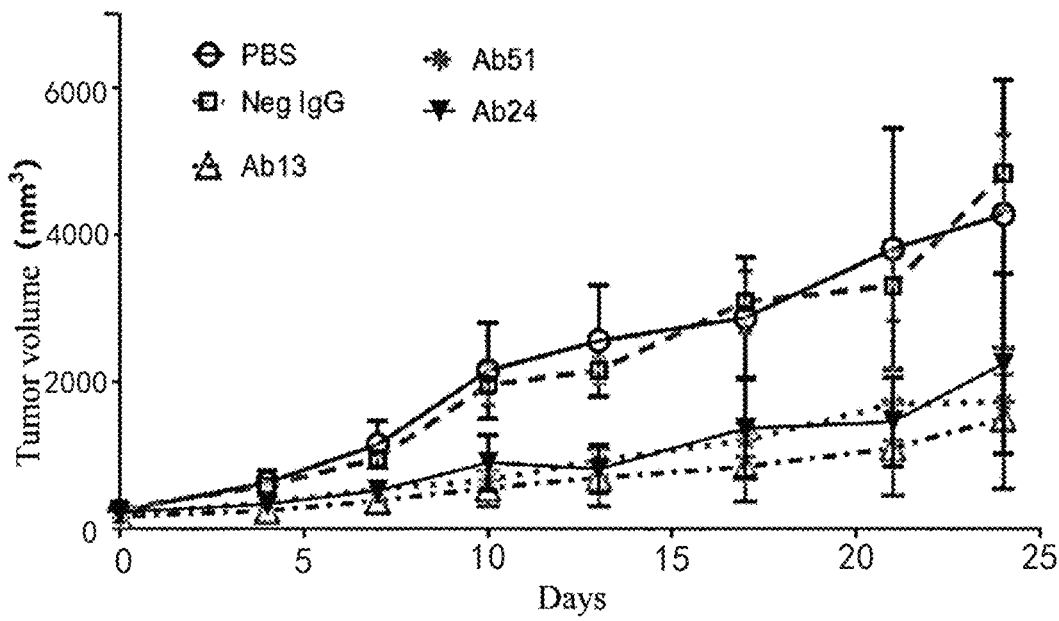

The results of efficacy in vivo of animals are shown in FIGS. 5a and 5b (hCLDN118.2+ cell allograft model) and Table 24 below (NUGC4 tumor cell allograft model).

In a tumor allograft model established with cells which has a high expression level of human CLDN18.2 (hCLDN18.2+ cells), the results in FIG. 5a show that the antibodies Ab10 and Ab6 of the present disclosure, like the positive antibody molecule (Ref), show a very good in vivo pharmacodynamic activity, and inhibit tumor cell growth and/or kill tumor cells (inhibition rate) by more than 90%; unexpectedly, the deamination sensitive sites of the light chain CDR1 and heavy chain CDR3 are optimized, and the preferred antibody Ab36 optimized by humanizing light chain CDR1 completely inhibits tumor growth, and the efficacy thereof in vivo is significantly better than that of Ab6, Ab10 and the control positive antibody (Ref). The results in FIG. 5b show that the fully humanized antibody of the present disclosure (without reversion mutations) Ab13, and the fully humanized antibody Ab51 with the optimized light chain CDR1 and heavy chain CDR3 deamination sensitive sites thereof, as well as the humanized antibody Ab24 with the optimized light chain CDR1 and heavy chain CDR3 deamination sensitive sites and with only 2 reversion mutations in heavy chain shows the same in vivo efficacy as the control antibody.

TABLE 24

Pharmacodynamic evaluation of the antibody of the present disclosure in gastric cancer cell line NUGC4 tumor model

| Sample | Dosage (mg/kg) | Number of animals | Day 0 tumor volume (mm³) Mean | SD | Day 21 tumor volume (mm³) Mean | SD | Day 21 tumor inhibition rate (%) |
|---|---|---|---|---|---|---|---|
| PBS | NA | 5 | 209.7 | 38.9 | 4167.2 | 1397.3 | 0 |
| Negative antibody | 10 | 5 | 191.3 | 46.5 | 4261.1 | 1852.9 | -3 |
| Ref | 3 | 6 | 218.5 | 28.3 | 4111.8 | 976.7 | 2 |
|  | 10 | 5 | 212.0 | 45.9 | 4108.3 | 862.3 | 2 |
| Ab10 | 3 | 6 | 176.7 | 43.6 | 3557.7 | 1286.4 | 15 |
|  | 10 | 6 | 211.4 | 37.6 | 3339.3 | 950.0 | 21 |
| Ab6 | 3 | 6 | 191.2 | 24.2 | 3765.9 | 929.6 | 10 |
|  | 10 | 6 | 188.5 | 60.3 | 3634.3 | 1680.8 | 13 |

[0423] NA: Not applicable, namely blank control.

In the tumor model established by the human gastric cancer cell line NUGC4, the above-mentioned results (T1able 24) indicate that the preferred humanized antibodies Ab10 and Ab6 of the present disclosure both show a certain efficacy, with a tumor inhibition rate of 10%-20%, and are dosage-dependent. In the same model, the control antibody (Ref), like the PBS control and the negative antibody (Neg IgG), has no inhibitory effects on tumor. This result indicates that the antibody of the present disclosure has an in vivo efficacy, which is superior to that of the positive control antibody.

Example 15: Evaluation of Pharmacokinetics (P1K) of the Antibody of the Present Disclosure in Mice As described in the above-mentioned Example 13, the antibody of the present disclosure has a very good binding activity to mice CLDN18.2, which provides the antibody of the present disclosure with a choice of non-primate species for preclinical studies. the present disclosure evaluates the pharmacokinetic (PK) properties of the antibody of the present disclosure in mice.

Specifically, the experimental Balb/c mice, female, 6 weeks old, were purchased from Shanghai Sippr-BK Laboratory Animal Co., Ltd. The mice were purchased, grouped into 6 mice per cage, and accessible to unlimited feed and water. The mice were fed in a laboratory environment for 3 days, and the temperature was 20-25 T.; humidity was 40-60%, with an adjusted cycle of 12/12 h light/darkness. The day before the start of the experiment, the weight of the mice was measured, and 20-25 g mice were taken and grouped for numbering with 3 mice/group. On the day of the experiment, each mouse was injected subcutaneously with the test drug Ab10 and the control antibody (Ref), respectively, and the dosage was 10 mg/kg with subcutaneous injection at 100 µl/mouse/time.

Blood of the mice was taken from the orbit at 0, 1, 6, 24, 26, 30, 50, 55, 71, 79, 98, 143, 167, 191, 215, 240 hours after injection. The blood sample was centrifuged, and the supernatant was taken, and stored at −20° C. for later testing. After the blood samples were collected, the ELISA method in preceding Example 2 was used to detect the blood drug concentration in the serum. before the formal detection, the serum from one mouse was taken for a serial dilution to determine the optimal dilution ratio of the serum. All samples were detected by ELISA according to the optimal dilution ratio, and the data of detected results was analyzed using the T1/2 calculation formula and EXCEL software. The results are as shown in Table 25 below.

TABLE 25

PK evaluation of the antibody of the present disclosure in mice

| Aantibody detection Mouse number and detection value | Ab10 | | | | | Ref | | | | |
|---|---|---|---|---|---|---|---|---|---|---|
|  | Mouse number | | | Average value | SD | Mouse number | | | Average value | SD |
|  | 1 | 2 | 3 |  |  | 4 | 5 | 6 |  |  |
| $t_{max}$ (h) | 24 | 24 | 24 | 24.0 | 0 | 26 | 24 | 24 | 24.7 | 1.2 |
| $C_{max}$ (mg/ml) | 633 | 459 | 131 | 407.7 | 254.9 | 326 | 214 | 238 | 259.3 | 59.0 |
| $t_{1/2}$ (h) | 133.3 | 203.8 | 173.3 | 170.1 | 35.4 | 141.4 | 150.7 | 126 | 139.4 | 12.5 |

The results in Table 25 above indicate that the Cmax of the antibody Ab10 of the present disclosure is 57% ([407.7-259.3]/259.3) higher than that of the control antibody (Ref). More surprisingly, the half-life T1/2 of the antibody Ab10 of the present disclosure is more than 30.7 hours (170.1-139.4) longer than that of the control antibody (Ref). The T1/2 advantage of up to 30 hours in mice is expected to be bigger in humans. These results indicate that the humanized antibody of the present disclosure has a better PK performance than that of the control antibody, especially the significant advantage in half-life T1/2, which is expected to provide such advantages as in efficacy (long-lasting) and cost (low administration frequency) in clinics.

Example 16: Affinity Analysis of the Antibody of the Present Disclosure (KinExA)

CLD18.2 is a cellular transmembrane protein, a tetraspanin, wherein the two extracellular regions ECL1 and ECL12 are only 20-50 amino acids in length. The antibody of the present disclosure specifically binds to the extracellular region of CLDN18.2. The conventional Biacore detection method that expresses the binding of an antigen (20-50 amino acids) to an antibody cannot effectively evaluate the specific affinity of the antibody of the present disclosure to the extracellular region of the target protein. Therefore, the KinExA method was used in the present disclosure to detect the affinity of the antibody to hCLDN18.2+ cells. The method refers to the instructions for KinExA 4000 instrument, namely, the antibodies Ref and Ab10 to be tested are used as Constant binding Partner (CBP) respectively, and hCLDN18.2+ cells are used as Titrant. The cells (Titrant) were serially diluted with a fixed concentration of antibodies (CBP), and after incubation, the free antibodies (free CBP) unbound to cells were captured by an anti-human IgG Fc column, and the signal value was obtained with an anti-human Fc Alexa Flour 647, and the affinity of the antibody was obtained by calculating with a KinExA built-in software.

Specifically, in order to determine an appropriate concentration of the antibody dilution solution, firstly, a reasonable concentration was calculated based on the estimated affinity for a signal test. It was determined that 500 ul 120 pM Ref antibody and 100 pM Ab10 antibody were used as Signal 100% respectively, and a satisfactory detection net signal value was obtained at this concentration, and PBS blank was used as negative signal value (NSB). The concentrations of 120 pM Ref antibody and 100 pM Ab10 antibody were determined as CBP concentrations. In the following balance experiment, centrifugation was performed at 300 g for 10 minutes to collect two tubes of hCLDN18.2+ cells, and the number of cells in each tube was $5\times10^8$ (the positive rate was 100% by FACS detection). The cells were washed once with PBS, centrifugation was performed at 300 g for 10 minutes, and the cells were collected into 15 ml of centrifuge tubes. 15 ml of 120 pM Ref and 100 pM Ab10 antibody solutions were prepared, respectively. 120 pM Ref antibody solution was added to $5\times10^7$ cells to 2 ml, and 120 pM Ref antibody solution was used as a buffer to serially dilute the cells by 2-fold, wherein the initial concentration was $2.5\times10^8$ cells/ml, with 18 gradients and 0.6 ml for each gradient. 100 pM Ab10 antibody solution was added to $5\times10^8$ cells to 2 ml, and 100 pM Ab10 antibody solution was used as a buffer to serially dilute the cells by 2-fold, wherein the initial concentration was $2.5\times10^8$ cells/Ml, with 18 gradients and 0.6 ml for each gradient. The suspension of cells and antibodies was incubated with shaking at room temperature for 2 h. After the incubation, centrifugation was performed at 450 g for 10 minutes and the supernatant was taken. 1 jig/ml of anti-human Fc Alexa Flour 647 solution was prepared. The sample was placed in the corresponding position in the tube rack. The KinExA3200 instrument was used to detect the signal value and the affinity data was obtained. The results are as shown in the following table. The results show that: the affinity of Ab10 (13.3 pM) is more than 10 times higher than that of the Ref antibody.

TABLE 26

Detection of affinity (M) of the antibody of the present disclosure

| Sample | Ab10 | Ref |
|---|---|---|
| KD | $1.33 \times 10^{-11}$ | $1.44 \times 10^{-10}$ |

Example 17: Detection of Endocytosis Activity of the Antibody of the Present Disclosure When the hCLDN18.2+ cells were grown to 90% confluence, the cells were digested with trypsin and resuspended in FACS buffer (PBS+1% BSA) to a final concentration of $1\times10^6$/ml cells. 500 μl of cell suspension was added to 1.5 ml of centrifuge tube, and added with fluorescently labeled antibody control antibody (an antibody not binding to hCLDN18.2+ cells), the control antibody Ref, and samples to be tested (preferred humanized antibodies Ab 10 and Ab6 of the present disclosure, which were labeled with mix-n-stain CF488 antibody labeling kit, Sigma-Aldrich, Cat #MX488S100-1kit, or labeled with mix-n-stain CF633 antibody labeling kit, Sigma-Aldrich, Cat #MX633S100-1kit, all the labeling steps carried out according to the instructions in the kit), the final concentration was 1 μg/ml or 10 ag/ml, incubated on ice for 1 hour, and washed three times with pre-cooled FACS buffer. 1/5 of the cells were taken out and placed on ice, which was used as the binding value sample for flow detection. For the remaining 4/5, the cells were resuspended in preheated RPMI 1640 containing 10% FBS at 37° C., and 1/4 of same placed directly on ice, which used as a sample for endocytosis at 0 hour, and the rest was incubated in a 37° C. incubator, taken out at 1 hr, 2 hr, and 3 hr, respectively, pre-cooled on ice to stop endocytosis, and centrifuged at 4° C. at 1300 rpm for 3 minutes to discard the supernatant. 250 pI of strip buffer (0.05 M glycine, pH 2.45+0.1 M NaCl) was added at 0 hr, 1 hr, 2 hr and 3 hr at room temperature for 7 minutes, centrifuged for 3 minutes at 4° C. at 1300 rpm to discard the supernatant, and washed once with FACS buffer. All samples were added with 150 μl of 4% paraformaldehyde (Sangon Biotech Cat #E672002), fixed at 4° C. for half an hour, and then detected on the machine (Beckman CytoFLEX flow cytometer). The results are shown in the table below.

TABLE 27

Endocytosis activity of the antibody of the present disclosure (FACS fluorescence intensity, CF488 labeled antibody)

| | 1 µg/ml of antibody | | | | | 10 µg/ml of antibody | | | | |
|---|---|---|---|---|---|---|---|---|---|---|
| Sample | Binding value | 0 h | 1 h | 2 h | 3 h | Binding value | 0 h | 1 h | 2 h | 3 h |
| Negative antibody | 1747 | 1759 | 1934 | 1662 | 1635 | 3485 | 2001 | 2035 | 2229 | 1284 |
| Ref | 1939 | 1659 | 1814 | 1978 | 1863 | 17900 | 4823 | 6143 | 6335 | 6127 |
| Ab10 | 27200 | 7373 | 10900 | 12800 | 15100 | 138000 | 27900 | 33000 | 47000 | 59000 |
| Ab6 | 16300 | 3219 | 4531 | 5053 | 7294 | 86000 | 14900 | 27900 | 29600 | 30400 |

The above-mentioned results (the antibody to be tested was labeled with CF488) indicate that when the antibody concentration is 1 pig/ml (the left half of the above table), the binding fluorescence intensity (1939) of the control antibody (Ref) is close to the fluorescence intensity value (1747) of the negative antibody (the antibody that does not bind to hCLDN18.2+ cells), namely, the background value. Moreover, the fluorescence intensity values (underlined values) at 0 h, 1 h, 2 h, and 3 h are all close to the background (1747). However, the binding values (fluorescence intensity) of the antibodies Ab10 and Ab6 of the present disclosure are 27200 and 16300 respectively, which are 15 times and 9 times of the background, and are 14 times (27200/1939) and 8.4 times (16300/1939) of the control antibody, respectively. This further proves that the binding Emax of the antibody of the present disclosure is stronger than that of the control antibody (Ref).

When the antibody concentration increases to 10 µg/ml (the right half of the above table), the fluorescence intensity value of the negative antibody (the antibody that does not bind to hCLDN18.2+ cells), namely, the background value, is 1284-3485 (underlined values). The fluorescence intensity (binding value) of the control antibody (Ref) is 17900, which is 4 times higher than that of the background (3485), indicating that the specific binding of the fluorescently labeled antibody is detected when the Ref is at up to 10 µg/ml. However, at the same concentration, the binding intensities (fluorescence values) of the antibodies Ab10 and Ab6 of the present disclosure are respectively 138000 and 86000, which are 39 times and 24 times of the background (3485), and are 7.7 times (138000/17900) and 4.8 times (86000/17900) of Ref, respectively. This further indicates that the binding Emax of the antibody of the present disclosure is much stronger than that of the control antibody (Ref). This is also consistent with the above-mentioned KinExA detection results.

The data in the above table is calculated according to the formula: endocytosis percentage (%)=(fluorescence intensity at the time point for detection-fluorescence intensity at 0 h)/binding value to obtain the data as the following table.

TABLE 28

Endocytosis activity (endocytosis %) of the antibody of the present disclosure (CF488 labeled)

| | 1 µg/ml of antibody | | | | | 10 µg/ml of antibody | | | | |
|---|---|---|---|---|---|---|---|---|---|---|
| Sample | Binding value | 0 h | 1 h | 2 h | 3 h | Binding value | 0 h | 1 h | 2 h | 3 h |
| Negative antibody | Background | Background | Background | Background | Background | Background | Background | Background | Background | Background |
| Ref | Background | Background | Background | Background | Background | NA | 0 | 7 | 8 | 7 |
| Ab10 | NA | 0 | 13 | 20 | 28 | NA | 0 | 4 | 10 | 23 |
| Ab6 | NA | 0 | 8 | 11 | 25 | NA | 0 | 15 | 17 | 18 |

Background: Namely, reading value is the background value, without endocytosis; NA: Not applicable, no endocytosis at this time point The above-mentioned results indicate that the preferred antibodies Ab10 and Ab6 of the present disclosure at the concentration of 1 µg/ml (left half of the above table), all show better endocytosis at 1 h, 2 h, and 3 h, wherein the endocytosis at 3 h are 28% and 25%, respectively. However, under the same conditions, the Ref antibody, like the negative control antibody, shows no endocytosis.

When the amount of antibody is increased to 10 µg/ml (the right half of the above table), the control antibody still has very little endocytosis (7%-8%), which is almost close to the background, namely, without endocytosis. However, the endocytosis of the antibodies Ab10 and Ab6 of the present disclosure still increases over time, and at 3h, the endocytosis percentage are 23% and 18%, respectively. These are less than those of the antibody at a concentration of 1 µg/mil (28% and 25%), indicating that, because the binding activity of the antibody of the present disclosure is much better than that of Ref, 10 gg/ml is supersaturated for the antibody of the present disclosure, not the optimal antibody endocytosis concentration.

These results indicate that the preferred humanized antibody of the present disclosure is an endocytic antibody. The control antibody (Ref) is not an endocytic antibody, or the endocytosis is very weak. In order to further prove the endocytosis activity of the preferred antibody of the present disclosure, the fluorescent dye CF633 (Sigma-Aldrich, Cat #MX633S100-1kit), rather than CF488, was used for antibody labeling and analysis of endocytosis activity. The detection instrument was BD FACS Calibur flow cytometry. The results are as shown in the following table.

specific binding of the fluorescently labeled antibody is detected when the Ref is at up to 10 μg/ml. However, at the

TABLE 29

Endocytosis activity of the antibody of the present disclosure (FACS fluorescence intensity, CF633 labeled antibody)

| | 1 μg/ml of antibody | | | | | 10 μg/ml of antibody | | | | |
|---|---|---|---|---|---|---|---|---|---|---|
| Sample | Binding value | 0 h | 1 h | 2 h | 3 h | Binding value | 0 h | 1 h | 2 h | 3 h |
| Negative antibody | 23 | 12.7 | 13.2 | 11.9 | 13.7 | 23.2 | 19 | 17 | 16.5 | 14.9 |
| Ref | 62.5 | 15.5 | 33.9 | 33.7 | 33.4 | 198 | 72.8 | 86.2 | 88.2 | 132 |
| Ab10 | 854 | 134 | 205 | 322 | 434 | 3229 | 418 | 1163 | 1176 | 1299 |
| Ab6 | 690 | 56.6 | 205 | 263 | 266 | 2237 | 242 | 682 | 829 | 889 |

The above-mentioned results (the test antibody was labeled with CF633) indicate that when the antibody concentration is 1 μg/ml (the left half of the above table), the fluorescence intensity value of the negative antibody (the antibody that does not bind to hCLDN18.2+ cells), namely, the background value, is 23. The fluorescence intensity values (underlined values) at 0 h, 1 h, 2 h and 3 h are also close to the background (12.7-13.7, namely, the values within 2 times and less than 100 are the background values). The binding fluorescence intensity (62.5) of the control antibody (Ref) is close to the background (negative antibody, 23), which is in the range of 2 times (62.5/23=2.7). Moreover, the binding fluorescence intensity values at 0, 1, 2, and 3 h are relatively weak (15.5-33.4), especially the readings at 1, 2, and 3 h (33.9, 33, 7, 33.4) have no change, indicating that these values are basically close to the background level.

However, the binding values (fluorescence intensity) of the antibodies Ab10 and Ab6 of the present disclosure are respectively 854 and 690, which are 37 times (854/23) and 30 times (690/23) of the background, and are 14 times (854/62.5) and 11 times (690/62.5) of the control antibody, respectively. This further proves that the binding Emax of the antibody of the present disclosure is much stronger than that of the control antibody (Ret). This is also consistent with the above-mentioned KinExA results.

When the antibody concentration increases to 10 μg/ml (the right half of the above table), the fluorescence intensity value of the negative antibody (the antibody that does not bind to hCLDN18.2+ cells), namely, the background value, is 23.2-14.9 (underlined values). The fluorescence intensity (binding value) of the control antibody (Ref) is 198, which is 8.5 times of the background (23.2), indicating that the same concentration, the binding intensities (fluorescence values) of the antibodies Ab10 and Ab6 of the present disclosure are 3229 and 2237 respectively, which are 139 times and 96 times of the background (23.2), and are 16 times (3229/198) and 11 times (2237/198) of Ref, respectively. This further proves that the binding Emax of the antibody of the present disclosure is much higher than that of the control antibody (Ref) (the fluorescence reading is more than 10 times stronger).

The data in the above table is calculated according to the formula: endocytosis percentage (%)=(fluorescence intensity at the time point for detection-fluorescence intensity at 0 h)/binding value to obtain the data as the following table.

TABLE 30

Endocytosis activity (endocytosis %) of the antibody of the present disclosure (CF633 labeled)

| | 1 μg/ml of antibody | | | | | 10 μg/ml of antibody | | | | |
|---|---|---|---|---|---|---|---|---|---|---|
| Sample | Binding value | 0 h | 1 h | 2 h | 3 h | Binding value | 0 h | 1 h | 2 h | 3 h |
| Negative antibody | Background | Background | Background | Background | Background | Background | Background | Background | Background | Background |
| Ref | Background | Background | Background | Background | Background | NA | 0 | 6.8 | 7.8 | 4.6 |
| Ab10 | NA | 0 | 8.3 | 22.0 | 35.1 | NA | 0 | 23.1 | 23.5 | 27.3 |
| Ab6 | NA | 0 | 21.5 | 29.9 | 30.4 | NA | 0 | 19.7 | 26.2 | 28.9 |

Background: Namely, reading value is the background value, without endocytosis; NA: Not applicable, no endocytosis at this time point The above-mentioned results indicate that the preferred antibodies Ab10 and Ab6 of the present disclosure at the concentration of 1 μg/ml show better endocytosis at 1 h, 2 h, and 3 h, and the endocytosis at 3h are 35.1% and 30.4%, respectively. Under the same conditions, the Ref antibody (binding intensity within 2-3 times of the background) was the same as the negative control antibody, without endocytosis.

Figure 6:
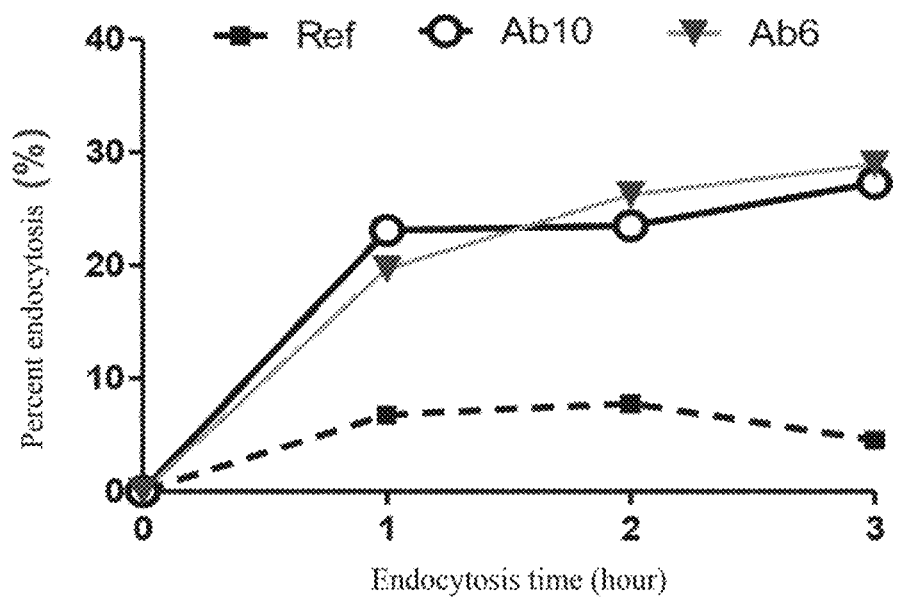
FIG. 6 is the analysis of endocytosis activity of the humanized antibodies Ab10 and Ab6 of the present disclosure.
Figure 7A:
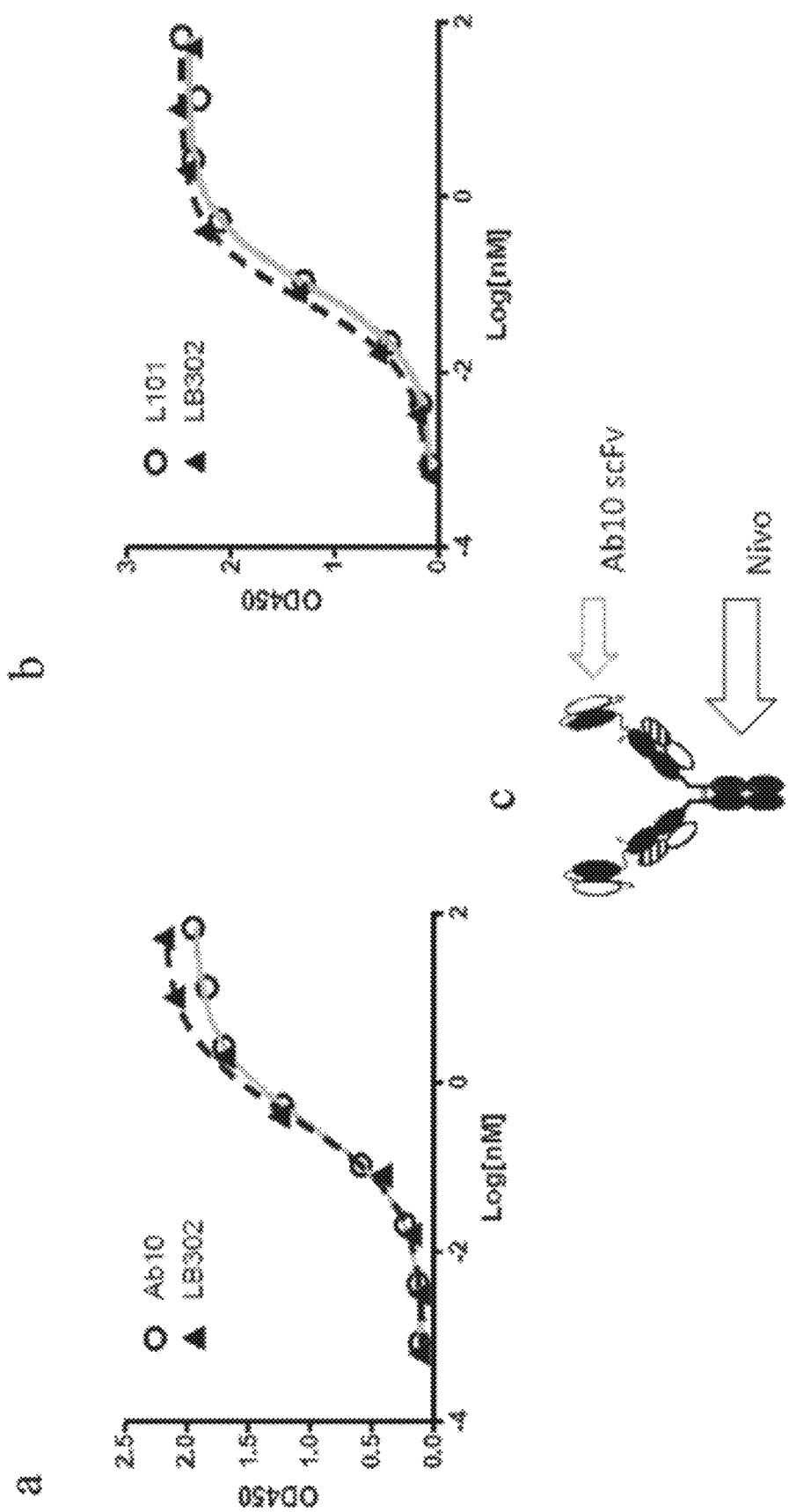
FIG. 7A is the structure of L13302 and a diagram of the related detection data, including a structure diagram (c), and the detection result of binding activity of LB302 to human CLDN18.2 (a) and the detection result of binding activity of LB302 to human PD-1 (b).
Figure 7B:
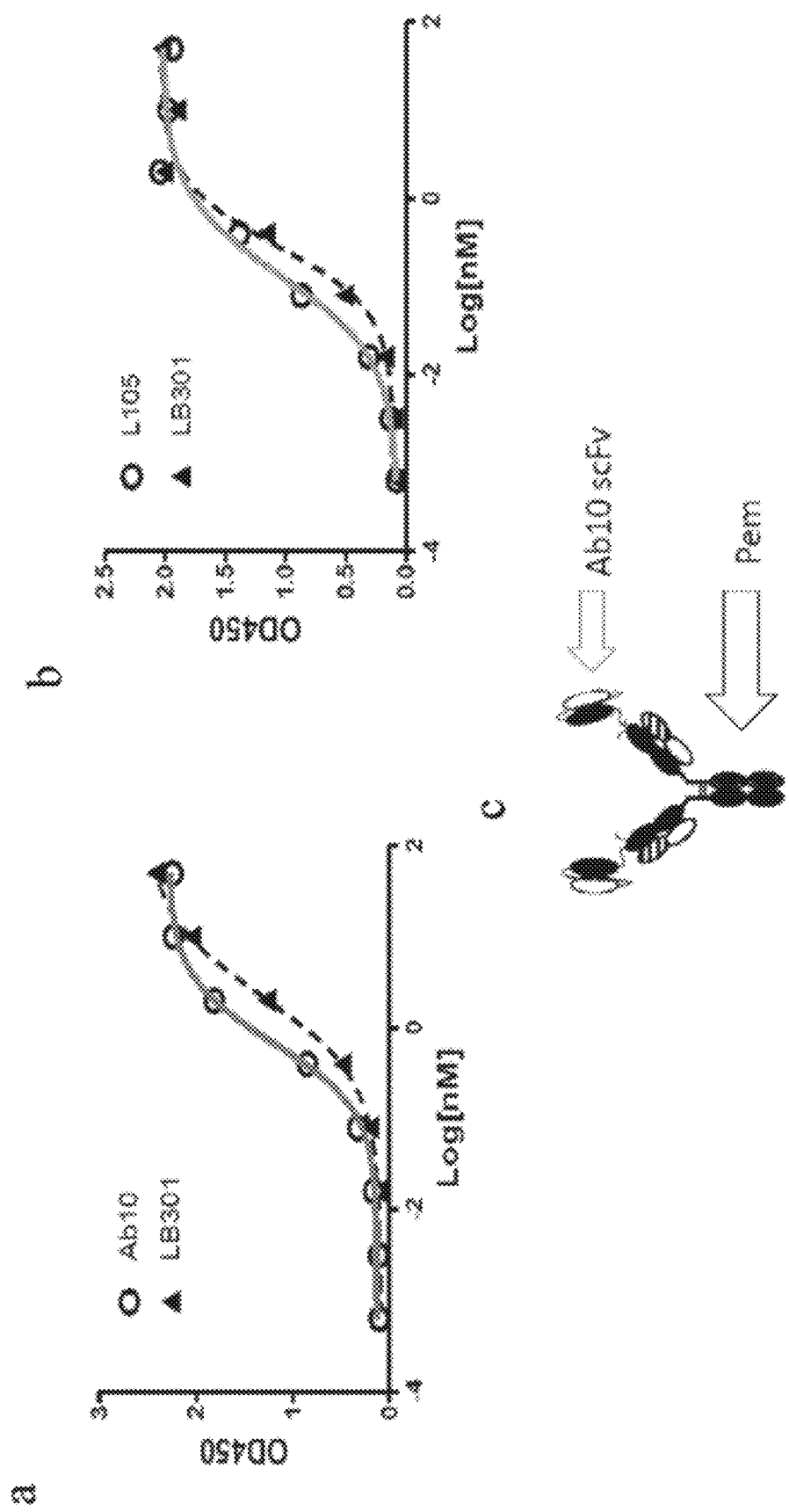
FIG. 7B is the structure of LB301 and a diagram of the related detection data, including a structure diagram (c), and the detection result of binding activity of LB301 to human CLDN18.2 (a) and the detection result of binding activity of LB301 to human PD-1 (b).
Figure 7C:
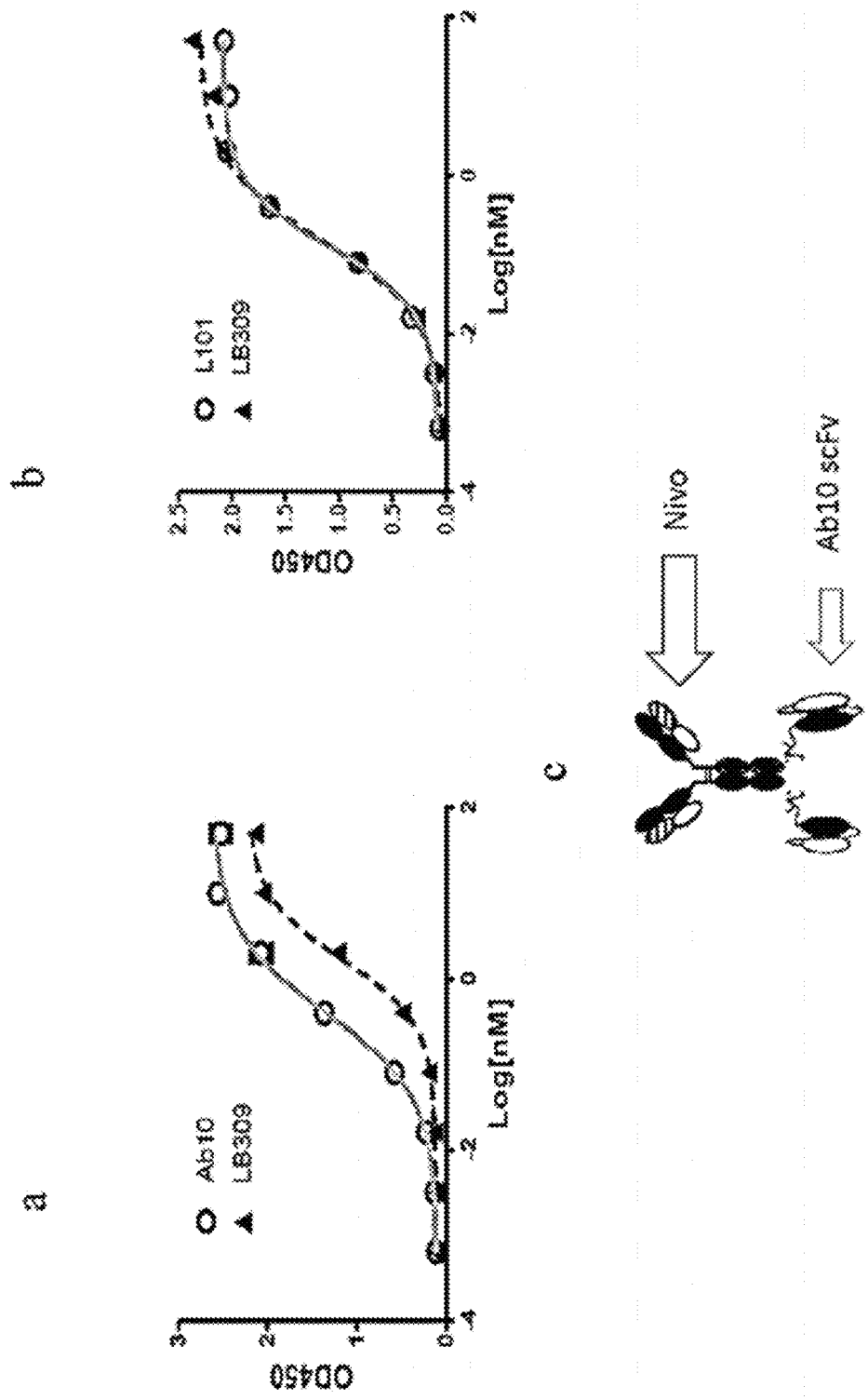
FIG. 7C is the structure of LB309 and a diagram of the related detection data, including a structure diagram (c), and the detection result of binding activity of LB309 to human CLDN18.2 (a) and the detection result of binding activity of LB309 to human PD-1 (b).
Figure 7D:
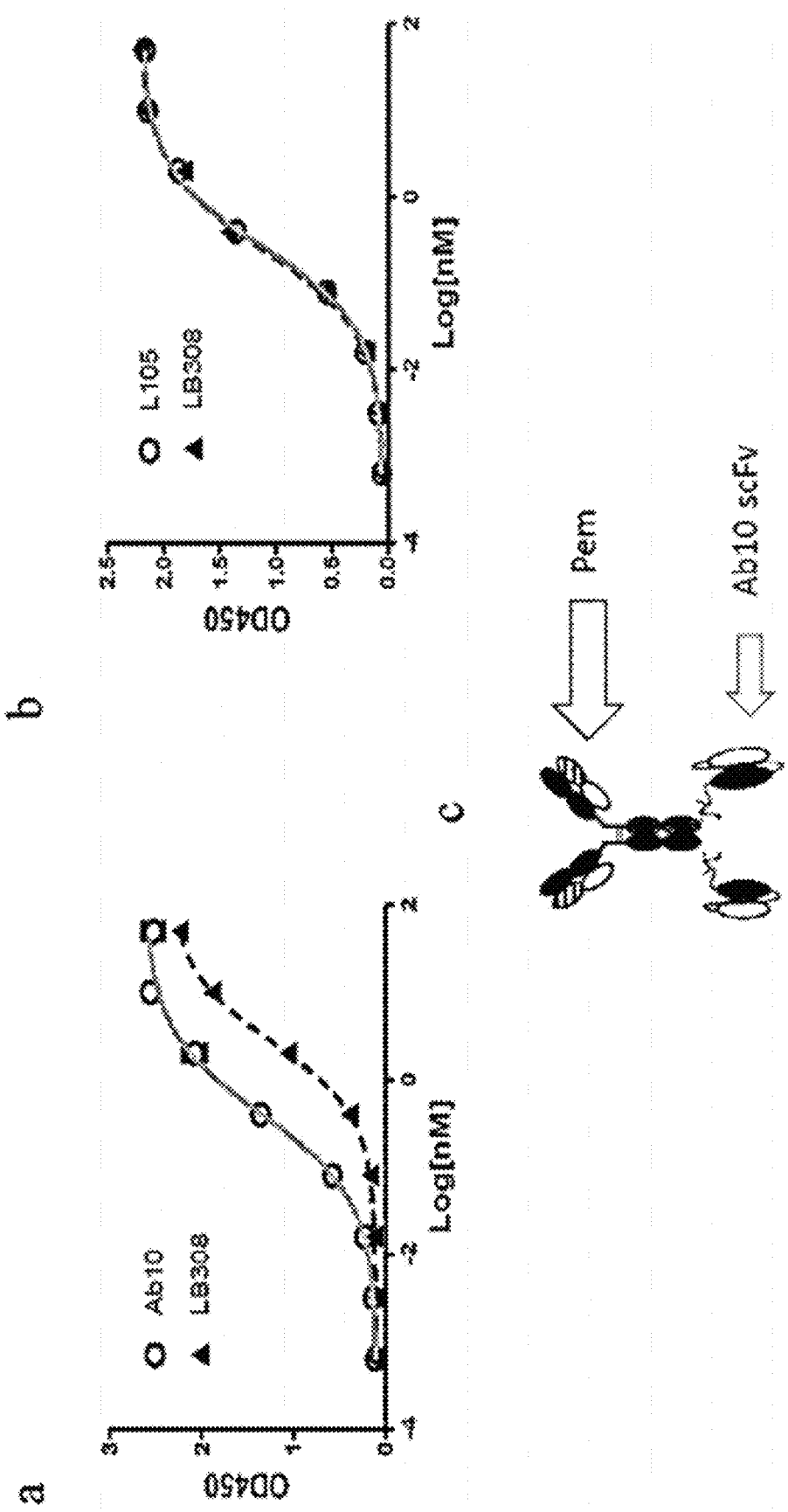
FIG. 7D is the structure of LB308 and a diagram of the related detection data, including a structure diagram (c), and the detection result of binding activity of LB308 to human CLDN18.2 (a) and the detection result of binding activity of LB308 to human PD-1 (b).

When the amount of antibody is increased to 10 μg/ml (the right half of the above table), the control antibody still has very little endocytosis (5%-8%), which is almost close to the background, namely, without endocytosis. However, the endocytosis of the antibodies Ab10 and Ab6 of the present disclosure increases over time, and at 3h, the values are 27.3% and 28.9%, respectively (see FIG. 6). These are less than those of the antibody at a concentration of 1 μg/ml (35.1% and 30.4%), indicating that, because the binding activity of the antibody of the present disclosure is much better than that of Ref, 10 µg/ml is supersaturated for the antibody of the present disclosure, not the optimal endocytosis concentration.

The results of the above-mentioned experiments with the two different fluorescent dyes (CF488 and CF633) indicate that the preferred humanized antibodies Ab10 and Ab6 of the present disclosure are endocytic antibodies. They are completely different from the control antibody (Ref). The control antibody has no endocytosis, or has very weak endocytosis, and the value thereof is close to the background level.

Example 18: Preparation of Anti-CLDN18.2 Antibody Ab10—Toxin SMCC-DM1 Conjugate (ADC1)

The preparation method of the anti-CLDN18.2 antibody Ab10—toxin SMCC-DMI conjugate (ADC1) of the present disclosure refers to the methods disclosed in patents CN 106188293 A and US 2009202536 A1, and the specific steps are as follows.

first and second steps in the above synthesis route, and concentrated to approximately 8 µg/ml for the next reaction.

Step 2. Antibody-toxin conjugation. 5 mg of the intermediate solution obtained in step 1 was taken and added with L-DMI ethanol solution (3.0 mg of L-DM1 ethanol). L-DM1 can be prepared by a well-known method in the document "Journal of Medicinal Chemistry. 2006, 49, 4392-4408", and the amount of L-DMI is added at a ratio of L-DM1:intermediate=3:8 mg. After being shaken and reacted at 25° C. for approximately 4.0 hours, the reaction solution was desalted and purified by Sephadex G25 gel column (elution phase: 0.05 M PBS solution, pH 6.5) to obtain the product of the anti-CLDN18.2 antibody Ab10—toxin SMCC-DM1 conjugate of the present disclosure, an ADC1 solution. The final concentration of ADC1 obtained was 1.3 µg/ml, which was split packed and stored at 4° C. for later use.

The obtained ADC1 sample was detected and analyzed by the LC-MS method, which proved that there were no free small toxic molecules in the obtained sample. The spectrophotometer (UV method) was used to detect the absorption peaks of A252 and A280 to determine the ratio DAR of the obtained ADC1 toxin to antibody=4.4.

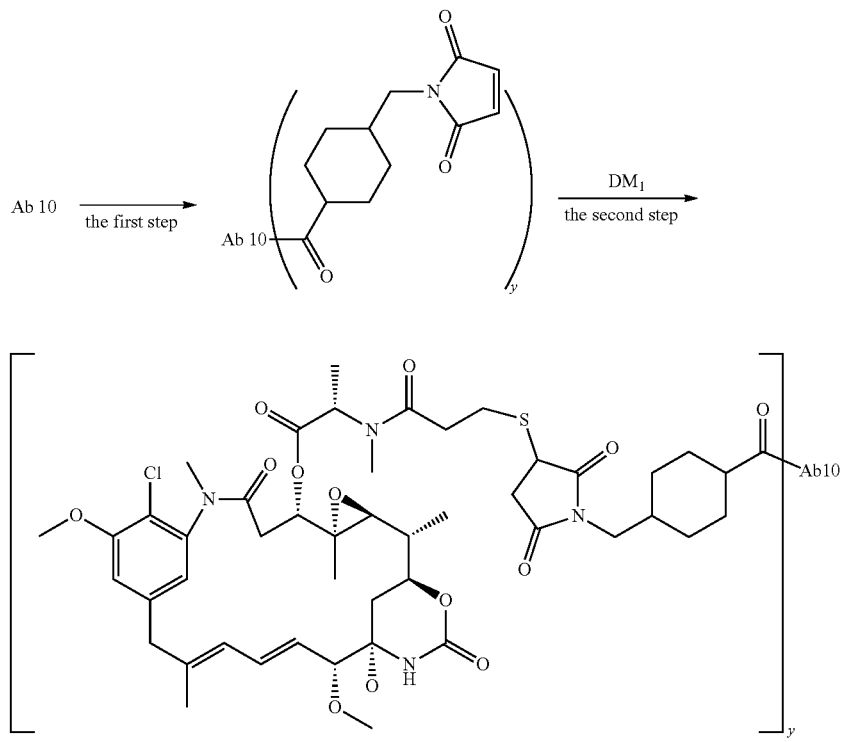

Step 1. Preparation of intermediates. 1 mg of SMCC (Succinimidyl-4-(N-maleimidomnethyl)cyclohexane-1-carboxylate, Shanghai Hanhong Chemical Technology Co., Ltd, batch No. BH-4857-111203) was dissolved in 0.55 mL of acetonitrile solution for later use; 50 mg (5 ml) of Ab1 0 antibody (pH=6.5, PBS buffer) was taken and added to the above spare acetonitrile solution of Succinimidyl-4-(N-maleimidomethyl)cy clohexane-1-carboxylate, shaken at 25° C. and reacted for 2 hours. After the reaction, the solution was desalted and purified with Sephadex G25 gel column (elution phase: 0.05 M PBS solution with pH 6.5) to obtain an intermediate solution, which is the molecule between the

Example 19: Preparation of Anti-CLDN18.2 Antibody Ab10—Toxin MC-VC-PAB-MMAF Conjugate (ADC2)

The preparation method of the anti-CLDN18.2 antibody Ab10—toxin MC-VC-PAB-MMAF conjugate (ADC2) of the present disclosure refers to the methods disclosed in patents CN 106188293 A and US 20140127211 A1, and the specific steps are as follows.

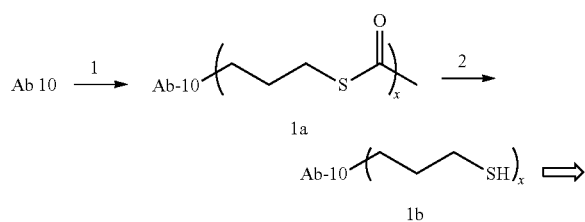

Step 1. Preparation of intermediates. 0.7 mg of thioacetic acid S-(3-carbonylpropyl)ester was taken and dissolved in 0.9 mL of acetonitrile solution for later use. 50 mg (5 ml) of Ab10 antibody (acetic acid/sodium acetate buffer with pH=4.3) was taken and added to the above spare acetonitrile solution of thioacetic acid S-(3-carbonylpropyl)ester, and then added dropwise with 1.0 ml of aqueous solution of sodium cyanoborohydride (14.1 mg), and reacted at 25° C. for 2 hours with shaking. After the reaction, the solution was desalted and purified by Sephadex G25 gel column (elution phase: 0.05M PBS solution with pH 6.5) to obtain the product 1a solution (see the above-mentioned route diagram), and 1a was concentrated to approximately 10 μg/ml for the preparation of intermediate 1 b. In this situation, the x≤y.

5 ml of the above 1a solution was taken, added with 0.15 ml of 2.0 M hydroxylamine hydrochloride solution, and reacted at 25° C. for 30 minutes with shaking, and then the reaction solution was desalted and purified by Sephadex G25 gel column (elution phase: 0.05 M PBS solution with pH 6.5) to obtain the intermediate 1b in the above route, namely the Ab10-propanethiol solution.

Step 2. Antibody-toxin conjugation. 1.6 mg of compound MC-VC-PAB-MMAF (prepared by the method disclosed in PCT patent WO 2005081711) was taken and dissolved in 0.3 ml of acetonitrile, added with 5 mg of the intermediate Ab10-propanethiol solution prepared above, and shaken at 25° C. and reacted for 4 hours, and then the reaction solution was desalted and purified by Sephadex G25 gel column (elution phase: 0.05 M PBS solution, pH 6.5) to obtain the anti-CLDN18.2 antibody Ab10—toxin MC-VC-PAB-MMAF conjugate ADC2 (the structure is as shown in the following formula) of the present disclosure.

The final concentration of ADC2 obtained was 1.21 μg/ml, which was split packed and stored at 4° C. for later use. The obtained ADC2 sample was detected and analyzed by the LC-MS method, which proved that there were no free small toxic molecules in the obtained sample. The spectrophotometer (LIV method) was used to detect the absorption peaks of A252 and A280 to determine the ratio DAR of the obtained ADC2 toxin to antibody, namely, y=4.8.

Example 20: Detection of the Binding Activities of Anti-CLDN18.2 Antibody Ab10 Cytotoxic Conjugates ADC1 and a DC2

The ELISA method described in Example 2 was used to detect the binding activities of the antibody Ab10 of the present disclosure and the Ab10 antibody—cytotoxin conjugates ADC1 and ADC2 to hCLDN18.2+ cells. The results are shown in the table below.

TABLE 31 binding activities (EC50) of Ab 10 antibody cytotoxic conjugates ADC1 and ADC2 of the present disclosure

| Sample | ADC1 | ADC2 | Ab10 |
|---|---|---|---|
| EC50 (nM) | 0.344 | 0.310 | 0.164 |

The above-mentioned results indicate that the binding activities (EC50) of Ab10 antibody cytotoxic conjugates ADC1 and ADC2 to target cells (hCLDN18.2+ cell) is slightly weaker than that of antibody Ab10, but within 2 times (error) range.

Example 21: Detection of Endocytosis Activities of Anti-CLDN18.2 Antibody Ab11 Cytotoxic Conjugates ADC1 and ADC2

The endocytosis activities of the antibody Ab10 of the present disclosure and the Ab 0 antibody—cytotoxin conjugates ADC1 and ADC2 were detected by the same method as that in the above-mentioned "detection of endocytosis activity of the antibody of the present disclosure" (Example 17). On the basis of the above examples, the labeling method (with CF633 dye), antibody concentration (2.5 μg/ml) and

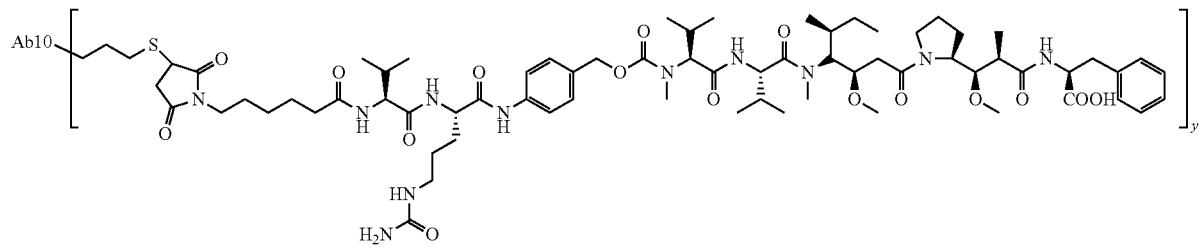

time (1 hour) and other endocytosis detection conditions were optimized. The results are as shown in the following table.

TABLE 32

Detection of endocytosis activities of Ab10 antibody cytotoxic conjugates ADC1 and ADC2 of the present disclosure

| Sample | Binding value [1] | Before endocytosis (0 h) | After endocytosis (1 h) | Endocytosis ratio (%) [3] |
|---|---|---|---|---|
| Negative antibody | 932 [2] | 935 | 944 | NA |
| Ab10 | 6135 | 1191 | 2055 | 14.1 |
| ADC1 | 4136 | 1200 | 2119 | 22.2 |
| ADC2 | 4254 | 1788 | 2754 | 22.7 |

1) Binding values, the values before and after endocytosis, are the FACS detection values of CF633 labeled antibodies;
2) The underlined number is the background value of the FACS binding;
3) Endocytosis ratio (1 hour)=100*(after endocytosis-before endocytosis)/binding value; NA: Not applicable The above-mentioned results indicate that the Ab10 antibody—cytotoxin conjugates ADC1 and ADC2 of the present disclosure retain the endocytosis activity of the antibody Ab10. That is to say, the antibody Ab10 linked to the toxin does not affect the endocytosis activity of the antibody.

Example 22: Activity of Anti-CLDN18.2 Antibody Ab10 Cytotoxic Conjugates ADC1 and ADC2 for Inhibiting the Proliferation of Target Cells In order to detect the activity of the Ab10 antibody cytotoxic conjugates ADC1 and ADC2 for inhibiting the proliferation of target cells, the CCK8 method (the kit was purchased from Dojindo Laboratories (Shanghai) Co., Ltd, Cat. No. CK04, operated according to the instructions) was used to detect cell proliferation. Specifically, hCLDN18.2+ cells (target cells) and hCLDN18.1±cells (non-CLDN18.2 target cells, as control cells) were cultured in DME1M/F12 medium containing 10% FBS, and at 2 hours before the end of the 72-hour culture, 10 μl of CCK8 was added to each well, and culture was performed for another 2 hours in the incubator, the OD450 nM reading was obtained by the Multiskan GO microplate reader, and the data was analyzed and processed with Graphpad prism 5. Percentage of cell proliferation inhibition (%)=100*(1-(OD450 samples/0D450 control wells)), the results are shown in the table below.

TABLE 33

Activity of Ab10 antibody cytotoxic conjugates ADC1 and ADC2 of the present disclosure for inhibiting the proliferation of target cells (IC50, nM)

| Target cell/sample | hCLDN18.2 + cells | hCLDN18.1 + cells | IC 50 ratio (hCLDN18.2 + cells/ hCLDN18.1 + cells) |
|---|---|---|---|
| ADC1 | 11.2 | 34519 | 3082 |
| ADC2 | 0.71 | 18.5 | 26.1 |

The above-mentioned results inhibition that the Ab10 antibody—cytotoxin conjugate ADC1 and ADC2 molecules of the present disclosure can significantly inhibit the proliferation of target-specific cells (hCLDN18.2+ cell), with IC50 being 11.2 nM and 0.71 nM, respectively. ADC1 has no inhibitory effect on non-target cells (hCLDN18.1+ cells that did not bind to Ab10 antibody were used in this experiment), and the safety window is up to 3000. ADC2 is seen to inhibit non-target specific cells at very high concentrations (IC50 is 18.5 nM), and this inhibition is due to non-targeted toxicity directly caused by a high dose (up to 10-100 nM). This is consistent with the highly toxic characteristic of MMAF connected to ADC2. The safety window of ADC2 reachs 26.

Example 23: Detection of Toxic Activity of Anti-CLDN18.2 Antibody Ab10 Cytotoxic Conjugate for Targeting Cells In order to detect the toxicity of the Ab10 antibody—cytotoxin conjugate of the present disclosure for specifically targeting CLDN18.2+ cells, ADC1 is used as an example in this example, and the toxic activity of anti-CLDN18.2 antibody Ab10 cytotoxic conjugate for targeting cells is evaluated by detecting the release of LDH in the cell supernatant.

Specifically, hCLDN18.2+ cells (target cells) and hCLDN18.]+ cells (non-CLDN18.2 target cells, as control cells) were cultured in DMEM/F12 medium containing 10% FBS to the logarithmic growth phase. The day before the experiment, the cultured hCLDN18.2+ cells and hCLDN18.1—cells were taken, and the cells were resuspended in DMEM/F12 medium containing 10% FBS, the cell concentration was adjusted to $4\times10^4$ cells/ml, and added at 100 μl/well to a 96-well cell culture plate; the cells were incubated overnight at 37° C. under 5% CO2; on the day of the experiment, the medium was removed from the cells in the 96-well plate and DMEM/F12 medium containing 2% FBS was added to each well for later use; the serially diluted drug ADC1 to be tested was prepared with DMEM/F12 medium containing 2% FBS, and 0 μg/ml antibody-containing wells were added with a fresh medium as control wells; the prepared antibody samples at different concentrations were added to the cells at 50 hi/well, with three replicate wells for each concentration; after being incubated in a 37° C. and 5% $CO_2$ incubator for 72 hours, the supernatant was taken out and the LDH kit (purchased from Dojindo Laboratories (Shanghai) Co., Ltd, Cat. No. CK12) was used to detect the release of LDH. The detection was carried out according to the instructions. Reading was performed on a Multiskan GO microplate reader at 490 nM, and the data was analyzed and processed with Graphpad prism 5. Cell killing percentage (%)=100*(OD490 samples to be tested-OD490 control wells)/(OD490 all cells lysed-OD490 control wells). The experimental results are as shown in the following table.

TABLE 34

Evaluation of the toxicity of the Ab10 antibody cytotoxic conjugate ADC1 for targeting cells (EC50, nM)

| Target cell/sample | hCLDN18.2 + cells | hCLDN18.1 + cells | EC 50 ratio (hCLDN18.2 + cells/ hCLDN18.1 + cells) |
|---|---|---|---|
| ADC1 | 0.983 | 153.4 | 156 |

The above-mentioned results indicate that the toxicity of Ab10 antibody cytotoxic conjugate of the present disclosure for specifically targeting hCLDN18.2+ positive cells is stronger, and the EC50 is below 1 nM. The cytotoxicity effect for the non-targeted cells (hCLDN18.1+ cells that did not bind to the Ab10 antibody were used in this experiment) is weak (no cytotoxicity). In particular, the ratio of ADC1 toxicity (EC50) of targeting specific cells and non-specific cells is up to 156. This specific window (safety window) shows that the non-targeted toxicity of the molecules is very weak and the safety is reliable.

Example 24: In Vivo Efficacy of Anti-CLDN18.2 Antibody Ab10 Cytotoxic Conjugate The same animal model of the BALB/c nude mice subcutaneously transplanted with hCLND18.2+ cell and test method as those in the method of Example 14 were used, and ADC1 was used as an example to evaluate the in vivo efficacy of the antibody Ab10 antibody cytotoxic conjugate of the present disclosure. The results are shown in Table 35.

TABLE 35

Pharmacodynamic evaluation of antibody drug conjugate ADC1 of the present disclosure in tumor models

| Sample | Dosage (mg/kg) | Number of animals | Day 0 tumor volume (mm³) Mean | SD | Day 14 tumor volume (mm³) Mean | SD | Day 14 tumor inhibition rate (%) | P value |
|---|---|---|---|---|---|---|---|---|
| PBS | NA | 5 | 153.28 | 26.20 | 2618.10 | 364.58 | 0 | NA |
| ADC1 | 2 | 5 | 143.41 | 14.50 | 1465.62 | 338.39 | 46 | 0.0004 |

NA: Not applicable, namely blank control.

The results in Table 35 indicate that the antibody-toxin drug conjugate ADC1 of the present disclosure has a very good tumor inhibiting effect at a low concentration (2 mg/kg) with only 4 administrations over 2 weeks (14 days), with an inhibition rate of 46%, and the difference from the control group is extremely significant (P value<0.001).

The same method as in Example 14 was used, the tumor cells, the cell lines of the gastric cancer cell line NUGC-4 overexpressing hCLDN18.2 were inoculated into BALB/c nude mice to evaluate the efficacy of ADC2 of the present disclosure in animals. Specifically, cells of the gastric cancer cell line NUGC-4 were purchased from the Cell Institute of the Chinese Academy of Sciences. The hCDLN18.2 overexpressing cell line NUGC-4-802 was constructed using the method of Example 1. NUGC-4-802 was cultured in RPMI1640 medium (Shanghai BasalMedia Technologies Co., Ltd, Cat. No.: L2IOKJ) containing 10% of fetal bovine serum (Shanghai BioSun Sic&Tech Co., Ltd, Cat. No.: BS-0002-500), and continuously cultured in a 37° C. cell incubator containing 5% $CO_2$. When NUGC-4-802 cells were at the logarithmic growth phase (the confluence rate was 80%-90%), the cells were digested with 0.25% trypsin, collected, washed twice with a serum-free RPM11640 medium, and resuspended and counted, and the cell concentration was adjusted to $5 \times 10^7$ cells/ml. The BALB/c-nude mice were inoculated with $5 \times 10^6$ cells/100 µl subcutaneously on the right ribs, the mice with a tumor cell size of approximately 120-150 mm³ were selected, and grouped randomly, with 6 mice in each group.

The samples ADC2 and Ab10 to be tested were prepared with PBS and sterilized. The blank group was PBS. The administration dosage was 5 mg/kg via intravenous injection, BIW for 2 weeks. The day of administration of the injection samples was day 0. Body weight and tumor volume were measured before each administration and recorded. The statistical analysis method of the data is the same as that in the preceding Example 14. The actual administration period in this experiment was 2 weeks. The results are shown in Table 35b.

TABLE 35

Pharmacodynamic evaluation of antibody drug conjugate ADC2 of the present disclosure in tumor models

| Sample | Dosage (mg/kg) | Number of animals | Day 0 tumor volume (mm³) Mean | SD | Day 14 tumor volume (mm³) Mean | SD | Day 14 tumor inhibition rate (%) |
|---|---|---|---|---|---|---|---|
| PBS | NA | 6 | 133.51 | 25.79 | 1671.72 | 880.89 | — |
| Ab10 | 5 | 6 | 134.79 | 33.22 | 1516.35 | 1085.40 | 10 |
| ADC2 | 5 | 6 | 134.86 | 25.35 | 720.15 | 565.91 | 62 |

The results in Table 35b indicate that the antibody-toxin drug conjugate ADC2 of the present disclosure has a very good tumor inhibiting effect on the NUGC-4-802 tumor model at 5 mg/kg with only 4 administrations for 2 weeks (14 days), with an inhibition rate of 62%, and the difference from the control group (PBS) is significant (P value<0.05). It is especially unexpected that in this model, the tumor inhibition effect of the antibody Ab10 at the same concentration is very weak (only 10%). This unexpected result indicates that the antibody-toxin drug conjugate ADC2 of the present disclosure has an outstanding tumor inhibiting effect, which is superior to that of the single antibody (antibody alone).

Example 25 Cloning, Expression and Purification of Antigens and Antibodies in Bispecific Antibodies The design of human CLDN18.2 used in the present disclosure is shown in the above-mentioned Examples. PD-1, PD-L1 extracellular region-human IgG1 Fe fusion protein,-his tag protein, monoclonal antibody and designed bispecific antibodies of different structures, etc. were either obtained by cloning, expression and purification of the present disclosure, or purchased from Beijing ACROBiosystems Biological Technology Co., Ltd and Beijing Sino Biological Co., Ltd (Sino Biological).

The antigen sequence was obtained by searching the NCBI database. The antibodies used in the present disclosure include recombinant antibodies and bispecific antibodies. Except for the sequence of the anti-human CLDN18.2 antibody discovered in the present disclosure, other sequences can be obtained from published literatures, including sequences of anti-PD-1 antibodies Nivo, Pem, Ba08 (the sequences are derived from patent WO 2016015685A1); sequences of anti-PD-L1 antibodies Atezo (Atezolizumab/Tecentriq), Avel (Avelumab/Bavencio), Durv (Durvalumab/imfinzi); anti-CD47 antibody hu5F9, and the light and heavy chain variable region sequences of anti-CD3 antibodies in iMab, Blincyto and AMG420. For example, the sequence of PD-1 antibody Nivo (Nivolumab/Opidivo) is derived from a published literature, such as www.drugbank.ca, or WO 2013019906. The sequence of PD-1 antibody Pem (Pembrolizumab/Keytruda) is derived from www.drugbank.ca (. The sequence of PD-1 antibody Ba08 is derived from patent WO 2016015685 A1. Atezo sequence, Avel sequence, and Durv sequence (Accession Number, DB11714) can all be accessible at www-.drugbank.ca. The light chain sequence of the CD47 antibody hu5F9 is derived from U.S. Pat. No. 9,382,320 B2_42, and the heavy chain sequence is derived from U.S. Pat. No. 9,382,320 B2_37. iMab light chain is derived from WO 2018075857_4, IF8; and the heavy chain is derived from WO 2018075857_3, IF8. The CD3 antibody is derived from the light chain and heavy chain variable regions of the anti-CD3 antibody from blincyto. The Blincyto sequence is the sequence disclosed in www.drugbank.ca. The other CD3 antibody sequence is derived from anti-CD3 in AMG420. AMG420 sequence is derived from WO 2014140248_340. The amino acid sequences of the light chain variable region and the heavy chain variable region of Tim3 are as shown in SEQ ID NO: 27 and SEQ ID NO: 36 in CN 201710348699.4, respectively; the patent has been published; the amino acid sequences of the light chain variable region and the heavy chain variable region of LAG3 are as shown in SEQ ID NO: 33 and SEQ ID NO: 44 in CN 201810917684X, respectively. The sequence of TGFβ receptor II (TGFβRII) is derived from the extracellular region of UniProtKB/Swiss-Prot: P37173.2 (namely, SEQ ID NO: 1 in the sequence listing of the present disclosure); IL10 sequence is derived from NCBI No. NP 000563.1 (namely, SEQ ID NO: 2 in the sequence listing of the present disclosure). The sequence of CD47 ligand SFRPα is derived from NCBI No. NP_001035111.1.

The synthesized fragments of all antigens and antibodies, including the single antibody, bispecific antibody, antibody-receptor (Trap), antibody-cytokine, etc., were obtained by gene synthesis, and the design, cloning and expression, and purification thereof were all completed by the present disclosure. The details are the same as the preceding Example 3.

His Tagged protein purification: the samples were centrifuged at a high speed to remove impurities. Nickel column equilibration (Ni smart beads 6FF Changzhou Smart-Life Sciences Biotechnology Co., Ltd, Cat #SA036010): the nickel column was equilibrated with PBS solution at pH7.4 containing 10 mM imidazole and 0.5M NaCl, and flushed with 2-5 times the column volume. The supernatant of the samples were passed through the column. Hybridprotein rinsing: the chromatographic column was flushed with PBS solution (pH 7.4) containing 10 mM imidazole and 0.5 M NaCl to remove non-specifically binding hybridproteins, and the effluent was collected. The target protein was eluted with PBS (pI 7.4) containing 250 mM imidazole and 0.5 M NaCl. Buffer replacement: the eluted target protein was centrifuged through an ultrafiltration tube at 12000 g for 10 min (Ultrafiltration tube Merck Millipore Cat #UFC500308), added with 1 ml of PBS, measured for the concentration, split packed and stored for later use. TGFβ1, TGFβ2, TGFβ3 and IL10 were all purchased from Peprotech.

Human antibody light chain constant region sequences Lc (κ chain) and Lc (, chain): the prior art; the human antibody heavy chain constant region sequence hIgG4 or He (hIgG4); hIgG1 or He (hIgG1); hIgG1p or He (hIgG1p), namely, another form of hIgG1 with EEM at positions 356-358, all of which are within the prior art. In addition to the sequences listed above, the heavy chain constant region can also be hIgG2 or hIgG3.

TABLE 36

Number, light and heavy chain sequences and description of part of the cloned and expressed monoclonal antibodies (for control) in bispecific antibody technical solution

| No. | Light chain sequence | Heavy chain sequence | Description |
| --- | --- | --- | --- |
| Ab10 | Ab10VL-Lc (κ chain) (SEQ ID: 38) | Ab10VH-Hc (hIgG1) (SEQ ID: 39) | Anti-CLDN18.2 antibody of the present disclosure |
| Ab6 | Ab6VL-Lc (κ chain) (SEQ ID: 42) | Ab6VH-Hc (hIgG1) (SEQ ID: 39) | Anti-CLDN18.2 antibody of the present disclosure |
| L101 | NivoVL-Lc (κ chain) | NivoVH-Hc (hIgG4) | Namely, Nivolumab |
| L105 | PemVL-Lc (κ chain) | PemVH-Hc (hIgG4) | Namely, Pembrolizumab |
| LB125 | Ba08VL-Lc (κ chain) | Ba08VH-Hc (hIgG4) | Namely, Ba08-1 in WO 2016015685A1 |
| LB185 | AtezoVL-Lc (κ chain) | AtezoVH-Hc (hIgG1p) | Namely, Atezolumab |
| LB315 | AvelVL-Lc (λ chain) | AvelVH-Hc (hIgG1) | Namely, Avelumab |
| LB318 | DurvVL-Lc (κ chain) | DurvVH-Hc (hIgG1p) | Namely, Durvalumab |
| LB192 | Hu5F9VL-Lc (κ chain) | Hu5F9VH-Hc (hIgG4) | Namely, Hu5F9-F4 or Hu5F9 |
| LS956 | iMabVL-Lc (κ chain) | iMabVH-Hc (hIgG4) | Namely, WO 20180758571F8 |

Example 26 Experiment of Antibodies Binding to T Cells (CD3) (FACS)

Flow cytometry (FACS) was used to detect the CD3 binding activity of the bispecific antibody which targets CD3 designed in the present disclosure. Specifically, the peripheral blood mononuclear cells (PBMC) of healthy humans were extracted and activated by Dynabeads Human T-Activator CD3/CD28 (Gibco, 11131D) for three days. The activated cells were washed once with FACS buffer (PBS, 0.5% FBS) (centrifuged at 800 g for 3 minutes) and then resuspended in FACS buffer with the cell density of $4 \times 10^6$/ml, and 25 µl of each sample for later use. The samples to be tested were serially diluted with FACS buffer, and the highest concentration was 250 nM, which was diluted 5 times downward, with 8 concentrations, and the volume was 25 µl; 25 µl of diluted sample was added to 25 µl of cell suspension, mixed well and gently, and incubated at room temperature for 20 minutes; the cells were washed with FACS buffer at a volume more than 5 times the staining volume, and then added with the secondary antibody (anti-hFc-PFE, Biolegend, 409304), stained for 20 minutes at room temperature, washed, resuspended, and detected with flow cytometry (Beckman, CytoFLEX Flow cytometer). FlowJo software was used to analyze the average fluorescence signal MFI of the tested samples. The curve was plotted by MFI and concentrations, and Graphpad Prism 5 software was used to calculate EC50.

Example 27 Experiment of Activating PBMC to Kill Target Cells

For the bispecific antibody targeting CD3 of the present disclosure, the function thereof was evaluated by this experiment. The hCLDN18.2+ cells constructed in the above-mentioned Example 1 were used as the target cells, and hCLDN18.14 cells were used as the negative control cells (the method for constructing hCLDN18.1+ cells is the same as that in Example 1, namely, the construction steps are same, wherein the hCLDN18.2 plasmid was replaced with hCLDN18.1 plasmid). The peripheral blood mononuclear cells (PBMC) of healthy humans were used as effector cells. Specifically, hCLDN18.2+ cells and hCLDN18.1+ cells were collected respectively, and the cell density was adjusted to $2 \times 10^5$/ml in 1640 complete medium (RPMI1640, 10% FBS), and the cells were added at 100 µl per well to a 96-well plate for later use. The cell density of PBMC was adjusted to $4 \times 10^6$/ml in 1640 complete medium, and the cells were added at 50 µl per well to hCLDN18.2+ cells or hCLDN18.1+ cells. The serially diluted samples to be tested were prepared with 1640 complete medium, with the concentrations of 4, 0.4, 0.04 and 0.004 µg/ml, and added at 50 µl/well to the cells, with the final concentrations of 1, 0.1, 0.01 and 0.001 µg/ml. Three replicate wells were set. After being incubated in a 37° C. and 5% $CO_2$ incubator for 48 hours, the supernatant was taken and the LDH kit (Shanghai Tongren Biotechnology Co., Ltd, catalog number: CK12) was used to detect the release of LDH, which reflects the killing of target cells. The operation was according to the instruction, Multiskan GO microplate reader was used for reading at 490 nM, and the data was analyzed and processed with Graphpad prism 5.

Cell killing percentage (%)=100*(OD490 concentration of certain drug-OD490 control wells)/($OD_{490}$ all cells lysed-$OD_{490}$ control wells)

Example 28 Stability Evaluation of Bispecific Antibodies of the Present Disclosure The bispecific antibodies designed in the present disclosure were uniformly purified using the Protein A gravity column. The purified samples were replaced into a PBS buffer with pH 7.4, 1 µg/ml. The samples were stored in different conditions, including storing at −80° C. for more than 60 days, 4° C. for 14 or 30 days, 37° C. for 7 day, 37° C. for 14 days, etc. The samples stored under different conditions were subjected to electrophoresis (PAGE) to evaluate the degradation degree of the samples. The binding activity was detected to evaluate whether different storage conditions affect the activities of the samples. Under the same detection conditions, the detected activity value (EC50) was compared with the activity value detected in the sample stored at −80° C. If the ratio changes is beyond the 2-fold range, it can be considered that the storage conditions have affected the stability/activity of the sample.

Example 29 Design and Activity Evaluation of Bispecific Antibodies for the Two Targets of CLDN18 and PD-1

In the present disclosure, bispecific antibodies were designed with different sequence structures for the two targets of CLDN18.2 and PD-1, which are shown in the following table.

TABLE 37a

| Bispecific antibodies designed for the two targets of CLDN18.2 and PD-1 | | |
|---|---|---|
| Antibody number | Light chain or sequence comprising a light chain | Heavy chain or sequence comprising a heavy chain |
| LB302 | NivoVL-Lc (κ chain*) | Ab10VL-($G_4S$)$_3$-Ab10VH-($G_4S$)$_3$-NivoVH-Hc (hIgG4) |
| LB309 | NivoVL-Lc (κ chain) | NivoVH-Hc (hIgG4)#-($G_4S$)$_3$-Ab10VH-($G_4S$)$_3$-Ab10VL |
| LB156 | Ab10VL-Lc (κ chain) | PemVL-($G_4S$)$_3$-PemVH-($G_4S$)$_3$-Ab10VH-Hc (hIgG1) |
| LB301 | Pem VL-Lc (κ chain) | Ab10VL-($G_4S$)$_3$-Ab10VH-($G_4S$)$_3$-PemVH-Hc (hIgG4) |
| LB308 | Pem VL-Lc (κ chain) | PemVH-Hc (hIgG4)-($G_4S$)$_3$-Ab10VH-($G_4S$)$_3$-Ab10VL |
| LB307 | Ba08VL-Lc (κ chain) | Ab10VL-($G_4S$)$_3$-Ab10VH-($G_4S$)$_3$-Ba08VH-Hc (hIgG4) |
| LB310 | Ba08VL-Lc (κ chain) | Ba08VH-Hc (hIgG4)-($G_4S$)$_3$-Ab10VH-($G_4S$)$_3$-Ab10VL |
| LB312 | Ab10VL-($G_4S$)$_3$-Ab10VH-($G_4S$)$_3$-PemVL-Lc (κ chain) | PemVH-Hc (hIgG4) |
| LB313 | PemVL-Lc (κ chain)-Ab10VH-($G_4S$)$_3$-Ab10VL | PemVH-Hc (hIgG4) |
| LB314 | NivoVL-Lc (κ chain) | Ab10VL-($G_4S$)$_3$-Ab10VH-($G_4S$)$_3$-NivoVH-Hc (hIgG4)-($G_4S$)$_3$-Ab10VH-($G_4S$)$_3$-Ab10VL |
| LB3022 | NivoVL-Lc (κ chain*) | Ab6VL-($G_4S$)$_3$-Ab6VH-($G_4S$)$_3$-NivoVH-Hc (hIgG4) |
| LB3012 | PemVL-Lc (κ chain) | Ab6VL-($G_4S$)$_3$-Ab6VH-($G_4S$)$_3$-PemVH-Hc (hIgG4) |

*: κ chain represents the κ-type light chain constant region of the human IgG. 4: When the C-terminal of IgG is linked to a linker, the terminal amino acid K is mutated to A. The terminal K was mutated to A in the following designs of introducing scFvs into the C-terminal of the heavy chains. The "sequence containing a heavy (light) chain" in the present disclosure not only includes a normal heavy (light) chain, but also is linked to one or more scFvs.

The above-mentioned bispecific antibodies were cloned, expressed, and purified according to the method of Example 25 of the present disclosure, and the binding activities of these designed bispecific molecules to human CDN18.2 and PD-1 were detected using the methods of preceding examples. The results are as shown in the following table.

TABLE 37b

Binding activity of bispecific antibodies designed for the two targets of CLDN18.2 and PD-1

| Antibody number | Binding activity to human CLDN18.2 | | Binding activity to human PD-1 | |
|---|---|---|---|---|
| | EC50, nM | EC50 fold change* | EC50, nM | EC50 fold change |
| LB302 | 0.39 (0.33#) | 1.18 | 0.065 (0.096) | 0.68 |
| LB309 | 1.72 (0.41) | 4.2 | 0.16 (0.12) | 1.33 |
| LB156 | 1.60 (0.33) | 4.8 | 0.11 (0.32) | 0.34 |
| LB301 | 2.24 (0.69) | 3.2 | 0.29 (0.14) | 2.1 |
| LB308 | 2.67 (0.41) | 6.5 | 0.25 (0.27) | 0.93 |
| LB307 | 2.0 (0.33) | 6.1 | 0.68 (0.44) | 1.5 |
| LB310 | 2.99 (0.41) | 7.3 | 0.29 (0.52) | 0.56 |
| LB312 | 0.80 (0.31) | 2.6 | 0.042 (0.014) | 3 |
| LB313 | 3.63 (0.31) | 11.7 | 0.048 (0.014) | 3.4 |
| LB314 | 0.45 (0.31) | 1.5 | 0.083 (0.016) | 5.2 |
| LB3022 | 0.49 (0.33) | 1.5 | 0.08 (0.096) | 0.8 |
| LB3012 | 1.1 (0.69) | 2.2 | 0.24 (0.14) | 1.7 |

The value in brackets is the binding activity $EC_{50}$ of the monoclonal antibody (control antibody) corresponding to the same target under the same experimental conditions.
*Under the same experimental conditions, the ratio of the binding activities $EC_{50}$ of the bispecific antibody and the corresponding monoclonal antibody.

The larger the ratio, the more weakened the binding ability of the designed bispecific antibody to a single target. For example, the ratio is 2indicating that the binding activity of the designed bispecific antibody to the target is weakened by 1 time compared with that of the corresponding monoclonal antibody. The ratio is within 2, indicating that the binding activity is not affected; the ratio is between 2 and 5, indicating that the binding activity is slightly affected. At this time, the ratio for the other target should be considered. If the ratio for the other target is smaller, for example, within 1, the bispecific antibody still has a certain application value.

The results in the above table respectively show the detection results of the binding activities of LB302, LB301, LB308 and LB309 to human CLDN18.2 (FIGS. 7A-7D, a), the detection results of the binding activity to human PD-1 (FIGS. 7A-7D, b) and structural diagrams of the bispecific antibodies (FIGS. 7A-7D, c). The effects of the binding activities of LB302 (Ab10 scFv at the N-terminal of NivoVH Hc), LB301 (Ab10 scFv at the N-terminal of PemVH Hc), and LB307 (Ab10 scFv at the N-terminal of Ba08VH Hc) to PD-1 were 0.68, 2.1, and 1.5-fold changes, respectively; the effects of the binding activities to CLDN18.2 were 1.18, 3.2, and 6.1, respectively. LB302 retained the binding activity thereof to human CLDN18.2 and PD-1, while the binding activity of LB307 to human CLDN18.2 was most affected, which was weakened by 5.1 times (6.1-1=5.1). That is to say, in the same IgG-like bispecific molecules, although LB302, LB301, and LB307 are all against PD-1, the sequences of the PD-1 antibodies Nivo, Pem, and Ba08 are different, so the effects thereof against CLDN18.2 are also different. It was unexpectedly discovered that the binding activity of the bispecific antibody LB302 designed by scFv and Nivolumab (Nivo) of the antibody Ab10 of the present disclosure to the two targets of CLDN18.2 and PD-1 was not affected.

These data indicate that the activity of the sequence-based IgG like bispecific antibody (SBody for short in the present disclosure) designed based on the anti-CLDN18.2 antibody sequence of the present disclosure and different PD-1 antibody sequences is related to the sequences and the positions of the scFv. SBody has unexpected activities to the two targets due to sequence combinations and the position of scFvs.

For example, the effects of the binding activities of LB309 (Ab10 scFv at the C-terminal of NivoVH-Hc), LB308 (Ab10 scFv at the C-terminal of Pem VH-Hc), and LB310 (Ab10 scFv at the C-terminal of Ba08 VH-Hc) to PD-1 were 1.33, 0.93, and 0.56-fold changes, respectively; the effects of the binding activities to CLDN18.2 were 4.2, 6.5, and 7.3, respectively. That is to say, designed in the same way, three bispecific antibody molecules with different PD-1 antibody sequences have almost no effect on the binding activity to PD-1. However, it has a great effect on the binding activity to CLDN18.2, and the molecules have better activities in such a design that Ab10 scFv is at the C-terminal of NivoVH-Hc (LB309).

Comparing the activity data of LB302/LB3301LB307 and 13309/LB308/LB310, it is found that with the same sequence, scFvs at the N-terminal of He has less effect on the activity than that at C-terminal. For the bispecific antibody designed based on the sequences of the CLDN18.2 antibody of the present disclosure and the PD-1 antibody, the scFv at the N-terminal of He is a more optimized bispecific antibody design.

Comparing LB301 and LB156, it is found that for the bispecific antibody designed by the present disclosure, with the scFvs being different, but the positions thereof being the same (all at the N-terminal of the heavy chain), if the scFv is directed to PD-1, the (LB156) binding activity thereof to PD-1 is not weakened (the activity is changed by 0.34 times, namely, the activity is enhanced), but the activity to CLDN18.2 is changed by 4.8 times, namely, the activity is weakened by 3.8 times. If the scFv at N-terminal is directed to CLDN18.2, the binding thereof (LB301) to PD-1 is changed by 3.2 times, namely, it is weakened by 2.2 times; the binding activity thereof to CLDN18.2 is changed by 2.1 times, namely, it is weakened by 1.1 times. The effect of this structure on activity is very different from that of LB156.

Comparing LB302 and LB309, it was found that for the scFvs for the same target, for example the scFvs for CLDN18.2, unexpectedly, different positions thereof have a very significant difference in the effects on the activities of LB302 and LB309. The binding activity of LB302 to PD-1 is changed by 0.68 times (close to 1, namely, no effect), and the binding activity thereof to CLDN18.2 is changed by 1.18 times (no effect). The binding activity of LB309 to PD-1 is changed by 4.2 times, namely, the activity is weakened by 3.2 times, and there is almost no effect on the binding activity thereof to CLDN18.2 (the activity is changed by 1.33 times). That is to say, scFv is better at the N-terminal of the heavy chain than at the C-terminal.

Comparing LB312 and LB313, it was found that with the scFv for the same target, such as for the bispecific antibodies designed with Ab10 scFv and PD-1 antibody (Pem), and Ab10 scFv linked to the light chain of PD-1 antibody, unexpectedly, different positions of scFvs have a very significant difference in the effects on the activities of LB312 and LB313. The Ab10 scFv of LB312 is at the N-terminal of Pem Lc, and the Ab10 scFv of LB313 is at the C-terminal of Pem Lc. The binding activity of LB313 to CLDN18.2 was weakened by more than 10 times, and the binding activity of LB312 was weakened by 1.6 times. Both have similar effects on binding activity to PD-1. That is to say, Ab10 scFv is better at the N-terminal of the light chain than at the C-terminal.

It was unexpectedly found that adding 1 copy of Ab10 scFv (LB314) to the C-terminal of the heavy chain of the PD-1 antibody did not increase the binding activity to CLDN18.2 (compared with LB302), and weakened the binding activity of PD-1, wherein the fold change was 5.2 times. That is to say, adding a copy of Ab10 scFv to the C-terminal of the Nivo heavy chain can weaken the binding activity to the two targets or even hinder the binding.

In addition, in order to more accurately evaluate the binding level of the bispecific antibody of the present disclosure, the affinity of LB302 and LB301 to PD-1 was detected by Biacore. Specifically, the affinities of LB302 vs Nivo (L101), LB301 vs Pem GL105) to human PD-1-his (expressed by the method in Example 1 of the present disclosure) were measured with Biacore T200 (GE Healthcare) instrument. Firstly, using a running buffer HBS-EP+ with pH 7.4 (10 mM of HEPES, 150 mM of NaCl, 3 mM of EDTA and 0.05% of P20), protein A (Thermo Pierce, Cat #21181) was conjugated with the biosensor chip CM5 (Cat. #BR-1005-30, GE), the chip was activated with freshly prepared 50 mM of NHS (N-hydroxysuccinimide) and 200 mM of EDC (1-ethyl-3-(3-dimethylamino propyl) carbodiimide hydrochloride), and then 10 μg/ml of Protein A prepared with 10 mM of NaAC with pH 4.0 was injected. The sample to be tested was diluted with the running buffer to a concentration of 1 pg/ml, the signal was captured at approximately 50RU, and the concentration gradient of the antigen PD-1-his started from 100 nM, diluted by 3 times, at a flow rate of 30 l/min, binding time of 180 seconds, and dissociation time of 300 seconds. After the experiment, the chip was washed with 10 mM of Glycine-HCl with pH 1.5 at 30 μl/min for 30s. The experimental data was fitted with a 1:1 Langmuir model using Biacore T200 evaluation version 3.0 (GE) software to obtain the affinity value KD. Results: LB302, 10.4 nM vs L101, 8.6 nM; LB301, 6.5 nM vs L105, 4.4 nM. The affinity (KD) measured by the Biacore is consistent with the results of preceding ELISA, namely, the SBody molecules LB302 and LB301 of the present disclosure retain the binding activities to PD-1, which are closed to that of the corresponding antibody.

The activities of LB3022 and LB3012 designed based on the Ab6 sequence (see above table) are similar to those of LB302 and LB301.

These data indicate that the IgG like bispecific antibody (anti-CLDN18.2 and human PD-1) SBody designed based on the antibodies Ab10 and Ab6 of the present disclosure is sequence-dependent and sequence position-dependent. For example, a bispecific antibody specifically designed based on the Ab10 sequence can achieve unexpected results, namely, a preferred design, for example, LB302 retains the binding activity to the two targets very well.

The methods in preceding examples are used to evaluate the activity (%) of the preferred molecules designed in the present disclosure in inducing the apoptosis to compare the functional activity of anti-CLDN18.2. Ab10 antibody under the same conditions and the same concentration (150 nM in this experiment) was used as a control for apoptotic activity. The activity (IC50) of preventing the binding of PD-1 antigen and the ligand PD-L1 was detected to evaluate the functional activity of anti-PD-1. The results are as shown in the following Table.

TABLE 38a

Evaluation of functional activities of preferred bispecific antibodies of the present disclosure

| Antibody number | Functional activity of CLDN18.2, in inducing the apoptosis of tumor cells (%) | PD-1 functional activity | |
|---|---|---|---|
| | | IC$_{50}$, nM | IC$_{50}$ fold change * |
| LB302 | 40.5 | 2.04 (3.17#) | 0.64 |
| LB309 | 18.4 | 0.8 (0.33) | 2.42 |
| LB301 | 26.7 | 11.2 (3.94) | 2.84 |
| LB308 | 10.7 | 1.93 (1.07) | 1.8 |
| LB307 | 24.2 | 19.6 (8.2) | 2.39 |
| LB310 | 10.0 | 1.86 (4.22) | 0.44 |
| Ab10 | 10.3 | NA | NA |

: The value in brackets is the activity IC50 of the monoclonal antibody corresponding to the same target in blocking the binding of antigens and ligands under the same experimental conditions. *: The IC50 fold change, namely, the ratio of the IC50 of the bispecific antibody and the corresponding monoclonal antibody (control antibody). The larger the ratio, the more weakened the functional activity of the designed bispecific antibody to a single target. For example, the ratio is 2, indicating that the functional activity of the designed bispecific antibody to the target is weakened by 1 time compared with that of the corresponding monoclonal antibody. A ratio within 2 is the experimental error range, namely, the activity is not affected. NA: Ab10 is not applicable for PD-1 functional activity detection, because Ab10 has no PD-1 functional activity.

The above-mentioned results indicate that LB302, LB308, and LB310 all retain the functional activity of anti-PD-1 antibody, which is no weakened, but enhanced (LB310). The enhanced activity may reflect the synergistic effects related to sequence design.

The functional activity data of anti-CLDN18.2 indicate that Ab10 scFv at the N-terminal of the heavy chain (LB302, 13301, LB307) has an enhanced/synergistic (compared with Ab10 antibody) effects on the anti-CLDN18.2 cell activity, and this is indeed the case for different PD-1 antibodies (Pem, Nivo, Ba08). Ab10 scFv at the C-terminal of the heavy chain (LB309, LB308, LB310) retains the anti-CLDN18.2 cell activity. These data indicate that the bispecific antibodies (SBody) designed based on the Ab10 antibody of the present disclosure have unexpected activity effects due to different designs.

According to Stability evaluation, it was found (see preceding examples for the method) that bispecific antibodies (SBody) LB302, LB309, LB156, LB301, LB308, LB307, LB310, LB312, LB313, LB314, LB3022 and LB3012 were degraded to varying degrees after being stored at 37° C. for 14 days, and the binding activity to PD-1 and CLDN18.2 was weakened, some weakened by more than 10 times. When stored at −80° C. for 60 days and at 4° C. for 14 days, the bispecific molecules show no change in activities, indicating that these bispecific molecules can be stored stably at −80° C. and 4°.

TABLE 38b

Expression levels of bispecific antibodies designed for the two targets of CLDN18.2 and PD-1

| Antibody number | Antibody expression level (mg/L) |
|---|---|
| LB302 | 2.57 |
| LB309 | 28.7 |
| LB156 | 0.42 |
| LB301 | 1.42 |
| LB308 | 8.85 |
| LB307 | 3.90 |
| LB310 | 8.86 |
| LB312 | 3.25 |
| LB313 | 5.83 |
| LB314 | 0.2 |

The above-mentioned results indicate that for the bispecific antibodies designed by the present disclosure, with the same Ab]0 antibody scFv sequence and different positions thereof in the PD-1 antibody (LB302 vs LB309, LB301 vs LB308, LB307 vs LB310), the same Ab10 sequence and scFv sequence position and different PD-1 antibodies (LB302 vs LB3 vs LB307, LB309 vs LB308 vs LB3310), and the same Ab10 and PD-1 antibody scFv or Ab10 scFv sequence and PD-1 antibody (LB156 vs LB301), it is unexpectedly found that in different designs, expression levels were significantly related to the sequence. The highest yield of LB3095as 67 times higher than the lowest yield of LB156 (28.7/042) The same Ab-O scFv has a different expression level at the N-terminal (LB312) from the C-terminal (LB1313) of the same PD-1 antibody (Pem) light chain. The expression level of the molecule added with one copy of AB10 scFv (LB314) is 12 times lower than that of the molecule with a single copy Ab10 scFv (LB302) (2,57/0.2=12.9). These data indicate that the expression level of the bispecific antibody (SBody) designed based on the anti-CLDN18.2 antibody of the present disclosure is sequence specific. The sequence position and structure of Ab10O antibody in the bispecific antibody design are all related to the expression level.

LB302 light chain sequence: SEQ ID NO: 53; Sequence comprising a heavy chain: SEQ ID NO: 54.

Example 30 Design and Activity Evaluation of Bispecific Antibodies for the Two Targets of CLDN18.2 and PD-L1

In the present disclosure, bispecific antibodies were designed with different sequence structures for the two targets of CLDN18.2 and PD-L1, which are shown in the following table.

TABLE 39

Bispecific antibodies designed for the two targets of CLDN18.2 and PD-L1

| Antibody number | Light chain sequence | Sequence comprising a heavy chain |
|---|---|---|
| LB157 | Ab10VL-Lc (κ chain) | AtezoVL-$(G_4S)_3$-AtezoVH-$(G_4S)_3$-Ab10VH-Hc (hIgG1) |
| LB305 | AtezoVL-Lc (κ chain) | Ab10VL-$(G_4S)_3$-Ab10VH-$(G_4S)_3$-AtezoVH-Hc (hIgG1p*) |
| LB311 | AtezoVL-Lc (κ chain) | AtezoVH-Hc(hIgG1p*)-$(G_4S)_3$-Ab10VH-$(G_4S)_3$-Ab10VL |
| LB316 | AvelVL-Lc (λ chain) | Ab10VL-$(G_4S)_3$-Ab10VH-$(G_4S)_3$-AvelVH-Hc (hIgG1) |
| LB317 | AvelVL-Lc (λ chain) | AvelVH-Hc (hIgG1*)-$(G_4S)_3$-Ab10VH-$(G_4S)_3$-Ab10VL |
| LB319 | DurvVL-Lc (κ chain) | Ab10VL-$(G_4S)_3$-Ab10VH-$(G_4S)_3$-DurvVH-Hc (hIgG1p) |
| LB320 | DurvVL-Lc (κ chain) | DurvVH-Hc (hIgG1p*)-$(G_4S)_3$-Ab10VH-$(G_4S)_3$-Ab10VL |
| LB1572 | Ab6VL-Lc (κ chain) | AtezoVL-$(G_4S)_3$-AtezoVH-$(G_4S)_3$-Ab6VH-Hc (hIgG1) |
| LB3052 | AtezoVL-Lc (κ chain) | Ab6VL-$(G_4S)_3$-Ab6VH-$(G_4S)_3$-AtezoVH-Hc (hIgG1p*) |

*The hIgG1 constant region sequence here is same as the corresponding hIgG1 sequence of PD-L1 antibody. For example, it is same as Fc of Atezo, with N297A mutation The above-mentioned bispecific antibodies were cloned, expressed, and purified according to the method of Example 25 of the present disclosure, and the binding activities of these bispecific molecules to human CLDN18.2 and PD-L1 were detected using the methods of preceding examples. The results are as shown in the following Table.

TABLE 40

Binding activities of bispecific antibodies designed for the two targets of CLDN18.2 and PD-L1

| Antibody number | Binding activity to human CLDN18.2 | | Binding activity to human PD-L1 | |
|---|---|---|---|---|
| | $EC_{50}$, nM | $EC_{50}$ fold change * | $EC_{50}$, nM | $EC_{50}$ fold change * |
| LB157 | 0.33 (0.51#) | 0.65 | 0.078 (0.099#) | 0.79 |
| LB305 | 0.44 (0.33) | 1.33 | 0.11 (0.086) | 1.28 |
| LB311 | 0.76 (0.41) | 1.85 | 0.114 (0.1) | 1.14 |
| LB316 | 0.58 (0.31) | 1.87 | 0.076 (0.04) | 1.9 |
| LB317 | 1.72 (0.31) | 5.55 | 0.104 (0.04) | 2.6 |
| LB319 | 1.3 (0.7) | 1.86 | 0.086 (0.072) | 1.19 |
| LB320 | 2.04 (0.7) | 2.91 | 0.078 (0.072) | 1.08 |
| LB1572 | 0.55 (0.51) | 1.1 | 0.06 (0.099) | 0.6 |
| LB3052 | 0.64 (0.33) | 1.9 | 0.17 (0.086) | 2.0 |

: The value in brackets is the EC50 of the binding activity of the monoclonal antibody corresponding to the same target under the same experimental conditions. *: Under the same experimental conditions, the ratio of the binding activities EC50 of the bispecific antibody and the corresponding monoclonal antibody. The larger the ratio, the more weakened the binding ability of the designed bispecific antibody to a single target. For example, the ratio is 2, indicating that the binding activity of the designed bispecific antibody to the target is weakened by 1 time compared with that of the corresponding monoclonal antibody. The ratio is within 2, indicating that the binding activity is not affected.

Comparing LB157 and LB305, it is found that, after the antibody Ab10 of the present disclosure and PD-L1 antibody Atezo are designed as IgG like bispecific antibodies, unexpectedly, no matter whether the N-terminal of the heavy chain is Ab10 scFv or Atezo scFv, it does not affect the binding activity of the obtained bispecific antibodies to CLDN18.2 and PD-L1. Not only that, the protein stability test results indicate that after being stored at 37° C. for 14 days, LB157 and LB305 show no change in activity, and electrophoresis (PAGE) analysis show that obvious degradation of the antibodies are not seen. It indicates that the IgG like bispecific antibodies designed by the combination of the sequences of the antibody Ab10 of the present disclosure and Atezo can retain the binding activity to the two targets, and can be obtained by the conventional method for antibody purification, Protein A purification, wherein the process is simple, and the stability is good.

LB311 data indicates that in the SBody obtained by linking Ab10 scFv to the C-terminal of the heavy chain of the PD-L1 antibody Atezo, the binding activity to hCLDN18.2 and PD-L1 is not affected.

The data of LB316 and LB317 indicate that in the SBody designed by Ab10 scFv and PD-L1 antibody Avel, the effect thereof with Ab10 scFv at the N-terminal of Avel heavy chain is better, while the effect thereof with Ab10 scFv at both ends of Atezo heavy chain is good.

The data of LB319 and LB320 indicate that in the SBody designed by Ab10 scFv and PD-L1 antibody Durv, Ab10 scFv at the N-terminal of Durv heavy chain has no effect on the binding activity to CLDN18.2 and PD-L1. Ab10 scFv at the C-terminal of Durv heavy chain has a slight effect on the binding activity to CLDN18.2, while has no effect on the binding activity to PD-L1.

These data indicate that in the SBody designed by the 3 PD-L1 antibodies and Ab10 scFv, there are differences between the sequences for the binding activity to the two targets. Namely, the activity of SBody is sequence dependent. It is unexpected that the SBody designed by Ab10 scFv and Atezo is the best.

In addition, in order to more accurately evaluate the binding level of the bispecific antibody of the present disclosure, the affinity of LB157 and LB305 vs LB185 (Atezo) to PD-L1 was detected by Biacore. The Biacore method is the same as the method described in LB302. PD-L1-his (purchased from Sino biological, Cat #: 10084-H108H) is used instead of PD-1-his. The obtained affinity (KD) results: LB157 is 5.22 nM, LB305 is 3.08 nM, and LB185 is 1.97 nM. This result shows that Ab10 scFv in the SBody designed by anti-CLDN18.2 and PD-L1 (atezo) of the present disclosure has almost no effect on the binding activity of atezo (LB305 vs LB185), and atezo scFv at the N-terminal of Ab10 heavy chain slightly weakens the binding ability thereof to PD-L1 (LB157 vs LB185). This is basically consistent with the above-mentioned ELISA detection results, namely, the optimized SBody LB1157 and LB305 designed in the present disclosure retain the binding activity thereof to the two targets.

In addition, based on the Ab6 sequence, the designed LB1572 and LB3052 have almost no effect on the activities to CLDN18.2 and PD-L1.

The functional evaluation of the above-mentioned bispecific antibody includes CDC cell activity for CLDN18.2 and activity in blocking the binding to PD-1/PD-L1. The results are shown in the following table.

TABLE 41

Evaluation of functional activities of preferred bispecific antibodies designed for CLDN18.2 and PD-L1 in the present disclosure

| Antibody number | CLDN18.2 functional activity | | PD-L1 functional activity | |
|---|---|---|---|---|
| | EC50, nM | EC50 fold change* | IC50, nM | IC50 fold change * |
| LB157 | 5.03 (3.02#) | 1.7 | 2.49 (1.31#) | 1.9 |
| LB305w## | 7.57 (5.07) | 1.49 | 3.21 (3.31) | 0.97 |

: The value in brackets is the $EC_{50}$ or $IC_{50}$ of activity of the monoclonal antibody corresponding to the same target under the same experimental conditions. *: Under the same experimental conditions, the ratio of the activities of the bispecific antibody and the corresponding monoclonal antibody. A ratio within 2 (experimental error range) indicates that there is no difference in activities. ##: The LB305w heavy chain constant region does not have the mutations in the LB305 heavy chain constant region, so as to evaluate the CDC activity of this molecule on CLDN18.2+ cells.

The mice of C57BL/6 cnc strain (purchased from Zhejiang Weitonglihua Laboratory Animal Technology Co., Ltd, production license number: SCXK (Zhejiang) 2018-0001) was used to establish an animal efficacy model to evaluate the in vivo efficacy of the bispecific antibodies LB157 and LB305 of the present disclosure.

MC38 cells (purchased from the Cell Institute of the Chinese Academy of Sciences) were used to construct the stably expressed cell line MC38-804 required for this experiment (the construction method is the same as that in the preceding Example 1, replacing MC38 with CHO-K1). MC38-804 was cultured in DMEM/high glucose medium (Shanghai BasalMedia Technologies CO., Ltd, Cat. No.: L110KJ) containing 10% of fetal bovine serum (Shanghai BasalMedia Technologies Co., LTD, Cat. No.: BS-0002-500) and 1% Hepes (Thermo Fisher Technology (China) Co., Ltd, Cat. No.: 15630080), and continuously cultured in a 37° C. cell incubator containing 5% CO2. C57BL/6 cnc female mice, 6 weeks old, fed in SPF environment with 5 mice/cage, at a temperature of 20-25° C.; at 40%-60% humidity, free to eat and drink water, and the beddings were changed regularly.

When MC38-804 cells were at the logarithmic growth phase (the confluence rate was 80%-90%), same were digested with 0.25% trypsin, the cells were collected, and the cells were washed twice with a serum-free DMEM/high glucose medium, and finally resuspended in a serum-free DMEM/high glucose medium, the cells were counted, and Matrigel (purchased from BD Medical Devices Shanghai Co., Ltd, Cat. No.: 354234) was used at a ratio of 1:1 to adjust the cell concentration to $1\times10^7$ cells/ml for inoculation. The mice were inoculated with 100 μl of MC38-804 cell suspension ($1\times10^6$ cells) subcutaneously on the right ribs, the mice with a tumor cell size of approximately 120-150 mm³ were selected, and then grouped randomly, with 6 mice in each group.

The sample to be tested and the positive control were prepared with PBS and sterilized. The blank group was PBS. The PD-L1 antibody LB185+Ab10 was the drug combination of control group. LB157 and LB305 are the test groups of the respective bispecific antibody drugs. The mode of administration was intraperitoneal injection, and the dose to mice in the control group of the drug combination of LB185+Ab10 was 20 μg each antibody/200 μl/mouse. The administration dose of LB157 to mice was 26 μg/200 μl/mouse, and the administration dose of LB305 to mice was 26 μg/200 ul/mouse (at the same molar dose as the combination group of LB185 and Ab10). The frequency of administration in each group was BIW for 1.5 weeks.

The day of administration of the injection samples was day 0. Body weight and tumor volume were measured before each administration and recorded. The actual administration period in this experiment was 1.5 weeks, and the measurement period was 21 days.

Calculation formula for tumor sizes: Tumor volume TV (mm³)=0.5x (tumor long diameter× tumor short diameter²); relative tumor growth rate (RTV)=T/TO or C/CO. Relative tumor growth rate (T/C %)=100%*(T−T0)/(C−C0); Tumor inhibition rate (TGI)=(1-TIC)*100%; wherein TO and T are the tumor volumes at the beginning and end of the experiment in the sample group, respectively; C0 and C are the tumor volumes at the beginning and end of the experiment in the control group, respectively.

The results are shown in the table below.

TABLE 41b

In vivo efficacy of the preferred bispecific antibody designed for CLDN18.2 and PD-L1 in the present disclosure

| Groups | Mean tumor volume (mm³) D0 | SD | Mean tumor volume (mm³) D21 | SD | Tumor inhibition rate (%) |
|---|---|---|---|---|---|
| PBS | 136.01 | 30.99 | 4994.34 | 3727.92 | — |
| LB157 | 135.58 | 26.92 | 2372.70 | 2568.16 | 54 |

TABLE 41b-continued

In vivo efficacy of the preferred bispecific antibody designed for CLDN18.2 and PD-L1 in the present disclosure

| Groups | Mean tumor volume (mm³) D0 | SD | Mean tumor volume (mm³) D21 | SD | Tumor inhibition rate (%) |
|---|---|---|---|---|---|
| LB305 | 135.96 | 26.64 | 1090.70 | 1426.79 | 80 |
| LB185 + Ab10 | 136.12 | 26.73 | 2463.57 | 2147.90 | 52 |

The above-mentioned results indicate that the bispecific antibody LB157 for CLDN18.2 and PD-L1 in the present disclosure produced the same efficacy as the combination of the two monoclonal antibodies at the same molar dose, and the tumor inhibition rates on day 21 were 54% and 52%, respectively. Very surprisingly, the tumor inhibition rate of LB305 reached 80% on day 21, which was significantly better than the tumor inhibition rate (52%) of the combination of the two monoclonal antibodies.

LB305 light chain sequence: SEQ ID NO: 55; Sequence comprising a heavy chain: SEQ ID NO: 56;

Example 31 Design and Activity Evaluation of Bispecific Antibodies for the Two Targets of CLDN18.2 and CD47

In the present disclosure, bispecific antibodies were designed with different sequence structures for the two targets of CLDN18.2 and CD47, which are shown in the following table.

TABLE 42

Bispecific antibodies designed for the two targets of CLDN18.2 and CD47

| Antibody number | Light chain sequence | Sequence comprising a heavy chain |
|---|---|---|
| LB158 | Ab10VL-Lc (κ chain) | Hu5F9VL-(G4S)₃-Hu5F9VH-(G4S)₃-Ab10VH-Hc (hIgG1) |
| LB304 | Hu5F9-Lc (κ chain) | Ab10VL-(G4S)₃-Ab10VH-(G4S)₃-Hu5F9VH-Hc (hIgG4) |
| LB321 | Ab10VL-Lc (κ chain) | iMabVL-(G4S)₃-iMabVH-(G4S)₃-Ab10VH-Hc (hIgG1) |

The above-mentioned bispecific antibodies were cloned, expressed, and purified according to the method of Example 25 of the present disclosure, and the binding activities of these bispecific molecules to human CLDN18.2 and CD47 were detected using the methods of preceding examples. The results are as shown in the following table.

TABLE 43

Binding activities of bispecific antibodies designed for the two targets of CLDN18.2 and CD47 (ELISA, nM)

| Antibody number | Binding activity to human CLDN18.2 | | Binding activity to human CD47 | |
|---|---|---|---|---|
| | EC50, nM. | EC50 fold change* | EC50, nM | EC50 fold change* |
| LB158 | 0.96 (0.39#) | 2.5 | 0.11 (0.057#) | 1.9 |
| LB304 | 2.82 (0.33) | 8.5 | 0.42 (0.15) | 2.8 |
| LB321 | 0.366 (0.151) | 2.4 | 0.484 (1.38) | 0.4 |

: The value in brackets is the EC50 of the binding activity of the monoclonal antibody corresponding to the same target under the same experimental conditions. *: Under the same experimental conditions, the ratio of the binding activities EC50 of the bispecific antibody and the corresponding monoclonal antibody. The larger the ratio, the more weakened the binding ability of the designed bispecific antibody to a single target. For example, the ratio is 2, indicating that the binding activity of the designed bispecific antibody to the target is weakened by 1 time compared with that of the corresponding monoclonal antibody. The ratio is within 2, indicating that the binding activity is not affected.

The above-mentioned results (LB158 and LB304) indicate that, after the antibody Ab10 of the present disclosure and CD47 antibody Hu5F9 are designed to a IgG like form, when the Ab10 scFv is at the N-terminal of Hu5F9-Hc (LB304), it has a great effect on the binding activity of Ab10, and the EC50 is weakened by 7.5 times (8.5−1=7.5, see above table). The same sequence combination at different positions may be different. For example, when Hu5F9 scFv is at the N-terminal of the bispecific antibody (LB158), it has little effect on the binding activity to CLDN18.2 and CD47, and the EC50 is weakened by approximately 1 time (see above table).

The detection results of the functional activity of LB158 indicate that the activity IC50 of preventing the binding of CD47 and the ligand SIR-Pa is 1.13 nM, which is increased by 1.1 times than CD47 monoclonal antibody Hu5F9 with IC50=2.37 nM, namely, the functional activity is not weakened. The functional activity of CLDN18.2 is evaluated by inducing the apoptosis of tumor cells, wherein LB158 induces the apoptosis of tumor cells by 11%. Under the same conditions, Ab10 at the same concentration induces the apoptosis of tumor cells by 10.3%. Namely, the functional activity of LB158 anti-CLDN18.2 is not weakened.

The detection results of stability indicate that after storage at −80° C. for 60 days, 4° C. for 14 days, and 37° C. for 7 days and 14 days, LB158 was not degraded by electrophoresis (PAGE) analysis. The detection results of activity indicate that the binding activities of these 4 samples to CLDN18.2 are 0.68 nM, 0.98 nM, 0.67 nM, and 0.73 nM, respectively. The binding activities to CD47 are 0.08 nM, 0.12 nM, 0.16 nM, and 0.10 nM, respectively. It shows that under these storage conditions, LB158 is not only stable in molecular form (indicated by the result of electrophoresis), but also has a stable activity.

The results of LB321 indicate that the bispecific antibodies (iMab scFv at the N-terminal of the heavy chain of Ab10) designed by anti-CLDN18.2 antibody of the present disclosure and another CD47 antibody (iMab) retain the binding activity of anti-CLDN18.2, and the binding activity to CD47 is increased by 1.5 times (ECO: 0.484 nM vs 1.38 nM). The detection results of functional activities indicate that the activity IC50 of LB321 in preventing the binding of CD47 and the ligand SIRPα and that of LS956 (iMab) were changed 1.64 times. It shows that the functional activity of the anti-CD47 antibody in 13321 is not affected.

The detection results regarding stability indicate that after being stored at −80° C. for 60 days and 4° C. for 14 days, the binding activities of LB321 to CLDN18.2 and CD47 are not changed; after being stored at 37° C. for 14 days, the binding activity EC50 thereof to CLDN18.2 is changed from 0.99 nM to 10.1 nM, and the activity is weakened by nearly 10 times; the binding activity to CD47 is changed from 0.77 nM to 12.3 nM, and the activity is weakened by 15 times. It shows that LB321 is stable when stored at 4° C. or below. It also shows that among the SBody designed in the same way, due to the difference in CD47 antibody sequence, for example, in terms of stability, the stability of LB158 is better than that of LB321.

To compare the expression levels of the bispecific antibodies designed in the present disclosure, the results are shown in the following table.

TABLE 44a

Expression levels of bispecific antibodies designed for the two targets of CLDN18.2 and CD47

| Antibody number | Antibody expression level (mg/L) |
|---|---|
| LB158 | 27.9 |
| LB304 | 14.8 |
| LB321 | 13.6 |

The above-mentioned results indicate that for the bispecific antibodies designed in the present disclosure, with the same sequence while at different position (LB158 vs LB304), the expression levels thereof are quite different under the same conditions. The level of LB158 is more than 1 time higher than that of LB304. It shows that for the bispecific antibodies LB158 vs LB321 designed in the same way by different sequences (for the same target) and Ab10, the expression levels thereof under the same conditions are also quite different (37.9 vs 13.6).

These results show that the optimized bispecific molecules obtained from the antibody Ab10 of the present disclosure and CD47 antibody through optimized design (including sequence composition, and scFv position, etc.) can retain the binding activity to the two targets at the same time, and have good stability. The IgG like molecules can be purified by the same process as a conventional IgG, making subsequent development simpler and easier to do.

Example 32 Design and Activity Evaluation of Bispecific Antibodies for the Two Targets of CLDN18.2 and CD3

In the present disclosure, bispecific antibodies were designed with different sequence structures for the two targets of CLDN18.2 and CD3, which are shown in the following table.

TABLE 45

Bispecific antibodies designed for the two targets of CLDN18.2 and CD3

| Antibody number | Light chain sequence | Sequence comprising a heavy chain |
|---|---|---|
| LB155 | Ab10VL-Lc (κ chain) | BlincytoCD3VL-$(G_4S)_3$-BlincytoCD3VH-$(G_4S)_3$-Ab10VH-Hc (hIgG1) |
| LB195 | Ab10VL-Lc (κ chain) | BlincytoCD3VH-$(G_4)_3$-BlincytoCD3VL-$(G_4S)_3$-Ab10VH-Hc (hIgG1) |
| LB194 | Ab10VL-Lc (κ chain) | AMG420.CD3VL $(G_4S)_3$-AMG420.CD3VH-$(G_4S)_3$-Ab10VH-Hc (hIgG1) |
| LB193 | Ab10VL-Lc (κ chain) | AMG420.CD3VH-$(G_4S)_3$-AMG420.CD3VL-$(G_4S)_3$-Ab10VH-Hc (hIgG1) |
| LB196 | Ab10VL-Lc (κ chain) | Ab10VH-Hc (hIgG1)-$(G_4S)_3$-AMG420.CD3VH-$(G_4S)_3$-AMG420.CD3VL |
| LB303 | BlincytoCD3VL-Lc (κ chain) | Ab10VL-$(G_4S)_3$-Ab10VH-$(G_4S)_3$-BlincytoCD3VH-Hc (hIgG1) |
| LB1952 | Ab6VL-Lc (κ chain) | BlincytoCD3VH-$(G_4S)_3$-BlincytoCD3VL-$(G_4S)_3$-Ab6VH-Hc (hIgG1) |
| LB1932 | Ab10VL-Lc-$(G_4S)_3$-AMG420.CD3VH-$(G_4S)_3$-AMG420.VL | Ab10VH-Hc (hIgG1) |
| LB1934 | Ab10VL-Lc-$(G_4S)_3$-AMG420.CD3VL-$(G_4S)_3$-AMG420.VH | Ab10VH-Hc (hIgG1) |

The above-mentioned bispecific antibodies were cloned, expressed, and purified according to the method of Example 25 of the present disclosure, and the binding activities of these bispecific molecules to human CLDN18.2+ cells (ELISA) and CD3 (T cell) FACS were detected using the methods of preceding examples. The results are as shown in the following Table.

TABLE 46

Binding activity of bispecific antibodies designed for the two targets of CLDN18.2 and CD3

| Antibody number | Binding activity to human CLDN18.2 | | Binding activity to human T cell CD3 | |
|---|---|---|---|---|
| | EC50, nM | EC50 fold change* | EC50, nM | EC50 fold change ** |
| LB155 | 0.59 (0.27#) | 2.2 | 16.2 (16.2) | 1 |
| LB195 | 0.50 (0.27) | 1.9 | 5.0 (16.2##) | 0.31 |
| LB194 | 1.42 (0.27) | 7.2 | 7.2 (16.2) | 0.43 |
| LB193 | 0.66 (0.27) | 2.4 | 10.3 (16.2) | 0.62 |
| LB196 | 1.26 (0.36) | 3.5 | 22.0 (28.6) | 0.77 |
| LB303 | 1.1 (0.69) | 1.6 | 6.0 (19.7) | 0.3 |
| LB1952 | 0.76 (0.27) | 2.8 | 14.2 (16.2) | 0.88 |

: The value in brackets is the EC50 of the binding activity of the monoclonal antibody (Ab10) corresponding to the same target under the same experimental conditions. *: Under the same experimental conditions, the ratio of the binding activities (ELISA) EC50 of the bispecific antibody and the corresponding monoclonal antibody (Abi 0). The larger the ratio is, the more the binding ability of the designed bispecific antibody to CLDN18.2 is weakened. For example, the ratio is 2, indicating that the binding activity of the designed bispecific antibody to CLDN18.2 is weakened by 1 time compared with that of Ab1O. The ratio is within 2, indicating that the binding activity is not significantly affected (1 time of the experimental error range). ##: The value in brackets is the binding EC50 (FACS) value for LB155 under the same experimental conditions. **: The ratio of the binding activities of the bispecific antibody and LB155 under the same conditions. The ratio reflects the difference in binding activities between different CD3 antibodies with different structures such as VH-linker-VL and VL-linker-VH.

The above-mentioned results (LB155, LB195; LB194, LB193) indicate that, after the IgG like bispecific antibodies are designed by the antibodies Ab10 and CD3 of the present disclosure, CD3 scFv (from Blincyto or AMG420) at the N-terminus has a significant effect on the binding activities to Ab10 and CLDN18.2, wherein, the bispecific antibody LB194 designed by AMG420 scFv and Ab10 has the greatest effect on the binding activity to CLDN18.2, and the EC50 is weakened by 6.2 times (7.2−1=6.2). The results of LB195 vs. LB155 and LB194 vs. LB195 indicate that for the bispecific antibodies designed by the CD3 antibody and Ab10 of the present disclosure, when the CD3 scFv is at the N-terminal, VH1-Linker-VL retains the binding activity to the two targets better than VL-linker-VH.

In addition, by comparing the results of LB155, LB195, LB194, LB193 and LB303, it shows that the binding activity of the IgG like bispecific antibody designed by antibodies Ab10 scFv and CD3 is better retained than that of the bispecific antibody by antibodies CD3 scFv and Ab10.

The results of LB196 show that CD3 scFv at the C-terminal has no effect on the binding activity to CD3 (the fold change of activity is 0.77 (less than 1)), but it has a greater effect on the binding activity to CLDN 8.2. Under the same conditions, the binding activity of LB196 to CLDN18.2 was 2.5 times weaker than that of Ab10 to CLDN18.2 (3.5−1=2.5). It shows that among the bispecific antibodies composed of CD3 scFv and Ab10 antibody, CD3 scFv at the N-terminus can better retain the binding activity to the two targets.

In the bispecific antibodies designed based on Ab6 and CD3 antibodies, the preferred molecule LB1952 basically retains the binding activity to CLDN18.2 and CD3.

The analysis of functional activity shows that the fold changes of the activities of LB195 and LB193 in activating CDC (the method of preceding examples is used to evaluate the function of anti-CLDN18.2) relative to Ab10 activity (EC5o) are 1.7 and 2.2 times, respectively. These fold changes are within the range of the experimental errors, that is to say, LB195 and LB193 retain the functional activity thereof on CLDN18.2. In the detection of the activity of activating PBMC to kill target cells (see preceding examples for the method), it was found that the activities of LB195 and LB193 are comparable, and the specific killing effect thereof on target cells is in a dose-effect relationship. At a concentration of 0.1 µg/ml, 30%-40% of target cells are lysed.

The analysis results regarding stability indicate that after being stored at −80° C. for 60 days, 4° C. for 14 days, 37° C. for 7 days, 37° C. for 14 days, etc., only for 37° C. for 14 days, on PAGE, a little degradation of LB195 and LB193 is found, and for other conditions, they are stable and no degradation is seen, and the activity does not change significantly.

These show that the preferred bispecific molecules LB195 and LB193 designed based on anti-CD3 scFv and Ab10 retain the binding activity to and the functional activity on the two targets. The molecules can be obtained by conventional IgG purification methods and can be stored stably.

TABLE 47a

Expression levels of bispecific antibodies designed for the two targets of CLDN18.2 and CD3

| Antibody number | Antibody expression level (mg/L) |
| --- | --- |
| LB155 | 11.5 |
| LB195 | 6.11 |
| LB194 | 14.7 |
| LB193 | 21.7 |
| LB196 | 67.0 |
| LB303 | 9.2 |

The above-mentioned results indicate that the bispecific antibody designed based on Ab10 and CD3 antibodies in the present disclosure with the optimal expression level is LB196.

Light chain sequence of the representing antibody LB193: SEQ ID NO: 38, which is the Ab10 light chain, see Example 6; Sequence comprising a heavy chain: SEQ ID NO: 4.

Example 33 Design and Activity Evaluation of Bispecific Antibodies for the Two Targets of CLDN18.2 and TGFβ

In the present disclosure, IgG like bispecific antibodies are designed with different sequences for the two targets of CLDN18.2 and TGFβ. Specifically, at the N or C-terminal of the light chain or heavy chain of the antibody Ab10 and Ab6 of the present disclosure, preferably the C-terminal of the heavy chain, TGFβ receptor II was fused, and the obtained molecule (TRAP) can bind to CLDN118.2, and can bind to TGFβ1, 2 and 3 at the same time. The design is shown in the table below.

TABLE 48

Bispecific antibodies designed for two targets of CLDN18.2 and TGFβ

| Antibody number | Light chain sequence | Sequence comprising a heavy chain* |
| --- | --- | --- |
| LB824** | AvelVL-Lc (λ chain) | AvelVH-Hc (hIgG1)-(G₄S)₃-TGFβRII |
| LB401 | Ab10VL-Lc (κ chain) | Ab10VH-Hc (hIgG1)-(G₄S)₃-TGFβRII |
| LB4012 | Ab6VL-Lc (κ chain) | Ab6VH-Hc (hIgG1)-(G₄S)₃-TGFβRII |

*The K at C-terminal of the heavy chain of hIgG1 is mutated to A.
**LB824 is the control molecule. The sequence is derived from WO 2015118175_1 (λ chain) and WO 2015118175_3. It is a trap molecule composed of PD-L1 antibody Avel and TGFβ receptor II (TGFβRII). The TGFβRII binding activity thereof can be used as a control for the molecule LB401 of the present disclosure.

The above-mentioned bispecific antibodies were cloned, expressed, and purified according to the method of Example 25 of the present disclosure, and the binding activities of these bispecific molecules to human CLDN18.2 and TGFβ were detected using the methods of preceding examples. The results are as shown in the following table.

TABLE 49

Binding activity of bispecific antibodies (TRAP) designed for CLDN18.2 and TGFB (ELISA, nM)

| Antibody number | Binding activity to human CLDN18.2 | Binding activity to human TGFβ | | |
| --- | --- | --- | --- | --- |
| | | TGFβI | TGFβII | TGFβIII |
| LB824 | NA | 0.28 | 22.5 | 12.7 |
| LB401 | 0.162 # | 0.26 | 11.8 | 7.6 |
| LB4012 | 0.151 | 0.31 | 14.2 | 8.9 |

: Under the same experimental conditions, the EC50 of Ab10=0.157 nM, namely, adding TGFβRII to the C-terminal of the heavy chain of LB401 did not affect the binding activity thereof to CLDN18.2. NA: Not applicable, the molecule does not target CLDN18.2.

The above-mentioned results of the binding activity of LB401 indicate that the antibody Ab10 of the present disclosure with TGFβRII linked to the C-terminal of the heavy chain thereof not only retains the binding activity thereof to human CLDN18.2, but also retains the binding activity thereof to TGFβI and the high selectivity to TGFβII and TGFβIII. In addition, comparing the binding activities of LB401 and LB824 to TGFβ, it is found that the binding activity of the LB401 obtained by fusing antibody Ab10 of the present disclosure with TGFβRII to TGFβ1, 2 and 3 is consistent with the binding profile of the Trap (LB824) of PD-L1 antibody fused with TGFβRII.

Ab10 is replaced by Ab6 to obtain LB4012, which also retains the binding activity to the two targets.

Figure 8:
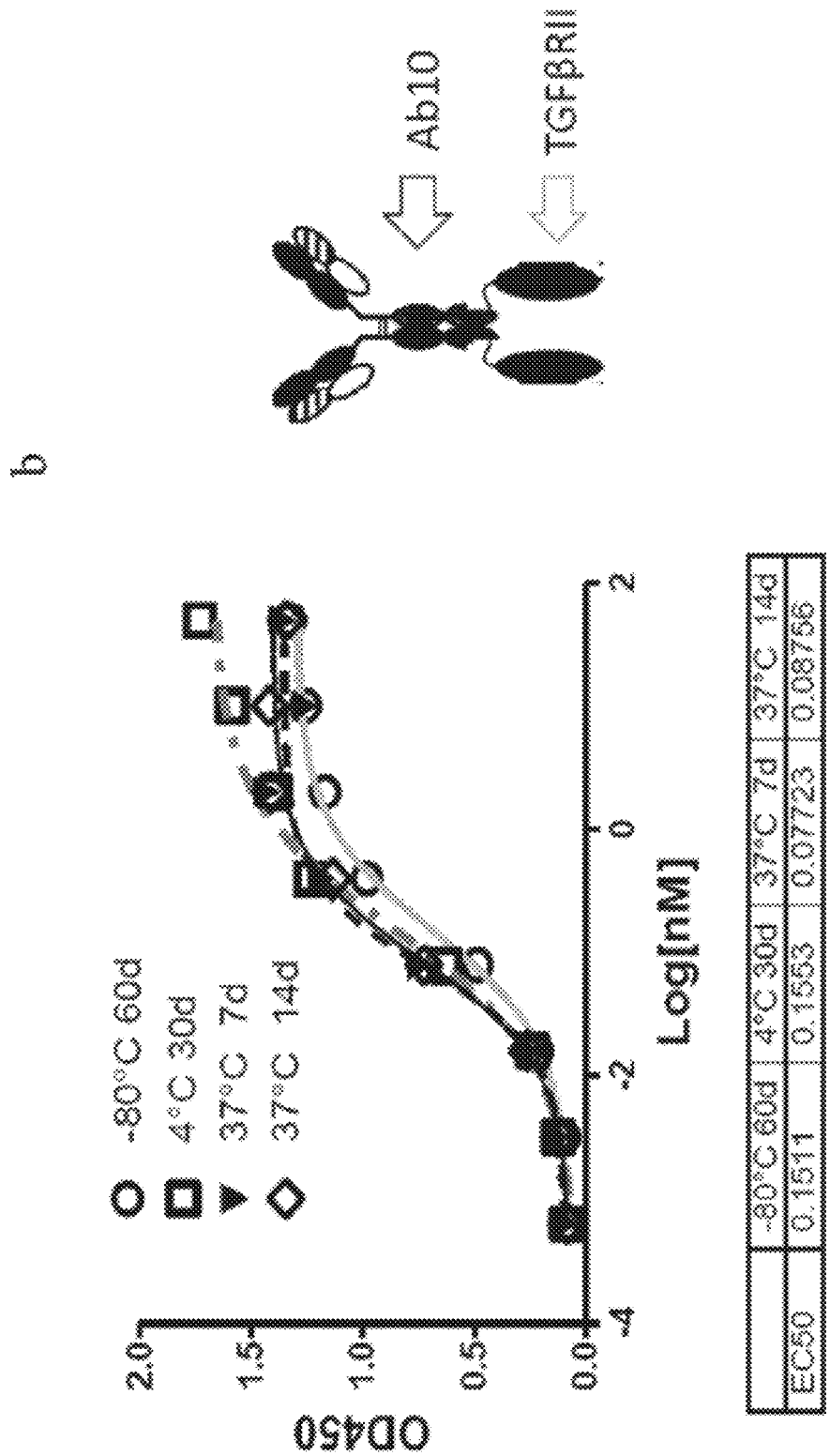
FIG. 8 is the structure of LB401 and a diagram of the related detection data, wherein a is the detection results of binding activity of samples stored at −80° C. for 60 days (60d), 4° C. for 30 days, and 37° C. for 7 days and 14 days to human CLDN18.2; b is the structure diagram of LB401.

The analysis results regarding stability indicate that LB401 is stable under storage conditions such as at −80° C. for 60 days, 4° C. for 30 days, 37° C. for 7 days, 37° C. for 14 days, etc. Electrophoresis (PAGE) analysis shows that degradation occurs when being stored at 37° C. for 14 days, and the binding activities to TGFβI, II, and III are weakened, and the binding activity to CLDN18.2 is not affected, as shown in FIG. 8. Therefore, LB401 is stable at −80° C. or 4° C.

In addition, LB401 and LB824 were evaluated for serum stability in parallel. Specifically, the blood of C57BL/6 mice (six weeks old, female, purchased from Shanghai Sippr-BK Laboratory Animal Co., Ltd) was taken, centrifuged at 12000 rpm for 10 minutes, and the serum was collected for later use. 3 µl of the sample (1 µg/µl, pH 7.4 PBS) was taken and diluted with 27 µl of the above serum to a final concentration of 0.1 µg/ml. The binding activity thereof to human CLDN18.2+ cells and TGFβI was detected after treatment at 37° C. for 0 h, 24 h and 72 h, respectively. Results are given below.

TABLE 50a

Serum stability test of bispecific antibodies (TRAP) designed for CLDN18.2 and TGFβ (ELISA, EC50, nM)

| Antibody number | Binding activity to human CLDN18.2 | | | Binding activity to human TGFβI | | |
|---|---|---|---|---|---|---|
| | 0 h | 24 h | 72 h | 0 h | 24 h | 72 h |
| LB824 | NA# | NA | NA | 1.58 | 1.73 | 4.95 |
| LB401 | 0.11 | 0.127 | 0.424 | 1.18 | 1.4 | 6.92 |

NA: Not applicable.

The above-mentioned results indicate that incubating LB401 in serum for 24 hours has no effect on the binding activity of LB401 to CLDN18.2 and TGFβI. After incubation for 72 hours, the binding activity to CLDN18.2 was weakened by more than 2 times (0.424 vs 0.11); the binding activity to TGFβI was also weakened, which is similar to the stability of the same type of molecule LB824 in current clinical trials.

The same animal model (MC38-804) and method as those in preceding Example 30 were used to evaluate the in vivo efficacy of the bispecific antibody (TRAP) designed for CLDN18.2 and TGFβ of the present disclosure. The sample to be tested and the positive control were prepared with PBS and sterilized. The blank group was PBS. Ab10 was the control group of a single drug, and LB824 was the control group of the bispecific antibody drug. LB401 is the test group of the preferred bispecific antibody drug of the present disclosure. The mode of administration is intraperitoneal injection. The dosage of Ab10 is 120 μg/200 μl/mouse, and the dosage of LB824 and LB401 is 160 μg/200 μl/mouse. The frequency of administration in each group is 2 times/week for 3 weeks. The results are shown in the table below.

TABLE 50b

In vivo efficacy of bispecific antibodies (TRAP) designed for CLDN18.2 and TGFβ in the present disclosure

| Groups | Mean tumor volume (mm³) D0 | SD | Mean tumor volume (mm³) D24 | SD | Tumor inhibition rate |
|---|---|---|---|---|---|
| PBS | 136.01 | 30.99 | 6820.98 | 4897.32 | — |
| LB824 | 137.25 | 30.42 | 3100.58 | 4142.46 | 56% |
| LB401 | 137.66 | 30.07 | 2770.72 | 2324.22 | 61% |
| Ab10 | 138.04 | 29.92 | 6048.36 | 2786.19 | 12% |

The above-mentioned results indicate that in this animal model, the efficacy of Ab10 alone is very weak, with a tumor inhibition rate of only 12% on day 24. The molecule LB824 (as a pharmacodynamic model control molecule) for PD-L1 and TGFβ shows a tumor inhibition rate of 56% on day 24. Very surprisingly, the bispecific antibody (TRAP) LB401 designed for CLDN18.2 and TGFβ in the present disclosure at the same molar dose as Ab10 has a tumor inhibition rate of 61% on day 24, which is better than that of LB824 (56%) and significantly better than that of Ab10 alone (12%).

The above-mentioned results indicate that the bispecific molecule optimally designed by anti-CLDN18.2 antibody and TGFβRII in the present disclosure retains a very good activity to the two targets, and has a significant efficacy in animals, and the molecule is stable, and the purification process (Protein A binding) is simple and easy to do.

LB401 light chain sequence (SEQ ID NO: 38), which is Ab10 light chain, see Example 6.

LB401 comprises the sequence of the heavy chain (SEQ ID NO: 57):

QVQLVQSGAEVKKPGSSVKVSCKASGYAFSNYLIEWVKQAPGQGLEWIGL

INPGSGGTNYNEKFKGKATITADKSTSTAYMELSSLRSEDTAVYYCARVY

YGNSFAYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGAGG

GGSGGGGSGGGGSGIPPHVQKSVNNDMIVTDNNGAVKFPQLCKFCDVRFS

TCDNQKSCMSNCSITSICEKPQEVCVAVWRKNDENITLETVCHDPKLPYH

DFILEDAASPKCIMKEKKKPGETFFMCSCSSDECNDNIIFSEEYNTSNPD

Example 34 Design and Activity Evaluation of Bispecific Antibodies for the Two Targets of CLDN18.2 and IL10

In the present disclosure, Abi 0 antibody and cytokine fusion molecules were designed for the two targets of CLDN18.2 and I10. Specifically, IL10 molecules were fused to the N and/or C-terminal of the light chain and heavy chain, preferably to the C-terminal and N-terminal of the heavy chain, of the antibodies Ab10 and Ab6 of the present disclosure. The design is shown in the following table.

TABLE 51

Bispecific antibodies designed for the two targets of CLDN18.2 and IL10

| Antibody number | Light chain sequence | Sequence comprising a heavy chain |
|---|---|---|
| LB432 | Ab10VL-Lc (κ chain) | IL10-(G₄S)₃-Ab10VH-Hc (hIgG1) |
| LB433 | Ab10VL-Lc (κ chain) | Ab10VH-Hc (hIgG1)-(G₄S)₃-IL10* |
| LB4331 | Ab10VL-Lc (κ chain) | Ab10VH-Hc (hIgG4)-(G₄S)₃-IL10 |
| LB4332 | Ab6VL-Lc (κ chain) | Ab6VH-Hc (hIgG1)-(G₄S)₃-IL 10 |
| LB4333# | Ab10VL-Lc (κ chain) | Ab10VH-Hc (hIgG1/L234A)-(G₄S)₃-IL 10* |
| LB4334 | Ab10VL-Lc (κ chain) | Ab10VH-Hc (hIgG1/L235A)-(G₄S)₃-IL 10* |
| LB4335 | Ab10VL-Lc (κ chain) | Ab10VH-Hc (hIgG1/L234A/L235A)-(G₄S)₃-IL10* |

*The K at C-terminal of the heavy chain of hIgG1 is mutated to A.
LB4333 is the same as LB433 except that the L234 of the Fc region thereof is mutated to A;
LB4334 is the same as LB433 except that the L235 of the Fc region thereof is mutated to A;
LB4335 is the same as LB433 except that the L234 and L235 of the Fc region thereof are mutated to A The above-mentioned bispecific antibodies were cloned, expressed, and purified according to the method of Example 25 of the present disclosure, and the binding activities of these bispecific molecules to human CLDN18.2 and IL10 were detected using the methods of the preceding examples. The results are as shown in the following table.

TABLE 52

Binding activities of bispecific antibodies designed for the two targets of CLDN18.2 and IL 10 (nM)

| Antibody number | Binding activity to human CLDN18.2 | | Binding activity to IL10 | |
|---|---|---|---|---|
| | EC50, nM | EC50 fold change* | Antigen-coated ELISA | Sandwich ELISA |
| LB432 | 0.74 (0.38#) | 1.9 | 0.34 | 11.3 |
| LB433 | 0.86 (0.38) | 2.3 | 0.14 | 0.77 |
| LB4332 | 0.78 (0.38) | 2.1 | 0.2 | 0.9 |

: The value in brackets is the EC50 of the binding activity of the monoclonal antibody (Ab10) corresponding to the same target under the same experimental conditions. *: Under the same experimental conditions, the ratio of the binding activities (ELISA) EC50 of the bispecific antibody and the corresponding monoclonal antibody (Ab10). The larger the ratio is, the more the binding ability of the designed bispecific antibody to CLDN18.2 is weakened. For example, the ratio is 2, indicating that the binding activity of the designed bispecific antibody to CLDN]8.2 is weakened by 1 time compared with that of Ab10. The ratio is within 2, indicating that the binding activity is not significantly affected (1 time of the experimental error range).

The above-mentioned results of binding activities show that the binding activities of the bispecific molecules LB432, LB433 and LB4332 to CLDN18.2 designed by the antibody Ab10 of the present disclosure and cytokine IL10 are the same as Ab10 and Ab6 (the activity change is approximately 2 times). The binding activity to IL10 was evaluated by antigen-coated ELISA and sandwich ELISA. Specifically, the antigen-coated ELISA detection method is seen in preceding Example 3. Results show that the EC5O of LB432, LB433 and LB4332 are 0.34, 0.14 and 0.2 nM, respectively. The difference in activity is approximately 2 times, which is close to the experimental error range.

Under the same conditions, the binding activity of IL10 (Peprotech, Cat #: 200-10) was detected by ELISA, with EC50=4.53 nM. That is to say, the binding activity of the bispecific molecules 13432, LB433 and LB4332 of the present disclosure to IL]10 is stronger than that of the recombinant to IL 10.

Sandwich ELISA method: Human CLDN18.2+ constructed in Example 2 was taken, and plated on a 96-well plate (Corning, Cat #CLS3599-100EA) at 10×10$^4$/well, and after overnight incubation in a 37° C. incubator, the supernatant was removed, and fixed with 100 μl/well of immunostaining fixative solution (Shanghai Beyotime Biotechnology Co., Ltd, Cat #P0098) for half an hour at room temperature. After being washed with PBS, the solution was blocked with 230 hl of 5% milk at 37° C. for 2 hours, and washed 3 times with PBST. The sample to be tested serially diluted by 5 times with 1% BSA was added at 50 hi/well, incubated at 37° C. for 1 hour, the plate was washed 5 times with PBST, and 1: 400 diluted HRP labeled rabbit anti-human IL10 (sino biological, Cat #SEKA10947) was added at 50 μl/well, incubated at 37° C. for 1 hour. After the plate was washed 5 times with PBST, TMB chromogenic substrate (KPL, 52-00-03) was added at 50 μl/well, incubated at room temperature for 5-10 min, added at 50 μl/well with 1M H2S04 to stop the reaction, and the absorption value at 450 nm was read using a MMLTISKAN Go microplate reader (ThermoFisher, 51119200) and the EC50 was calculated based on the OD value. The results of the sandwich ELISA indicate that the binding activity of LB432 (11.3 nM) is significantly weaker than that of LB433 (0.77 nM). It shows that the same IL10 sequence, no matter at the N-terminal or C-terminal of Ab10, has little effect on the binding activity thereof to CLDN18.2 and IL10, respectively; however, after LB432 binds to CLDN18.2, the activity of binding to IL10 is weakened by more than 10 times compared with LB433 (11.3 nM vs 0.77 nM)

That is to say, there is a "steric hindrance" when the N-terminal of LB432 is linked to IL10, namely, the activity of the obtained bispecific molecule in separately binding to the two targets is not affected, but the binding to either target prevents/affects the molecule from binding to the other target. In the other bispecific molecules SBody of the present disclosure, including LB302, LB301, LB157, LB305, LB158, LB195, LB196, LB401, etc., which have been detected by sandwich ELISA, it has not been found that the binding to either target affects the binding to the other target (steric hindrance).

The above-mentioned data indicates that it is unexpectedly discovered in the present disclosure that the optimized sequence of the bispecific antibody designed by antibodies Ab10 and IL10 is LB433, namely, the fusion of IL10 to the C-terminal of the heavy chain of Ab10 is optimal.

The analysis results of stability indicate that LB432 and LB433 are stable under storage conditions such as at −80° C. for 60 days, 4° C. for 30 days, 37° C. for 7 days, 37° C. for 14 days, etc. Electrophoresis (PAGE) analysis shows no significant degradation, indicating that LB432 and LB433 have a good stability.

In addition, LB432 and LB433 were evaluated for serum stability. Specifically, the blood of C57BL/6 mice (six weeks old, female, purchased from Shanghai Sippr-BK Laboratory Animal Co., Ltd) was taken, centrifuged at 12000 rpm for 10 minutes, and the serum was collected for later use. 3 μl of the sample (1 μg//μl pH 7.4 PBS) was taken and diluted with 27 μl of the above serum to a final concentration of 0.1 μg/ml. The binding activity thereof to human CLDN 182+ cells and IL10 antibody was detected after treatment at 37° C. for 0 h, 24 h and 72 h, respectively. Results are given below.

TABLE 53a

Serum stability test of the bispecific antibodies designed for the two targets of CLDN18.2 and IL10 (ELISA, EC50, nM)

| Antibody number | Binding activity to human CLDN18.2 | | | Binding activity to IL10 Ab | | |
|---|---|---|---|---|---|---|
| | 0 h | 24 h | 72 h | 0 h | 24 h | 72 h |
| LB432 | 0.357 | 0.535 | 1.20 | 0.083 | 0.083 | 0.115 |
| LB433 | 0.161 | 0.286 | 0.264 | 0.168 | 0.104 | 0.113 |

The above-mentioned results regarding serum stability indicate that after the incubation of LB433 serum for 72 hours, the binding activity thereof to CLDN18.2 is changed by 1.64 times (0.264/0.161), and under the same conditions, the binding activity of LB432 changed by 3.4 times (1.2/0.357); the binding activity of LB433 to IL10 changed by 0.67 times (0.113/0.168), and under the same conditions, that of LB432 changed by 1.4 times (0.115/0.083). It shows that the serum stability of LB433 is better than that of LB432.

TABLE 53b

Binding activity of Fc mutants of the bispecific antibodies designed for the two targets of CLDN18.2 and IL10 (nM)

| Antibody number | Binding activity to human CLDN18.2 | | Binding activity to IL10 (ELISA) | Binding activity to CD64 ELISA) |
|---|---|---|---|---|
| | EC50, nM | EC50 fold change | | |
| LB433 | 0.86 (0.42#) | 2 | 0.18 | Strong |
| LB4331 | 0.75 (0.42) | 1.8 | 0.15 | Weak |
| LB4333 | 0.91 (0.42) | 2.2 | 0.19 | Weak |
| LB4334 | 0.83 (0.42) | 1.98 | 0.23 | Weak |
| LB4335 | 0.88 (0.42) | 2.1 | 0.31 | Weak |

Description is the same as Table 52:

The above-mentioned results indicate that the binding activities of LB4331, LB4333, LB4334, and LB4335 (CLDN18.2, IL10) are similar to that of LB433. The difference of these molecules with LB433 lies in that the binding activity thereof to CD64 (FcγR I) is significantly weakened.

The same animal model (MC38-804) and method as in preceding Example 30 were used to evaluate the in vivo efficacy of the bispecific antibody designed for CLDN18.2 and IL10 of the present disclosure. The sample to be tested and the positive control were prepared with PBS and sterilized. The blank group was PBS. Ab10 is the control group of single drug administration. LB433 is the test group of the bispecific antibody drug. The mode of administration is intraperitoneal injection. The dosage of Ab10 is 60 μg/200 μl/mouse, and the dosage of LB433 is 80 μg/200 μl/mouse. The frequency of administration in each group was 2 times/week for 1.5 weeks. The results are shown in the table below.

TABLE 53c

In vivo efficacy of the bispecific antibody designed for CLDN18.2 and I10 in the present disclosure

| Groups | Mean tumor volume (mm³) | | Mean tumor volume (mm³) | | Tumor inhibition rate |
|---|---|---|---|---|---|
| | D0 | SD | D21 | SD | |
| PBS | 136.01 | 30.99 | 4994.34 | 3727.92 | — |
| LB433 | 137.95 | 29.92 | 1078.45 | 1864.76 | 81% |
| Ab10 | 137.13 | 29.35 | 4806.72 | 6524.25 | 4% |

The above-mentioned results indicate that in this animal model, the efficacy of Ab10 alone is very weak, and only 4% of tumor inhibition rate was shown on day 21, namely, no efficacy was seen in animals. Very surprisingly, the bispecific antibody LB433 designed for CLDN18.2 and I1 in the present disclosure at the same molar dose as Ab10 has a tumor inhibition rate of 81% on day 21, which is significantly better than that of Ab10 alone (4%), and P value of T test analysis<0.05.

LB433 light chain sequence (SEQ ID NO: 38) is same with Ab10 light chain, see Example 6.

LB433 sequence comprising a heavy chain (SEQ ID NO: 58):

QVQLVQSGAEVKKPGSSVKVSCKASGYAFSNYLIEWVKQAPGQGLEWIGL

INPGSGGTNYNEKFKGKATITADKSTSTAYMELSSLRSEDTAVYYCARVY

YGNSFAYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGAGG

GGSGGGGSGGGGSSPGQGTQSENSCTHFPGNLPNMLRDLRDAFSRVKTFF

QMKDQLDNLLLKESLLEDFKGYLGCQALSEMIQFYLEEVMPQAENQDPDI

KAHVNSLGENLKTLRLRLRRCHRFLPCENKSKAVEQVKNAFNKLQEKGIY

KAMSEFDIFINYIEAYMTMKIRN

LB4333 light chain sequence (SEQ ID NO: 38); LB4333 sequence comprising a heavy chain (SEQ ID NO: 59);

LB433 1 light chain sequence (SEQ ID NO: 38); LB4331 sequence comprising a heavy chain (SEQ ID NO: 60);

LB4335 light chain sequence (SEQ ID NO: 38); LB4335 sequence comprising a heavy chain (SEQ ID NO: 61):

QVQLVQSGAEVKKPGSSVKVSCKASGYAFSNYLIEWVKQAPGQGLEWIGL

INPGSGGTNYNEKFKGKATITADKSTSTAYMELSSLRSEDTAVYYCARVY

YGNSFAYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPEAAGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGAGG

GGSGGGGSGGGGSSPGQGTQSENSCTHFPGNLPNMLRDLRDAFSRVKTFF

QMKDQLDNLLLKESLLEDFKGYLGCQALSEMIQFYLEEVMPQAENQDPDI

KAHVNSLGENLKTLRLRLRRCHRFLPCENKSKAVEQVKNAFNKLQEKGIY

KAMSEFDIFINYIEAYMTMKIRN

Example 35 Design and Activity Evaluation of Bispecific Antibodies for the Two Targets of CLDN18.2 and LAG3, CLDN18.2 and Tim3

In the present disclosure, bispecific antibodies are designed for the two targets of CLDN18.2 and LAG3 and the two targets of CLDN18.2 and Tim3 respectively, shown in the following table.

TABLE 54

Bispecific antibodies designed for the two targets of CLDN18.2 and LAG3, and the two targets of CLDN18.2 and Tim3

| Antibody number | Light chain sequence | Sequence comprising a heavy chain |
|---|---|---|
| LB154 | Ab10VL-Lc (κ chain) | LAG3VL-(G$_4$S)$_3$-LAG3VH-(G$_4$S)$_3$-Ab10VH-Hc (hIgG1) |
| LB1541 | Ab10VL-Lc (κ chain) | Tim3VL-(G$_4$S)$_3$-Tim3VH-(G$_4$S)$_3$-Ab10VH-Hc (hIgG1) |

The above-mentioned bispecific antibodies were cloned, expressed, and purified according to the method of Example 25 of the present disclosure, and the binding activities of these bispecific molecules to human CLDN18.2 as well as LAG3 and Tim3 were detected using the preceding ELISA method. The results are as shown in the following table.

TABLE 55

Binding activities of bispecific antibodies for CLDN18.2 and LAG3, CLDN18.2 and Tim3 (ELISA, nM)

| Bispecific antibody number | Binding activity to human CLDN18.2 | | ELISA binding activity | |
|---|---|---|---|---|
| | EC50, nM | EC50 fold change* | EC50, nM | EC50 fold change ** |
| LB154 | 1.01 (0.33 #) | 3.1 | 0.20 (0.39) | 0.51 |
| LB1541 | 0.64 (0.33) | 1.9 | 0.1 (0.06) | 1.7 |

: The value in brackets is the EC50 of the binding activity of the monoclonal anti body (Ab10) corresponding to the same target under the same experimental conditions. *: Under the same experimental conditions, the ratio of the binding activities (ELISA) EC50 of the bispecific antibody and the corresponding monoclonal antibody (Ab10). The larger the ratio is, the more the binding ability of the designed bispecific antibody to CLDN18.2 is weakened. For example, the ratio is 2, indicating that the binding activity of the designed bispecific antibody to CLDN18.2 is weakened by 1 time compared with that of Ab10. The ratio is within 2, indicating that the binding activity is not significantly affected (the experimental error range). **: Under the same experimental conditions, the ratio of the binding activities ELISA (LAG3 antibody EC50: 0.39 nM; Tim3 antibody EC50: 0.06 nM) EC50 of the bispecific antibody and the corresponding monoclonal antibody. For LAG3 antibody sequence and other information, see the patent number: 201810917684.X. For Tim3 antibody sequence and other information, see the patent application number: 201710348699.4.

The above-mentioned results indicate that the IgG like bispecific antibody molecules (scFv at the N-terminal of the heavy chain of Ab10) designed by the antibody Ab10 of the present disclosure and antibodies LAG3 and Tim3 retain the binding activities to CLDN18.2, LAG3 and Tim3, and can be stably expressed and purified.

Example 36 Design and Evaluation of DVD Structure of the Two Target Antibodies of CLDN18.2 with PD-1, PD-L1, CD47, Respectively In the present disclosure, bispecific antibodies are designed in DVD form for CLDN18.2 and PD-1, PD-L1, and CD47 respectively, shown in the following table.

TABLE 56

Design of the bispecific antibodies in DVD form for the two targets of CLDN18.2/PD-1, CLDN18.2/PD-L1, CLDN18.2/CD47

| Antibody number | Sequence comprising a light chain | Sequence comprising a heavy chain |
|---|---|---|
| LB3021 | Ab10VL-$(G_4S)_3$-NivoVL-Lc (κ chain) | Ab10VH-$(G_4S)_3$-NivoVH-Hc (hIgG4) |
| LB1571 | Atezo VL-$(G_4S)_3$-Ab10VL-Lc (κ chain) | AtezoVH-$(G_4S)_3$-Ab10VH-Hc (hIgG1) |
| LB1581 | Hu5F9VL-$(G_4S)_3$-Ab10VL-Lc (κ chain) | Hu5F9VH-$(G_4S)_3$-Ab10VH-Hc (hIgG1) |

According to the method in Example 25 of the present disclosure, the above-mentioned bispecific antibodies were cloned, expressed, and purified, and the results of gel electrophoresis (PAGE) indicate that the light and heavy chains of these antibodies are prone to breakage between linkers. One target antibody is linked to the N or C-terminal of the light or heavy chain of another target antibody in the form of scFvs, and the designed optimized bispecific antibodies are obtained through screening, which can avoid/reduce the breakage between linkers (see preceding examples), and retain the binding activity to and functional activity on the two targets. The preferred bispecific antibody (called SBody in the present disclosure) is not only stable, but also similar to a conventional IgG, and the purification process is simple, which provides great convenience for the process and purification in the later development process.

Example 37 CAR Molecule Design for CLDN18.2

In the present disclosure, the new CAR molecule was designed for CLDN18.2, with reference to the previously published patent CN 106755107 A.

Specifically, the general formula of the nucleic acid construct of the CAR molecule designed in the present disclosure is CAR-[(IRES)-f]$_q$. In this general formula, CAR represents a chimeric antigen receptor, including scFv-H-TM-S-CD3ζ wherein scFv (single chain Fv) is a single chain variable fragment specifically targeting CLDN18.2 antigen, or called a single chain antibody or a single chain variable region. The sequence thereof is composed of the variable region sequence of the anti-CLDN18.2 antibody (see preceding examples) discovered in the present disclosure. The structure thereof is VL-Linker-VH or VH-Linker-VL, wherein the Linker is preferably $(G_4S)_w$, w is 0, 1, 2, 3, 4; preferably, w=3 or w=4. H is the hinge domain, TM is the transmembrane domain, and S is the co-stimulatory signaling domain. The co-stimulatory signaling domain includes a co-stimulatory molecule derived from CD28, and/or a co-stimulatory molecule derived from 4-1BB. In the general formula, CD3ζ is the cytoplasmic signaling sequence (intracellular region) derived from CD3.

IRES represents the sequence of internal ribosome entry site (IRES); f represents a coding functional protein F, and q is 0 or a non-zero natural number. The functional protein includes cytokines IL10, IL15 or active fragments thereof, and/or receptors of the cytokines such as IL15 receptor or active fragments thereof, and/or fusion fragments of the cytokines such as IL10, IL15 or active fragments thereof with IL15 receptor sushi+ fragment.

If there is no f part in the designed CAR molecule structure, the CAR molecule also has no IRES sequence. In addition, IRES and (IRES) represent the same meaning. When there are brackets "( )" outside IRES, it means that the IRES sequence is only present in the nucleic acid construct. When the nucleotide containing the IRES sequence is used to encode a protein, the IRES sequence does not encode the corresponding protein, so the nucleotide sequences before and after the IRES sequence encode different protein fragments (i.e., CAR and f), and the different protein fragments are separated.

In the above-mentioned CAR or CAR-(IRES)-f molecule, the scFv sequence designed according to the variable region of the anti-CLDN18.2 antibody sequence is a new antibody sequence of the present disclosure, see the above examples. The scFV can also be a Fab or the structure of a single domain antibody (sdFv). Other sequences (sequences other than scFvs) can be searched from the National Library of Medicine website http://xvwxv.pubmed.com, and GenBank database, including human CD8α signal peptide, human CD8α hinge region, CD8α transmembrane region, human CD28 intracellular region, human 4-1BB intracellular region, human CD3ζ intracellular region, internal ribosome entry elements (IRES elements), human IL15 (same as SEQ ID NO. 22 in patent CN 106755107 A), human IL15 receptor alpha (IL15Rα) wild type and mutant/sushi part (US 2014/01314; WO 2007/046006), human IL10 (SEQ ID NO: 2) protein sequence, etc. All base sequences constructed into the clone were codon-optimized according to the protein sequence to ensure that it is more suitable for human cell expression without changing the coding amino acid sequence.

The nucleotide sequence of IL10 is, for example, the sequence shown in GenBank Accession No. NM000572.

Specifically, the construction of the representative CAR molecule of the present disclosure refers to the method described in the patent application with publication number CN 106755107 A. The scFv encoding the c-Met antibody in the JX005 plasmid (derived from pBABEpuro) in Example 3 of the patent is replaced with the Ab10 scFv of the present disclosure to obtain the plasmid JX1a of the new CAR molecule CAR1a of the present disclosure. The amino acid sequence of CAR1a encoded by plasmid JX1a is:

```
                                         (SEQ ID NO: 3)
DIVMTQSPDSLAVSLGERATISCKSSQSLLNSGNQKNYLTWYQQKPGQPP

KLLIYWASTRESGVPDRFSGSGSGTDFTLTISSLQAEDVAVYYCQNDYFY

PFTFGQGTKLEIKGGGGSGGGGSGGGGSQVQLVQSGAEVKKPGSSVKVSC

KASGYAFSNYLIEWVKQAPGQGLEWIGLINPGSGGTNYNEKFKGKATITA

DKSTSTAYMELSSLRSEDTAVYYCARVYYGNSFAYWGQGTLVTVSSTTTP

APRPPTPAPTIASQPLSLRPEACRPAAGGAVHTRGLDFACDIYIWAPLAG

TCGVLLLSLVITLYCKRGRKKLLYIFKQPFMRPVQTTQEEDGCSCRFPEE

EEGGCELRVKFSRSADAPAYKQGQNQLYNELNLGRREEYDVLDKRRGRDP

EMGGKPRRKNPQEGLYNELQKDKMAEAYSEIGMKGERRRGKGHDGLYQGL

STATKDTYDALHMQALPPR
```

Specifically, at positions 1-246 are the coding sequence of Ab10 scFv; at positions 247-293 are the coding sequence of human CD8α hinge region (underlined part); at positions 294-315 are the coding sequence of human CD8α transmembrane region; at positions 316-357 are the coding sequence of 4-1BB intracellular region; and at positions 358-469 are the coding sequence of CD3zeta (Q intracellular signal region.

The nucleotides 1 to 63 (underlined part) are the signal peptide coding region. At positions 64-801 are the scFv coding sequence of the Ab10 antibody binding to CLDN18.2; at positions 802-942 are the coding sequence of human CD8α hinge region; at positions 943-1008 are the coding sequence of human CD8α transmembrane region; at positions 1009-1134 are the coding sequence of 4-11BB intracellular region; and at positions 1135-1470 are the coding sequence of CD3zeta (( ) intracellular signal region.

The scFv encoding the c-Met antibody in the JX007 plasmid constructed in Example 5 of the patent application with the publication number CN 106755107 A is replaced with the Ab10 scFv of the present disclosure (the method is the same as the construction method for JX1a of the present disclosure) to obtain the plasmid JX3ab of the new CAR molecule CAR3ab of the present disclosure. The amino acid sequence encoded by the plasmid JX3ab is the same as the above-mentioned encoding sequence of JX1a; in addition, the plasmid also encodes the active fragment of the cytokine IL15 (wild type). The nucleotide sequence of the IL1]5 active fragment can be any sequence used in the prior technology to encode the fragment, such as the nucleotide sequence at positions 699-1040 of SEQ ID NO: 31 of CN 106755107 A.

The sequence encoding IL15 in the plasmid JX3ab constructed above (for example, the nucleotide sequence at positions 699-1040 of SEQ ID NO: 31 of CN 106755107 A) was replaced with a sequence encoding IL10 (for example, the sequence shown in GenBank accession number NM_000572) to obtain the plasmid JX3ab10, the new CAR molecule CAR3ab10 of the present disclosure.

The above-mentioned plasmid JX3ab10 encodes the following IL10 protein sequence:

```
                                         (SEQ ID NO: 2)
SPGQGTQSENSCTHFPGNLPNMLRDLRDAFSRVKTFFQMKDQLDNLLLKE

SLLEDFKGYLGCQALSEMIQFYLEEVMPQAENQDPDIKAHVNSLGENLKT

LRLRLRRCHRFLPCENKSKAVEQVKNAFNKLQEKGIYKAMSEFDIFINYI

EAYMTMKIRN
```

The scFv encoding the c-Met antibody in the JX008 plasmid constructed in Example 6 of the patent CN 106755107 A is replaced with the Ab10 scFv of the present disclosure (the method is the same as the construction method for JX1a of the present disclosure) to obtain the plasmid JX4a of the new CAR molecule CAR4a of the present disclosure. In addition to the above-mentioned CAR1a coding sequence, the amino acid sequence encoded by JX4a also encodes the fusion protein of the active fragment (mutant) of the cytokine IL15 and IL15Rα (sushi+); sushi+ means that in addition to sushi fragments, other polypeptide fragments are also included.

Using the same method as above, the scFv of the Ab10 antibody was replaced with the scFv of the Ab6 antibody sequence to construct and obtain plasmids JX1a.2, JX3ab.2, JX3ab10.2 and JX4a.2 corresponding to new CAR molecules CAR1a.2, CAR3ab.2, CAR3ab10.2, and CAR4a.2.

Example 38 Identification of CAR Molecules Designed for CLDN18.2

Packaging, preparation and concentration of viruses: The preparation method of viruses refers to the method used in the patent CN 106755107 A, the three-plasmid virus packaging system of pGag-Pol, pVSVG and the new CAR molecule expression plasmid pBABEpuro of the present disclosure (all purchased from Youbao Bio), such as JX1a, JX3ab, JX3ab10 or JX4a were used to co-transfect the 293 cells to obtain the viral supernatant, which was concentrated by ultracentrifugation to obtain concentrated viruses.

Specifically, 6 μg of each of the packaging plasmids pGag-Pol, pVSVG and the expression plasmid JX1a, JX3ab, JX3ab10 or JX4a, and 36 μg of PEI (Polysciences, Inc, Cat #: 23966-2) were taken, mixed well, left to stand at room temperature for 5 minutes, and added to 293 cells (Cell Bank of the Type Culture Collection Committee of the Chinese Academy of Sciences). The mixture was cultured for 48 h to collect the first supernatant; on the next day, when cultured for 72 hours, the second supernatant was collected. The two batches of the supernatant were combined, added with 3 ml of 20% sucrose solution, and the viral supernatant was carefully plated on top of the sucrose solution centrifuged at 125000 g for 1.5 hours, and the precipitation was resuspended with PBS at a low temperature, split packed, and freeze-stored at −80° C. The viruses are marked as 1a, 3ab, 3ab10, and 4a, respectively. Ultra-centrifuge model: Beckman Coulter Optima XPN-100; rotor model: SW32i, ultra-centrifuge tube: Beckman 344058.

Detection of virus titer: The 293 cells were infected with serially diluted viruses, and after 48 hours, the virus titer was determined by the method of staining with protein L to determine the positive rate of the cells expressing scFvs. Specifically, 20 d of viruses (1a, 3ab, 3ab10, 4a) were taken, and 5-fold serial dilution was performed with RPMI 1640 medium (BasalMedia, Cat #L210KJ) containing 10% FBS (Gibco, Cat #: 10099141) and 0.8 µg of polybrene (Shanghai Yeasen Biotech Co., Ltd, Cat #: 40804ES76), with a final volume of 250 µl. The mixture was added to pre-plated 293, with the total culture system of 500 K/well, at 293 $5 \times 10^4$/well. After 48 hours, the cells were collected and 293 was labeled with biotin-protein L (GenScript, Cat. No. M00097) at 1 µl/sample. After incubation at room temperature for 20 min, 1 ml of FACS buffer was added to wash the cells by centrifugation. The cells were resuspended in 100 K of FACS buffer, added with PE labeled Strepavidin (eBioscience, Cat. No. 12-4317-87) at 0.4 K/sample, and after incubation at room temperature for 20 minutes, 1 ml of FACS buffer was added to wash the cells by centrifugation. The ratio of positive cells was detected by FACS, and the samples with a positive ratio of 10% are selected to calculate the virus titer: titer (IU/ml)=positive rate*number of 293 cells*dilution factor/volume of virus solution. The results indicate that the titers of 1a, 3ab, 3ab10 and 4a viruses obtained this time are 9.2, 1.3, 3.2 and $1.5 \times 10^6$ IU/m, respectively.

Preparation of CART cells: Fresh peripheral blood from healthy volunteers was taken, and peripheral blood mononuclear cells (PBMC) were separated using the same method as in patent CN 106755107 A. PBMC was activated with magnetic beads (Gibco, Cat. No. 1113 ID) conjugated with anti-human CD3 and CD28 antibodies for 40-48 h and then added with viruses 1a, 3a, 3ab10 and 4a (MOI in the range of 0.05-5) and polybrene (at a final concentration of 8 µg/ml). After infection for 3 hours, the fluid was refilled to 1 ml, and changed at night. The medium was RPMI 1640 containing 10% FBS and 500 IU/mL of $1L_2$ (Beijing Sihuan Biopharmaceutical Co., Ltd, Cat #: S20040007). The medium was changed every other day and the culture volume was expanded at 1: 2 until enough cells were obtained for in vivo and in vitro experiments. After infection, the T cells of each CAR molecule (CART cells) were marked as CART1a, CART3ab, CART3ab10 and CART4a cells; uninfected T cells (empty vector) were used as negative cells (control).

Expression identification of the Ab10 antibody scFv of the CART molecule of the present disclosure: The above-mentioned CART cells were stained by Protein L to determine the expression of CART molecule scFv and the positive rate of infected cells. Specifically, $2 \times 10^5$ of infected T cells (CART cells) were collected, and the cells were labeled with biotin-protein L (Nanjing GenScript Biotechnology Co., Ltd, Cat. No. M00097) (the labeling method was the same as the preceding virus titer detection). FACS was used to detect the proportion of CART positive cells, and negative cells were used as controls. Positive rate=CART cell FACS (%)-negative cell (control) FACS (%), and the results are shown in Table 57a below.

CART1a.2, CART3ab.2, CART3ab10.2 and CART4a.2 were prepared in the same method as above. The positive rate of Ab6 antibody scFv was detected, which was close to those of CART1a CART3ab CART3ab10 and CART4a as shown in Table 57b.

TABLE 57a

Positive rate of Ab 10 antibody scFv expressed by CART cells of the present disclosure

| CART cells | Positive rate (%) |
|---|---|
| CART1a | 47.1 |
| CART3ab | 24.1 |
| CART3ab10 | 28.6 |
| CART4a | 25.7 |

TABLE 57b

Positive rate of Ab6 antibody scFv expressed by CART cells of the present disclosure

| CART cells | Positive rate (%) |
|---|---|
| CART1a.2 | 34.2 |
| CART3ab.2 | 23.3 |
| CART3ab10.2 | 27.5 |
| CART4a.2 | 20.9 |

The above-mentioned results indicate that the positive rate of the four CART cells (including Ab10 and Ab6 scFvs) in this experiment is 20%-47%, confirming that the obtained CART cells all express the scFv of Ab10 or Ab6 antibody normally. The CART1a, CART3ab, CART3ab10 and CART4a are used as examples to evaluate the activity and function of the CAR cells of the present disclosure below.

Identification of cytokines expressed and secreted by the CART cells designed in the present disclosure: the new CART cells CART3ab and CART4a designed in the present disclosure express and secrete cytokines IL15, IL15/IL15R; and CART3ab10 expresses and secretes the cytokine IL10. In order to identify the CART cells expressing and secreting the cytokines, the supernatant of the cultured CART cells was taken, and the expressions of IL10 and IL15 were respectively detected with an ELISA kit (Beijing Sinobiological Biotechnology Co., Ltd, Cat. No. SEKA10947, SEK10360). The results show that cytokines at 2256 µg/ml and 844 µg/ml can be only detected in the supernatant of CART3ab10 (repeated preparation of CART cells obtained from infecting with PBMC-derived T cells from different donors), and only the background values of 13.7 pg/ml and 5.3 µg/ml were detected in the CART1a supernatant prepared at the same time (repeated preparation of CART cells obtained from infecting with PBMC-derived T cells from different donors). The data shows that the CART3ab10 designed by the present disclosure specifically expresses and secretes the cytokine IL10. The ELISA method failed to detect the expression and secretion of IL]15 and IL15/IL15Rα, in the supernatant of CART3ab and CART4a, indicating that the amounts of cytokines IL15 and IL15/IL15Rα secreted by the cultured CART3ab and CART4a are low.

In view of the expression of IL15 and IL15/IL15Rα could not be detected in the supernatant of the cultured cells, the 4 CART cells produced were injected into mice respectively. Balb/c nude mice were taken and administered $1 \times 10^6$ CART cells via intravenous injection. Serum was collected on day 7 and day 14 after injection, and the levels of IL10 and IL15 in the serum were detected by ELISA. The results are shown in the table below.

TABLE 58

Evaluation of cytokine expression levels by CART cells of the present disclosure in mouse serums

| CART cells | IL10 (pg/ml) | | IL15 (pg/ml) | |
| --- | --- | --- | --- | --- |
|  | Day 7 | Day 14 | Day 7 | Day 14 |
| CART1a | 0 | 152.7 | 0 | 0 |
| CART3ab | NA* | NA | 0 | 118.8 |
| CART3ab10 | 5154.7 | 350.7 | NA | NA |
| CART4a | NA | NA | 206.4 | 18 |
| CART (blank) | 14 | 128.7 | 0 | 0 |

*Not applicable

The above-mentioned results indicate that the expression level of IL 10 reaches 5154.7 pg/ml on day 7 after CART3ab10 being administered to mice. On day 14, the expression level of IL10 is decreased to 350.7 pg/ml. No expression of IL10 was detected from CART1a and CART (blank) which were used as control samples, and the detected values of 14, 152.7 and 128.7 pg/ml were all background values. Il5 active fragment expression by CART3ab was detected on day 14, and the expression level was 118.8 pg/ml. IL15/IL15Rα expression by CART4a was detected on day 7, and the expression level was 206.4 pg/ml. No expression of IL15 was detected from CART1a and CART (blank) which were used as control samples, and the reading value was 0 (background).

The above-mentioned results indicate that the CAR-transfected T cells CART3ab and CART4a cells designed by the present disclosure express and secrete IL15 active fragments. CART3ab10 cells express and secrete IL10.

Example 39 Activity of CAR Cells Designed for CLDN18.2

In order to evaluate the in vitro activity of CART cells of the present disclosure, cells which highly express human CLDN18.2 (hCLDN18.2+ cells) were used as target cells, and cells which highly express human CLDN18.1 (hCLDN18.1+ cells) were used as negative control. With the killing of the two cells by CART cells, the survival ratio of the target cells was compared to evaluate the specific in vitro killing activity of CART cells. Specifically, hCLDN18.2+ cells were labeled with CFSE (Biolegend, Cat. No. 423801). The suspension of target cells was prepared with mixing the hCLDN18.1+ cells and CFSE labeled hCLDN18.2+ cells in equal proportions, each at $1.5 \times 10^7$ cells/ml. The killing experiments for target cells was carried out in a 24-well plate, with 100 µl of the suspension of target cells per well. CART1a, CART3ab, CART3ab10 and CART4a cells and negative cells (empty vectors) were diluted with the same medium to form different ratios of CART cells and target cells, which were 20:1,10:1,3: 1 and 1:1, respectively. In addition, a killing-free group was set up, namely, the group contains no CART cells, only the above-mentioned target cells. After CART cells and target cells were co-cultured for 16 hours, the supernatant was discarded, the remaining CART cells and the killed target cells were gently washed off with PBS, digested with trypsin and the target cells adhering to the culture plate were collected, and after staining with 7AAD (Biolegend: 420404), FACS was used to detect the ratio of 7AAD negative CFSE labeled hCLDN18.2+ cells/hCLDN18.1+ cells.

Specific lysis (killing) rate of target cells=1-[CART cells 7AAD negative hCLDN18.2+/hCLN18.1+]/[Negative control (empty vector) cells 7AAD negative hCLDN18.2+/hCLN18.1+]. The specific lysis (killing) rate of the target cells is high, namely, the specific killing effect of CART cells is strong. The following is the calculation result of killing rate of CART1a when the ratio of CART cells to target cells is 10:1. The data of the results of the negative control CART cells show that CLDN18.1: CLDN18.2 of live cells is 50.5% vs 48.6%, which is close to 1: 1, indicating that the negative control CART cells have no killing effect on non-target cells and target cells. The data of the results of CART1a cells show that CLDN18.1: CLDN18.2 of live cells is 57.5% vs 37.5%, indicating that CART1a cells have no killing effect on non-target cells (close to 50%), but have killing effect on target cells (CLDN18.2) (reduced from 50% to 37.5%). The calculation method of killing rates (%) is: 1-[(37.5%/57.5%)/(48.6%/50.5%)]=32.2%. The results are shown in the table below.

TABLE 59

In vitro cell activity of CART cells of the present disclosure (specific killing rate of target cells, %)

| CART cells | Ratio of CART cells to target cells | | | |
| --- | --- | --- | --- | --- |
|  | 20:1 | 10:1 | 3:1 | 1:1 |
| CART1a | 34.8 | 32.2 | 18.3 | 19.1 |
| CART3a | 24.3 | 21.8 | 3.1 | 3.9 |
| CART3ab10 | 21.2 | 12.2 | 0 | 0 |
| CART4a | 19.8 | 8.8 | 1.2 | 0 |

The above-mentioned results (for more than three repeated experiments, and for the negative control in each experiment, CART cells having no killing effect on non-target cells and target cells) indicate that the four CART cells of the present disclosure have killing effects on target cells at 20:1, and the killing rate is 19.8%-34.8%. As the ratio of CART cells:target cells decreases, the killing effect on target cells weakens, and the fastest weakening is shown in CART4a, CART3ab10 and CART3a. When the 3 CART cells are at a ratio of 3:1,1:1, basically no killing effect on the target cells was seen. This shows that the CART design of the present disclosure is related to cell function, and the effects produced show unexpected effects according to the different design.

Example 40 In Vivo Efficacy of CART Cells Designed for CLDN18.2 in Animals

The Balb/c nude mice were subcutaneously inoculated with hCLDN18.2+ cells to establish a tumor model. The mice were intravenously injected with CART cells, and the tumor volume (TV) and body weight (BW) were measured to evaluate the anti-tumor effect and safety of CART cells. Specifically, hCLDN18.2+ cells were cultured in DMEM/F12 medium containing 10% fetal bovine serum, and continuously cultured to the logarithmic growth phase in a 37° C. cell incubator containing 5% CO2 (the confluence rate was 80%-90%), and then digested with trypsin, and the cells were collected, washed twice with serum-free DMEM/F12, resuspended in PBS, and counted, and the cell concentration was adjusted to $1 \times 10^8$/ml. Balb/c nude mice were inoculated with 100 µl/mouse of the suspension of hCLDN18.2+ cells, subcutaneously on the right rib. Three weeks later, mice with a tumor volume of 80-130 mm³ were selected and grouped (2 mice/group) and intravenously injected with $2 \times 10^6$ CART cells/mouse. The day of administration was day 0. After that, the tumor volume was measured twice a week, the body weight was weighed, and the data was recorded.

Calculation formula for tumor sizes: Tumor volume TV (mm)=0.5×(tumor long diameter× tumor short diameter 2); Relative tumor volume (RTV)=TV/TV0, wherein TV0 is the tumor volume at the beginning (Day 0), which is set as 1. TV is the tumor volume at detection. Relative tumor volume (RTV) is the fold of tumor volume increase at each detection time point. Relative tumor growth rate (T/C %)=100%*(T-T0)/(C-C0); tumor inhibition rate (TGI)=(1-T/C)*100%. T0 and T are the tumor volumes at the beginning and end of the experiment in the sample group, respectively; C0 and C are the tumor volumes at the beginning and end of the experiment in the control group, respectively.

Figure 9:
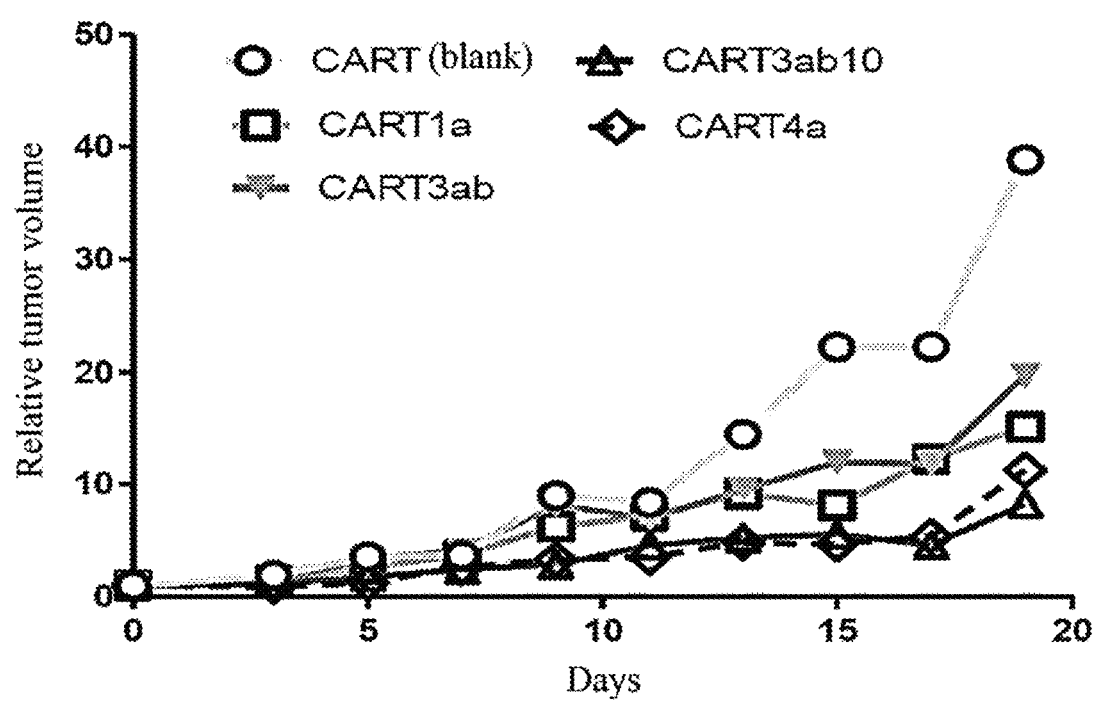
FIG. 9 shows the in vivo efficacy in animals of CART cells designed against CLDN18.2, and shows the tumor volume changes in mice injected with CART (empty vector), CART1a, CART3ab, CART3ab10 and CART4a cells.

The results indicate that two weeks after CART injection, the body weight of each mouse did not change significantly, indicating that CART cells did not have significant safety issues. In terms of efficacy, the tumor volume continued to increase from the day 13 to day 19 of CART (empty vector) injection into mice, and the increase fold (relative tumor volume) changed from 14 to 39 (FIG. 9). The tumor volume of mice injected with CART1a, CART3ab, CART3ab10 and CART4a cells all increased by less than 10 times (tumor inhibition rate was 40%-90%). In particular, the tumor volume of mice injected with CART3ab10 and CART4a cells showed almost no increase during the period from day 13 to day 17, achieving the effect of continuous inhibition (close to 100% inhibition). This result indicates that the CART cells produced by the different CAR molecules designed by anti-CLND18.2 antibodies of the present disclosure show an unexpected efficacy in animals.

Example 40 CARNK Cell Activity Obtained by Transfecting NK Cells with CAR Designed for CLDN18.2

NK92 (purchased from BeNa Culture Collection Co., Ltd) cells in a good state in the logarithmic growth phase were taken and added with viruses 1a, 3a, 3ab10, 4a (MOI in the range of 0.5-5) and polybrene (at a final concentration of 8 μg/mL). After infection for 3 hours, the fluid was refilled to 1 mL, and changed the next day. The medium was NK92 special medium (BeNa Culture Collection Co., Ltd). The medium was changed every other day and the culture volume was expanded at 1: 2 until enough cells were obtained for in vivo and in vitro experiments. The infected NK92 cells were marked as CARNK1a, CARNK3a, CARNK3ab10, and CARNK4a cells, respectively; uninfected NK92 cells were marked as CARNK (empty vector) and used as the negative control. 7 days after infection, the same method as in Example 38 was used to detect the expression on the surface of CARNK cells. The results are as shown in the following table.

TABLE 60

Positive rates of antibody scFvs expressed by CARNK cells constructed by anti-CLDN18.2 antibody of the present disclosure

| CARNK cells | Positive rate (%) |
|---|---|
| CARNK1a | 21 |
| CARNK3a | 22 |
| CARNK3ab10 | 30 |
| CARNK4a | 41 |

The above-mentioned results indicate that the newly designed CAR of the present disclosure can also express the scFv of antibody Ab10 and recognize human hCLDN18.2 well in NK cells.

Example 41 In Vivo Efficacy of CARNK Cells Designed for CLDN18.2 in Animals

The same animal model as in Example 7 above was used to evaluate the efficacy of CARNK cells of the present disclosure in animals. The prepared CARNK (empty vector) control, CARNK1a, CARNK3ab, CARNK3ab10, and CARNK4a cells were injected at $2 \times 10^5$/mouse, 2 mice in each group, once on Day 0 and Day 3, respectively. After that, the tumor size was detected 2 times a week, and the results are shown in Table 61 below.

TABLE 61

In vivo efficacy of CARNK cells constructed by anti-CLDN18.2 antibody of the present disclosure

| | Mean tumor volume (mm$^3$) and tumor inhibition rate (%) | | | | |
|---|---|---|---|---|---|
| Groups | Day 0 tumor volume | Day 11 tumor volume | Day 11 tumor inhibition rate | Day 13 tumor volume | Day 13 tumor inhibition rate |
| CARNK (blank) | 63.7 | 1094.3 | 0 | 1408.4 | 0 |
| CARNK1a | 74.0 | 934.5 | 16.5 | 972.4 | 33.2 |
| CARNK3ab | 65.9 | 883.9 | 20.6 | 933.2 | 35.5 |
| CARNK3ab10 | 67.2 | 576.8 | 50.6 | 596.3 | 60.7 |
| CARNK4a | 78.3 | 686.8 | 41.0 | 797.1 | 46.5 |

The results in Table 61 indicate that the CARNK cells constructed by the anti-CLDN18.2 antibody of the present disclosure still show tumor inhibitory effect on day 11 and day 13. The tumor inhibition rate was in the range of 16.5%-60.7%. CARNK3ab10 shows the best efficacy in animals.

All documents mentioned in this application are hereby incorporated by reference as if each document were individually incorporated by reference. In addition, it should be understood that after reading the above teachings of the disclosure, those skilled in the art can make various changes or modifications to the disclosure, and these equivalent forms also fall within the scope defined by the appended claims of this application.

What is claimed is:

1. An antibody targeting CLDN18.2, wherein the antibody targeting CLDN18.2 comprises a light chain variable region (VL) or a heavy chain variable region (VH), wherein the VL comprises the following complementary determining region (CDR) sequences:
   a VL CDR1 amino acid sequence as shown in SEQ ID NO: 11 or SEQ ID NO: 12; a VL CDR2 amino acid sequence as shown in SEQ ID NO: 13; and a VL CDR3 amino acid sequence as shown in SEQ ID NO: 14;
   and the VH comprises the following CDR sequences:
   a VH CDR1 amino acid sequence as shown in SEQ ID NO: 15; a VH CDR2 amino acid sequence as shown in SEQ ID NO: 16; and a VH CDR3 amino acid sequence as shown in SEQ ID NO: 17.

2. The antibody targeting CLDN18.2 as defined in claim 1, wherein the antibody targeting CLDN18.2 is a humanized antibody;
   wherein the BL comprises the amino acid sequence as shown in SEQ ID NO: 29; the NG comprises the amino acid sequence as shown in SEQ ID NO: 34; or, the VL comprises the amino acid sequence as shown in SEQ ID NO: 31; the VH comprises the amino acid sequence as shown in SEQ ID NO: 34.

3. The antibody targeting CLDN18.2 as defined in claim 1, comprising the following light chain and heavy chain, the heavy chain is as shown in the amino acid sequence of SEQ ID NO: 39, and the light chain is as shown in the amino acid sequence of SEQ ID NO: 38; or, the heavy chain is as shown in the amino acid sequence of SEQ ID NO: 39, and the light chain is as shown in the amino acid sequence of SEQ ID NO: 42.

4. A bispecific antibody, comprising a first protein functional region and a second protein functional region, wherein the first protein functional region is the antibody targeting CLDN18.2 as defined in claim 1; and the second protein functional region is an antibody targeting a non-CLDN18.2 antigen, or, the second protein functional region is a cytokine or a cytokine receptor, or a fragment thereof;
   the non-CLDN18.2 antigen is an immune checkpoint antigen or a tumor therapeutic target, the immune checkpoint antigen includes PD-1, PD-L1, Tim3, LAG3 and CD47, and the tumor therapeutic target-includes SIRPα; the second protein functional region is an anti-PD-1 antibody, an anti-PD-L1 antibody, an anti-Tim3 antibody, an anti-LAG3 antibody, an anti-CD47 antibody, an anti-CD3 antibody and an anti-CSF-1R antibody.

5. The bispecific antibody as defined in claim 4, wherein the first protein functional region is an immunoglobulin, and the second protein functional region is one or more scFvs, cytokines or fragments thereof, or cytokine receptors or fragments thereof; or, the second protein functional region is an immunoglobulin, and the first protein functional region is one or more scFvs; wherein, the scFv comprises a heavy chain variable region and a light chain variable region, and the heavy chain variable region is linked to the light chain variable region via a linker; the scFv, the cytokine or the fragment thereof, or the cytokine receptor or the fragment thereof is linked to the immunoglobulin via a linker.

6. The bispecific antibody as defined in claim 5, wherein the structure of the scFv is light chain variable region-linker-heavy chain variable region, and the N-terminal of the light chain variable region of the scFv or the C-terminal of the heavy chain variable region of the scFv is respectively linked to the C-terminal or N-terminal of the light chain or heavy chain of the immunoglobulin via a linker; or the structure of the scFv is heavy chain variable region-linker-light chain variable region, and the N-terminal of the heavy chain variable region of the scFv or the C-terminal of the light chain variable region of the scFv is respectively linked to the C-terminal or N-terminal of the light chain or heavy chain of the immunoglobulin via a linker; the linker is $(G_4S)_3$ (residues 449-463 of SEQ ID NO: 61), or, the bispecific antibody has two scFvs and the two scFvs are symmetrically linked to the light chain or heavy chain of the immunoglobulin; the scFv targeting CLDN18.2 or non-CLDN18.2 antigen.

7. The bispecific antibody as defined in claim 5, wherein the first protein functional region is an immunoglobulin, and the second protein functional region is a cytokine or fragment thereof, or a cytokine receptor or a fragment thereof; the number of the cytokine or the fragment thereof, or the number of the cytokine receptor or the fragment thereof is two or four; the cytokine or the fragment thereof, or the cytokine receptor or the fragment thereof is symmetrically linked to the C-terminals or N-terminals of the two light chains or two heavy chains of the immunoglobulin via a linker.

8. The bispecific antibody as defined in claim 6, wherein the bispecific antibody comprises the following amino acid sequences of light chain and the amino acid sequences containing heavy chains:
   the light chain amino acid sequence as shown in SEQ ID NO: 53, and the amino acid sequence comprising a heavy chain as shown in SEQ ID NO: 54; or, the light chain amino acid sequence as shown in SEQ ID NO: 55, and the amino acid sequence comprising a heavy chain as shown in SEQ ID NO: 56; or, the light chain amino acid sequence as shown in SEQ ID NO: 38, and the amino acid sequence comprising a heavy chain as shown in SEQ ID NO: 57; or, the light chain amino acid sequence as shown in SEQ ID NO: 38, and the amino acid sequence comprising a heavy chain as shown in SEQ ID NO: 58; or, the light chain amino acid sequence as shown in SEQ ID NO: 38, and the amino acid sequence comprising a heavy chain as shown in SEQ ID NO: 59; or, the light chain amino acid sequence as shown in SEQ ID NO: 38, and the amino acid sequence comprising a heavy chain as shown in SEQ ID NO: 60; or, the light chain amino acid sequence as shown in SEQ ID NO: 38, and the amino acid sequence comprising a heavy chain as shown in SEQ ID NO: 61; or, the light chain amino acid sequence as shown in SEQ ID NO: 38, and the amino acid sequence comprising a heavy chain as shown in SEQ ID NO: 4.

9. An isolated nucleic acid, encoding the antibody targeting CLDN18.2 as defined in claim 1.

10. An antibody drug conjugate (ADC), having a structure as shown in formula I:

$$Ab\text{-}[(L_2)_n\text{-}L_1\text{-}D]_y \qquad \text{formula I}$$

wherein D is a small molecule drug having cytotoxicity, and L1 and L2 are linkers respectively linking the drug and the antibody; n is 0 or 1; y represents the average of the number of D conjugated to Ab, and $0 < y \leq 10$;
and the Ab is the antibody targeting CLDN18.2 as defined in claim 1.

11. The antibody drug conjugate as defined in claim 10, wherein the small molecule drug is DM1, the linker L1 is SMCC, and n is 0, thereby forming an antibody drug conjugate as shown in the following formula III:
formula III;

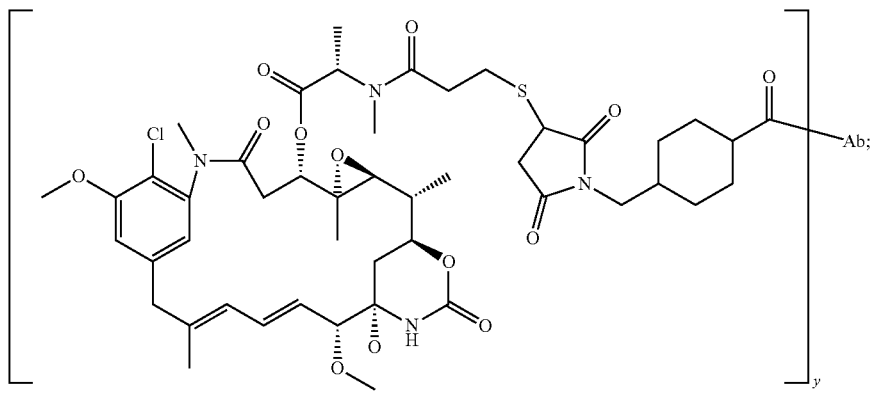

or, the small molecule drug is MMAF, the linker L1 is MC-VC-PAB, L2 is S-(3-carbonylpropyl) thioacetate ester, and n is 1, thereby forming an antibody drug conjugate as shown in the following formula IV:
formula Iv

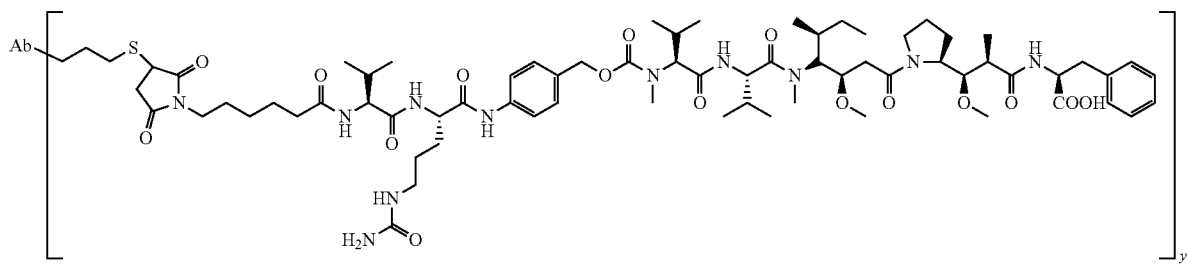

12. A chimeric antigen receptor (CAR), wherein the CAR comprises: (a) an extracellular binding domain scFv specifically recognizing CLDN18.2; (b) a hinge domain; (c) a transmembrane domain; (d) a co-stimulatory intracellular domain; and (e) a signaling domain; wherein the extracellular binding domain comprises the light chain variable region and the heavy chain variable region of the antibody targeting CLDN18.2 as defined in claim 1.

13. A nucleic acid construct, wherein the nucleic acid construct has a structure as shown in formula car-[(IRES)-f]q, and wherein IRES is an internal ribosome entry site sequence; f encodes a functional protein F, q is 0 or a non-zero natural number; and car encodes the car as defined in claim 12.

14. An expression vector, comprising the isolated nucleic acid as defined in claim 9, the expression vector is selected from a retrovirus vector, a lentiviral vector, an adenovirus vector and an adeno-associated virus vector.

15. A method for treating a patient in need of a medicament for tumors: wherein the method comprises administering to the patient a medicament comprising an effective amount of the antibody targeting CLDN18.2 as defined in claim 1.

16. An antibody targeting CLDN18.2, wherein the antibody targeting CLDN18.2 comprises alight chain variable region (VL) or a heavy chain variable region (VHI), wherein the VL comprises the following mutated complementary determining region (CDR) sequences: a VL CDR1 amino acid sequence as shown in SEQ ID NO: 11 or SEQ ID NO: 12; a VL CDR2 amino acid sequence as shown in SEQ ID NO: 13; and a VL CDR3 amino acid sequence as shown in SEQ TD NO: 14; and the mutated VHI comprises the following CDR sequences: a VH CDR1 amino acid sequence as shown in SEQ TD NO: 15, a VH CDR2 amino acid sequence as shown in SEQ TD NO: 16; and a VHI CDR3 amino acid sequence as shown in SEQ ID NO: 17, wherein mutation sequence of the CDR of the antibody targeting CLDN18.2 is a sequence with a deamination sensitive site mutation in a CDR region; the deamination sensitive site in the CDR region is position L30A or L30B of light chain CDR1; or, position H99 or H100 of heavy chain CDR3; amino acid residues at positions L30A and L30B of light chain CDR1 are mutated from NS to TS or NT, provided that position L30E is not Q and position L34 is not T; amino acid residues at positions H99 and H100 of heavy chain CDR3 are mutated from NS to TS or NT, provided that in light chain CDR1, position L30E is not Q and position L34 is not T.

17. The antibody targeting CLDN18.2 as defined in claim 1, wherein the antibody targeting CLDN18.2 comprises an immunoglobulin, Fab, Fab', F(ab')$_2$ or a single-chain Fv (scFv).

18. The bispecific antibody as defined in claim 4, wherein the anti-PD-1 antibody is Nivolumab, Pembrolizumab or Ba08, the anti-PD-L1 antibody is Atezolumab, Avelumab or Durvalumab, the anti-CD47 antibody is hu5F9 or iMab, and the anti-CD3 antibody is an antibody constructed using the sequences of light and heavy chain variable regions that bind to CD3 in Blinatumomab or AMG420; or, the cytokine includes TGF3, IL10 and CSF-1, and the cytokine receptor includes TGFj3RII, IL10 receptor and CSF-1R.

19. The bispecific antibody as defined in claim 6, wherein the bispecific antibody is selected from any one of the following:
- (1) the first protein functional region is an immunoglobulin, and the immunoglobulin comprises a light chain amino acid sequence as shown in SEQ ID NO: 38 and a heavy chain amino acid sequence as shown in SEQ ID NO: 39; the second protein functional region is scFv; wherein
  the C-terminals of the heavy chain variable regions of the two scFvs are symmetrically linked to the N-terminals of the two heavy chains of the immunoglobulin via a linker; and, the light chain variable region of the scFv is the light chain variable region of Atezolumab, and the heavy chain variable region of the scFv is the heavy chain variable region of Atezolumab; or,
  the C-terminals of the heavy chain variable regions of the two scFvs are symmetrically linked to the N-terminals of the two heavy chain variable regions of the immunoglobulin via a linker; and, the light chain variable region of the scFv is the light chain variable region of Hu5F9, and the heavy chain variable region of the scFv is the light chain variable region of Hu5F9; or,
  the N-terminals of the heavy chain variable regions of the two scFvs are symmetrically linked to the C-terminals of the two heavy chains of the immunoglobulin via a linker; and, the light chain variable region of the scFv is the light chain variable region of AMG420, and the heavy chain variable region of the scFv is the heavy chain variable region of AMG420;
- (2) the first protein functional region is scFv, and the second protein functional region is an immunoglobulin; the C-terminals of the heavy chain variable regions of the two scFvs are symmetrically linked to the N-terminals of the two heavy chains of the immunoglobulin via a linker; the sequence of the light chain variable region of the scFv is as shown in SEQ ID NO: 29, and the sequence of the heavy chain variable region of the scFv is as shown in SEQ ID NO: 34; wherein
  the immunoglobulin comprises the amino acid sequences of the light chain variable region of Nivolumab, the light chain constant region κ chain, the heavy chain variable region of Nivolumab and the heavy chain constant region of hIgG4; or,
  the immunoglobulin comprises the amino acid sequences of the light chain variable region of Pembrolizumab, the light chain constant region κ chain, the heavy chain variable region of Pembrolizumab and the heavy chain constant region of hIgG4; or,
  the immunoglobulin comprises the amino acid sequences of the light chain variable region of Atezolumab, the light chain constant region κ chain, the heavy chain variable region of Atezolumab and the heavy chain constant region of hIgG1.

20. The bispecific antibody as defined in claim 7, wherein the immunoglobulin comprises a light chain amino acid sequence as shown in SEQ ID NO: 38 and a heavy chain amino acid sequence as shown in SEQ ID NO: 39; wherein
  the cytokine or the fragment thereof, or the cytokine receptor or the fragment thereof is TGFβRII, and the sequence of TGFβRII is as shown in SEQ ID NO: 1, and there are two copies of TGFβRII; the two TGFβRIIs are symmetrically linked to the C-terminals of the two heavy chains of the immunoglobulin, and the C-terminal amino acid is mutated from K to A, respectively; or,
  the cytokine or the fragment thereof, or the cytokine receptor or the fragment thereof is IL10, and the sequence of IL10 is as shown in SEQ ID NO: 2, and there are two copies of IL10; the two copies of IL10 are symmetrically linked to the C-terminals of the two heavy chains of the immunoglobulin, and the C-terminal amino acid is mutated from K to A, respectively.

\* \* \* \* \*